US009670253B2

(12) United States Patent
Barouch et al.

(10) Patent No.: US 9,670,253 B2
(45) Date of Patent: *Jun. 6, 2017

(54) ANTIVIRAL VACCINES WITH IMPROVED CELLULAR IMMUNOGENICITY

(71) Applicants: Beth Israel Deaconess Medical Center, Inc., Boston, MA (US); Los Alamos National Security, LLC, Los Alamos, NM (US)

(72) Inventors: Dan H. Barouch, Boston, MA (US); Bette T. Korber, Los Alamos, NM (US); William M. Fischer, Los Alamos, NM (US)

(73) Assignees: Beth Israel Deaconess Medical Center, Inc., Boston, MA (US); Los Alamos National Security, LLC, Los Alamos, NM (US)

( * ) Notice: Subject to any disclaimer, the term of this patent is extended or adjusted under 35 U.S.C. 154(b) by 15 days.

This patent is subject to a terminal disclaimer.

(21) Appl. No.: 14/632,869

(22) Filed: Feb. 26, 2015

(65) Prior Publication Data

US 2016/0024156 A1 Jan. 28, 2016

Related U.S. Application Data

(63) Continuation of application No. 13/130,018, filed as application No. PCT/US2009/064999 on Nov. 18, 2009, now Pat. No. 9,017,691.
(Continued)

(51) Int. Cl.
*A61K 39/21* (2006.01)
*A61K 39/12* (2006.01)
(Continued)

(52) U.S. Cl.
CPC ............ *C07K 14/005* (2013.01); *A61K 39/12* (2013.01); *A61K 39/21* (2013.01); *A61K 39/235* (2013.01);
(Continued)

(58) Field of Classification Search
None
See application file for complete search history.

(56) References Cited

U.S. PATENT DOCUMENTS

| 4,603,112 A | 7/1986 | Paoletti et al. |
| 5,639,649 A | 6/1997 | Almond et al. |

(Continued)

FOREIGN PATENT DOCUMENTS

| WO | WO-2006/040330 A2 | 4/2006 |
| WO | WO-2007/024941 A2 | 3/2007 |

(Continued)

OTHER PUBLICATIONS

Abbink et al., "Comparative seroprevalence and immunogenicity of six rare serotype recombinant adenovirus vaccine vectors from subgroups B and D," J Virol. 81(9):4654-63 (2007).
(Continued)

*Primary Examiner* — Janet L Andres
*Assistant Examiner* — Stuart W Snyder
(74) *Attorney, Agent, or Firm* — Panitch Schwarze Belisario & Nadel LLP

(57) ABSTRACT

The invention provides compositions, methods, and kits for the treatment or prevention of viral infections. The polyvalent (e.g., 2-valent) vaccines described herein incorporate computationally-optimized viral polypeptides that can increase the diversity or breadth and depth of cellular immune response in vaccinated subjects.

20 Claims, 54 Drawing Sheets

Related U.S. Application Data

(60) Provisional application No. 61/248,188, filed on Oct. 2, 2009, provisional application No. 61/152,184, filed on Feb. 12, 2009, provisional application No. 61/115,703, filed on Nov. 18, 2008.

(51) Int. Cl.
*A61K 39/00* (2006.01)
*C07K 14/005* (2006.01)
*A61K 39/235* (2006.01)
*A61K 39/275* (2006.01)
*C12N 7/00* (2006.01)

(52) U.S. Cl.
CPC .............. *A61K 39/275* (2013.01); *C12N 7/00* (2013.01); *C12N 2710/10043* (2013.01); *C12N 2710/10343* (2013.01); *C12N 2710/24043* (2013.01); *C12N 2740/16122* (2013.01); *C12N 2740/16134* (2013.01); *C12N 2740/16171* (2013.01); *C12N 2740/16222* (2013.01); *C12N 2740/16234* (2013.01); *C12N 2740/16271* (2013.01); *C12N 2740/16322* (2013.01); *C12N 2740/16334* (2013.01)

(56) References Cited

U.S. PATENT DOCUMENTS

| | | |
|---|---|---|
| 5,643,576 A | 7/1997 | Johnston et al. |
| 5,762,938 A | 6/1998 | Paoletti et al. |
| 6,913,922 B1 | 7/2005 | Bout et al. |
| 7,153,509 B2 | 12/2006 | Haynes et al. |
| 7,172,761 B2 | 2/2007 | Haynes et al. |
| 7,195,768 B2 | 3/2007 | Haynes et al. |
| 7,270,811 B2 | 9/2007 | Bout et al. |
| 7,598,078 B2 | 10/2009 | Havenga et al. |
| 7,741,099 B2 | 6/2010 | Havenga et al. |
| 7,906,113 B2 | 3/2011 | Bout et al. |
| 7,951,377 B2 | 5/2011 | Korber et al. |
| 7,968,286 B2 | 6/2011 | Havenga et al. |
| 8,012,467 B2 | 9/2011 | Havenga et al. |
| 8,052,967 B2 | 11/2011 | Vogels et al. |
| 8,071,107 B2 | 12/2011 | Haynes et al. |
| 8,076,131 B2 | 12/2011 | Vogels et al. |
| 2003/0147888 A1 | 8/2003 | Haynes et al. |
| 2003/0207287 A1 | 11/2003 | Short |
| 2003/0219452 A1 | 11/2003 | Haynes et al. |
| 2004/0001851 A1 | 1/2004 | Haynes et al. |
| 2004/0086506 A1 | 5/2004 | Haynes et al. |
| 2005/0196384 A1 | 9/2005 | Vogels et al. |
| 2005/0221493 A1 | 10/2005 | Vogels et al. |
| 2005/0232900 A1 | 10/2005 | Vogels et al. |
| 2007/0178562 A1 | 8/2007 | Haynes et al. |
| 2007/0298051 A1 | 12/2007 | Barouch et al. |
| 2008/0153083 A1 | 6/2008 | Vogels et al. |
| 2008/0171018 A1 | 7/2008 | Bout et al. |
| 2008/0199939 A1 | 8/2008 | Havenga et al. |
| 2008/0279879 A1 | 11/2008 | Zolla-Pazner |
| 2009/0198042 A1 | 8/2009 | Korber et al. |
| 2009/0324631 A1 | 12/2009 | Korber et al. |
| 2010/0015176 A1 | 1/2010 | Vogels et al. |
| 2010/0034774 A1 | 2/2010 | Vogels et al. |
| 2010/0104596 A1 | 4/2010 | Haynes et al. |
| 2010/0143302 A1 | 6/2010 | Havenga et al. |
| 2011/0150915 A1 | 6/2011 | Korber et al. |
| 2011/0301328 A1 | 12/2011 | Korber et al. |

FOREIGN PATENT DOCUMENTS

| | | |
|---|---|---|
| WO | WO-2007/104792 A2 | 9/2007 |
| WO | WO-2010/042817 A1 | 4/2010 |
| WO | WO-2010/059732 A1 | 5/2010 |
| WO | WO-2010/096561 A1 | 8/2010 |

OTHER PUBLICATIONS

Abrahams et al., "Quantitating the multiplicity of infection with human immunodeficiency virus type 1 subtype C reveals a non-poisson distribution of transmitted variants," J Virol. 83(8):3556-67 (2009).
Barouch et al., "Adenovirus vector-based vaccines for human immunodeficiency virus type 1," Hum Gene Ther. 16(2):149-56 (2005).
Barouch et al., "Dynamic immune responses maintain cytotoxic T lymphocyte epitope mutations in transmitted simian immunodeficiency virus variants," Nat Immunol. 6(3):247-52 (2005).
Barouch et al., "Immunogenicity of recombinant adenovirus serotype 35 vaccine in the presence of pre-existing anti-Ad5 immunity," J Immunol. 172(10):6290-7 (2004) (9 pages).
Barouch et al., "International seroepidemiology of adenovirus serotypes 5, 26, 35, and 48 in pediatric and adult populations," Vaccine. 29(32):5203-9 (2011) (14 pages).
Barouch et al., "Mosaic HIV-1 vaccines expand the breadth and depth of cellular immune responses in rhesus monkeys," Nat Med. 16(3):319-23 (2010) (14 pages).
Barouch et al., "Vaccine protection against acquisition of neutralization-resistant SIV challenges in rhesus monkeys," Nature. 482(7383):89-93 (2012) (6 pages).
Barouch et al.,"HIV-1 vaccine development after STEP," Annu Rev Med. 61:153-67 (2010) (19 pages).
Barouch, "Novel adenovirus vector-based vaccines for HIV-1," Curr Opin HIV AIDS. 5(5):386-90 (2010) (8 pages).
Beerenwinkel et al., "Computational methods for the design of effective therapies against drug resistant HIV strains," Bioinformatics. 21(21):3943-50 (2005).
Burgers et al., "Measurements of immune responses for establishing correlates of vaccine protection against HIV," AIDS Res Hum Retroviruses. 27(00):1-8 (2011).
Cao et al., "Cytotoxic T-lymphocyte cross-reactivity among different human immunodeficiency virus type 1 clades: implications for vaccine development," J Virol. 71(11):8615-23 (1997).
Communication pursuant to Rules 70(2) and 70a(2) EPC for European Application No. 09828172.8, dated Jul. 18, 2013 (1 page).
Doria-Rose et al., "Breadth of human immunodeficiency virus-specific neutralizing activity in sera: clustering analysis and association with clinical variables," J. Virol. 84(3):1631-6 (2010).
Engelhardt et al., "Ablation of E2A in recombinant adenoviruses improves transgene persistence and decreases inflammatory response in mouse liver," Proc Natl Acad Sci USA. 91(13):6196-200 (1994).
Examination and Search Report for African Regional Intellectual Property Organization Patent Application No. AP/P/2011/005767, dated Mar. 19, 2015 (8 pages).
Examination Report for African Regional Intellectual Property Organization Patent Application No. AP/P/2011/005767, dated Oct. 8, 2015 (5 pages).
Examination Report for Australian Patent Application No. 2009316629, dated Dec. 17, 2014 (4 pages).
Fourth Office Action for Chinese Patent Application No. 200980154787.4, dated Apr. 3, 2015 (7 pages).
Frahm et al., "Consistent cytotoxic-T-lymphocyte targeting of immunodominant regions in human immunodeficiency virus across multiple ethnicities," J Virol. 78(5):2187-200 (2004).
Frahm et al., "Control of human immunodeficiency virus replication by cytotoxic T lymphocytes targeting subdominant epitopes," Nat Immunol. 7:173-8 (2006).
Frahm et al., "Increased detection of HIV-specific T cell responses by combination of central sequences with comparable immunogenicity," AIDS. 22(4):447-56 (2008).
Gao et al., "Antigenicity and immunogenicity of a synthetic human immunodeficiency virus type 1 group m consensus envelope glycoprotein," J Virol. 79(2):1154-63 (2005).
Gao et al., "Broadly reactive monoclonal antibodies to multiple HIV-1 subtype and SIVcpz envelope glycoproteins," Virology. 394(1):91-8 (2009) (16 pages).

(56) References Cited

OTHER PUBLICATIONS

Gao et al., "Centralized HIV-1 envelope immunogens and neutralizing antibodies," Curr HIV Res. 5(6):572-7 (2007).
Genbank Accession No. AAY23526. Retrieved on Feb. 13, 2010<http://www.ncbi.nlm.nih.gov/protein/62956393> (2 pages).
Gnanakaran et al., "Genetic signatures in the envelope glycoproteins of HIV-1 that associate with broadly neutralizing antibodies," PLoS Comput Biol. 6(10):e1000955 (2010) (26 pages).
Haynes et al., "Analysis of HIV-1 subtype B third variable region peptide motifs for induction of neutralizing antibodies against HIV-1 primary isolates," Virology. 345(1):44-55 (2006).
Hudgens et al., "Power to detect HIV vaccine effects in repeated low-dose challenge experiments," J Infect Dis. 200(4):609-13 (2009) (8 pages).
Hulot et al., "Vaccine-induced CD8+ T lymphocytes of rhesus monkeys recognize variant forms of an HIV epitope but do not mediate optimal functional activity," J Immunol. 186(10):5663-74 (2011).
Kaufman et al., "Focus and breadth of cellular immune responses elicited by a heterologous insert prime-boost vaccine regimen in rhesus monkeys," Vaccine. 30(3):506-9 (2012).
Kaufman et al., "Route of adenovirus-based HIV-1 vaccine delivery impacts the phenotype and trafficking of vaccine-elicited CD8+ T lymphocytes," J Virol. 84(12):5986-96 (2010).
Kaufman et al., "Translational Mini-Review Series on Vaccines for HIV: T lymphocyte trafficking and vaccine-elicited mucosal immunity," Clin Exp Immunol. 157(2):165-73 (2009).
Korber et al., "The implications of patterns in HIV diversity for neutralizing antibody induction and susceptibility," Curr Opin HIV AIDS. 4(5):408-17 (2009).
Kothe et al., "Ancestral and consensus envelope immunogens for HIV-1 subtype C," Virology. 352(2):438-49 (2006).
Kothe et al., "Antigenicity and immunogenicity of HIV-1 consensus subtype B envelope glycoproteins," Virology. 360(1):218-34 (2007) (29 pages).
Koup et al., "Priming immunization with DNA augments immunogenicity of recombinant adenoviral vectors for both HIV-1 specific antibody and T-cell responses," PLoS One. 5(2):e9015 (2010) (15 pages).
Kulkarni et al., "Highly complex neutralization determinants on a monophyletic lineage of newly transmitted subtype C HIV-1 Env clones from India," Virology. 385(2):505-20 (2009) (33 pages).
Launay et al., "Immunological efficacy of a three-dose schedule of hepatitis A vaccine in HIV-infected adults: HEPAVAC study," J Acquir Immune Defic Syndr. 49(3):272-5 (2008).
Li et al., "Genetic and neutralization properties of subtype C human immunodeficiency virus type 1 molecular env clones from acute and early heterosexually acquired infections in Southern Africa," J Virol. 80(23):11776-90 (2006).
Li et al., "Mapping HIV-1 vaccine induced T-cell responses: bias towards less-conserved regions and potential impact on vaccine efficacy in the Step study," PLoS One. 6(6):e20479 (2011) (9 pages).
Liao et al., "A group M consensus envelope glycoprotein induces antibodies that neutralize subsets of subtype B and C HIV-1 primary viruses," Virology. 353(2):268-82 (2006) (30 pages).
Liu et al., "Immune control of an SIV challenge by a T-cell-based vaccine in rhesus monkeys," Nature. 457(7225):87-91 (2009) (13 pages).
Liu et al., "Magnitude and phenotype of cellular immune responses elicited by recombinant adenovirus vectors and heterologous prime-boost regimens in rhesus monkeys," J Virol. (82)10:4844-52 (2008).
Liu et al., "Modulation of DNA vaccine-elicited CD8+ T-lymphocyte epitope immunodominance hierarchies," J Virol. 80(24):11991-7 (2006).
Létourneau et al., "Design and pre-clinical evaluation of a universal HIV-1 vaccine," PLoS One. 2(10):e984 (2007) (11 pages).
Masek-Hammerman et al., "Mucosal trafficking of vector-specific CD4+ lymphocytes following vaccination of rhesus monkeys with adenovirus serotype 5," J Virol. 84(19):9810-6 (2010).
Moore et al., "Inter- and intraclade neutralization of human immunodeficiency virus type 1: genetic clades do not correspond to neutralization serotypes but partially correspond to gp120 antigenic serotypes," J Virol. 70(1):427-44 (1996).
Mothe et al., "Definition of the viral targets of protective HIV-1-specific T cell responses," J Transl Med. 9:208 (2011) (20 pages).
Nanda et al., "Immunogenicity of recombinant fiber-chimeric adenovirus serotype 35 vector-based vaccines in mice and rhesus monkeys," J Virol. 79(22):14161-8 (2005).
Ndhlovu et al., "Mosaic HIV-1 Gag antigens can be processed and presented to human HIV-specific CD8+ T cells," J Immunol. 186(12):6914-24 (2011) (24 pages).
Nkolola et al., "Breadth of neutralizing antibodies elicited by stable, homogeneous clade A and clade C HIV-1 gp140 envelope trimers in guinea pigs," J Virol. 84(7):3270-9 (2010).
O'Brien et al., "Adenovirus-specific immunity following immunization with an Ad5 HIV-1 vaccine candidate in humans," Nat Med. 15(8):873-5 (2009) (8 pages).
Office Action for Israeli Patent Application No. 212984, dated Aug. 26, 2013 (4 pages).
Office Action for Israeli Patent Application No. 212984, dated Oct. 14, 2015 (6 pages).
Office Action for Israeli Patent Application No. 212984, dated Oct. 14, 2014 (6 pages).
Office Action for Japanese Patent Application No. 2015-021128, mailed Dec. 15, 2015 (7 pages).
Priddy et al., "Safety and immunogenicity of a replication-incompetent adenovirus type 5 HIV-1 clade B gag/pol/nef vaccine in healthy adults," Clin Infect Dis. 46(11):1769-81 (2008).
Rhee et al., "Translational Mini-Review Series on Vaccines for HIV: Harnessing innate immunity for HIV vaccine development," Clin Exp Immunol. 157(2):174-80 (2009).
Roberts et al., "Hexon-chimaeric adenovirus serotype 5 vectors circumvent pre-existing anti-vector immunity," Nature. 441(7090):239-43 (2006).
Salazar-Gonzalez et al., "Deciphering human immunodeficiency virus type 1 transmission and early envelope diversification by single-genome amplification and sequencing," J Virol. 82(8):3952-70 (2008).
Santra et al., "A centralized gene-based HIV-1 vaccine elicits broad cross-clade cellular immune responses in rhesus monkeys," Proc Natl Acad Sci U S A. 105(30):10489-94 (2008).
Santra et al., "Mosaic vaccines elicit CD8+ T lymphocyte responses in monkeys that confer enhanced immune coverage of diverse HIV strains," Nat Med. 16(3):324-8 (2010) (12 pages).
Santra et al., "Replication-defective adenovirus serotype 5 vectors elicit durable cellular and humoral immune responses in nonhuman primates," J Virol. 79(10):6516-22 (2005).
Seaman et al., "Tiered categorization of a diverse panel of HIV-1 Env pseudoviruses for assessment of neutralizing antibodies," J Virol. 84(3):1439-52 (2010).
Sumida et al., "Neutralizing antibodies and CD8+ T lymphocytes both contribute to immunity to adenovirus serotype 5 vaccine vectors," J Virol. 78(6):2666-73 (2004).
Sumida et al., "Neutralizing antibodies to adenovirus serotype 5 vaccine vectors are directed primarily against the adenovirus hexon protein," J Immunol. 174(11):7179-85 (2005).
Tang et al., "Epitopes immediately below the base of the V3 loop of gp120 as targets for the initial autologous neutralizing antibody response in two HIV-1 subtype B-infected individuals," J Virol. 85(18):9286-99 (2011).
Weaver et al., "Cross-subtype T-cell immune responses induced by a human immunodeficiency virus type 1 group m consensus env immunogen," J Virol. 80(14):6745-56 (2006).
Yusim et al., "Genotype 1 and global hepatitis C T-cell vaccines designed to optimize coverage of genetic diversity," J Gen Virol. 91( Pt 5):1194-206 (2010).
Blondelle et al., "Immunogenically optimized peptides derived from natural mutants of HIV CTL epitopes and peptide combinatorial libraries," Biopolymers. 90(5):683-694 (2008).
Fischer et al., "Coping with viral diversity in HIV vaccine design: A response to Nickle et al.," PLoS Comput Biol. 4(1):e15 (2008) (5 pages).

(56) References Cited

OTHER PUBLICATIONS

Fischer et al., "Polyvalent vaccines for optimal coverage of potential T-cell epitopes in global HIV-1 variants," Nat Med. 13(1):100-106 (2007).
Kong et al., "Expanded breadth of the T-cell response to mosaic human immunodeficiency virus type 1 envelope DNA vaccination," J Virol. 83(5):2201-2215 (2009).
Korber et al., "T-Cell vaccine strategies for human immunodeficiency virus, the virus with a thousand faces," J Virol. 83(17):8300-8314 (2009).
NCBI Blast for Accession No. AAY23526. Retrieved on Feb. 13, 2010 (2 pages).
Thurmond et al., "Web-based design and evaluation of T-cell vaccine candidates," Bioinformatics. 24(14):1639-1640 (2008).
Office Action in Chinese Patent Application No. 200980154787.4 mailed Feb. 7, 2014 (with English Translation) (5 pages).
Communication Pursuant to Rules 161(2) and 162 EPC for European Patent Application No. 09828172.8, dated Jul. 4, 2011 (2 pages).
Extended European Search Report for European Patent Application No. 09828172.8, dated Jul. 1, 2013 (16 pages).
First Examination Report for New Zealand Patent Application No. 593598, dated Jul. 7, 2011 (3 pages).
First Examination Report for New Zealand Patent Application No. 602504, dated Sep. 24, 2012 (4 pages).
Second Examination Report for New Zealand Patent Application No. 593598, dated Oct. 9, 2012 (3 pages).
Third Examination Report for New Zealand Patent Application No. 593598, dated Dec. 21, 2012 (1 page).
English Translation of the Notification of the First Office Action for Chinese Patent Application No. 200980154787.4, mailed Mar. 7, 2013 (4 pages).
International Search Report for International Application No. PCT/US2009/064999, mailed Mar. 5, 2010 (4 pages).
International Preliminary Report on Patentability and Written Opinion of the International Searching Authority for International Application No. PCT/US2009/064999, issued May 24, 2011 (9 pages).
Barouch, "Challenges in the development of an HIV-1 vaccine" Nature. 455(7213):613-9 (2008).
Cohen, J. "AIDS research. Did Merck's failed HIV vaccine cause harm?" Science. 318(5853):1048-9 (2007).
Girard, et al. "A review of vaccine research and development: the human immunodeficiency virus (HIV)" Vaccine. 24(19):4062-81 (2006).
Gotch, et al. "Candidate vaccines for immunotherapy in HIV" HIV Med. 2(4):260-5 (2001).
Office Action in Japanese Patent Application No. 2011-537586 mailed May 27, 2014 (with English Translation) (4 pages).
Examination Report for Singapore Patent Application No. 201103573-0, mailed Sep. 8, 2014 (13 pages).
Third Office Action for Chinese Patent Application No. 200980154787.4, dated Sep. 30, 2014 (4 pages) (Chinese language only).
Cohen, J. "Naked DNA points way to vaccines," Science. 259(5102):1691-2 (1993).
Fynan et al., "DNA vaccines: protective immunizations by parenteral, mucosal, and gene-gun inoculations," Proc Natl Acad Sci U.S.A. 90(24):11478-82 (1993).
Kochanek et al., "A new adenoviral vector: Replacement of all viral coding sequences with 28 kb of DNA independently expressing both full-length dystrophin and beta-galactosidase," Proc Natl Acad Sci U.S.A. 93(12):5731-6 (1996).
Mangeat et al., "Lentiviral vectors and antiretroviral intrinsic immunity," Hum Gene Ther. 16(8):913-20 (2005).
Stemmer et al., "Single-step assembly of a gene and entire plasmid from large numbers of oligodeoxyribonucleotides," Gene. 164(1):49-53 (1995).
Wattanapitayakul et al., "Recent developments in gene therapy for cardiac disease," Biomed Pharmacother. 54(10):487-504 (2000).
Wiznerowicz et al., "Harnessing HIV for therapy, basic research and biotechnology," Trends Biotechnol. 23(1):42-7 (2005).
Office Action issued Aug. 15, 2016 in IL Application No. 243991.

Fig. 6

- CD8 T cells: median (range)
  - 2 Mosaic: 16 (12-29)
  - Mcon: 6 (0-7)
  - OptC: 3 (0-7)
- CD4 T cells:
  - 2 Mosaic: 4 (2-6)
  - Mcon: 1 (0-2)
  - OptC: 0.5 (0-2)

Fig. 9

OptC 366-07:

5 CD8 responses:

| | | | |
|---|---|---|---|
| OptC | IVQQQSNLLRAIEAQQ | Env | |
| E54 | VVQQSNLLRAIEAQ | Env | 548 562 |
| E72 | -VQQMNLLRAIEAQH | Env | 549 563 |
| | | | |
| OptC | AVFIHNFKRKGGIGGY | Pol | |
| P22 | AVFIHNFKRKGIGG | Pol | 894 908 |
| P236 | -VLIHNFKRKGIGGY | Pol | 895 909 |
| | | | |
| OptC | MAICEEMEKEGKITK | Pol | |
| P224 | TAICEMEREGKITK | Pol | 190 204 |
| | | | |
| OptC | CTHGIKPVVSTQLLL | Env | |
| E15 | CTHGIKPVVSTQLL | Env | 247 261 |
| | | | |
| OptC | GGPSHKARVLAEAMS | Gag | |
| G76 | GGPSHKARVLAEAMG | Gag | 354 368 |

1 CD4 response:

| | | | |
|---|---|---|---|
| OptC | LIGQVRDQAEHLKTA | Pol | |
| P86 | LIGQVRDQAEHLKTA | Pol | 876 890 |

Fig. 10

```
Mos1   ICTTTVPWNASWSNKSL
Mos2   ICTTAVPWNTSWSNKSQ  T...A
E334   ICTTTVPWNASWSNR    T...S
E214   -CTTTVPWNSSWSNKT   A...A
E158   ---TTAVPWNASWSNKSL A...T
E290   ---TTAVPWNTSWSNKSL
```

Fig. 11

8 CD8 responses:

| | | | | |
|---|---|---|---|---|
| Mos1 | EQLIKKERVYLSWVPAHKGIG | | | |
| Mos2 | EQLIKKEKVYLAWVPAHKGIG | | | |
| P221 | EELIKKEKVYLAWVP | Pol | 678 | 692 |
| P250 | EPLIKKEKVYLSWVP | Pol | 678 | 692 |
| P316 | -KLIEKDKVYLSWVPA | Pol | 679 | 693 |
| P223 | --LIKKERVYLSWVPAH | Pol | 680 | 694 |
| P169 | ------EKVYLAWVPAHKGIG | Pol | 684 | 698 |
| P83 | ------EKVYLSWVPAHKGIG | Pol | 684 | 698 |
| | | | | |
| Mos1 | CTHGIRPVVSTQLLL | | | |
| Mos2 | CTHGIKPVVSTQLLL | | | |
| E15 | CTHGIKPVVSTQLLL | Env | 247 | 261 |
| E47 | CTHGIRPVVSTQLLL | Env | 247 | 261 |
| | | | | |
| Mos1 | ICTTTVPWNASWSNKSL | | | |
| Mos2 | ICTTAVPWNTSWSNKSQ | | | |
| E334 | ICTTTVPWNASWSNR | Env | 603 | 617 |
| E214 | -CTTTVPWNSSWSNKT | Env | 604 | 618 |
| E158 | --TTAVPWNASWSNKSL | Env | 605 | 619 |
| E290 | --TTAVPWNTSWSNKSL | Env | 605 | 619 |
| | | | | |
| Mos1 | ACQGVGGPGHKARVLAEAMS | | | |
| Mos2 | ACQGVGGPSHKARVLAEAMS | | | |
| G166 | ACQEVGGPGHKARVL | Gag | 349 | 363 |
| G76 | -----GGPSHKARVLAEAMG | Gag | 354 | 368 |
| | | | | |
| Mos1 | AAEWDRVHPVHAGPIAPGQ | | | |
| Mos2 | AAEWDRLHPVHAGPVAPGQ | | | |
| G319 | AAE-DRLHPVHAGPIP | Gag | 209 | 225 |
| G242 | -ADWDRLHPVHAGPVA | Gag | 210 | 224 |
| G44 | -AEWDRLHPVHAGPIA | Gag | 210 | 224 |
| G277 | ---WDRVHPVHAGPNPPG | Gag | 212 | 226 |
| G102 | ----DRVHPVHAGPIPPGQ | Gag | 212 | 226 |
| | | | | |
| Mos1 | HSNWRAMASDFNLPP | | | |
| Mos2 | HSNWRAMASEFNLPP | | | |
| P93 | HSNWRAMASDFNLPP | Pol | 731 | 745 |
| | | | | |
| Mos1 | KGRPGNFLQNRPEPT | | | |
| Mos2 | KGRPGNFLQSRPEPT | | | |
| G86 | KGRPGNFLQNRPEPT | Gag | 442 | 456 |
| | | | | |
| Mos1 | SRELERFAVNPGLLE | | | |
| Mos2 | SRELERFALNPGLLE | | | |
| G39 | SRELERFALNPGLLE | Gag | 38 | 52 |

Fig. 11 cont.

5 CD4 responses:

| | | | | |
|---|---|---|---|---|
| Mos1 | RSLYNTVATLYCVHQR | | | |
| Mos2 | RSLFNTVATLYCVHAE | | | |
| G289 | KSLFNTVATLYCVHA | Gag | 76 | 90 |
| G54 | -SLYNTVATLYCVHQR | Gag | 77 | 91 |
| Mos1 | YVTDRGRQKIVSLTE | | | |
| Mos2 | YVTDRGRQKVVSLTD | | | |
| P134 | YVTDRGRQKVVSLTE | Pol | 612 | 626 |
| Mos1 | CTTTVPWNASWSNKS | | | |
| Mos2 | CTTAVPWNTSWSNKS | | | |
| E53 | CTTNVPWNSSWSNKS | Env | 604 | 618 |
| Mos1 | WWAGIQQEFGIPYNP | | | |
| Mos2 | WWAGIKQEFGIPYNP | | | |
| P135 | WWAGIQQEFGIPYNP | Pol | 846 | 860 |
| Mos1 | GPGHKARVLAEAMSQ | | | |
| Mos2 | GPSHKARVLAEAMSQ | | | |
| G15 | GPGHKARVLAEAMSQ | Gag | 355 | 369 |

Fig. 14

- CD8 T cells: median (range)
  – 2 Mosaic: 8 (7-14)
  – Mcon: 3 (0-6)
  – OptC: 1.5 (0-5)
- CD4 T cells:
  – 2 Mosaic: 3 (2-5)
  – Mcon: 1 (0-2)
  – OptC: 0.5 (0-2)

Fig. 20A

CD8 Gag

Natural C
M Consensus
B+C
Mosaic

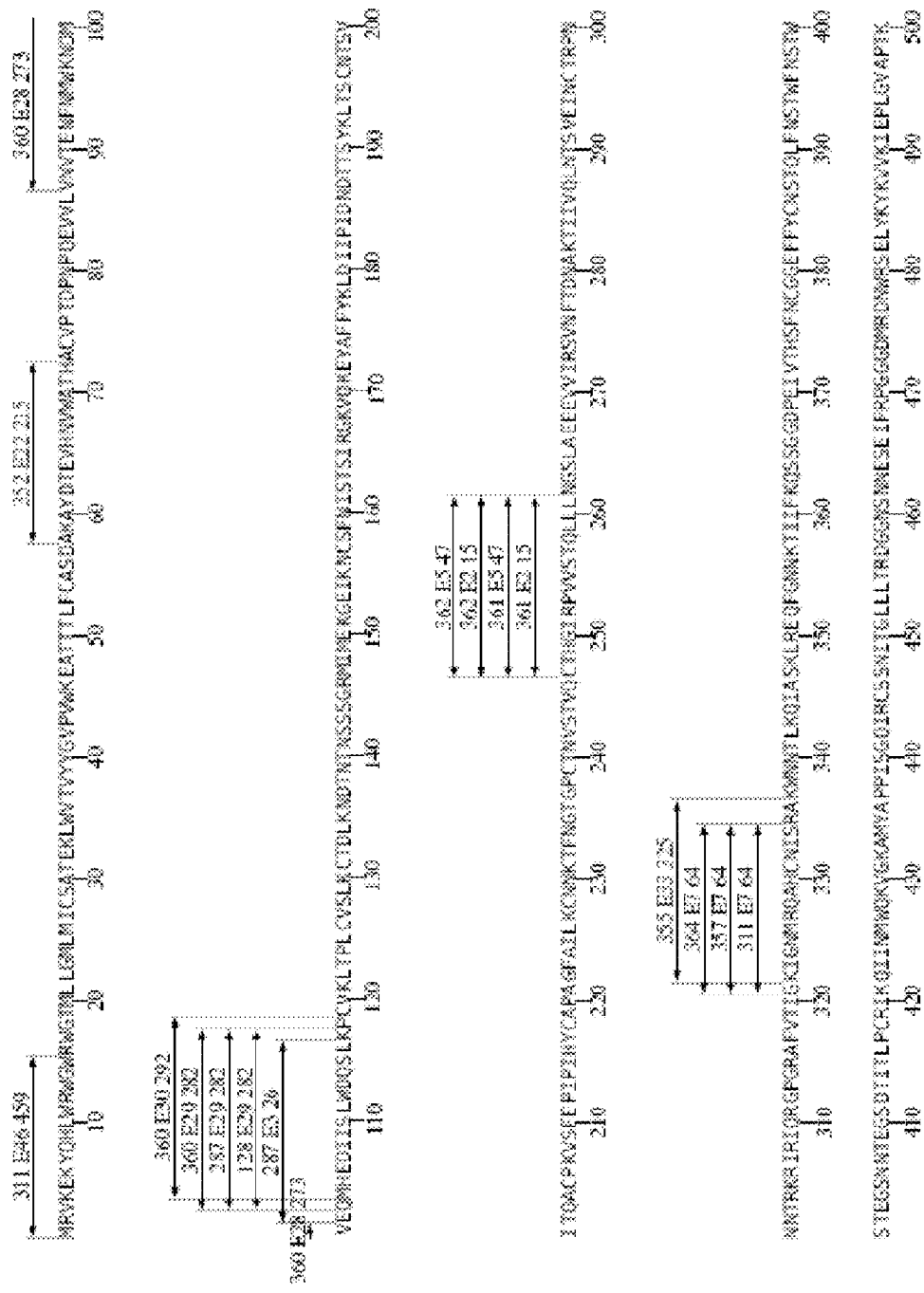

Fig. 21B

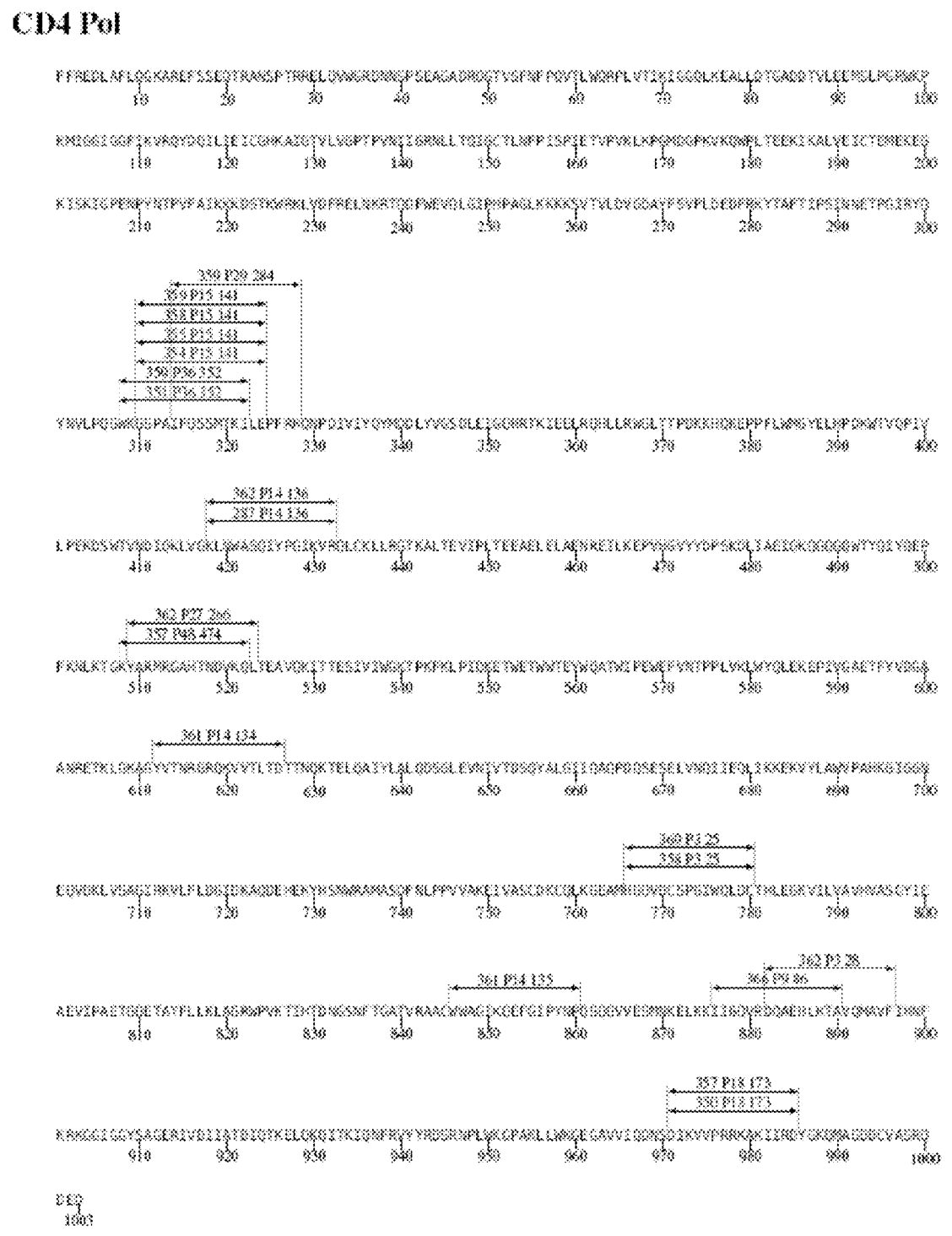

CD4 Pol

[Sequence alignment figure with amino acid sequence positions 10–1000, showing peptide mapping annotations at various positions including 359 P29 284, 359 P15 141, 358 P15 141, 354 P15 141, 354 P15 141, 398 P36 358, 351 P36 152, 363 P14 136, 357 P14 136, 362 P27 266, 357 P48 474, 361 P14 134, 360 P1 25, 358 P3 25, 361 P14 135, 366 P8 86, 362 P3 28, 357 P18 173, 358 P18 173]

SEQ
1603

Fig. 21C

CD4 Env

Fig. 22

Reactive peptides and breadth and depth of responses: Clade B+C Vaccine

```
Clade B+C 287-95:
3 CD8 PTE+, 1 CD4 PTE+
3 CD8+ regions, 1 CD4+ region
Number of overlapping peptides per region: CD8: 1 1 1 CD4: 1

3 CD8 responses:
C     AAEWDRLHPVHAGPIA
B     AAEWDRLHPVHAGPIA
G319  AAE-DRLHPVHAGPIP Gag   209   225

C     IQMHEDIISLWDQSLK
B     IQMHEDIISLWDQSLK
E26   IQMHEDIISLWDQSL  Env   103   116
E282  MMHEDIISLWDESLK  Env   103   117

1 CD4 response:
C     KLNWASQIYSGIKVR
B     KLNWASQIYPGIKVR
P136  KLNWASQIYAGIKVK  Pol   418   432
```

```
Clade B+C 128-92:
5 CD8 PTE+, 2 CD4 PTE+
5 CD8+ regions, 2 CD4+ regions
Number of overlapping peptides per region: CD8: 1 1 1 1 1 CD4: 1 1

5 CD8 responses:
C     KHLVWASRELERFAL
B     KHIVWASRELERFAV
G20   KHLVWASRELERFAL  Gag   32    46

C     LQEQIAWMTNNPPVP
B     LQEQISWMTNNPPIP
G174  LAEQIAWMTSNPPIP  Gag   243   257

C     QMHEDIISLWDQSLK
B     QMHEDIISLWDQSLK
E282  MMHEDIISLWDESLK  Env   103   117

C     DIWDNMTWMQWDREI
B     EIWDNMTWMEWEREI
E297  EIWNRMTWMEWEKEI  Env   621   635

C     WPVKVIHTANGSNFT
B     WPVKTIHTANGSNFT
P814  WPVKVVHTDNGSNFT  Pol   823   837

2 CD4 responses:
C     AQTGTEELRSLYNTV
B     LQTGSEELRSLYNTV
G146  LQTGSEELKSLFNTV  Gag   68    82

C     YFNMWKNDMVDQMHE
B     NFNMWKNDMVEQMHE
E544  NFNMWKNDMVEQMHE  Env   92    106
```

Fig. 22 cont.

```
Clade B+C 263-00:
3 CD8 PTE+, 1 CD4 PTE+
3 CD8+ regions, 1 CD4+ region
Number of overlapping peptides per region: CD8: 1 1 1 CD4: 1

3 CD8 responses:
C       GRPGNFLQSRPEPT
B       GRPGNFLQSRPEPT
G86     GRPGNFLQNRPEPT   Gag   442   456

C       PVHAGPIAPGQMREP
B       PVHAGPIAPGQMREP
G213    PVQAGPIAPGQMREP  Gag   217   231

C       VQQSNLLRAIEAQQ
B       VQQSNLLRAIEAQQ
E72     VQQSNLLRAIEAQH   Env   549   563

1 CD4 response:
C       LLEESQNQQEKNEKD
B       LEEESQNQQEKNEQE
E49     LEEESQNQQEKNEQD  Env   645   659
```

```
Clade B+C 311-00:
5 CD8 PTE+, 0 CD4 PTE+
5 CD8+ regions, 0 CD4+ region
Number of overlapping peptides per region: CD8: 1 1 1 1 1 CD4: 0

5 CD8 responses:
C       DRLHPVHAGPIAPGQ
B       DRLHPVHAGPIAPGQ
G102    DRVHPVHAGPIPPGQ  Gag   213   227

C       GDIIGDIRQAHCNIS
B       GEIIGDIRQAHCNIS
E64     GDIIGDIRQAHCNIS  Env   301   334

C       TGMLRNCQPWWIWGI
B       KGIRKNYQSLWRWGT
E459    KEIRKNYQSLWRWGT  Env   4     18

C       MTKILEPFRAKNPEI
B       MTKILEPFRKQNPDI
P144    MTKILEPFRKQNPDI  Pol   319   333

C       RAMASEFNLPPVVAK
B       RAMASDFNLPPVVAK
P193    RAMASDFNLPPVVAK  Pol   735   749
```

Fig. 22 cont.

```
Clade B+C 335-96:
6 CD8 PTE+, 0 CD4 PTE+
2 CD8+ regions, 0 CD4+ region

Number of overlapping peptides per region: CD8: 3 3 CD4: 0

6 CD8 responses:
C      AAEWDRLHPVHAGPIAPGQ
B      AAEWDRLHPVHAGPIAPGQ
G319   AAE-DRLHPVHAGPIP       Gag   209   225
G44     AEWDRLHPVHAGPIA       Gag   210   224
G102       DRVHPVHAGPIPPGQ    Gag   213   227

C      QLINKERVYLSWVPAHKGIS
B      QLIKKEKVYLNWVPAHKGIS
P316   KLIEKDKVYLSWVPA        Pol   679   693
P223   LIKKERVYLSWVPAH        Pol   680   694
P83        EKVYLSWVPAHKGIG    Pol   684   698

Clade B+C 414-95:
0 CD8 PTE+, 1 CD4 PTE+
0 CD8+ regions, 1 CD4+ region
Number of overlapping peptides per region: CD8: 0 CD4: 1

1 CD4 responses:
C      SLYNTVATLYCVHAG
B      SLYNTVATLYCVHQK
G54    SLYNTVATLYCVHQR  Gag   77   91

Clade B+C 431-01:
3 CD8 PTE+, 1 CD4 PTE+
2 CD8+ regions, 1 CD4+ region
Number of overlapping peptides per region: CD8: 2 1 CD4: 1

3 CD8 responses:
C      HQAAMQMLKDTINEE
B      HQAAMQMLKETINEE
G24    HQAAMQMLKDTINEE  Gag  194  208
G51    HQAAMQMLKETINEE  Gag  194  208

C      AVFIHNFKRKGGIGG
B      AVFIHNFKRKGGIGG
P22    AVFIHNFKRKGGIGG  Pol  894  908

1 CD4 response:
C      YFNMWKNDMVDQMHE
B      NFNMWKNNMVEQMHE
E44    NFNMWKNNMVEQMHE  Env   92  106
```

Fig. 22 cont.

Reactive peptides and breadth and depth of responses: M Consensus Vaccine

```
M consensus 349-07:
7 CD8 PTE+, 2 CD4 PTE+
3 CD8+ regions, 2 CD4+ regions
Number of overlapping peptides per region: CD8: 3 2 2 CD4: 1 1

3 CD8 responses:
Mcon   EQATQDVKNWMTDTLLVQNANP
G197   EQATQEVKNWMTDTL             Gag   307   321
G198   ---TQEVKNWMTDTLLIQ          Gag   310   324
G55    --------KNWMTDTLLVQNANP     Gag   314   329

Mcon   IVQQQSNLLRAIEAQQ
E54    VVQQQSNLLRAIEAQ             Env   548   562
E72    -VQQQNLLRAIEAQH             Env   549   563

Mcon   AVFIHNFKRKGGIGGY
P22    AVFIHNFKRKGGIGG             Pol   894   908
P236   -VLIHNFKRKGGIGGY            Pol   895   909

2 CD4 responses:
Mcon   SELYKYKVVKIEPLG
E42    SELYKYKVVKIEPLG             Env   481   495

Mcon   NFNMWKNDMVEQMHE
E44    NFNMWKNDMVEQMHE             Env   92    106

M consensus 350-07:
0 CD8 PTE+, 2 CD4 PTE+
0 CD8+ regions, 2 CD4+ regions
Number of overlapping peptides per region: CD8: none CD4: 1 1

2 CD4 responses:
Mcon   GKKKYRLKHLVWASR
G230   GKKKYRLKHIVWASR             Gag   25    39

Mcon   DIKVVPRRKAKIIRD
P173   DIKVVPRRKVKIIRD             Pol   971   985

M consensus 351-07:
7 CD8 PTE+, 1 CD4 PTE+
4 CD8+ regions, 1 CD4+ regions
Number of overlapping peptides per region: CD8: 2 2 2 1 CD4: 1
```

Fig. 22 cont.

```
4 CD8 responses:
Mcon  KHLVWASRELERFALNPGLL
G20   KHLVWASRELERFAL          Gag    32     46
G68   -----ASRELERFAVNPGLL     Gag    37     5

Mcon  IVQQQSNLLRAIEAQQ
E6    VVQQQSNLLRAIEAQ          Env    548    562
E8    -VQQNNLLRAIEAQH          Env    549    563

Mcon  AVFIHNFKRKGGIGGY
P22   AVFIHNFKRKGGIGG          Pol    894    908
P236  -VLIHNFKRKGGIGGY         Pol    895    909

Mcon  KNWMTDTLLVQNANP
G55   KNWMTDTLLVQNANP          Gag    314    328

1 CD4 response:
Mcon  WKGSPAIFQSSMTKI
P352  WKGSPAIFQASMTKI          Pol    308    322
```
---
```
M consensus 352-07:
6 CD8 PTE+, 2 CD4 PTE+
6 CD8+ regions, 2 CD4+ regions
Number of overlapping peptides per region: CD8: 1 1 1 1 1 1  CD4: 1

6 CD8 responses:
Mcon  QPALQTGSEELRSLY
G268  LPALKTGSEELRSLY          Gag    65     79

Mcon  IVQQQSNLLRAIEAQ
E54   VVQQQSNLLRAIEAQ          Env    548    562

Mcon  CSGKLICTTTVPWNS
E73   CSGKLICTTAVPWNS          Env    598    612

Mcon  AKAYDTEVHNVWATH
E215  AKAYEKEVHNVWATH          Env    58     72

Mcon  KKDSTKWRKLVDFRE
P23   KKDSTKWRKLVDFRE          Pol    220    234

Mcon  VFIHNFKRKGGIGGY
P236  VLIHNFKRKGGIGGY          Pol    895    909

2 CD4 responses:
Mcon  NKIVRMYSFVSILDI
G13   NKIVRMYSFVSILDI          Gag    271    285

Mcon  KGNSSKVSQNYPIVQ
G97   TGNSSQVSQNYPIVQ          Gag    122    136
```

Fig. 22 cont.

```
M consensus 353-07:
2 CD8 PTE+, 0 CD4 PTE+
2 CD8+ regions, 0 CD4+ regions
Number of overlapping peptides per region: CD8: 1 1  CD4: none 2 CD8 responses:
Mcon  GCKQIIGQLQPALQT
G151  GCRQILGQLQPSLQT       Gag   56    70

Mcon  PVHAGPIPPGQMREP
G213  PVQAGPIAPGQMREP       Gag   217   231

M consensus 354-07:
3 CD8 PTE+, 1 CD4 PTE+
3 CD8+ regions, 1 CD4+ regions
Number of overlapping peptides per region: CD8: 2 2 1  CD4: 1

3 CD8 responses:
Mcon  EQATQDVKNWMTDTLLVQNANP
G197  EQSTQEVKNWMTDTL       Gag   307   321
G55   -------KNWMTDTLLVQNANP Gag  314   328

Mcon  IVQQQSNLLRAIEAQQ
E54   VVQQQSNLLRAIEAQ       Env   548   562
E72   -VQQNNLLRAIEAQH       Env   549   563

Mcon  HSNWRAMASDFNLPP
P93   HSNWRAMASDFNLPP       Pol   731   745

1 CD4 response:
Mcon  GSPAIFQSSMTKILE
P141  GSPAIFQSSMTKILD       Pol   310   324

M consensus 355-07:
3 CD8 PTE+, 1 CD4 PTE+
2 CD8+ regions, 1 CD4+ regions
Number of overlapping peptides per region: CD8: 1 3  CD4: 1

2 CD8 responses:
Mcon  IIGDIRQAHCNISGT
E325  ITGDIRQAHCNVSRS       Env   322   336

Mcon  SNWRAMASDFNLPPIVAK
P93   SNWRAMASDFNLPP        Pol   731   745
P149  ----RAMASDFNLPPIVAK   Pol   735   749
P193  -----AMASDFNLPPIVAK   Pol   735   749

1 CD4 response:
Mcon  GSPAIFQSSMTKILE
P141  GSPAIFQSSMTKILD       Pol   310   324
```

Fig. 22 cont.

```
Reactive peptides and breadth and depth of responses: Mosaic Vaccine

Mosaic 356-07:
15 CD8 PTE+, 2 CD4 PTE+
8 CD8+ regions, 2 CD4+ regions
Number of overlapping peptides per region: CD8: 5 3 1 3 1 1 1 2  CD4: 1 1

8 CD8 responses:
Mos1   AAEWDRVHPVHAGPIAPGQ
Mos2   AAEWDRLHPVHAGPVAPGQ
G319   AAE-DRLHPVHAGPIP       Gag    209    225
G44    -AEWDRLHPVHAGPIA       Gag    210    224
G242   -ADWDRLHPVHAGPVA       Gag    210    224
G577   ---WDRVHPVHAGPNFPG     Gag    213    226
G162   ----DPVHPVHAGPIPPGQ    Gag    213    227

Mos1   IVQQQNLLRAIEAQQ
Mos2   IVQQSNLLRAIEAQQ
E54    VVQQQNLLRAIEAQ         Env    548    562
E72    -VQQQNLLRAIEAQH        Env    549    563
E191   -VQQSNLLRAIEAQQ        Env    549    563

Mos1   ASQDVKNWMTETLLV
Mos2   ATQDVKNWMTDTLLV
G66    ASQEVKNWMTETLI         Gag    309    323

Mos1   AVFIHNFKRKGGIGGY
Mos2   AVFIHNFKRKGGIGGY
P22    AVFIHNFKRKGGIGG        Pol    894    908
P236   -VFIHNFYRKGGIGGY       Pol    895    909

Mos1   PLVKLWYQLEKDPIA
Mos2   PLVKLWYQLEKEPIV
P73    PLVKLWYQLEKEPIV        Pol    576    590

Mos1   TIPSTNNETPGIRYQ
Mos2   TIPSINNETPGIRYQ
P79    TIPSINNETPGIRYQ        Pol    286    300

Mos1   YPGIKVRQLCKLLRG
Mos2   YAGIKVRQLCKLLRG
P136   YPGIKVRQLCKLLRG        Pol    426    440

Mos1   LIKKERVYLSWVPAHKGIG
Mos2   LIKKERVYLAWVPAHKGIG
P125   LIKKERVYLSWVPAH        Pol    680    694
P83    ----ERVYLSWVPAHKGIG    Pol    684    698

2 CD4 responses:
Mos1   SLYNTVATLYCVHQR
Mos2   SLFNTVATLYCVHAS
G54    SLYNTVATLYCVHQR        Gag    77     91

Mos1   ANPDCKTILKALGPA
Mos2   ANPDCKTILKALGPG
G63    ANPDCKTILKALGPS        Gag    326    340
```

Fig. 22 cont.

```
Mosaic 357-07:
29 CD8 PTE+, 4 CD4 PTE+
14 CD8+ regions, 4 CD4+ regions
Number of overlapping peptides per region: CD8: 5 2 2 5 5 2 1 1 1 1 1 1 1 1 CD4: 1 1 1 1

14 CD8 responses:
Mos1  EQLIKKERVYILSWVPAHKGIG
Mos2  EQLIKKERVYLNWVPAHKSIG
P250  EFLIKKERVYILSWVP           Pol    673    692
P316  -FLIKKDKVYILSWVPA          Pol    679    693
P223  --LIKKERVYILSWVPAH         Pol    680    694
P169  ------ERVYLNWVPAHKGIG      Pol    684    698
P83   ------ERVYILSWVPAHKGIG     Pol    684    698

Mos1  IVQQQNNLLRAIEAQQ
Mos2  IVQQQNNLLRAIEAQQ
E54   VVQQQNNLLRAIEAQ            Env    540    562
E72   -VQQQNNLLRAIEAQQ           Env    549    563

Mos1  EQASQEVKNWMTETLLVQNANP
Mos2  EQATQEVKNWMTDTLLVQNANP
G197  EQGTQEVKNWMTDTL            Gag    307    321
G59   ---------KNWMTDTLLVQNANP   Gag    314    328

Mos1  HSNWRAMASDFNLPPVVAK
Mos2  HSNWRAMASKFNLPPIVAK
P93   HSNWRAMASDFNLPP            Pol    731    745
P062  -SNWRAMASKFNLPPI           Pol    732    746
P473  --NWRTSASDFNLPPVI          Pol    733    747
P149  ----STMASDFNLPPVVAK        Pol    735    749
P193  ----KAMASDFNLPPIVAK        Pol    735    749

Mos1  AENDRVHPVHAGPIAPGQ
Mos2  AENDRLHPVRAGPVAPGQ
G819  AENDRLHPVHAGPIF            Gag    209    223
G340  ENDRLHPVHAGPVR             Gag    210    224
G44   AENDRLHPVHAGPIA            Gag    210    224
G077  ---NDKVHPVHAGPNPPG         Gag    213    226
G192  ---DRVHPVHAGPIPPGQ         Gag    213    227

Mos1  SVFIHNFKRKGGIGGY
Mos2  SVFIHNFKRKGGIGGY
P22   SVFIHNFKRKGGIGG            Pol    894    908
P236  -VLIHNFKRKGGIGGY           Pol    895    909

Mos1  PLDEGFRKYTAFTIP
Mos2  PLDEDFRKYTAFTIP
P043  ELDESFRKYTAFTIP            Pol    274    288

Mos1  TKILEPFRAKNPEIV
Mos2  TKILEPFRKQNPDIV
P394  TKIISPFRAQSEIV             Pol    320    334

Mos1  ICEEMEKEGKITKIG
Mos2  ICTEMEKEGKISKIG
P162  ICTEMEKEGKISKIG            Pol    192    206

Mos1  VKLWYQLEKDPIAGV
Mos2  VKLNYQLEKEPIVGA
P260  VELNYQLEKDPIVGA            Pol    579    593

Mos1  GDIIGDIRQAHCNIS
Mos2  GDIIGDIRQAHCNLS
E764  GDIIGDIRQAHCNIS            Env    321    334

Mos1  ICTTTVPWNASWSNK
Mos2  ICTTAVPWNTSWSNK
E334  ICTTTVPWNASWSNK            Env    603    617
```

Fig. 22 cont.

```
Mos1   IGQVRDQAEHLKTAV
Mos2   IGQVRDQAEHLKTAV
P174   IGQVREQAEHLKTAV           Pol    877    891

Mos1   GKQMAGADCVAGRQD
Mos2   GKQMAGDDCVASRQD
P95    GKQMAGDDCVAGRQD           Pol    987   1001

4 CD4 responses:
Mos1   KYARMRTAHTNDVKQ
Mos2   KYARMRGAHTNDVKQ
P474   KYARMRTAHTNDVKQ           Pol    508    522

Mos1   AGDIIGDIRQAHCNI
Mos2   SGDIIGDIRQAHCNL
E412   TGEIIGDIRQAHCNL           Env    320    333

Mos1   NQQEKNEKDLLALDS
Mos2   NQQEKNEQELLELDK
E68    NQQEKNEQDLLALEK           Env    651    665

Mos1   DIKVVPRRKVKIIRD
Mos2   DIKVVPRRKAKIIRD
P173   DIKVVPRRKVKIIRD           Pol    971    985
```
---
```
Mosaic 358-07:
19 CD8 PTE+, 3 CD4 PTE+
7 CD8+ regions, 3 CD4+ regions
Number of overlapping peptides per region: CD8: 3 4 2 6 3 1 1  CD4: 1 1 1

7 CD8 responses:
Mos1   LIKKERVYLSWVPAHKGIG
Mos2   LIKKEKVYLAWVPAHKGIG
P233   LIKKERVYLSWVPAH           Pol    680    694
P83    ----ERVYLSWVPAHKGIG       Pol    684    698

Mos1   IVQQQNLLRAIEAQQHLLQL
Mos2   IVQQQSNLLRAIEAQQHMLQL
E54    VVQQQSNLLRAIEAQ           Env    548    562
E191   -VQQQSNLLRAIEAQQ          Env    549    563
E72    -VQQQNLLRAIEAQQ           Env    549    563
E19    ------NLLRAIEAQQHLLQL     Env    554    568

Mos1   AVFIHNFKRKGGIGGY
Mos2   AVFIHNFKRKGGIGEY
```

Fig. 22 cont.

```
P222  RVFIHNFKRKGGIGG           Pol    894    908
P236  -VLIHNFKRKGGIGGY          Pol    895    909

Mos1  EQASQDVKNWMTETLLVQNANP
Mos2  EQATQDVKNWMTDTLLVQNANP
G122  EQASQDVKNWMTETL           Gag    307    321
G197  EQSTQEVKNWMTDTL           Gag    307    321
G66   --ASQEVKNWMTETLLI         Gag    309    323
G128  ---TQDVKNWMTDTLLIQ        Gag    310    324
G30   --------KNWMTETLLVQNANP   Gag    314    328
G55   --------KNWMTDTLLVQNANP   Gag    314    328

Mos1  AEWDRVHPVHAGPIAPGQ
Mos2  AEWDRLHPVHAGPVAPGQ
G319  AEWDRLHPVHAGPIP           Gag    209    225
G44   AEWDRLHPVHAGPIA           Gag    210    224
G11   ---DRVHPVHAGPIPPGQ        Gag    213    227

Mos1  WKGSPAIFQCSMTRI
Mos2  WKGSPAIFQSSMTRI
P238  NKGSPAIFQCSMTKI           Pol    308    322

Mos1  MTKILEPFRAKNPEI
Mos2  MTKILEPFRKQNPDI
P144  MTKILEPFRKQNPDI           Pol    319    333

3 CD4 responses:
Mos1  GSPAIFQCSMTRILE
Mos2  GSPAIFQSSMTKILE
P141  GSPAIFQCSMTKILD           Pol    310    324

Mos1  HGQVDCSPGIWQLAC
Mos2  HGQVDCSPGIWQLAC
P25   HGQVDCSPGIWQLDC           Pol    766    780

Mos1  DRFYKTLRAEQASQD
Mos2  DRFYKTLRAEQATQD
G57   DRFYKTLRAEQASQE           Gag    298    312
```

Mosaic 359-07:
12 CD8 PTE+, 5 CD4 PTE+
10 CD8+ regions, 3 CD4+ regions
Number of overlapping peptides per region: CD8: 2 2 1 1 1 1 1 1 1 1  CD4: 3 2

10 CD8 responses:
Mos1  LIKKERVYLSWVPAHKGIG

Fig. 22 cont.

```
Mos2  LIKKEKVYLAWVPAHKGIG
P223  LIKKERVYLSWVPAH              Pol    680    694
P83   ----EKVYLSWVPAHKGIG          Pol    684    698

Mos1  AEWDRVHPVHAGPIAPGQ
Mos2  AEWDRLHPVHAGPVAPGQ
G44   AEWDRLHPVHAGPIA              Gag    210    224
G102  ---DRVHPVHAGPIPPGQ           Gag    213    227

Mos1  AIFQCSMTRILEPFR
Mos2  AIFQSSMTKILEPFR
P358  AIFQSSMTRILEPFR              Pol    313    327

Mos1  ASQIYPGIKVRQLCK
Mos2  ASQIYAGIKVKQLCK
P365  WSQIYAGIKVRQLCK              Pol    421    436

Mos1  RELNKRTQDFWEVQL
Mos2  RELNKRTQDFWEVQL
P233  RELNKRTQDFWEVQL              Pol    233    247

Mos1  LLRAIEAQQHLLQLT
Mos2  LLRAIEAQQHMLQLT
E227  LLMAIEAQQHLLQLT              Env    555    569

Mos1  LICTTTVPWNASWSN
Mos2  LICTTAVPWNTSWSN
E432  HICTTNVPWNASWSN              Env    602    616

Mos1  KHIVWASRELERFAV
Mos2  KHLVWASRELERFAL
G20   KHLVWASRELERFAL              Gag    32     46

Mos1  RSLYNTVATLYCVHQ
Mos2  RSLFNTVATLYCVHA
G220  KSLYNTVAVLYCVHQ              Gag    76     90

Mos1  EEKAFSPEVIPMFSA
Mos2  EEKAFSPEVIPMFTA
G14   EEKAFSPEVIPMFSA              Gag    160    174

2 CD4 responses:
Mos1  WKGSPAIFQCSMTRILEPFRA
Mos2  WKGSPAIFQSSMTKILEPFRK
P352  WKGSPAIFQASMTKI              Pol    308    322
P141  --GSPAIFQSSMTKILD            Pol    310    324
```

Fig. 22 cont.

```
P284  -------IFQCGNTKILEPFRA       Pol    314

Mos1  KARVLAEAMSQVTNSAT
Mos2  KARVLAEAMSQTNSTIL
G234  KAKVLAEAMSQVQQT              Gag    359    373
G91   ---RVLAEAMSQVTNSAT           Gag    361    375

Mosaic 360-07:
16 CD8 PTE+, 2 CD4 PTE+
12 CD8+ regions, 2 CD4+ regions
Number of overlapping peptides per region: CD8: 2 2 3 1 1 1 1 1 1 1 1 1 CD4: 1 1

12 CD8 responses:
Mos1  SDLEIGQHRAKIEELR
Mos2  SDLEIGQHRTKIEELR
P385  SDLEIGQHRIKIEEL              Pol    346    360
P133  -DLEIGQHRAKIEELR             Pol    347    361

Mos1  QMHEDIISLWDQSLKP
Mos2  QMHEDIISLWDQSLKP
E282  RMHEDIISLWDESLK              Env    103    117
E292  -MHEDVISLWDQSLKP             Env    104    118

Mos1  EEKAFSPEVIPMFSAL
Mos2  EEKAFSPEVIPMFSAL
G14   EEKAFSPEVIPMFSA              Gag    160    174
G180  EEKGFNPEVIPMFSA              Gag    160    174
G111  -EKGFSPEVIPMFSAL             Gag    161    175

Mos1  KYTAFTIPSTNNETP
Mos2  KYTAFTIPSINNETP
P186  KYTAFTIPSTNNETP              Pol    281    295

Mos1  EKIKALTAICEEMEK
Mos2  EKIKALVRICTEMEK
P439  EKIKALTAICEEMEK              Pol    184    198

Mos1  GKYAKMRTAHTNDVK
Mos2  GKYAKMRGAHTNDVK
P444  GKYAKMRGAHTNDVK              Pol    507    521

Mos1  LPIQKETWETWWTDY
Mos2  LPIQKETWEAWWTEY
P356  LPIQKETWEAWWTEY              Pol    546    560

Mos1  WYQLEKDPIAGVETF
```

Fig. 22 cont.

```
Mos2   WYQLEKEPIVGAETF
P370   WYQLEKDPIAGAETF         Pol    581    595

Mos1   ENVTENFNMWKNDMV
Mos2   ENVTENFNMWKNDMV
E273   ENVTENFNMWKNMV          Env     87    101

Mos1   VIQDNSDIKVVPRRK
Mos2   VIQDNSDIKVVPRRK
P765   VIQDNSDIKVVPRRK         Pol    965    979

Mos1   VSQNYPIVQNIQGQM
Mos2   VSQNYPIVQNLQGQM
G19    VSQNYPIVQNLQGQM         Gag    128    142

Mos1   VLAEAMSQVTNSATIM
Mos2   VLAEAMSQ-TNSTILM
G307   VLAEAMSQ-AQQTNIM        Gag    362    377

2 CD4 responses:
Mos1   HGQVDCSPGIWQLAC
Mos2   HGQVDCSPGIWQLAC
P15    HGQVDCSPGIWQLDC         Pol    766    780

Mos1   RVLAEAMSQVTNSAT
Mos2   RVLAEAMSQTNSTIL
G305   RVLAEAMSQTNSAIL         Gag    361    376
```
---
```
Mosaic 361-07:
21 CD8 PTE+, 6 CD4 PTE+
7 CD8+ regions, 5 CD4+ regions
Number of overlapping peptides per region: CD8: 6 3 4 2 5 1 1 CD4: 2 1 1 1 1

7 CD8 responses:
Mos1   SQLIKKERVYLSWVPAHKGIG
Mos2   SQLIKKEKVYLAWVPAHKGIG
P221   EELIKKEKVYLAWVP         Pol    678    692
P220   EPLIKKEKVYLSWVP         Pol    678    692
P316   -KLIEKDKVYLSWVPA        Pol    679    693
P223   --LIKKERVYLSWVPAH       Pol    680    694
P169   -------EKVYLAWVPAHKGIG  Pol    684    698
P83    -------EKVYLSWVPAHKGIG  Pol    684    698

Mos1   CTHGIRPVVSTQLLL
Mos2   CTHGIRPVVSTQLLL
E15    CTHGIRPVVSTQLLL         Env    247    261
```

Fig. 22 cont.

```
E47     CTHGIRPVVSTQLLL          Env    247     261

Mos1    ICTTTVPWNASWSNKSL
Mos2    ICTTAVPWNTSWSNKSQ
E334    ICTTTVPWNASWSNR          Env    603     617
E214    -CTTTVPWNSSWSNKT         Env    604     618
E158    --TTAVPWNASWSNKSL        Env    605     619
E290    --TTAVPWNTSWSNKSL        Env    605     619

Mos1    ACQGVGGPGHKARVLAEAMS
Mos2    ACQGVGGPSHKARVLAEAMS
G166    ACQGVGGPGHKARVL          Gag    349     363
G76     -----GGPSHKARVLAEAMG     Gag    354     368

Mos1    AAEWDRVHPVHAGPIAPGQ
Mos2    AAEWDRLHPVHAGPVAPGQ
G319    AAE-DRLHPVHAGPIP         Gag    209     225
G242    -AEWDRLHPVHAGPVA         Gag    210     224
G44     -AEWDRLHPVHAGPIA         Gag    210     224
G277    ---WDRVHPVHAGPNPPG       Gag    212     226
G102    ----DRVHPVHAGPIPPGQ      Gag    212     226

Mos1    HSNWRAMASDFNLPP
Mos2    HSNWRAMASEFNLPP
P93     HSNWRAMASDFNLPP          Pol    731     745

Mos1    KGRPGNFLQNRPEPT
Mos2    KGRPGNFLQSRPEPT
G86     KGRPGNFLQNRPEPT          Gag    442     456

5 CD4 responses:
Mos1    RSLYNTVATLYCVHQR
Mos2    RSLFNTVATLYCVHAE
G289    KSLFNTVATLYCVHA          Gag    76      90
G54     -SLYNTVATLYCVHQR         Gag    77      91

Mos1    YVTDRGRQKIVSLTE
Mos2    YVTDRGRQKVVSLTD
P134    YVTDRGRQKVVSLTE          Pol    612     626

Mos1    CTTTVPWNASWSNKS
Mos2    CTTAVPWNTSWSNKS
E53     CTTNVPWNSSWSNKS          Env    604     618

Mos1    WWAGIQQEFGIPYNP
Mos2    WWAGIKQEFGIPYNP
```

Fig. 22 cont.

```
P135  WKASIQQEFGIPYNP           Pol   846   860

Mos1  GPGHKARVLAEAMSQ
Mos2  GPSHKARVLAEAMSQ
G15   GPGHKARVLAEAMSQ           Gag   355   369
```

Mosaic 362-07:
13 CD8 PTE+, 5 CD4 PTE+
7 CD8+ regions, 5 CD4+ regions
Number of overlapping peptides per region: CD8: 2 2 4 2 1 1 1 CD4: 1 1 1 1 1

7 CD8 responses:
```
Mos1  CTHGIRPVVSTQLLL
Mos2  CTHGIRPVVSTQLLL
E15   CTHGIRPVVSTQLLL           Env   247   261
E47   CTHGIRPVVSTQLLL           Env   247   261

Mos1  KRIVWASRELERFAVNPGLL
Mos2  KRLVWASRELERFALNPGLL
G30   KRLVWASRELERFAL           Gag   32    46
G68   -----ASRELERFAVNPGLL      Gag   37    51

Mos1  QPSLQTGSEELRSLYNTVATL
Mos2  QPALQTGTEELRSLFNTVATL
G268  LPALKTSSEELRSLY           Gag   65    79
G249  --ALQTGSEELRSLFNT         Gag   67    81
G132  ---LQTGTEELRSLFNTV        Gag   68    82
G100  ------GSEELRSLYNTVATL     Gag   71    85

Mos1  ACQEVGGPGHKARVLAEAMS
Mos2  ACQEVGGPSHKARVLAEAMS
G166  ACQEVGGPGHKARVL           Gag   349   363
G76   ------GPSHKARVLAEAMS      Gag   354   368

Mos1  RELNKRTQDFWEVQL
Mos2  RELNKRTQDFWEVQL
P032  RELNKRTQDFWEVQL           Pol   233   247

Mos1  LLRAIEAQQHLLQLT
Mos2  LLRAIEAQQHMLQLT
E127  LLRAIEAQQHLLQLT           Env   555   569

Mos1  KTAVQMAVFIHNFKR
Mos2  KTAVQMAVFIHNFKR
P5    KTAVQMAVFIHNFKR           Pol   888   902
```

Fig. 22 cont.

```
5 CD4 responses:
Mos1  KLNWASQIYPGIKVR
Mos2  KLNWASQIYXGIKVR
P136  KLNWASQIYXGIKVR         Pol  418  432

Mos1  YAKMRTAHTNDVKQL
Mos2  YASMRGAHTNDVKQL
P264  YARKRGAHTNDVKQL         Pol  509  523

Mos1  DQAEHLKTAVQMAVF
Mos2  DQAEHLKTAVQMAVF
P13   DQAEHLKTAVQNAVF         Pol  882  896

Mos1  SLQTGSEELRSLYNT
Mos2  ALQTGTEELRSLPNT
G182  ALKTGTEELRSLYNT         Gag   67   81

Mos1  GPGHKARVLAEAMSQ
Mos2  GPSHKARVLAEAMSQ
G15   GPGHKARVLAEAMSQ         Gag  355  369
```

Reactive peptides and breadth and depth of responses: Optimal Natural Clade C Vaccine

Natural Clade C 363-07:
2 CD8 PTE+, 0 CD4 PTE+
1 CD8+ regions, 0 CD4+ regions
Number of overlapping peptides per region: CD8: 2 CD4: none 1 CD8 responses:
C     QPALQTGTEELRSLYNTVATL
G168  LEALKTGSEELRSLY
G120  ------GSEELRSLYNTVATL Natural Clade C 364-07:
5 CD8 PTE+, 2 CD4 PTE+
5 CD8+ regions, 2 CD4+ regions
Number of overlapping peptides per region: CD8: 1 1 1 1 1 CD4: 1 1

5 CD8 responses:
C     AHTNDVKQLTEAVQK
P99   AHTNDVKQLTEAVQK  Pol  515  529

C     GDIIGDIRQAHCNIS
E64   GDIIGDIRQAHCNIS  Env  321  334

Fig. 22 cont.

```
C       SEKSAVGIGAVFLGF
E182    REKRAVGIGAVFLGF    Env    508    522

C       RASILRGGKLDKWEK
G283    SASILRGGKLDKWEK    Gag    4      18

C       TNNPPVPVGDIYKRW
G185    TSNPPVPVGDIYKRW    Gag    251    265

2 CD4 responses:
C       CKSNITGLLLTRDGG
E216    CTSNITGLLLVRDGG    Env    445    459

C       SLYNTVATLYCVHAG
G54     SLYNTVATLYCVHQR    Gag    77     91
```

---

Natural Clade C 365-07:
2 CD8 PTE+, 1 CD4 PTE+
2 CD8+ regions, 1 CD4+ regions
Number of overlapping peptides per region: CD8: 1 1 CD4: 1

```
2 CD8 responses:
C       EQLINKERVYLSWVP
P250    EPLIKKERVYLSWVP    Pol    678    692

C       AEWDRLHPVHAGPIA
G44     AEWDRLHPVHAGPIA    Gag    210    224

1 CD4 response:
C       HQAAMQMLKDTINEE
G24     HQAAMQMLKDTINEE    Gag    194    208
```

---

Natural Clade C 366-07:
6 CD8 PTE+, 1 CD4 PTE+
4 CD8+ regions, 1 CD4+ regions
Number of overlapping peptides per region: CD8: 2 2 1 1 CD4: 1

```
4 CD8 responses:
C       IVQQQSNLLRAIEAQQ
E54     VVQQQSNLLRAIEAQ    Env    548    562
E73     -VQQQNNLLRAIEAQH   Env    549    563

C       AVFIHNFKRKGIGGY
P22     AVFIHNFKRKGIGG     Pol    894    908
P236    -VFIHNFKRKGIGGY    Pol    895    909
```

Fig. 22 cont.

```
C      MAICEEMEKEGKITK
P114   TAICEEMEKEGKITK          Pol   190   204

C      GGPSHKARVLAEAMS
G76    GGPSHKARVLAEAMG          Gag   354   368

1 CD4 response:
C      IIGQVRDQAEHLKTA
P86    LIGQVRDQAEHLKTA  Pol     876   890
```

---

Natural Clade C 367-07:
0 CD8 PTE+, 0 CD4 PTE+
0 CD8+ regions, 0 CD4+ regions
Number of overlapping peptides per region: none

0 CD8 responses

0 CD4 responses

---

Natural Clade C 368-07:
2 CD8 PTE+, 0 CD4 PTE+
1 CD8+ regions, 0 CD4+ regions
Number of overlapping peptides per region: CD8: 2 CD4: 0

```
1 CD8 response
C      AVFIHNFKRKGGIGGY
P22    AVFIHNFKRKGGIGG          Pol   894   908
P136   -VIHNFKRKGGIGGY          Pol   895   909
```

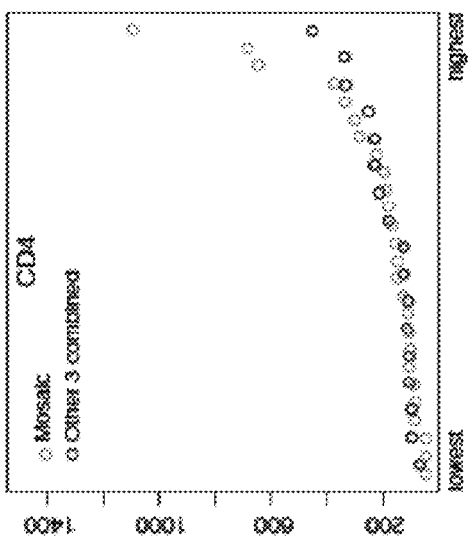
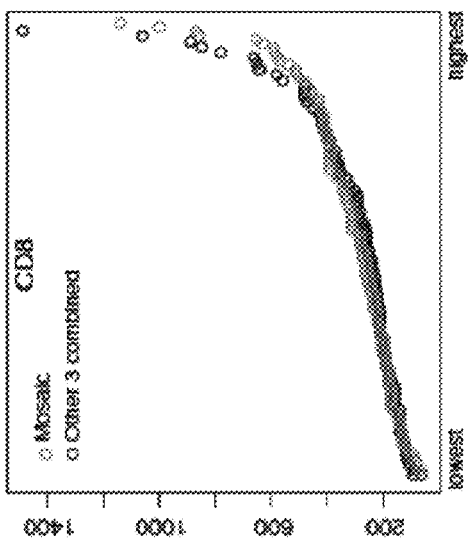
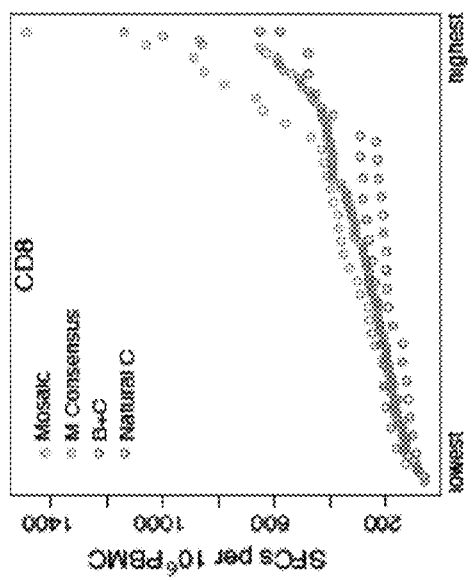

Fig. 24A

Monkey 366 (Natural C)

| | |
|---|---|
| OptC | IVQQQSNLLRAIEAQQ |
| E54 | VVQQQSNLLRAIEAQ |
| E72 | -VQQQSNLLRAIEAQH |
| | |
| OptC | AVFIHNFKRKGGIGGY |
| P02 | AVFIHNFKRKGGIGG |
| P236 | -VLIHNFKRKGGIGGY |
| | |
| OptC | MAICEEMEKEGKITK |
| P224 | TAICEEMEKEGKITK |
| | |
| OptC | GGPSHKARVLAEAMS |
| G76 | GGPSHKARVLAEAMS |

Fig. 24B

Monkey 361 (Mosaic)

| | |
|---|---|
| Mos1 | EQLIKKERVYLSWVPAHKGIG |
| Mos2 | EQLIKKERVYLAWVPAHKGIG |
| P221 | EELIKKERVYLAWVP |
| P250 | EELIKKEKVYLSWVP |
| P316 | -RLIKKERVYLSWVPA |
| P223 | --LIKKERVYLSWVPAH |
| P169 | ------ERVYLAWVPAHKGIG |
| P83 | ------EKVYLSWVPAHKGIG |
| | |
| Mos1 | CTHGIRPVVSTQLLL |
| Mos2 | CTHGIKPVVSTQLLL |
| E15 | CTHGIRPVVSTQLLL |
| E47 | CTHGIRPVVSTQLLL |
| | |
| Mos1 | ICTTTVPWNASWSNKSL |
| Mos2 | ICTTAVPWNTSWSNKSQ |
| E334 | ICTTTVPWNASWSNK |
| E314 | -CTTTVPWNSSWSNKS |
| E158 | --TTAVPWNASWSNKSL |
| E293 | --TTAVPWNTSWSNSL |
| | |
| Mos1 | ACQGVGGPGHKARVLAEAMS |
| Mos2 | ACQGVGGPGHKARVLAEAMS |
| G166 | ACQEVGGPGHKARVL |
| G76 | ------GGPSHKARVLAEAMS |
| | |
| Mos1 | AAENDRVHPVHAGPIAPGQ |
| Mos2 | AAENDRLHPVHAGPVAPGQ |
| G319 | AAD-DRLHPVHAGPIP |
| G242 | -ADNDRLHPVHAGPVA |
| G44 | -AENDRLHPVHAGPIA |
| G277 | ---NDRVHPVHAGPNPPG |
| G102 | ----DRVHPVHAGPIPPGQ |
| | |
| Mos1 | HSNWRAMASDFNLPP |
| Mos2 | HSNWRAMASEFNLPP |
| P83 | HSNWRAMASDFNLPP |
| | |
| Mos1 | KGRPGNFLQNRPEPT |
| Mos2 | KGRPGNFLQSRPEPT |
| G56 | KGRPGNFLQNRPEPT |

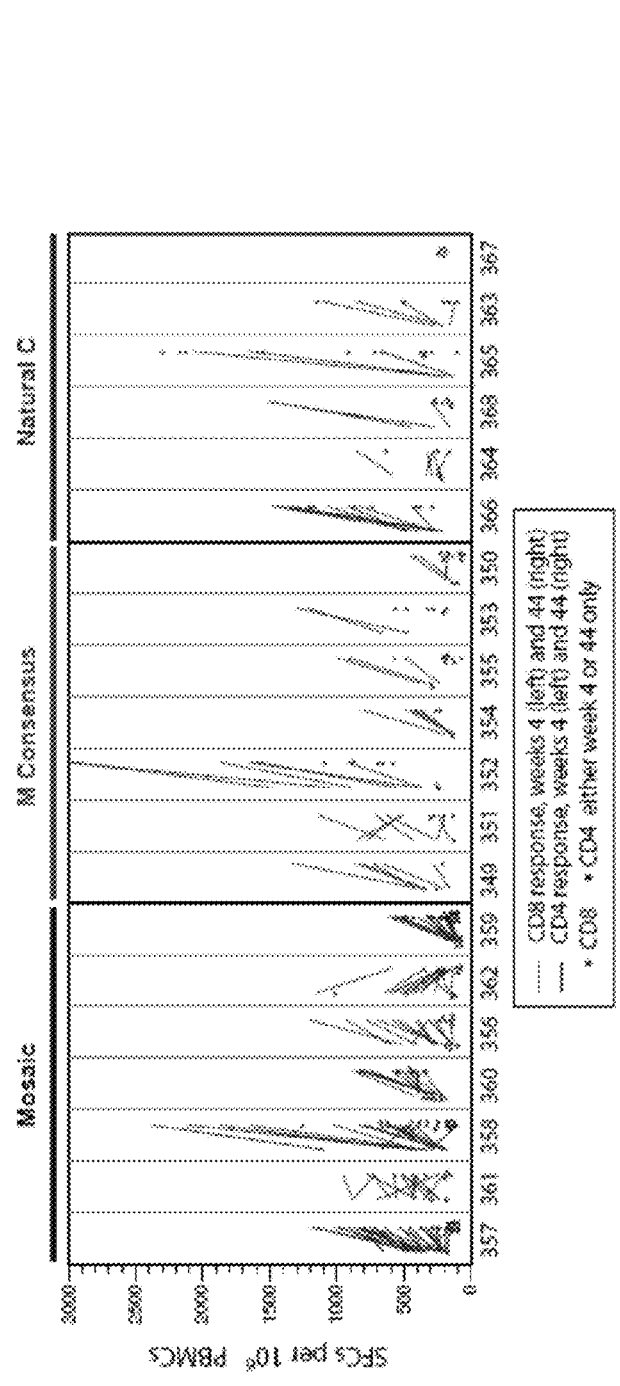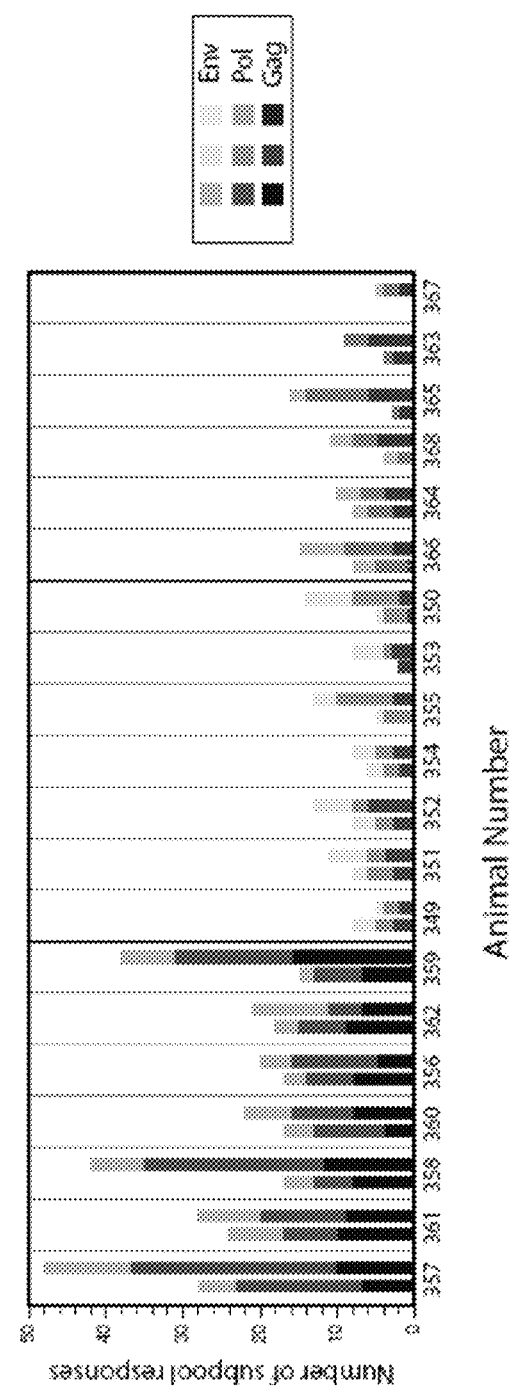
Fig. 26A
Fig. 26B

US 9,670,253 B2

ANTIVIRAL VACCINES WITH IMPROVED CELLULAR IMMUNOGENICITY

STATEMENT OF FEDERALLY FUNDED RESEARCH

This invention was made with government support under grants AI066305 and AI078526 awarded by NIH. The government has certain rights in the invention.

FIELD OF THE INVENTION

The invention provides compositions, methods, and kits for the treatment or prevention of viral infections. The polyvalent (e.g., 2-valent) vaccines described herein incorporate computationally-optimized viral polypeptides that can increase the diversity or breadth and depth of cellular immune response in vaccinated subjects.

BACKGROUND OF THE INVENTION

Vaccines that elicit cellular immune responses against viruses must reflect global viral diversity in order to effectively treat or prevent viral infection. For example, the initiation of intense and diverse HIV-1-specific T cell responses is likely crucial for an effective HIV-1 vaccine. Cytotoxic T lymphocyte (CTL) responses are correlated with slow disease progression in humans, and the importance of CTL responses in non-human primate vaccination models is well established. While the highly variable Envelope (Env) is the primary target for neutralizing antibodies against HIV, and vaccine antigens will also need to be tailored to elicit these antibody responses, T cell vaccine components can target more conserved proteins to trigger responses that are more likely to cross-react. But even the most conserved HIV-1 proteins are diverse enough that variation will be an issue. Artificial central-sequence vaccine approaches, such as consensus and ancestral HIV-1 sequences, essentially "split the differences" between strains, can stimulate responses with enhanced cross-reactivity compared to natural strain vaccines. Consensus antigens represent synthetic antigen sequences that are the single best "average" of all circulating strains. While these antigens can elicit directed cellular immune responses, the breadth and intensity of these responses are not substantially improved over previous vaccine strategies. The development of next-generation vaccines to treat or prevent viral infection must elicit an increased breadth of cellular immunity in order to allow for successful vaccination outcomes. The need for such vaccines is particularly urgent for the treatment or prevention of HIV-1.

SUMMARY OF THE INVENTION

In a first aspect, the invention features a vaccine for treating or reducing the risk of a viral infection in a mammal, such as a human, that includes at least two distinct optimized viral polypeptides (e.g., 2, 3, 4, 5, or more distinct optimized viral polypeptides), wherein the optimized viral polypeptides correspond to the same viral gene product. In one embodiment, the viral infection is caused by a retrovirus, reovirus, picornavirus, togavirus, orthomyxovirus, paramyxovirus, calicivirus, arenavirus, flavivirus, filovirus, bunyavirus, coronavirus, astrovirus, adenovirus, papillomavirus, parvovirus, herpesvirus, hepadnavirus, poxvirus, or polyomavirus. In other embodiments, the retrovirus is human immunodeficiency virus type 1 (HIV-1), and the viral gene products include Gag, Pol, Env, Nef, Tat, Rev, Vif, Vpr, or Vpu. In a further embodiment, the vaccine includes no more than two optimized viral polypeptides corresponding to one of the Gag, Pol, Env, Nef, Tat, Rev, Vif, Vpr, or Vpu viral gene products. In another embodiment, the vaccine does not include optimized viral polypeptides corresponding to Gag and Nef. In yet another embodiment, the vaccine includes at least two distinct optimized viral polypeptides (e.g., 2, 3, 4, 5, or more distinct optimized viral polypeptides) for a first viral gene product selected from Gag, Pol, Env, Nef, Tat, Rev, Vif, Vpr, and Vpu and one or more distinct optimized viral polypeptides (e.g., 2, 3, 4, 5, or more distinct optimized viral polypeptides) for a second viral gene product different from the first viral gene product selected from Gag, Pol, Env, Nef, Tat, Rev, Vif, Vpr, and Vpu.

In a second aspect, the invention features a vaccine for treating or reducing the risk of human immunodeficiency virus type 1 (HIV-1) infection in a mammal, such as a human, that includes an optimized viral polypeptide that has at least seven contiguous amino acids (e.g., at least 8, 9, 10, 11, 12, 13, 14, 15, 16, 17, 18, 19, 20, 21, 22, 23, 24, 25, 26, 27, 28, 29, 30, 50, 100, 150, 175, 200, 250, 300, 350, 400, 450, 500 or more contiguous amino acids in length) having at least 85% amino acid sequence identity to any one of the sequences set forth in SEQ ID NOS:1-29. In one embodiment, the optimized viral polypeptide has at least seven contiguous amino acids (e.g., at least 8, 9, 10, 11, 12, 13, 14, 15, 16, 17, 18, 19, 20, 21, 22, 23, 24, 25, 26, 27, 28, 29, 30, 50, 100, 150, 175, 200, 250, 300, 350, 400, 450, 500 or more contiguous amino acids in length) having amino acid sequence identity to any one of the sequences set forth in SEQ ID NOS:1-29. In another embodiment, the optimized viral polypeptide has the amino acid sequence of any one of the sequences set forth in SEQ NOS:1-29. In a further embodiment, the vaccine includes at least two optimized viral polypeptides selected from any one or more of groups a)-k): a) SEQ ID NOS:1 and 2; b) SEQ ID NOS:3, 4, and 5; c) SEQ ID NOS:6 and 7; d) SEQ ID NOS:8-12; e) SEQ ID NOS:13, 14, and 15; SEQ ID NOS:16, 17, and 18; g) SEQ ID NOS:19 and 20; h) SEQ ID NOS:21, 22, and 23; i) SEQ ID NOS:24 and 25; j) SEQ ID NOS:26 and 27; k) and SEQ ID NOS:21-22. In another embodiment, the vaccine can include a pair of optimized viral polypeptides selected from any one of groups a)-k) above and one or more different optimized viral polypeptides from the same or a different group a)-k). In other embodiments, the vaccine can include at least three or four or more optimized viral polypeptides from one or more of groups a)-k).

In a third aspect, the invention features a vaccine for treating or reducing the risk of a viral infection in a mammal, such as a human, that includes at least two pairs of distinct optimized viral polypeptides, wherein each pair of optimized viral polypeptides corresponds to the same viral gene product, and wherein no more than two optimized viral polypeptides incorporated in the vaccine correspond to the same viral gene product. In one embodiment, the vaccine includes at least three pairs of distinct optimized viral polypeptides. In another embodiment, the vaccine includes at least four pairs of distinct optimized viral polypeptides. In one embodiment, the viral infection is caused by a retrovirus, reovirus, picornavirus, togavirus, orthomyxovirus, paramyxovirus, calicivirus, arenavirus, flavivirus, filovirus, bunyavirus, coronavirus, astrovirus, adenovirus, papillomavirus, parvovirus, herpesvirus, hepadnavirus, poxvirus, or polyomavirus. In other embodiments, the retrovirus is human immunodeficiency virus type 1 (HIV-1), and the viral gene products include Gag, Pol, Env, Nef, Tat, Rev, Vif, Vpr, or Vpu. In a further embodiment, the vaccine includes no more than two optimized viral polypeptides corresponding to one of the Gag, Pol, Env, Nef, Tat, Rev, Vif, Vpr, or Vpu viral gene products. In another embodiment, the vaccine does not include optimized viral polypeptides corresponding to Gag and Nef. In a further embodiment, the vaccine includes at least three pairs of distinct optimized viral polypeptides corresponding to any three of the Gag, Pol, Env, Nef, Tat, Rev, Vif, Vpr, or Vpu viral gene products. In another embodiment, the vaccine includes at least four pairs of distinct optimized viral polypeptides corresponding to any four of the Gag, Pol, Env, Nef, Tat, Rev, Vif, Vpr, or Vpu viral gene products.

In one embodiment of any of the first three aspects of the invention, the vaccine elicits a cellular immune response against a viral gene product. In another embodiment, the vaccine elicits a cellular immune response against HIV-1. In a further embodiment, the nucleotide sequence of at least one distinct optimized viral polypeptide is encoded by a nucleic acid or vector. In one embodiment, the vector is a recombinant adenovirus, such as adenovirus serotype 26 (Ad26), adenovirus serotype 34 (Ad34), adenovirus serotype 35 (Ad35), adenovirus serotype 48 (Ad48), or adenovirus serotype 5 HVR48 (Ad5HVR48). In a further embodiment, the vaccine is in combination with a pharmaceutically acceptable carrier, excipient, or diluent.

In a fourth aspect, the invention features a nucleic acid that includes the nucleotide sequence of an optimized viral polypeptide that has at least seven contiguous amino acids (e.g., at least 8, 9, 10, 11, 12, 13, 14, 15, 16, 17, 18, 19, 20, 21, 22, 23, 24, 25, 26, 27, 28, 29, 30, 50, 100, 150, 175, 200, 250, 300, 350, 400, 450, 500 or more contiguous amino acids in length) having at least 85% amino acid sequence identity to any one of the amino acid sequences set forth in SEQ ID NOS:1-29. In one embodiment, the optimized viral polypeptide has at least seven contiguous amino acids (e.g., at least 8, 9, 10, 11, 12, 13, 14, 15, 16, 17, 18, 19, 20, 21, 22, 23, 24, 25, 26, 27, 28, 29, 30, 50, 100, 150, 175, 200, 250, 300, 350, 400, 450, 500 or more contiguous amino acids in length) having sequence identity to any one of the amino acid sequences set forth in SEQ ID NOS:1-29. In another embodiment, the optimized viral polypeptide has any one of the amino acid sequences set forth in SEQ ID NOS:1-29. In a further embodiment, the nucleic acid includes a vector. In one embodiment, the vector is a recombinant adenovirus, such as adenovirus serotype 26 (Ad26), adenovirus serotype 34 (Ad34), adenovirus serotype 35 (Ad35), adenovirus serotype 48 (Ad48), or adenovirus serotype 5 HVR48 (Ad5HVR48).

In a fifth aspect, the invention features an optimized viral polypeptide that has at least seven contiguous amino acids (e.g., at least 8, 9, 10, 11, 12, 13, 14, 15, 16, 17, 18, 19, 20, 21, 22, 23, 24, 25, 26, 27, 28, 29, 30, 50, 100, 150, 175, 200, 250, 300, 350, 400, 450, 500 or more contiguous amino acids in length) having at least 85% amino acid sequence identity to any one of the amino acid sequences set forth in SEQ ID NOS:1-29. In one embodiment, the optimized viral polypeptide has at least seven contiguous amino acids (e.g., at least 8, 9, 10, 11, 12, 13, 14, 15, 16, 17, 18, 19, 20, 21, 22, 23, 24, 25, 26, 27, 28, 29, 30, 50, 100, 150, 175, 200, 250, 300, 350, 400, 450, 500 or more contiguous amino acids in length) having sequence identity to any one of the amino acid sequences set forth in SEQ ID NOS:1-29. In another embodiment, the optimized viral polypeptide has any one of the amino acid sequences set forth in SEQ ID NOS:1-29.

In a sixth aspect, the invention features a method for treating or reducing the risk of a viral infection in a mammal, such as a human, by administering a vaccine or nucleic acid of the invention. In one embodiment, the viral infection is caused by a retrovirus, reovirus, picornavirus, togavirus, orthomyxovirus, paramyxovirus, calicivirus, arenavirus, flavivirus, filovirus, bunyavirus, coronavirus, astrovirus, adenovirus, papillomavirus, parvovirus, herpesvirus, hepadnavirus, poxvirus, or polyomavirus. In further embodiments, the retrovirus is human immunodeficiency virus type 1 (HIV-1), and the viral gene products include Gag, Pol, Env, Nef, Tat, Rev, Vif, Vpr, or Vpu. In one embodiment, the vaccine or nucleic acid elicits a cellular immune response against a viral gene product.

In a seventh aspect, the invention features a method of manufacturing a vaccine for treating or reducing the risk of a viral infection in a mammal, such as a human, by synthesizing a vaccine of the invention.

In an eighth aspect, the invention features a method of manufacturing a vaccine for treating or reducing the risk of a viral infection in a mammal, such as a human, by contacting a nucleic acid of the invention with a cell and isolating a optimized viral polypeptide.

In one embodiment of the seventh or eighth aspects of the invention, the optimized viral polypeptide elicits a cellular immune response when administered to a mammal. The cellular immune response can be against a viral gene product. In another embodiment, the viral infection is caused by a retrovirus, reovirus, picornavirus, togavirus, orthomyxovirus, paramyxovirus, calicivirus, arenavirus, flavivirus, filovirus, bunyavirus, coronavirus, astrovirus, adenovirus, papillomavirus, parvovirus, herpesvirus, hepadnavirus, poxvirus, or polyomavirus. In further embodiments, the retrovirus is human immunodeficiency virus type 1 (HIV-1), and the viral gene products include Gag, Pol, Env, Nef, Tat, Rev, Vif, Vpr, or Vpu.

In a ninth aspect, the invention features a kit that includes a vaccine of the invention, a pharmaceutically acceptable carrier, excipient, or diluent, and instructions for the use thereof. In one embodiment, the kit also includes an adjuvant.

In a final aspect, the invention features a kit that includes a nucleic acid of the invention, a pharmaceutically acceptable carrier, excipient, or diluent, and instructions for the use thereof. In one embodiment, the kit also includes an adjuvant.

In an embodiment of all aspects of the invention, the optimized viral polypeptide is encoded by a nucleic acid sequence that is optimized for expression in humans (e.g., any one of SEQ ID NOS:5, 10, 11, 12, 15, 18, and 23).

DEFINITIONS

By "optimized viral polypeptide" or "computationally-optimized viral polypeptide" is meant an immunogenic polypeptide that is not a naturally-occurring viral peptide, polypeptide, or protein. Optimized viral polypeptide sequences are initially generated by modifying the amino acid sequence of one or more naturally-occurring viral gene products (e.g., peptides, polypeptides, and proteins) to increase the breadth, intensity, depth, or longevity of the antiviral immune response (e.g., cellular or humoral immune responses) generated upon immunization (e.g., when incorporated into a vaccine of the invention) of a mammal (e.g., a human). Thus, the optimized viral polypeptide may correspond to a "parent" viral gene sequence; alternatively, the optimized viral polypeptide may not correspond to a specific "parent" viral gene sequence but may correspond to analogous sequences from various strains or quasispecies of a virus. Modifications to the viral gene sequence that can be included in an optimized viral polypeptide include amino acid additions, substitutions, and deletions. In one embodiment of the invention, the optimized viral polypeptide is the composite or merged amino acid sequence of two or more naturally-occurring viral gene products (e.g., natural or clinical viral isolates) in which each potential epitope (e.g., each contiguous or overlapping amino acid sequence of 5, 6, 7, 8, 9, 10, 11, 12, 13, 14, 15, 16, 17, 18, 19, 20, 21, 22, 23, 24, 25, 26, 27, 28, 29, 30 or more amino acids in length) is analyzed and modified to improve the immunogenicity of the resulting optimized viral polypeptide. Optimized viral polypeptides that correspond to different viral gene products can also be fused to facilitate incorporation in a vaccine of the invention. Methods of generating an optimized viral polypeptides are described in, e.g., Fisher et al. "Polyvalent Vaccine for Optimal Coverage of Potential T-Cell Epitopes in Global HIV-1 Variants," *Nat. Med.* 13(1):100-106 (2007) and International Patent Application Publication WO 2007/024941, herein incorporated by reference. Once the optimized viral polypeptide sequence is generated, the corresponding polypeptide can be produced or administered by standard techniques (e.g., recombinant viral vectors, such as the adenoviral vectors disclosed in International Patent Application Publications WO 2006/040330 and WO 2007/104792, herein incorporated by reference).

By "pharmaceutically acceptable carrier" is meant a carrier which is physiologically acceptable to the treated mammal while retaining the therapeutic properties of the compound with which it is administered. One exemplary pharmaceutically acceptable carrier is physiological saline. Other physiologically acceptable carriers and their formulations are known to one skilled in the art and described, e.g., in *Remington's Pharmaceutical Sciences* ($18^{th}$ edition, ed. A. Gennaro, 1990, Mack Publishing Company, Easton, Pa.), incorporated herein by reference.

By "vector" is meant a DNA construct that contains a promoter operably linked to a downstream gene or coding region (e.g., a cDNA or genomic DNA fragment, which encodes a polypeptide or polypeptide fragment). Introduction of the vector into a recipient cell (e.g., a prokaryotic or eukaryotic cell, e.g., a bacterium, yeast, insect cell, or mammalian cell, depending upon the promoter within the expression vector) or organism (including, e.g., a human) allows the cell to express mRNA encoded by the vector, which is then translated into the encoded optimized viral polypeptide of the invention. Vectors for in vitro transcription/translation are also well known in the art and are described further herein. A vector may be a genetically engineered plasmid, virus, or artificial chromosome derived from, e.g., a bacteriophage, adenovirus, retrovirus, poxvirus, or herpesvirus.

By "viral gene product" is meant any naturally-occurring viral peptide, polypeptide, or protein, or fragment thereof. In one embodiment of the invention, the viral gene product is derived from the human immunodeficiency virus type 1 (HIV-1). HIV-1 viral gene products include the Gag, Pol, Env, Nef, Tat, Rev, Vif, Vpr, and Vpu polypeptides.

BRIEF DESCRIPTION OF THE DRAWINGS

FIG. 1 is a chart that illustrates the expanded breadth of computationally-optimized HIV-1 Gag, Pol, and Env viral polypeptides against global potential T-cell epitopes (PTE) peptides in Rhesus macaques. Animals immunized with the optimized viral polypeptides (blue) reacted with the greatest number of recall peptide pools.

FIG. 2 is a chart that shows that computationally-modified HIV-1 Gag, Pol, and Env viral polypeptides expand the breadth of epitope-specific cellular immune response.

FIG. 3 illustrates the breadth of cellular immune responses detected in Rhesus macaques following immunization with HIV-1 viral gene products Gag, Pol, and Env derived from the computationally-modified viral polypeptides of the invention, as well as animals immunized with consensus HIV-1 antigens or HIV-1 clade C isolate antigens. Animals immunized with the optimized viral polypeptides (blue) reacted with the greatest number of recall peptide pools. Since the animals are outbred, the pools differ from animal to animal. Gag, Pol, and Env each elicit many cellular immune responses and can have shared patterns of reactivity.

FIGS. 4A-4C are graphs showing the potential epitopes shared between the different vaccines tested (2 valent mosaic (Mos2), M consensus (Mcon), and optimized clade C (OptC)) by viral polypeptide (Pol (FIG. 4A), Gag (FIG. 4B), and Env (FIG. 4C)). FIGS. 4A-C show the relative coverage of the current HIV database full length genome set and the PTE peptides by the different vaccine candidates.

FIG. 5 is a graph showing that the number of PTE peptide responses (where each response is considered an independent event regardless of overlap) to the 2 valent mosaic (Mos2) vaccine is greater than the number of responses to the M group consensus (Mcon) vaccine and the natural viral strain vaccine (optimized clade C (C Natural (optimal)), which has been selected to give optimal coverage of the M group collection (OptC) vaccine antigens. FIG. 5 shows the number of PTE peptide responses per animal by protein, CD8+ T cell, and CD4+ T cell. Statistically, Mos2>Mcon~OptC (Mcon shows a trend for more response than OptC). The Wilcoxon p-value for Mos2 compared to Mcon: p-value=0.001058.

FIG. 6 is a chart showing the number of PTE peptides that trigger T cell responses. A median number of 16 (range; 12-29) PTE peptides of the 2 valent mosaic (Mos2) vaccine trigger a response in CD8+ T cells, while only a median number of 6 (range: 0-7) Mcon peptides and only a median number of 3 peptides (range: 0-3) of OptC peptides trigger a response in CD8+ T cells. A median number of 4 (range; 2-6) PTE peptides of the 2 valent mosaic (Mos2) vaccine trigger a response in CD4+ T cells, while only a median number of 1 (range: 0-2) Mcon peptides and only a median number of 0.5 peptides (range: 0-2) of OptC peptides trigger a response in CD4+ T cells. Thus, the trend for responses is Mos2>Mcon>OptC.

FIG. 7 is a schematic summarizing the mapping of all CD8+ T cell Gag PTE peptides that are recognized by T cells from each of the animals studied (see Example 3 below). The animal number, peptide pool and peptide number label the boundaries of each reactive peptide. The symbol signifies the group: *, Mos2; ¥, ConM; ±, OptC. Gag is included here as an example. There tends to be clustering of CD8 responses even though the animals are outbred. Mosaics have potential advantages over the monovalent vaccines. Mosaics have a better chance of stimulating a response that reacts with more common variants. Mosaics also stimulate multiple responses to the different forms that are present in the cocktail. Thus, mosaics have the potential to block common escape routes. In our study, the mosaic vaccine tended to stimulate T cell responses that recognized more overlapping peptides. There are many hotspots of localization of reactive peptides. PTE peptides are designed to maximize the potential epitope (or 9-mer for a 9 amino acid contiguous stretch) coverage of the HIV-1 M group in the peptide reagents used to assess vaccines. Inevitably, there is a lot of overlap in PTE peptides, but because of the algorithm, overlap is usually an overlap with some variation. FIG. 7 discloses SEQ ID NO: 42.

FIG. 8 is a schematic summarizing the mapping of CD4+ T cell Gag PTE peptides that are recognized by T cells from each of the animals studied. FIG. 8 discloses SEQ ID NO: 43.

FIG. 9 is a chart illustrating typical patterns of PTE responses to the ConM vaccine or to the optimal natural vaccine, aligning peptides that elicit a response with the relevant region of the vaccine. Good matches with solid stretches of identity between vaccine and target PTE peptide are necessary to achieve a reaction to these vaccines. FIG. 9 discloses SEQ ID NOS 44-57, respectively, in order of appearance.

FIG. 10 is a chart illustrating that mosaic vaccines generated many responses that recognized multiple variant overlapping peptides with no apparent antigenic competition and with broad local responses. In particular, four variable PTE peptides were recognized. Moreover, in the region of overlap both mosaic forms were recognized, as well a combination of the two. Finally, a new form (S) was recognized. FIG. 10 discloses SEQ ID NOS 58-63, respectively, in order of appearance.

FIG. 11 is a chart illustrating a typical pattern of CD8+ PTE peptide responses in mosaic vaccinated animal (361-07). 22 PTE peptides were tested and 8 CD8 responsive regions were identified; 5 regions included variable peptides that match amino acids in one or the other of the mosaics. 5 CD4 responsive regions were identified. Thus, T cell responses to Mosaics see more variable peptides in a given region. This seemed to be true of CD8 T cell responses in particular. This could be the result of triggering multiple T cell clones that recognize variants of epitopes, and these may block fit escape routes, Not only are there more responses, they are deeper and cover more variants. FIG. 11 discloses CD8 responses as SEQ ID NOS 64-101, respectively, in order of appearance. CD4 responses disclosed as SEQ ID NOS 102-117, respectively, in order of appearance.

FIG. 12 is a graph showing the number of overlapping variable PTE peptides that span regions targeted by vaccine elicited T cells.

FIG. 13 is graph showing that the 2 mosaic antigen vaccine yields more T cell responses, relative to the Mcon and OptC vaccines, to regions that contain one or more overlapping PTE peptides. FIG. 13 is similar to FIG. 5, monkeys shown in the same order from right to left, but with the scale changed to reflect number of responses to regions that contain one or more overlapping PTE peptides rather than single peptides.

FIG. 14 is a chart showing the number of T cell responses in animals following administration of 2 valent mosaic (Mos2), Mcon, and OptC vaccines. The 2 valent mosaic (Mos2) vaccine triggers a median number of 8 responses in CD8+ T cells, while only a median number of 3 (range: 0-6) and 1.5 peptides (range: 0-5) CD8+ T cell responses are triggered by Mcon and OptC vaccines, respectively. The 2 valent mosaic (Mos2) vaccine triggers a median number of 3 (range: 2-5) responses in CD4+ T cells, while only a median number of 1 (range: 0-2) and 0.5 (range: 0-2) CD4+ T cell response are triggered by Mcon and OptC vaccines, respectively. Thus, the trend for responses is Mos2>Mcon>OptC.

FIG. 15 is a graph showing that the mosaic vaccines can elicit more responses that cross-react with C clade natural proteins than can a C clade natural vaccine: GAG pooled peptides representing 5 proteins. Animals vaccinated with the M group consensus or the optimal coverage C clade natural protein had 0-2 responses to the peptides derived from these proteins, while the Mosaic vaccinated animals could respond to 1-5 peptide pools. The Mosaic vaccine elicits more responses to each of the proteins tested than either M con or the optimal C. T cell responses elicited by mosaic vaccines also recognized more pooled peptide sets spanning actual Gag proteins. 10-12 Subpools=10×15mer peptides (except 96ZM Gag, which is 5×20mer peptides).

Figure 1:
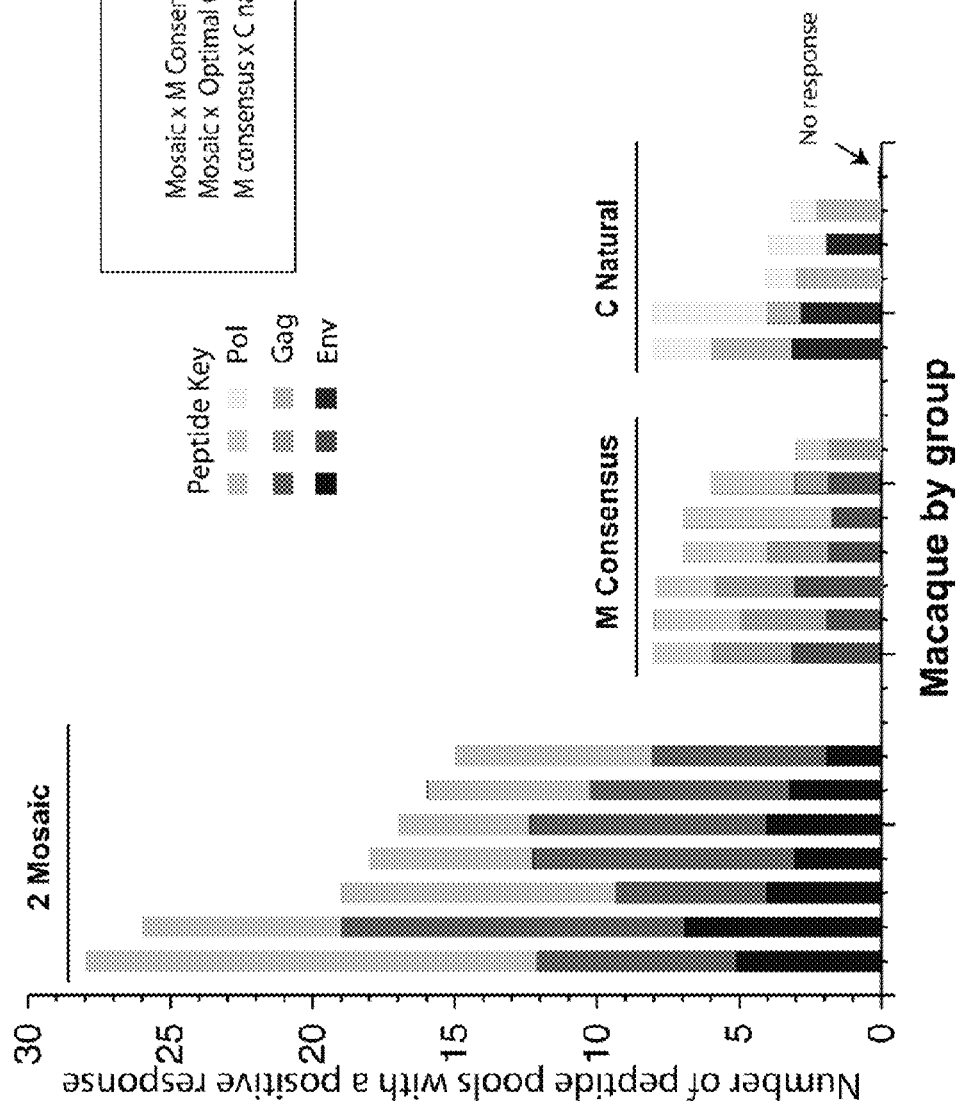
Figure 2:
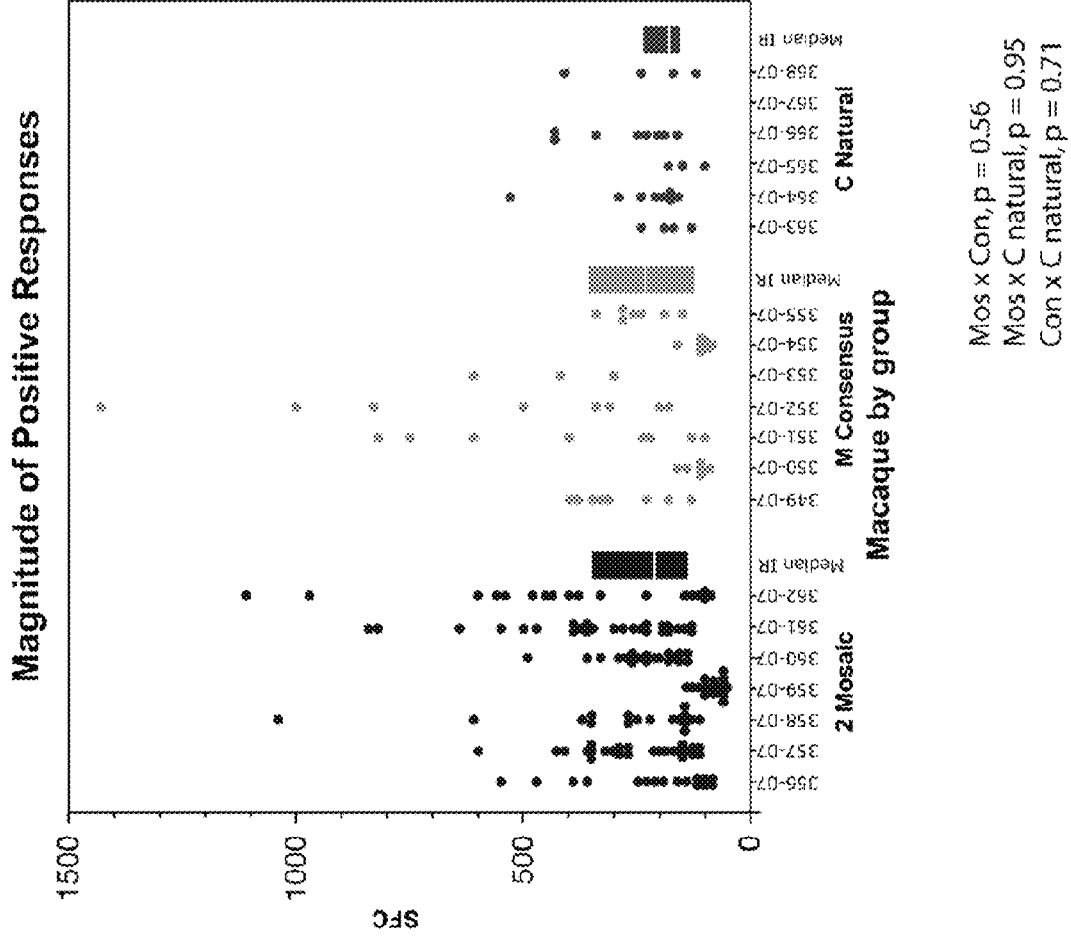
Figure 3:
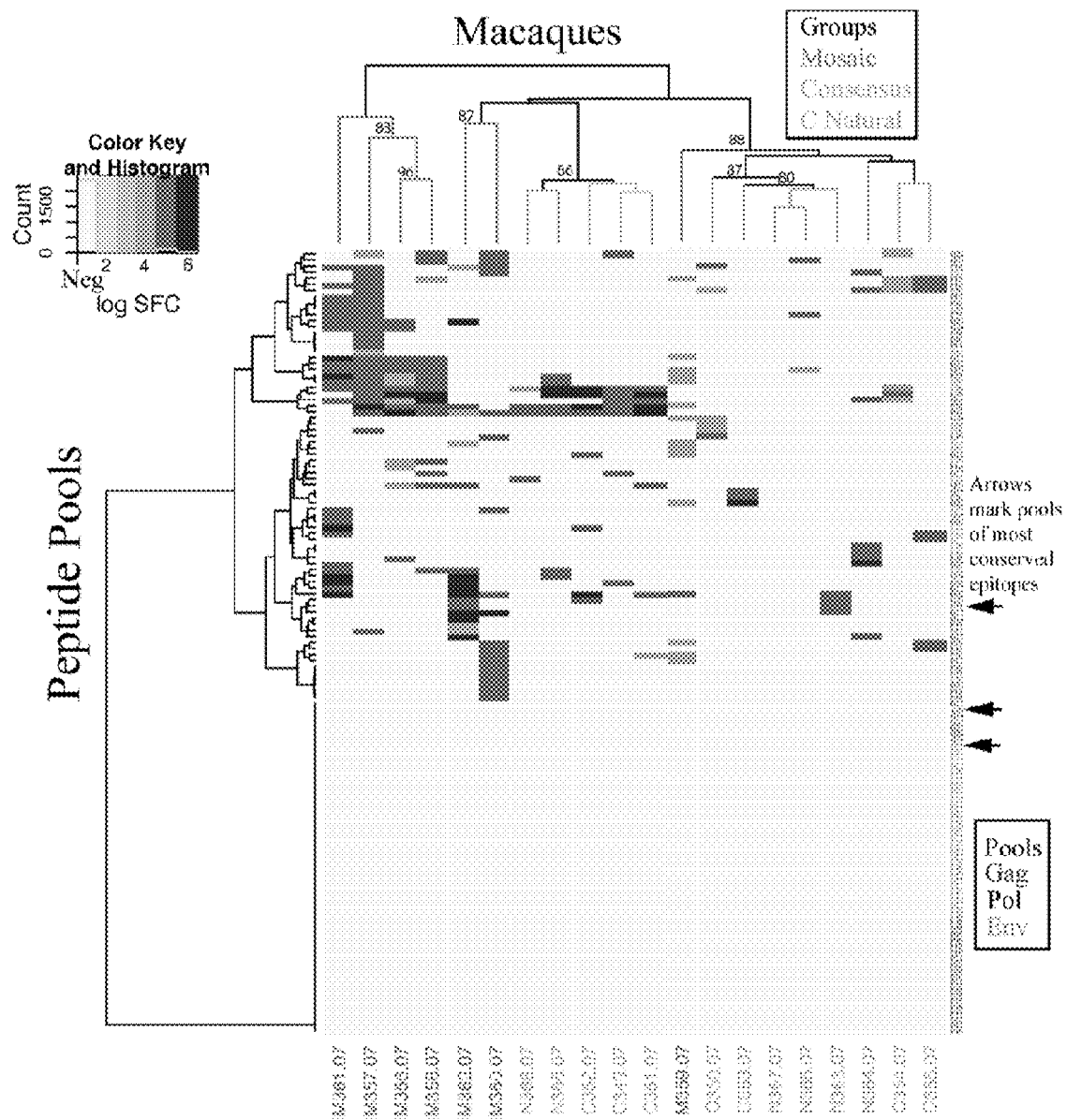
Figures 4A, 4B, 4C:
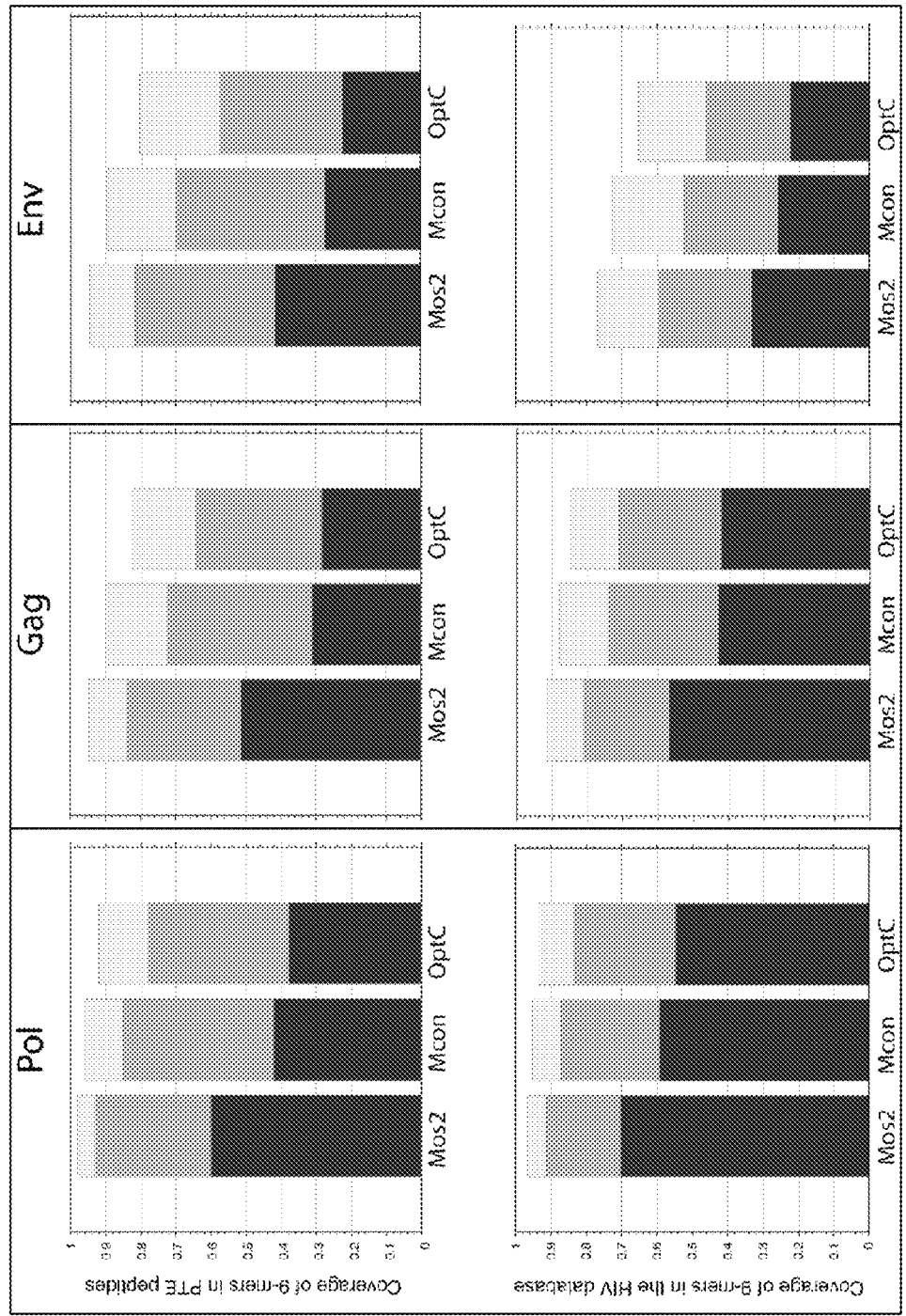
Figure 5:
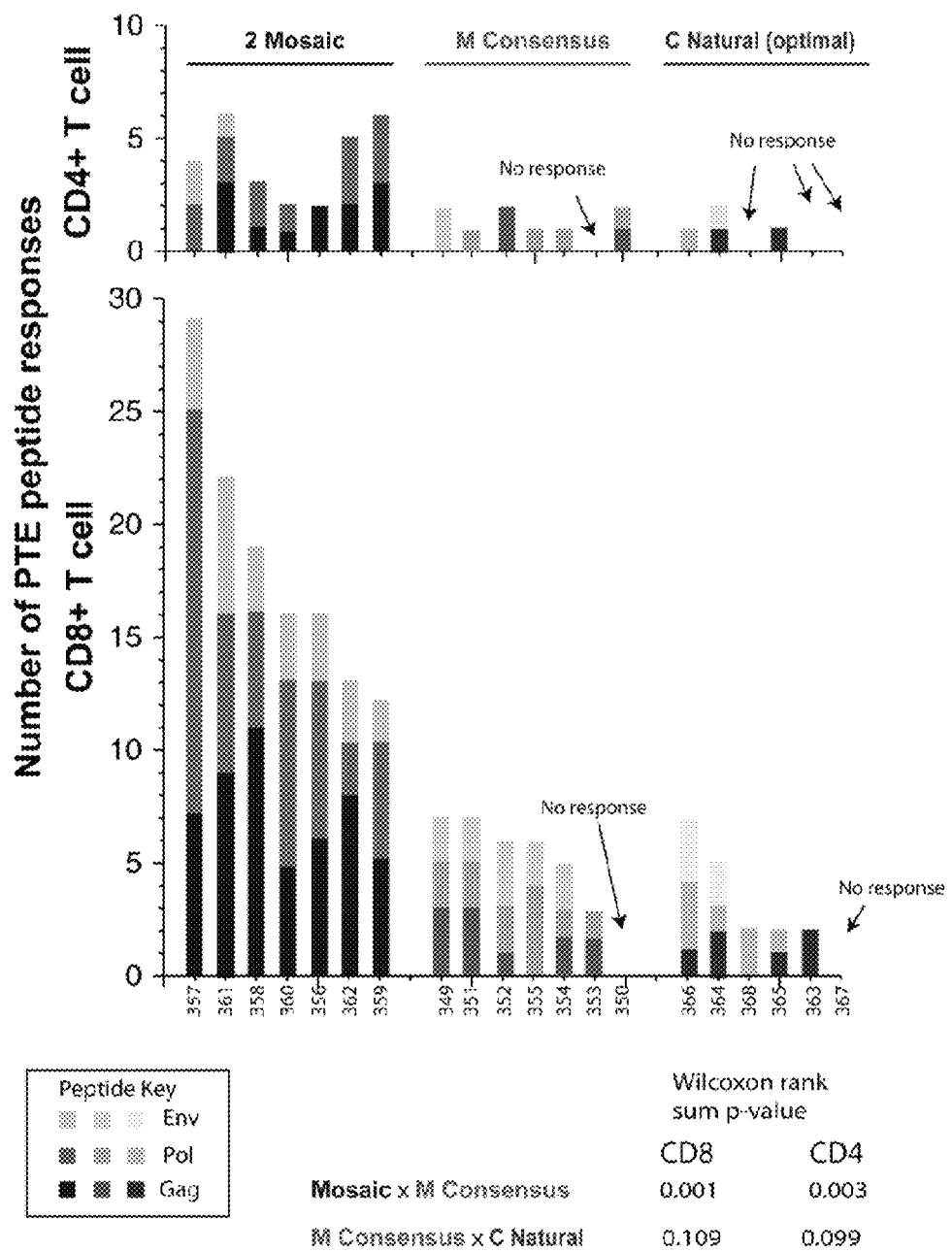
Figure 7:
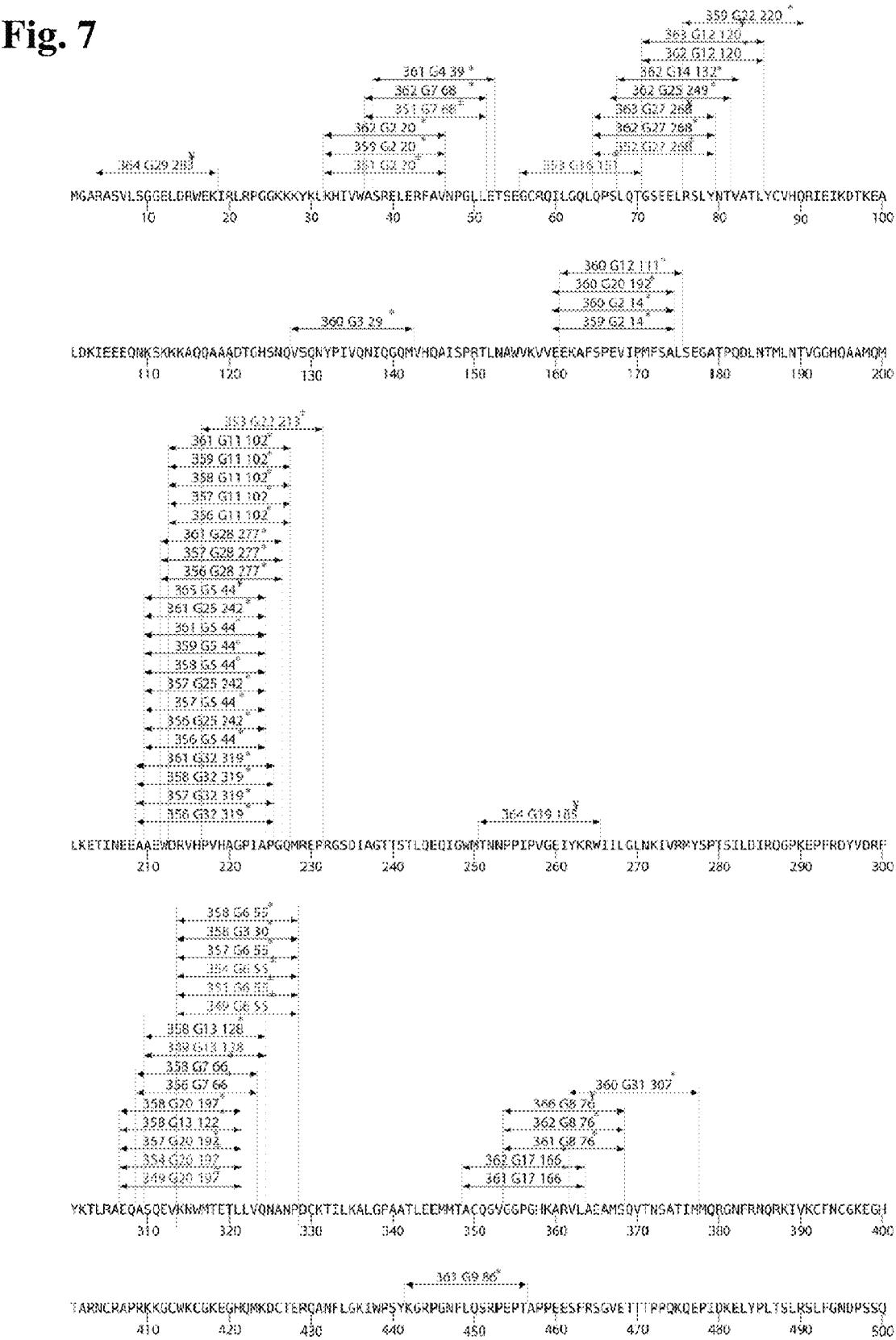
Figure 8:
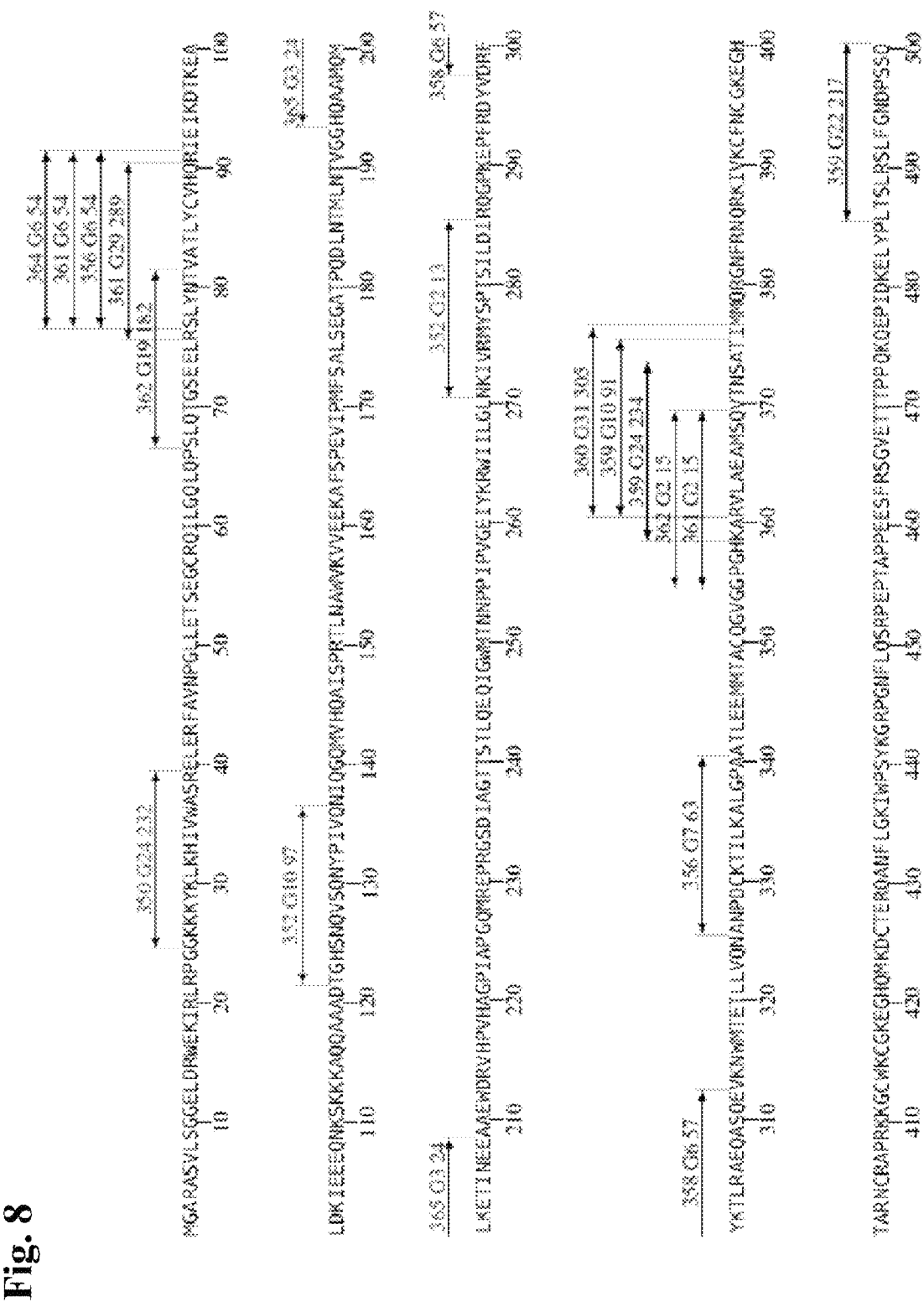
Figure 12:
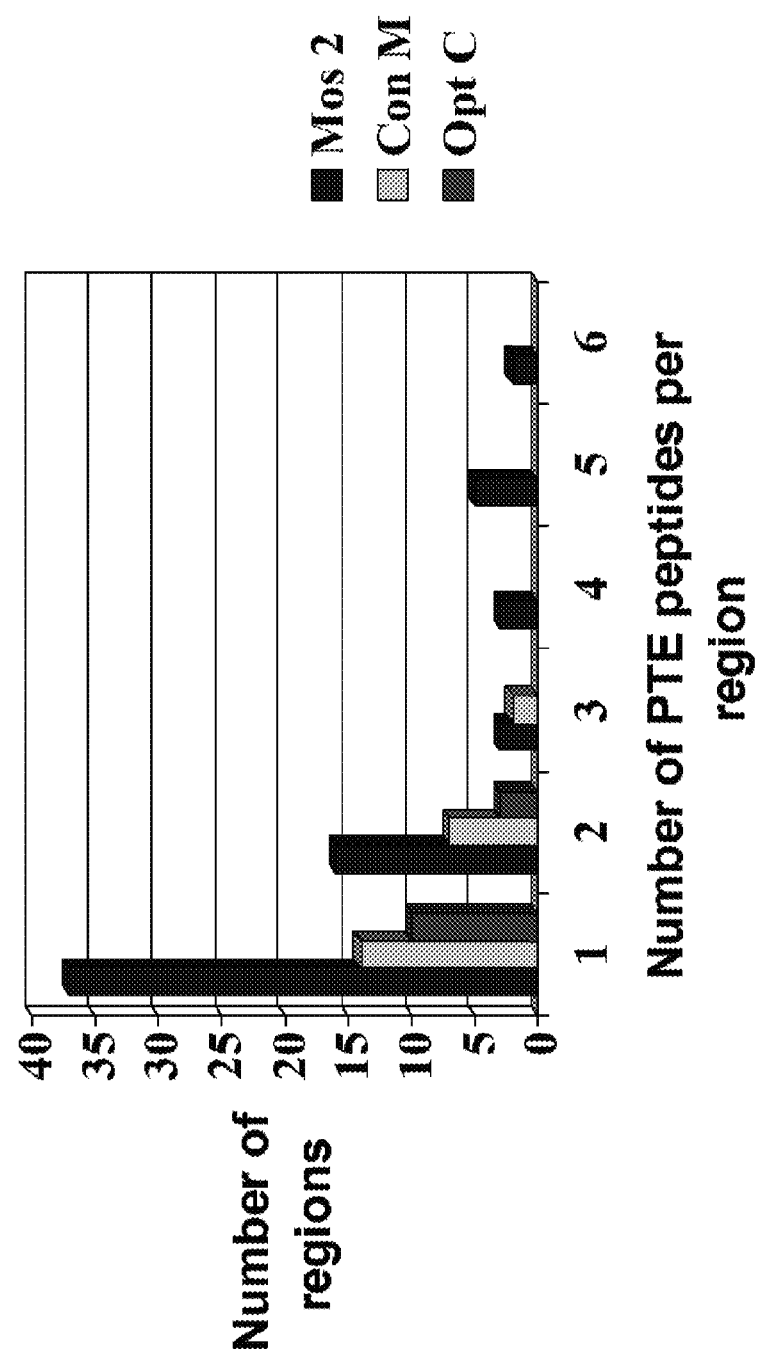
Figure 13:
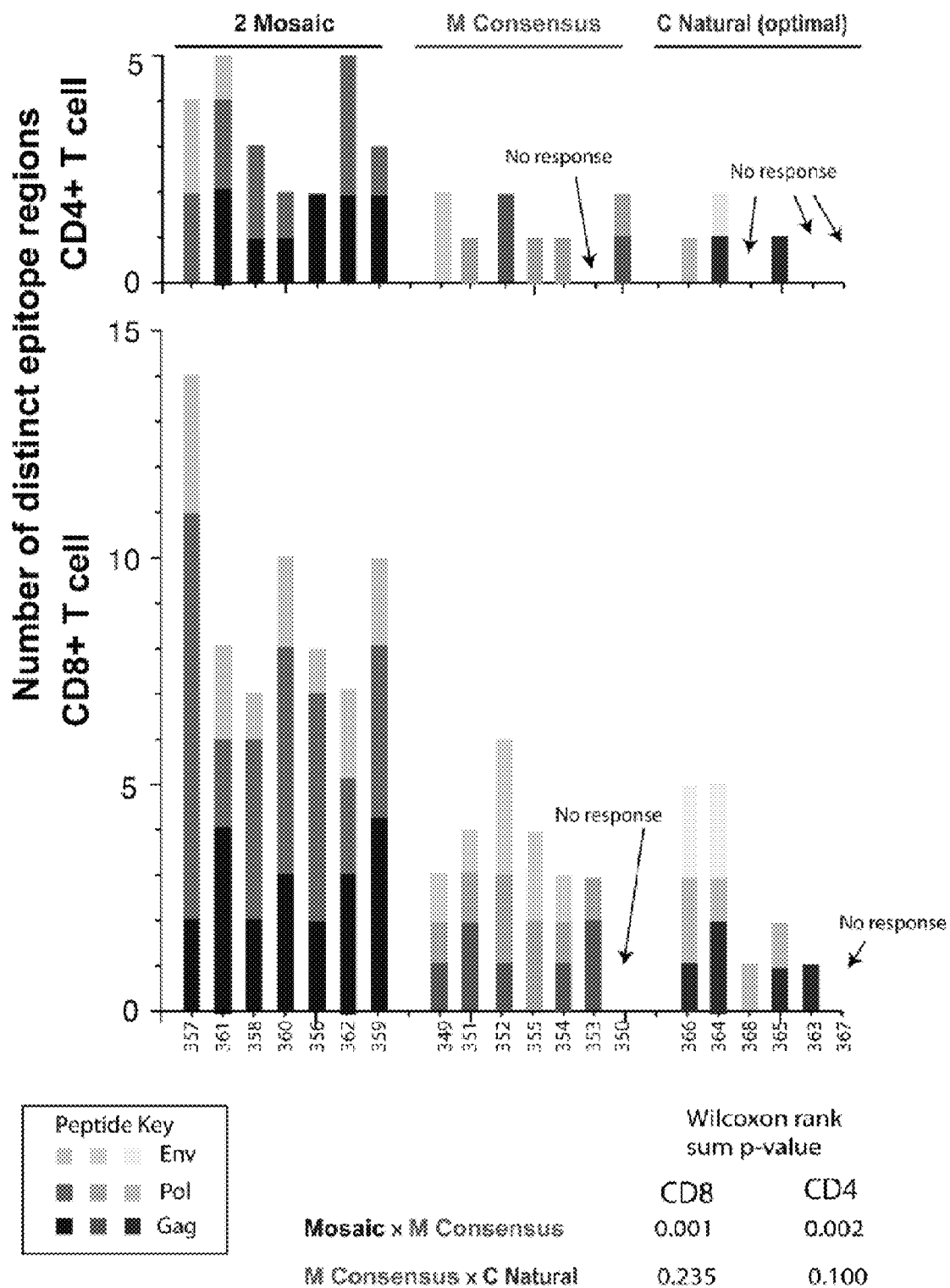
Figure 15:
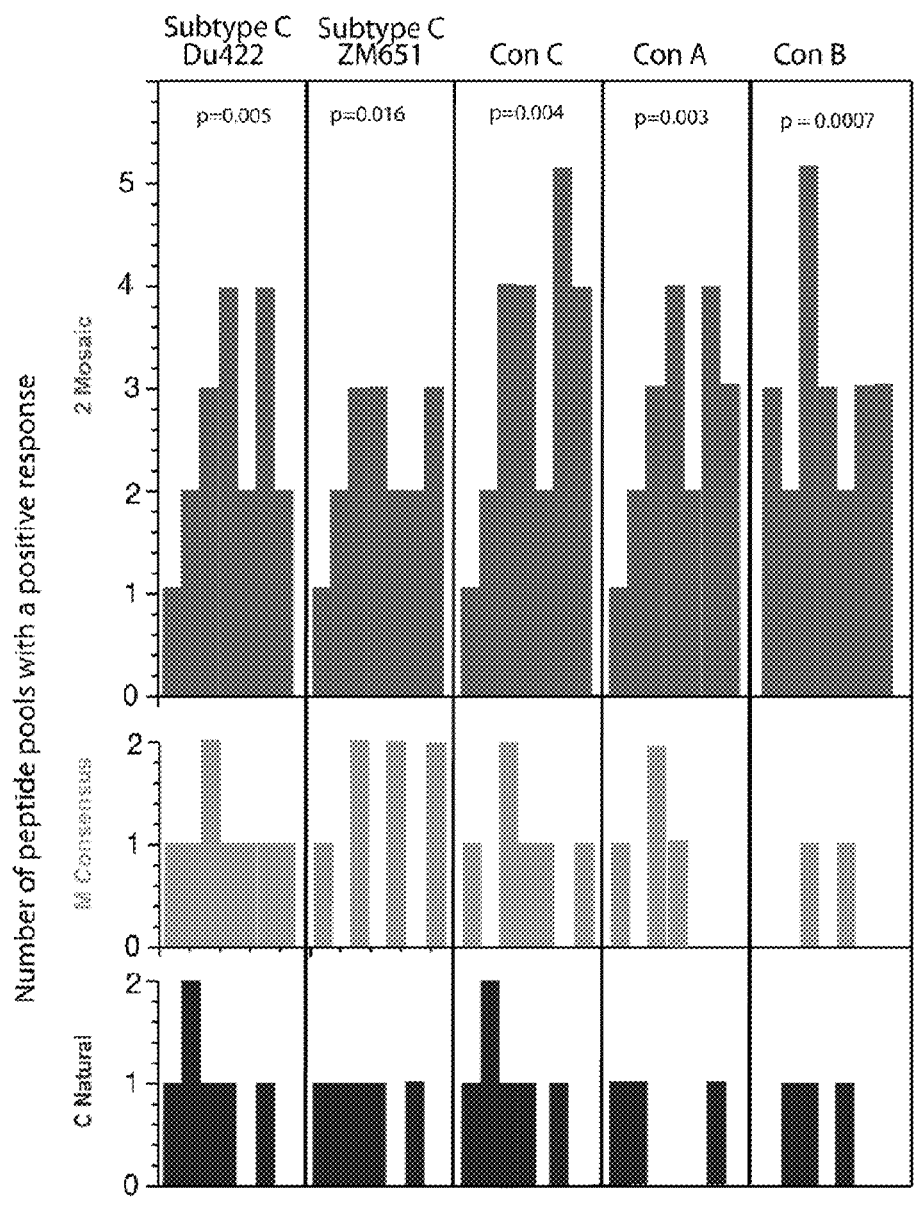
Figure 16:
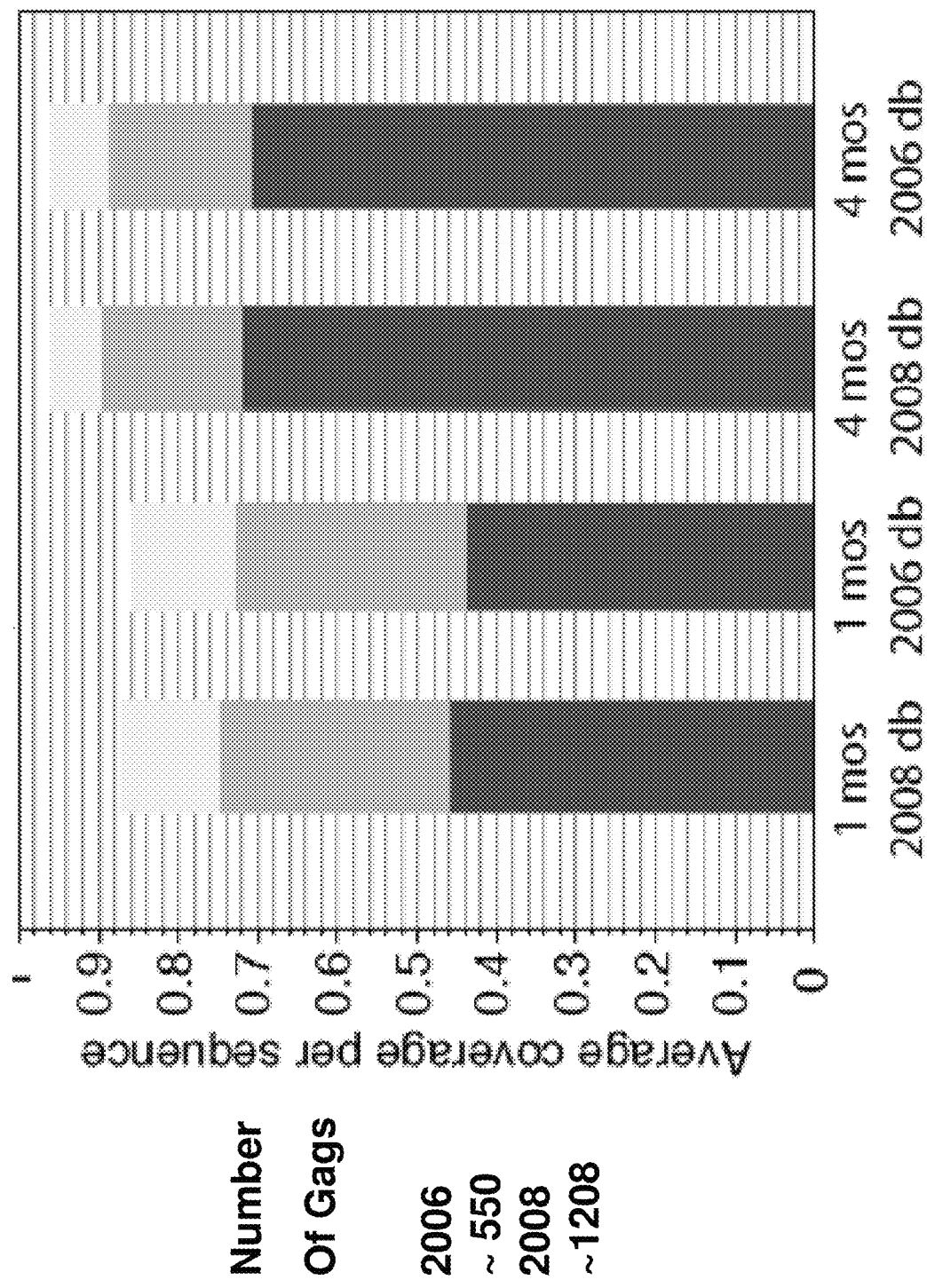
FIG. 16 is a graph showing that the mosaic design is robust to changes in viral polypeptides over time (e.g., Gag M).
Figure 17:
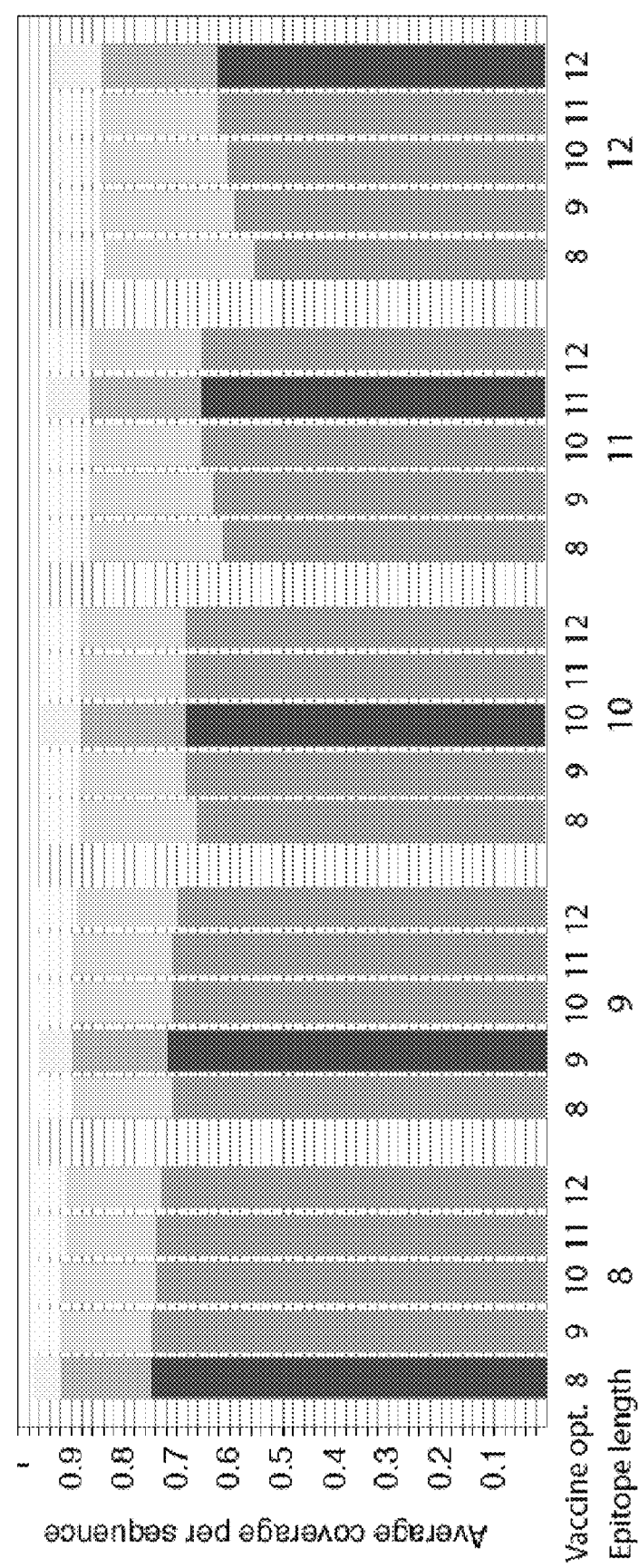
FIG. 17 is a graph showing that coverage using 9-mer optimization is robust over near (e.g., 8-12 mers) optimization lengths (Gag is shown).
Figure 18:
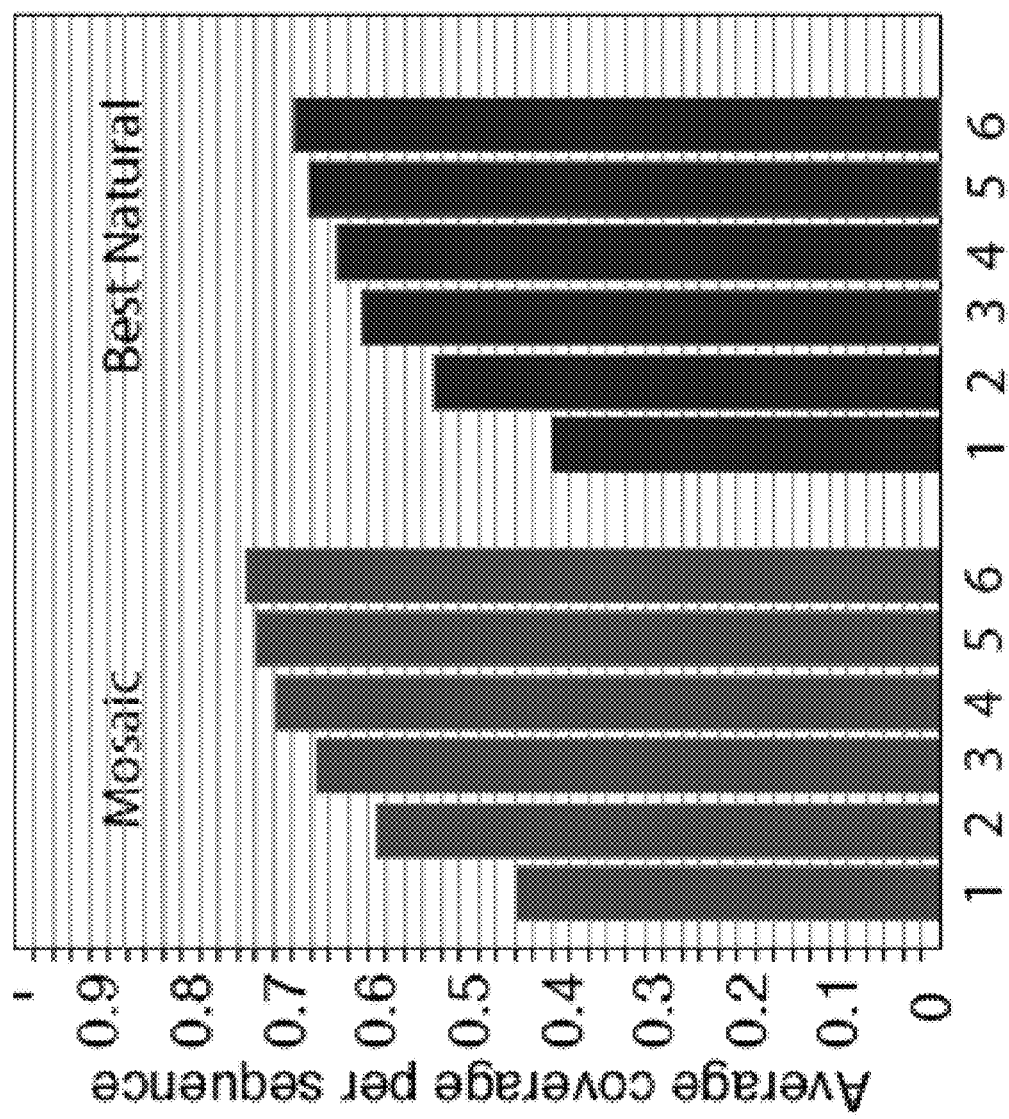
FIG. 18 is a graph showing that an increase in the number of variants increases coverage, but has only diminishing returns (Gag is shown).
Figure 19A:
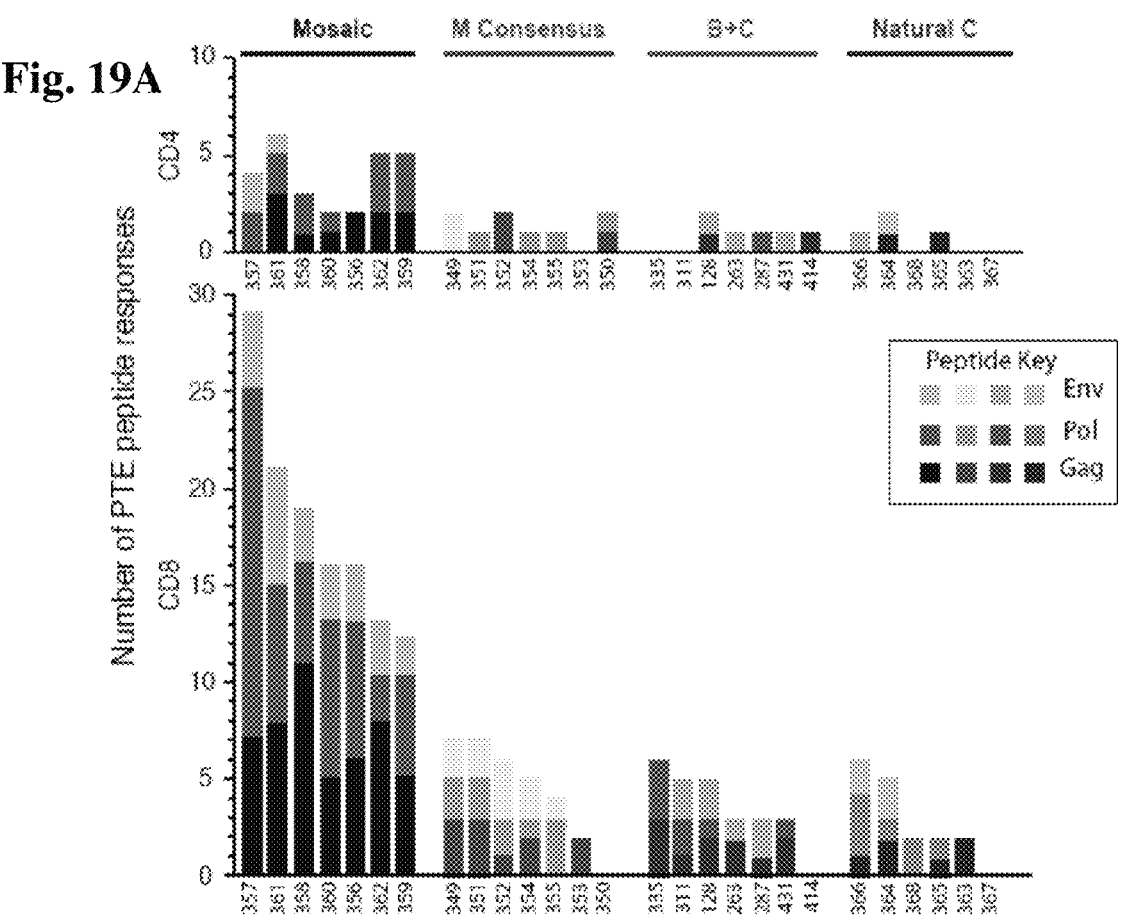
Figure 19B:
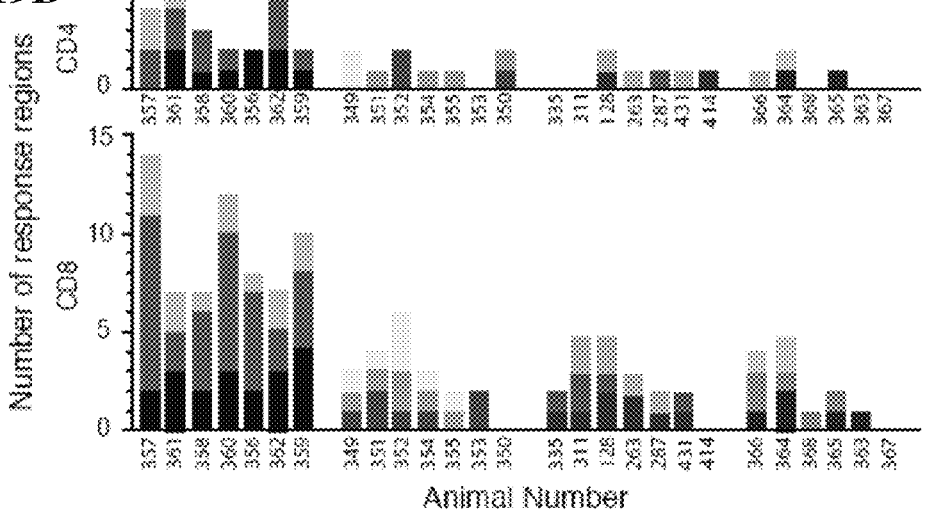

FIGS. 19A-19B are graphs showing the breadth and magnitude of epitope-specific T lymphocyte responses to PTE peptides. FIG. 19A is a graph showing the numbers of epitope-specific CD4+(top) and CD8+(bottom) T lymphocyte responses to individual PTE peptides following a single immunization of rAd26 vectors expressing mosaic (blue), M consensus (green), clade B+clade C (purple), or optimal natural clade C (red) HIV-1 Gag, Pol, and Env antigens. Individual monkeys are depicted on the x-axis. The different shades of each color reflect responses to the different antigens (Gag, Pol, Env). FIG. 19B is a graph showing the numbers of CD4+(top) and CD8+(bottom) T lymphocyte response regions.

Figure 20A:
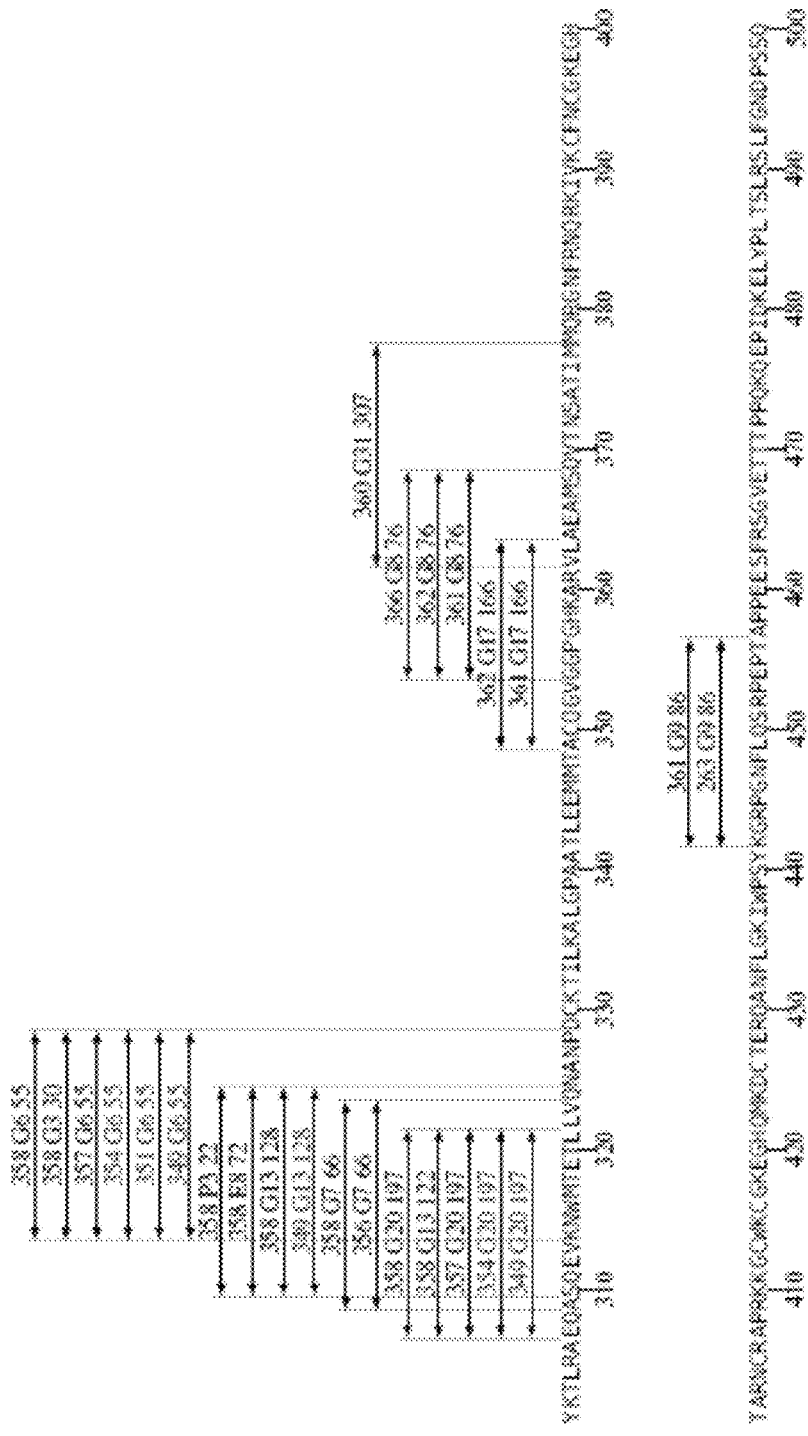
Figure 20B:
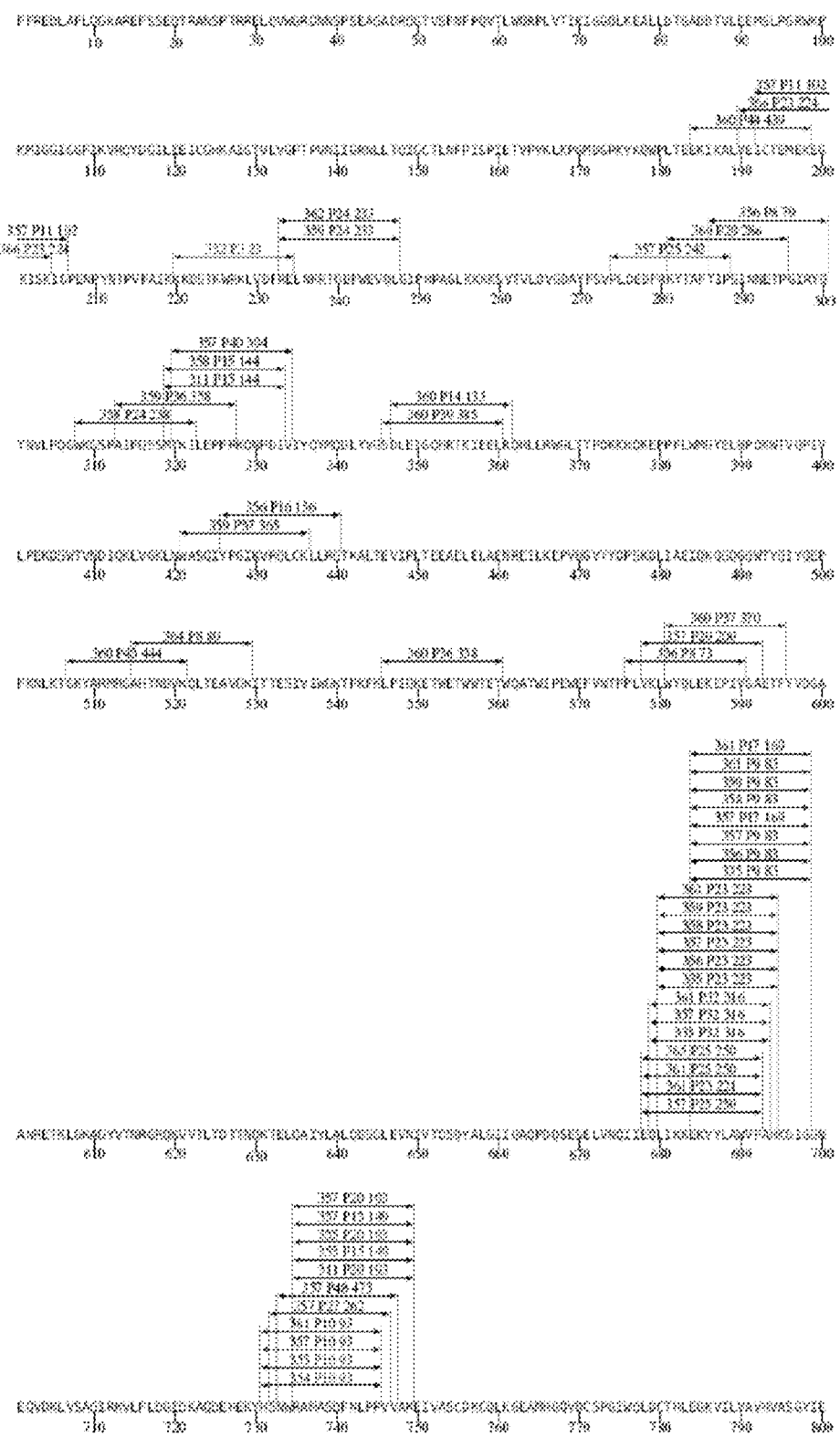
Figure 20B:
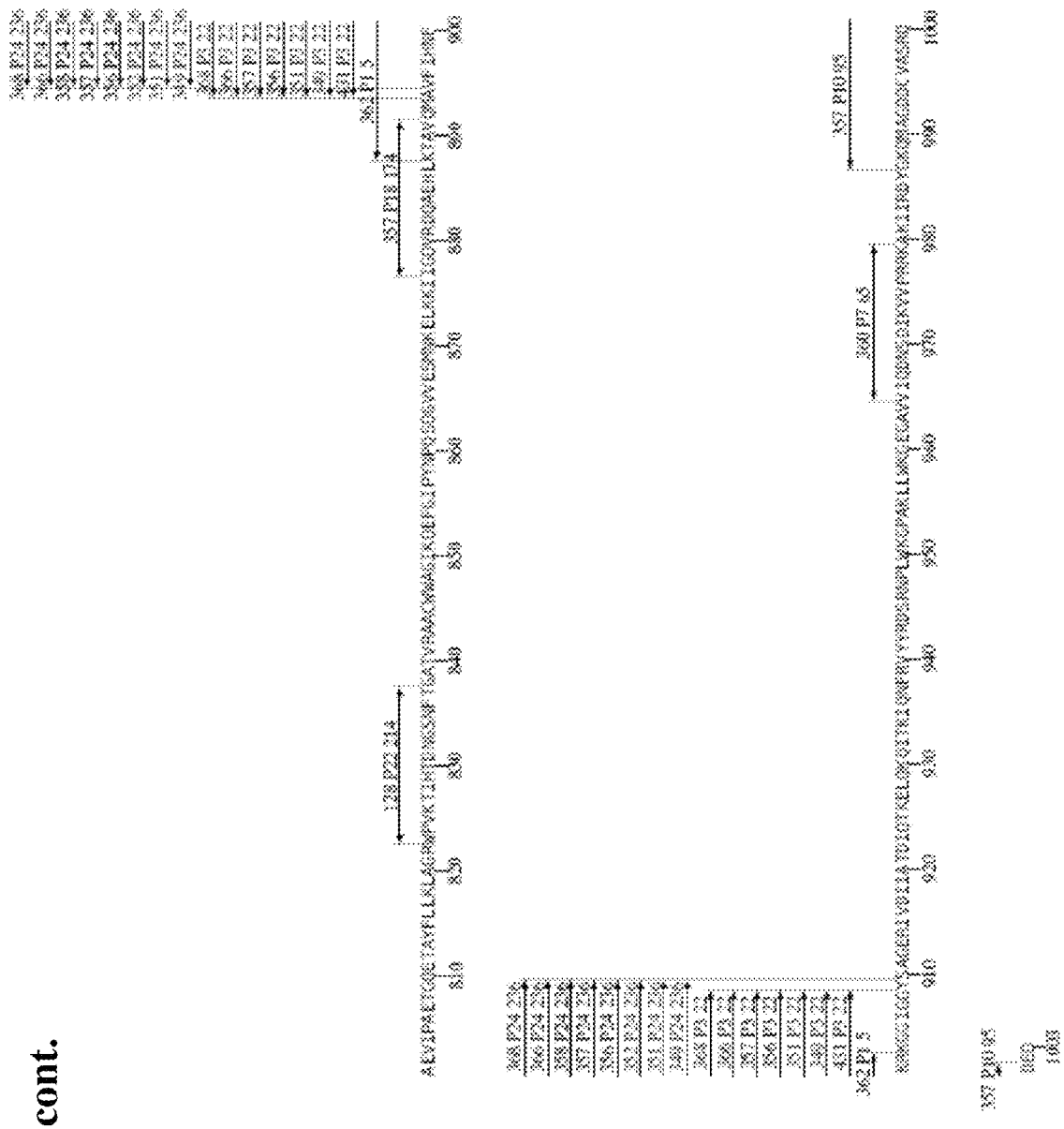
Figure 20C:
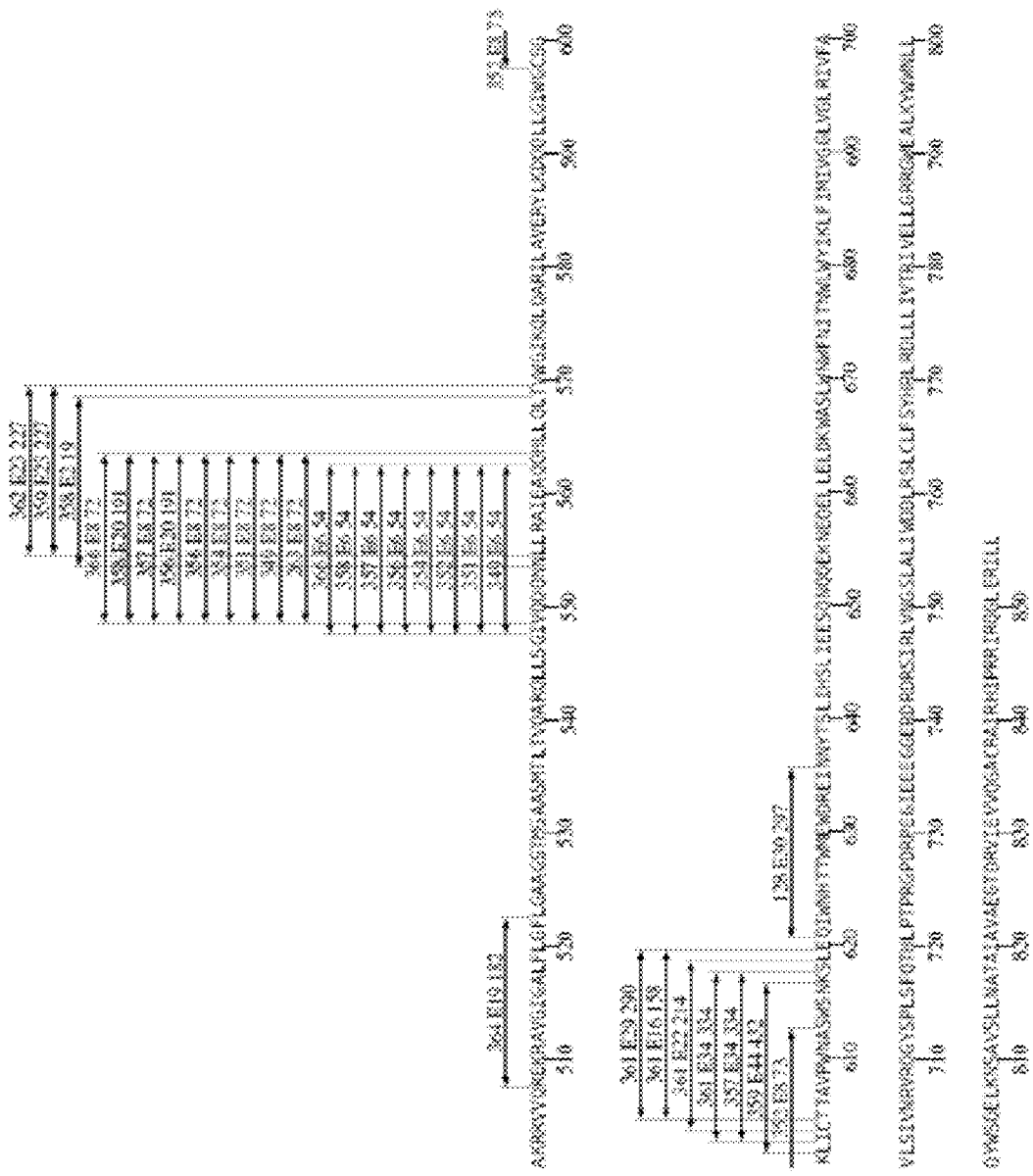

FIGS. 20A-20C show a schematic showing CD8+ T lymphocyte responses to PTE peptides at week 4 following immunization mapped on HIV-1 Gag (FIG. 20A) (SEQ ID NO: 118), Pol (FIG. 20B) (SEQ ID NO: 119), and Env (FIG. 20C) (SEQ ID NO: 120) protein sequences. Colors denote monkeys that received the mosaic (blue), M consensus (green), clade B+clade C (purple), or optimal natural clade C (red) HIV-1 Gag, Pol, and Env antigens. For each epitope, the monkey number, antigen (G, Gag; P, Pol; E, Env), subpool number, and individual PTE peptide number are indicated.

Figure 21A:
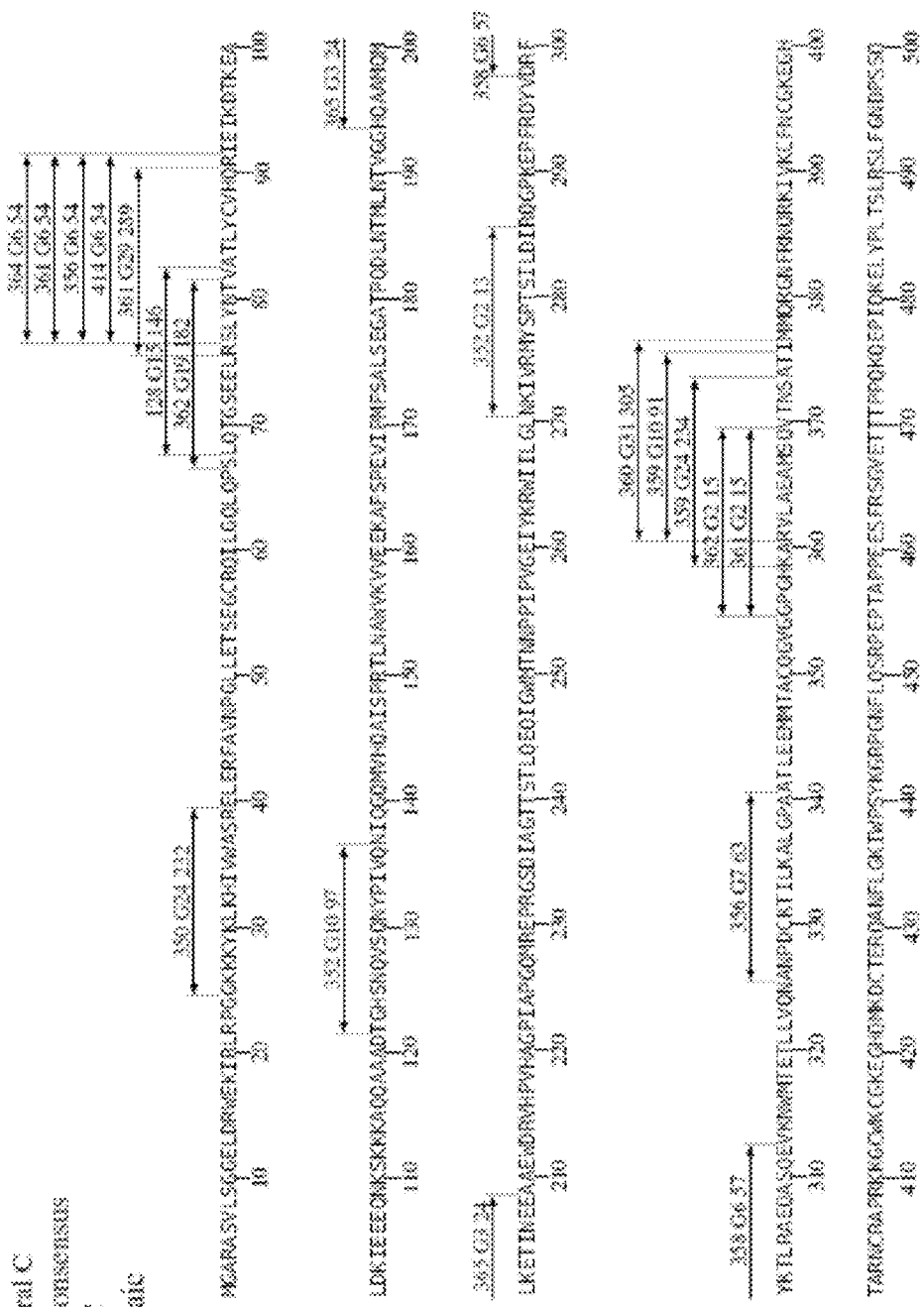
Figure 21C:
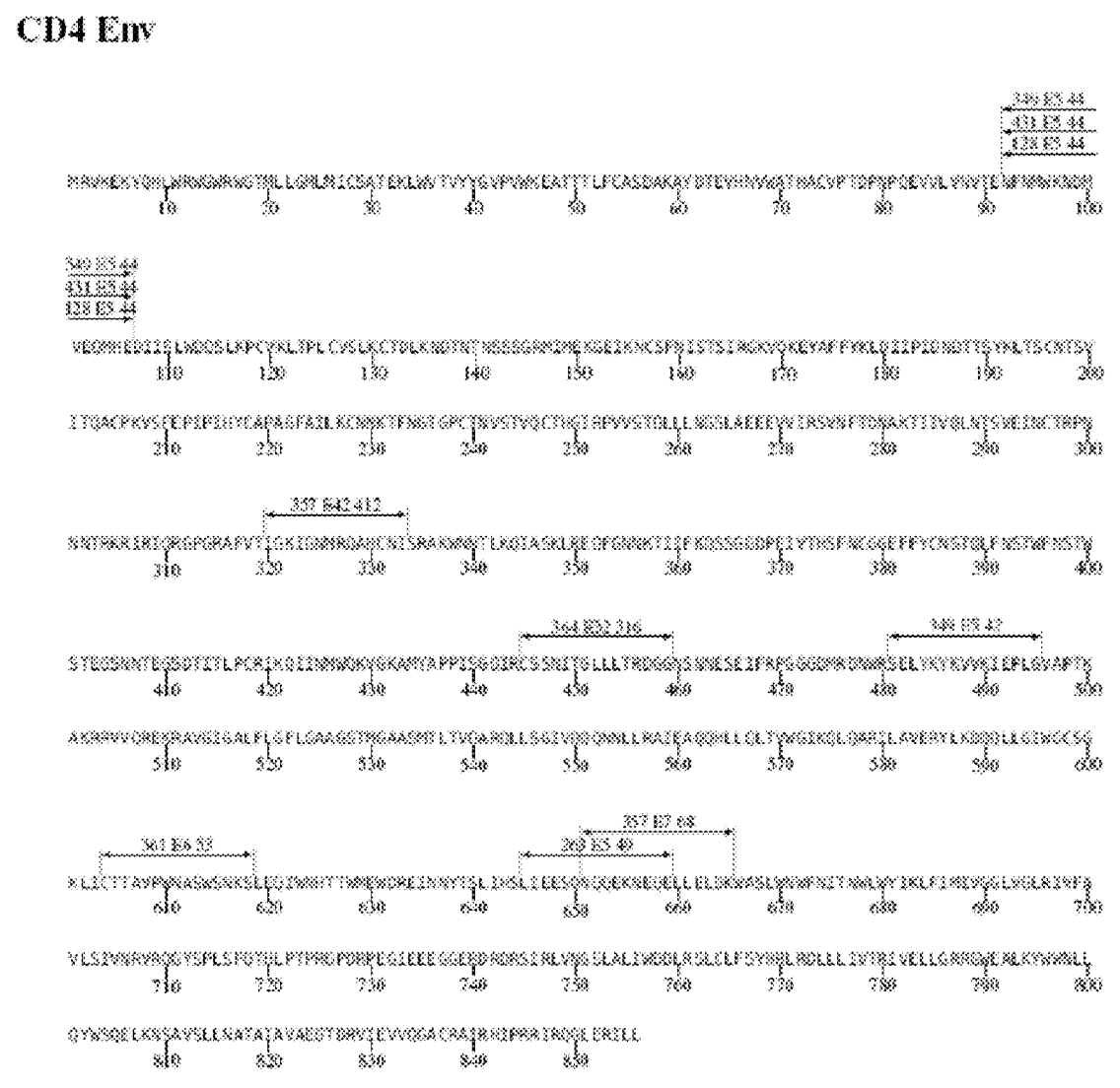

FIGS. 21A-21C show a schematic showing CD4+ T lymphocyte responses to PTE peptides at week 4 following immunization mapped on HIV-1 Gag (FIG. 21A) (SEQ ID NO: 121), Pol (FIG. 21B) (SEQ ID NO: 122), and Env (FIG. 21C) (SEQ ID NO: 123) protein sequences. Colors denote monkeys that received the mosaic (blue), M consensus (green), clade B+clade C (purple), or optimal natural clade C (red) HIV-1 Gag, Pol, and Env antigens. For each epitope, the monkey number, antigen (G, Gag; P, Pol; E, Env), subpool number, and individual PTE peptide number are indicated.

FIG. 22 is a schematic showing the alignment of vaccine sequences with reactive PTE peptides in all monkeys at week 4 following immunization with rAd26 vectors expressing mosaic, M consensus, clade B+clade C, or optimal natural clade C HIV-1 Gag, Pol, and Env antigens. For each monkey, vaccine sequences are shown on the top, and reactive PTE peptides are shown beneath the vaccine sequences denoted by the antigen (G, Gag; P, Pol; E, Env) and PTE peptide numbers. The minimal overlap region is shown in bold. Sequence polymorphisms between the two mosaic or the two clade B+clade C antigens are shown in blue. Differences between the vaccine sequences and the reactive PTE peptides are shown in red. FIG. 22 discloses SEQ ID NOS 124-640, respectively, in order of appearance.

Minimal regions within the peptides that are likely to contain the immune response epitope, based on overlap between reactive peptides when it occurs, are in bold in the vaccines. If there is no overlapping peptide, we assume the epitope can be anywhere in the peptide, so the whole region is bold. We cannot differentiate between different T cell responses targeting epitopes with different boundaries within a peptide, or more promiscuous clonal T cell responses that can tolerate variation when variants are present; either scenario could be advantageous in a vaccine immune response. The number of targeted regions corresponds to the minimum number of T cell responses required to account for the data.

Amino acids where the vaccine and the peptides don't match are written in red; if they fall within the region likely to carry the epitope, they are bold red. Amino acid differences outside of the overlapping regions when multiple peptides overlap are marked in red, but not bold.

The vaccines are always at the top. The letter for each protein (Gag is G, Pol is P, Envelope is E) and the peptide number are used to label for each reactive PTE peptide. The protein and HXB2 numbers follow each peptide.

For the mosaic and clade B+C vaccines, there are 2 antigens each and both are included in the alignment; amino acid differences in the vaccines are noted in blue, and if the reactive peptide carries the variant amino acid in the second mosaic, it is also in blue. In each of the positions where the two vaccine antigens differ, the reactive peptides are also marked in bold to indicate the positions where including two variants may have impacted the vaccine immune response and allowed greater breadth and depth.

For example, the first vaccine summarized is the clade B+C vaccine, and animal 287-95 is the first animal for which responses are listed. There were 3 CD8 responses to PTE peptides, 1 to CD4. Two of the CD8 peptides show substantial overlap, E26 and E282, so both may be targets for the same CTL response; thus we also note there are only 2 CD8 responsive regions, and 1 CD4 responsive region. For each responsive region, we write out the number of overlapping peptides per region (e.g., CD8: 1 2 CD4: 1) to assess depth of responses; the two is red to indicate that the region of overlap is variable in the reactive peptides. If the vaccine differs, like the D/E in the second reactive region, it is marked in blue. Only the region of overlap is bold. The H in E282 was not found in either vaccine so it is marked with red; it is within the region of overlap so it is bold. Each reactive peptide has its protein and corresponding HXB2 numbering noted on the right.

FIGS. 23A-23C are graphs showing the magnitude of all Gag-, Pol-, and Env-specific CD8+ (FIGS. 23A and 23B) and CD4+ (FIG. 23C) T lymphocyte responses arranged from lowest to highest.

Figure 24C:
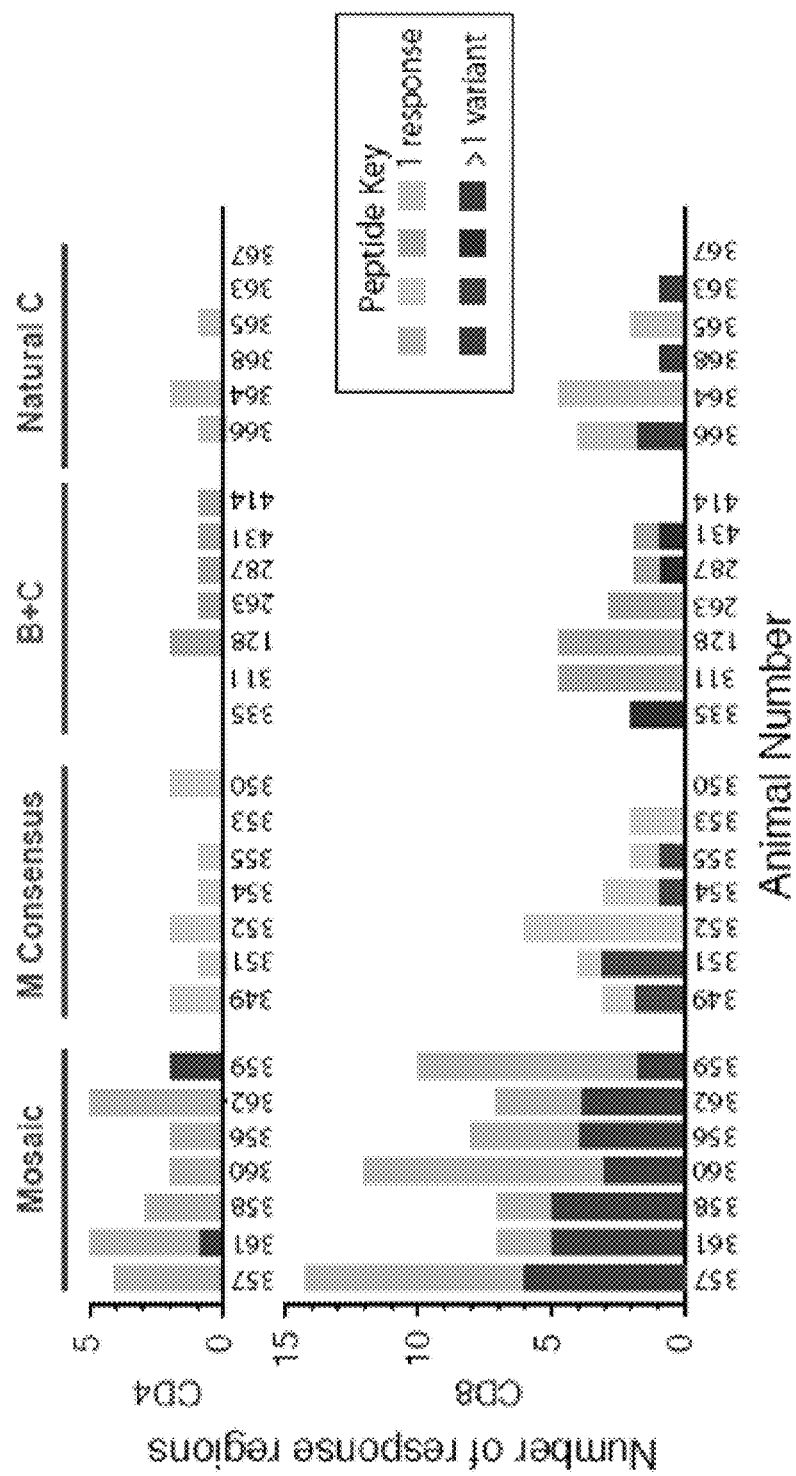

FIGS. 24A-C show the depth of epitope-specific T lymphocyte responses to PTE peptides. FIG. 24A is a schematic showing an example of mapped T lymphocyte responses in monkey 366 that received the optimal natural clade C antigens. FIG. 24B is a schematic showing an example of mapped T lymphocyte responses in monkey 361 that received the 2-valent mosaic antigens. In FIGS. 24A and 24B, vaccine sequences are shown on the top (OptC; Mos1, Mos2), and reactive PTE peptides are shown beneath the vaccine sequences denoted by the antigen (G, Gag; P, Pol; E, Env) and the PTE peptide numbers. The minimal overlap region is shown in bold. Sequence polymorphisms between the two mosaic antigens are shown in blue. Differences between the vaccine sequences and the reactive PTE peptides are shown in red. Complete alignments of all positive peptides organized by response regions are shown in FIG. 22. FIG. 24C is a graph showing the depth of CD4+(top) and CD8+(bottom) T lymphocyte responses following immunization with rAd26 vectors expressing mosaic, M consensus, clade B+clade C, or optimal natural clade C antigens. Individual monkeys are depicted on the x-axis. One response variant (light shade) or >1 response variants (dark shade) are shown for each epitopic region. FIG. 24A discloses SEQ ID NOS 641-650, respectively, in order of appearance. FIG. 24B discloses SEQ ID NOS 651-685, respective), in order of appearance.

Figure 25:
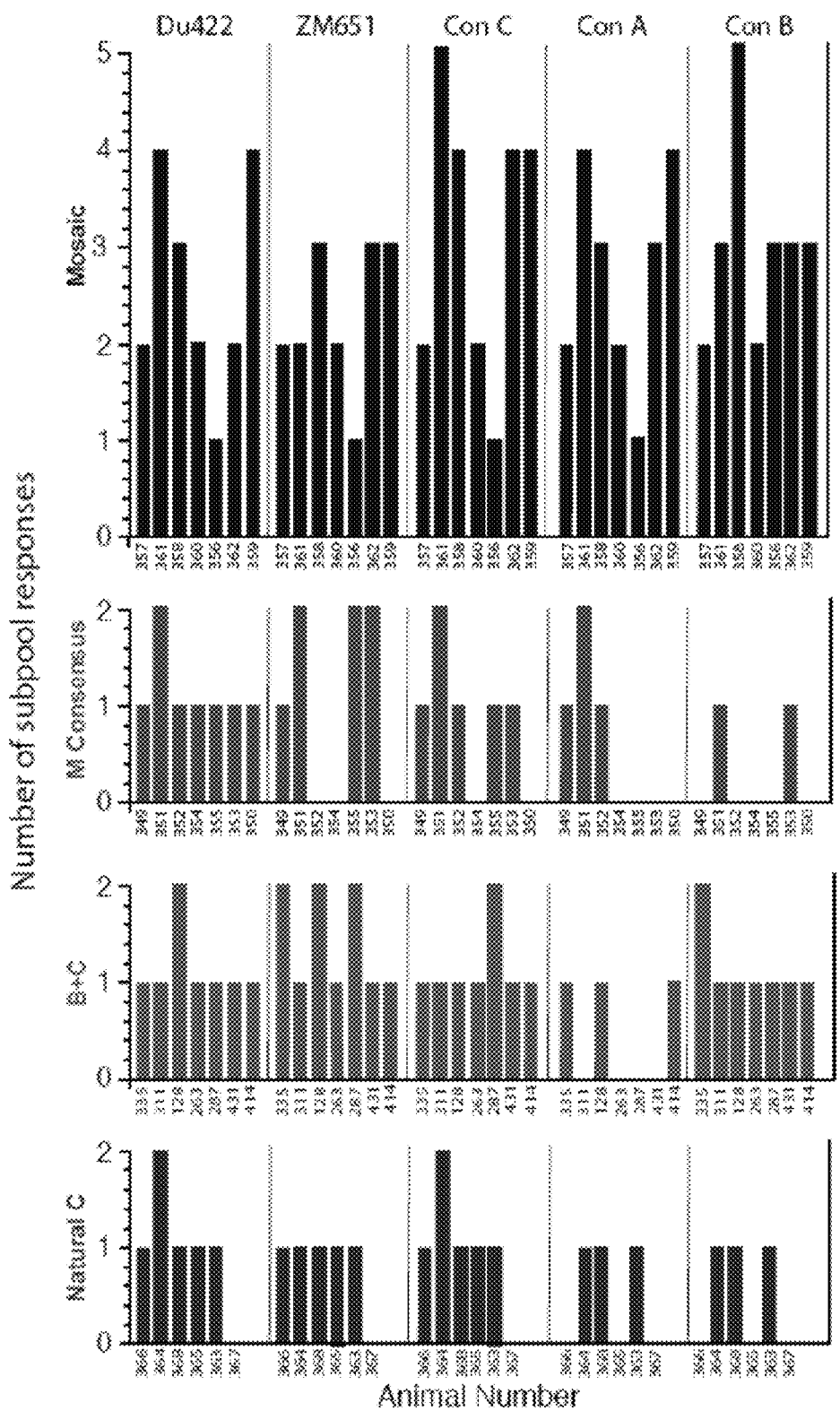

FIG. 25 is a graph showing the breadth of epitope-specific T lymphocyte responses to HIV-1 Gag peptides from clades A, B, and C. Breadth of cellular immune responses was assessed utilizing subpools of overlapping peptides from the following strains of HIV-1 Gag: clade C DU422, clade C ZM651, consensus C, consensus A, and consensus B. Numbers of positive subpools are shown following a single immunization of rAd26 vectors expressing mosaic (blue), M consensus (green), clade B☐clade C (purple), or optimal natural clade C (red) HIV-1 Gag, Pol, and Env antigens. Individual monkeys are depicted on the x-axis.

Figure 26D:
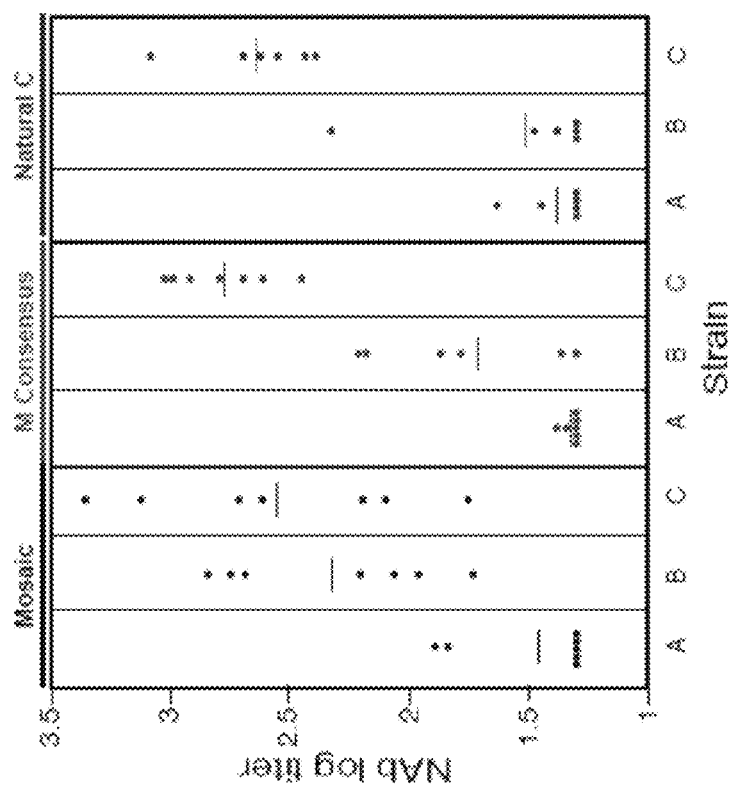
Figure 26C:
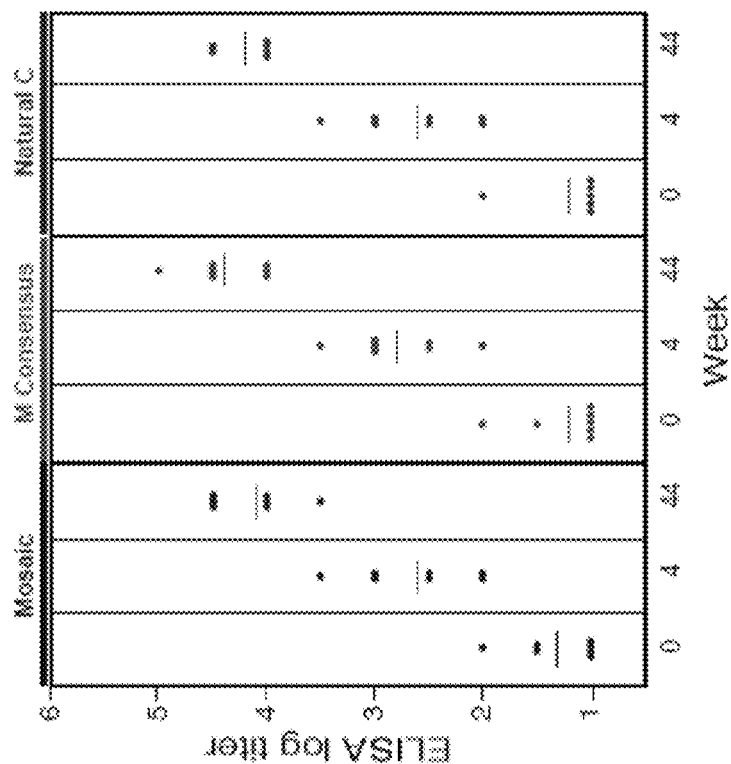

FIG. 26A-D are graphs showing the cellular and humoral immune responses following the boost immunization. Shown are the magnitude (FIG. 26A) and breadth (FIG. 26B) of individual T lymphocyte responses at week 4 post-prime (left side of each panel) and at week 44 post-boost (right side of each panel) for each monkey. Monkeys were primed at week 0 with rAd26 vectors and were boosted at week 40 with rAd5HVR48 vectors expressing mosaic, M consensus, or optimal natural clade C HIV-1 Gag, Pol, and Env antigens. Individual monkeys are depicted on the x axis. In FIG. 26A, red denotes CD8+ T lymphocyte responses, blue denotes CD4+ T lymphocyte responses, lines depict responses observed at both timepoints, and dots depict responses observed at only one timepoint. In FIG. 26B, different shades of each color reflect responses to the different antigens (Gag, Pol, Env), FIG. 26C is a graph showing the Env-specific ELISA endpoint titers at weeks 0, 4, and 44. FIG. 26D is a graph showing the neutralizing antibody (NAb) titers to the tier 1 clade A (DJ263.8), clade B (SF162.LS), and clade C (MW965.26) viruses at week 44. NAb titers to murine leukemia virus as a negative control were <20 for all samples.

Figure 27:
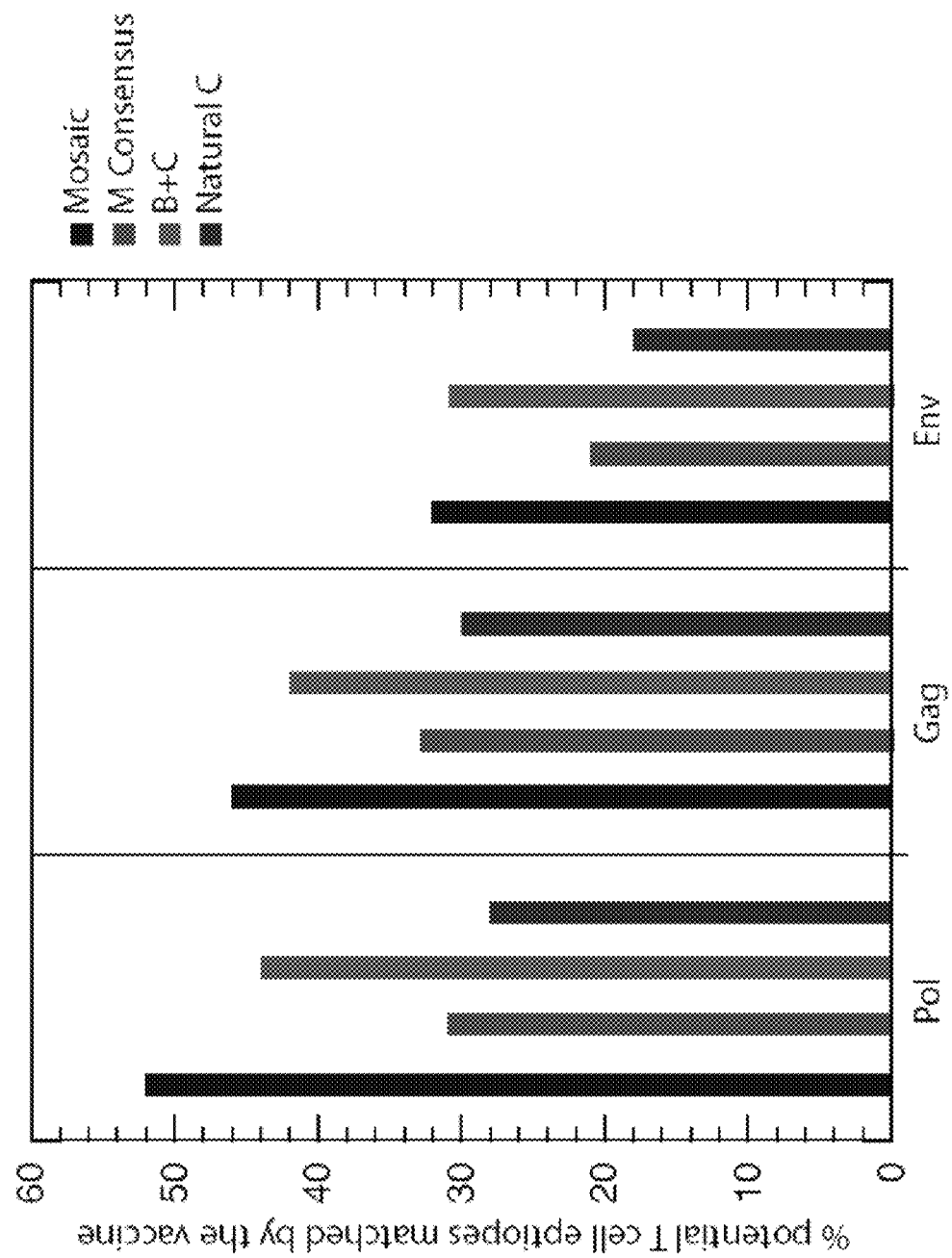

FIG. 27 is a graph showing the theoretical coverage of PTE peptides by the various vaccine antigens. Percentage of 9 amino acid PTE peptides that are covered by the mosaic (blue), M consensus (green), clade B+clade C (purple), or optimal natural clade C (red) HIV-1 Gag, Pol, and Env antigens are shown.

DETAILED DESCRIPTION OF THE INVENTION

The invention features optimized viral polypeptides that are computationally derived from naturally-occurring viral gene products. The optimized viral polypeptides of the invention allow for an increased breadth and depth of virus-specific immunity (e.g., cellular immunity, such as T cell-based immune responses) following immunization of a subject (e.g., a human) with one or more optimized viral polypeptides of the invention or vaccines (e.g., a vector) that incorporate one or more optimized viral polypeptides of the invention. The invention provides vaccines that can be administered to a subject (e.g., a human) infected with or at risk of becoming infected with a viral infection. The vaccines of the invention incorporate at least two distinct optimized viral polypeptides for each corresponding viral gene product represented. The incorporation of at least two distinct optimized viral polypeptides allows for increased coverage and representation of immunogenic epitopes in the vaccine, which the inventors have found results in an increase in the total number of virus-specific immune responses following vaccination of a subject. The present invention also provides methods of administering and manufacturing vaccines, vectors, and optimized viral polypeptides that to a subject (e.g., a human). The compositions, methods, and kits described herein can substantially increase the diversity, breadth, and/or depth of the virus-specific cellular immune responses by providing at least two distinct optimized viral polypeptides.

Optimized Viral Polypeptides of the Invention

The present invention provides for polyvalent (e.g., 2-valent) vaccines that incorporate computationally-optimized viral polypeptides that correspond to and are derived from viral gene products that naturally circulate. Polyvalent mosaic proteins are assembled from natural sequences by in silico recombination and optimized to provide maximal coverage of potential T cell epitopes (PTEs) for a given valency. Mosaic antigens are full-length proteins that are designed to preserve natural antigen expression and processing.

The inventors have discovered that immunization with two distinct optimized viral polypeptides corresponding to and derived from a single viral gene product (i.e., a 2-valent vaccine) elicits a substantially higher number of cellular immune responses (e.g., T cell responses) than conventional monovalent or polyvalent vaccines that incorporate naturally-occurring polypeptides derived from the same viral gene product (e.g., sequences based on clinical isolates), or a consensus sequence of such naturally-occurring polypeptides derived from the same viral gene product. Accordingly, a vaccine that incorporates computationally-optimized viral polypeptides, the sequences of which provide maximum coverage of non-rare short stretches of circulating viral sequences, can increase the breadth and depth of the immune response.

A genetic algorithm is used to create sets of optimized viral polypeptides as "mosaic" blends of fragments of an arbitrary set of naturally-occurring viral gene product sequences provided as inputs. This genetic algorithm strategy uses unaligned protein sequences from a general viral population as an input data set, and thus has the virtue of being "alignment independent." It creates artificial optimized viral polypeptides that resemble viral proteins found in nature, but are not naturally-occurring. The genetic algorithm can be adjusted to optimize viral polypeptides of different lengths, depending on the intended target or desired immune response. As most T cell epitopes are nine amino acids in length, the genetic algorithm utilized to design the optimized viral polypeptides of the invention was based on optimizing each consecutive 9-mer amino acid sequence of a given viral gene product (e.g., HIV-1 Gag). In accordance with this approach, 9-mers (for example) that do not exist in nature or that are very rare can be excluded—this is an improvement relative to consensus sequence-based vaccine strategies since the latter can contain some 9-mers (for example) that occur rarely or not at all in nature. The definition of fitness used for the genetic algorithm is that the most "fit" polyvalent cocktail is the combination of input viral sequences that gives the best coverage (highest fraction of perfect matches) of all of the 9 mers in the population and is subject to the constraint that no 9 mer is absent or rare in the population. The genetic algorithm used to generate the optimized viral polypeptides of the invention is further described in International Patent Application Publication WO 2007/024941, herein incorporated by reference.

In one embodiment, the invention provides polyvalent (e.g., 2-valent) HIV-1 vaccines that incorporate single optimized HIV-1 polypeptides (e.g., the polypeptides set forth in SEQ ID NOS:1-29). In another embodiment, the invention features a polyvalent vaccine that incorporates two or more optimized HIV-1 polypeptides. In each case, the optimized HIV-1 polypeptides are based on all HIV-1 variants in global circulation, known as the HIV-1 Main (M) group. The inventors have generated a set of optimized HIV-1 polypeptides (SEQ ID NOS:1-29) that augment the breadth and depth of cellular immunity based on group M mosaic genes that utilize only two variants per gene (e.g., two polypeptide sequences each for Gag, Pol, Env, Nef, Tat, Rev, Vif, Vpr, and Vpu). We have obtained the novel and surprising result in Rhesus macaques that the use of these optimized HIV-1 polypeptides in a polyvalent (e.g., 2-valent) HIV-1 group M vaccine elicits a significantly greater breadth and depth of HIV-1-specific cellular immune responses when compared with two other leading vaccine antigen strategies (M consensus antigens and optimal natural clade C antigens).

The invention provides for the fusion of optimized viral polypeptides that correspond to different viral gene products. The genetic algorithm described above can be used to generate fused polypeptides for use in a vaccine of the invention. For example, the optimized HIV-1 polypeptide fusions of Gag/Nef (SEQ ID NOS:19-20), Gag/Pol (SEQ ID NOS:21-27), and Gag/Pol/Nef (SEQ ID NOS:28-29) can be incorporated into a vector of the invention for administration to a subject (e.g., a human) infected with or at risk of being infected with HIV-1. The vaccines of the invention (whether in polypeptide or nucleic acid form) can also include one or more of the non-"mosaic" polypeptides (or sequences encoding them, respectively), such as, e.g., the optimal clade C sequences (SEQ ID NOS: 30-36) or the consensus sequences (SEQ ID NOS: 37-39).

The optimized viral polypeptides disclosed in this invention can be prepared conventionally by chemical synthesis techniques, such as described by Merrifield, *J. Amer. Chem. Soc.* 85:2149 (1963) (see also, e.g., Stemmer et al., 164 *Gene* 49 (1995)). For example, the vaccines can be readily prepared using solid phase peptide synthesis (SPPS). Automated solid phase synthesis can be performed using any one of a number of well known, commercially available automated synthesizers, such as the Applied Biosystems ABI 433A peptide synthesizer. Alternatively, the optimized viral polypeptides of the invention can be recombinantly produced by transfecting or transducing a cell or organism with a nucleic acid or vector (e.g., a viral vector, such an adenovirus) that allows for the intracellular expression of the optimized viral polypeptide. Nucleic acids and vectors that encode the nucleotide sequence of optimized viral polypeptides of the invention can be synthesized by well-known recombinant DNA techniques, including those described herein.

Vaccines of the Invention

The invention also features vaccines that can be administered to a patient infected with or at risk of becoming infected with a virus (e.g., HIV-1). A vaccine of the invention contains at least one of the optimized viral polypeptides of the invention, as discussed herein. The vaccine of the invention can be a nucleic acid encoding the nucleotide sequence of two or more optimized viral polypeptides of the invention (e.g., the immunogenic component of a recombinant (e.g., subunit) or whole-organism (e.g., whole-virus) viral vector). Nucleic acids include vectors (e.g., viral vectors, such as adenoviruses) that incorporate the nucleotide sequence of two or more optimized viral polypeptides of the invention. The optimized viral polypeptides of the invention, as well as vaccines, nucleic acids, and vectors that incorporate optimized viral polypeptides, can be recombinantly expressed in a cell or organism, or can be directly administered to subject (e.g., a human) infected with, or at risk of becoming infected with, a virus.

Vectors of the Invention

The invention also features vectors encoding the nucleotide sequences (e.g., DNA or RNA) of one or more optimized viral polypeptides of the invention. The vector can be a carrier (e.g., a liposome), a plasmid, a cosmid, a yeast artificial chromosome, or a virus that includes a nucleotide sequence encoding one or more optimized viral polypeptides of the invention. The vector can include additional nucleic acid sequences from several sources.

Vectors encoding one or more optimized viral polypeptides of the invention can be constructed using any recombinant molecular biology technique known in the art. The vector, upon transfection or transduction of a target cell or organism, can be extrachromosomal or it can be integrated into the host cell chromosome. The nucleic acid component of a vector can be in single or multiple copy number per target cell, and can be linear, circular, or concatamerized.

Vectors of the invention can also include internal ribosome entry site (IRES) sequences to allow for the expression of multiple peptide or polypeptide chains from a single nucleic acid transcript. For example, a vector of the invention can encode one or more optimized viral polypeptides of the invention as well as another polypeptides (e.g., a detectable label, such as green fluorescent protein (GFP)).

Vectors of the invention further include gene expression elements that facilitate the expression of optimized viral polypeptides of the invention. Gene expression elements useful for the expression of an vector encoding an optimized viral polypeptide of the invention include, but are not limited to (a) regulatory sequences, such as viral transcription promoters and their enhancer elements, such as the SV40 early promoter, Rous sarcoma virus LTR, and Moloney murine leukemia virus LTR; (b) splice regions and polyadenylation sites such as those derived from the SV40 late region; and (c) polyadenylation sites such as in SV40. Also included are plasmid origins of replication, antibiotic resistance or selection genes, multiple cloning sites (e.g., restriction enzyme cleavage loci), and other viral gene sequences (e.g., sequences encoding viral structural, functional, or regulatory elements, such as the HIV long terminal repeat (LTR)).

Vectors of the invention can also include optimized viral polypeptides of the invention that have been optimized for expression in humans, such as, e.g., any one of SEQ ID NOS:11, 14-18, and 23.

Vectors of the invention can also be engineered to include a multiple cloning site (MCS) having the following enzyme cleavage sites: XbaI-EcoRI-Kozak-Start . . . Stop-BamHI-NheI; and the following sequence: TCTAGA GAATTC GCCACC [ATG gene TAA TGA] GGATCC GCTAGC. Vectors having this MCS can be used with optimized viral polypeptides having no internal XbaI, EcoRI, BamHI, NheI sites and no stretches of 6 or more C's or G's.

In Vivo Administration

The invention features methods for the in vivo administration of one or more vaccines of the invention (e.g., a vector encoding two or more optimized viral polypeptides of the invention) to a subject (e.g., a human) to facilitate the expression of two or more optimized viral polypeptides of the invention. Upon administering the vaccine to the subject, one or more optimized viral polypeptides of the invention will be expressed that can elicit protective or therapeutic immune responses (e.g., cellular or humoral immune responses) directed against the viral immunogens.

Several types of vectors can be employed to deliver a nucleotide sequence encoding one or more optimized viral polypeptides of the invention directly to a subject (e.g., a human). Vectors of the invention include viruses, naked DNA, oligonucleotides, cationic lipids (e.g., liposomes), cationic polymers (e.g., polysomes), virosomes, and dendrimers. The present invention provides for the ex vivo transfection or transduction of cells (e.g., blood cells) followed by administration of these cells back into the donor subject to allow for the expression of optimized viral polypeptides of the invention that have immunogenic properties. Cells that can be isolated and transfected or transduced ex vivo according to the methods of invention include, but are not limited to, blood cells, skin cells, fibroblasts, endothelial cells, skeletal muscle cells, hepatocytes, prostate epithelial cells, and vascular endothelial cells. Stem cells are also appropriate cells for transduction or transfection with a vector of the invention. Totipotent, pluripotent, multipotent, or unipotent stem cells, including bone marrow progenitor cells and hematopoietic stem cells (HSC), can be isolated and transfected or transduced with an vector encoding one or more optimized viral polypeptides of the invention, and administered to a subject according to the methods of the invention.

The method of transfection or transduction used to express an optimized viral vector of the invention has a strong influence on the strength and longevity of protein expression in the transfected or transduced cell, and subsequently, in the subject receiving the cell. The present invention provides vectors that are temporal (e.g., adenoviral vectors) or long-lived (e.g., retroviral vectors) in nature. Regulatory sequences (e.g., promoters and enhancers) are known in the art that can be used to regulate protein expression. The type of cell being transfected or transduced also has a strong bearing on the strength and longevity of protein expression. For example, cell types with high rates of turnover can be expected to have shorter periods of protein expression.

Ex Vivo Transfection and Transduction

The invention also features methods for the ex vivo transfection and transduction of cells (e.g., blood cells, such as lymphocytes), followed by administration of these cells to a subject (e.g., a human). In one embodiment, the cells are autologous to the treated subject. Cells can be transfected or transduced ex vivo with one or more vectors encoding the nucleotide sequence of one or more optimized viral polypeptides of the invention to allow for the temporal or permanent expression of the optimized viral polypeptides in the treated subject. Upon administering these modified cells to the subject, one or more optimized viral vectors of the invention will be expressed that can elicit protective or therapeutic immune responses (e.g., cellular or humoral immune responses) directed against the viral immunogens.

Several types of vectors can be employed to deliver a nucleotide sequence encoding one or more optimized viral polypeptides of the invention to a cell (e.g., a blood cell, such as a lymphocyte). Vectors of the invention include viruses, naked DNA, oligonucleotides, cationic lipids (e.g., liposomes), cationic polymers (e.g., polysomes), virosomes, and dendrimers. The present invention provides for the ex vivo transfection or transduction of cells (e.g., blood cells) followed by administration of these cells back into the donor subject to allow for the expression of optimized viral polypeptides of the invention that have immunogenic properties. Cells that can be isolated and transfected or transduced ex vivo according to the methods of invention include, but are not limited to, blood cells, skin cells, fibroblasts, endothelial cells, skeletal muscle cells, hepatocytes, prostate epithelial cells, and vascular endothelial cells. Stem cells are also appropriate cells for transduction or transfection with a vector of the invention. Totipotent, pluripotent, multipotent, or unipotent stem cells, including bone marrow progenitor cells and hematopoietic stem cells (HSC), can be isolated and transfected or transduced with an vector encoding one or more optimized viral polypeptides of the invention, and administered to a subject according to the methods of the invention.

The method of transfection or transduction used to express an optimized viral vector of the invention has a strong influence on the strength and longevity of protein expression in the transfected or transduced cell, and subsequently, in the subject receiving the cell. The present invention provides vectors that are temporal (e.g., adenoviral vectors) or long-lived (e.g., retroviral vectors) in nature. Regulatory sequences (e.g., promoters and enhancers) are known in the art that can be used to regulate protein expression. The type of cell being transfected or transduced also has a strong bearing on the strength and longevity of protein expression. For example, cell types with high rates of turnover can be expected to have shorter periods of protein expression.

Viral Vectors

Viral vectors encoding the nucleotide sequence of one or more optimized viral polypeptides of the invention can be used as a vaccine of the invention. For example, the nucleotide sequence of one or more optimized viral polypeptides of the invention can be inserted recombinantly into that of a natural or modified (e.g., attenuated) viral genome suitable for the transduction of a subject (e.g., in vivo administration) or cells isolated from a subject (e.g., for ex vivo transduction followed by administration of the cells back to the subject). Additional modifications can be made to the virus to improve infectivity or tropism (e.g., pseudotyping), reduce or eliminate replicative competency, or reduce immunogenicity of the viral components (e.g., all components not related to the immunogenic vaccine agent). A vector of the invention can be expressed by the transduced cell and secreted into the extracellular space or remain with the expressing cell (e.g., as an intracellular molecule or displayed on the cell surface). Chimeric or pseudotyped viral vectors can also be used to transduce a cell to allow for expression of one or more optimized viral polypeptides of the invention. Exemplary vectors are described below.

Adenoviruses

Recombinant adenoviruses offer several significant advantages for use as vectors for the expression of one or more optimized viral polypeptides of the invention. The viruses can be prepared to high titer, can infect non-replicating cells, and can confer high-efficiency transduction of target cells ex vivo following contact with a target cell population. Furthermore, adenoviruses do not integrate their DNA into the host genome. Thus, their use as expression vectors has a reduced risk of inducing spontaneous proliferative disorders. In animal models, adenoviral vectors have generally been found to mediate high-level expression for approximately one week. The duration of transgene expression (expression of a nucleic acid encoding an optimized viral polypeptide of the invention) can be prolonged by using cell or tissue-specific promoters. Other improvements in the molecular engineering of the adenoviral vector itself have produced more sustained transgene expression and less inflammation. This is seen with so-called "second generation" vectors harboring specific mutations in additional early adenoviral genes and "gutless" vectors in which virtually all the viral genes are deleted utilizing a Cre-Lox strategy (Engelhardt et al., Proc. Natl. Acad. Sci. USA 91:6196 (1994) and Kochanek et al., Proc. Natl. Acad. Sci. USA 93:5731 (1996), each herein incorporated by reference).

The rare serotype and chimeric adenoviral vectors disclosed in International Patent Application Publications WO 2006/040330 and WO 2007/104792, each incorporated by reference herein, are particularly useful as vectors of the invention. For example, recombinant adenoviruses rAd26, rAd34, rAd35, rAd48, and rAd5HVR48 can encode one or more optimized viral polypeptides of the invention. One or more recombinant viral vectors encoding optimized viral polypeptides of the invention can be administered to a subject to treat or prevent a viral infection.

Adeno-Associated Viruses (AAV)

Adeno-associated viruses (rAAV), derived from non-pathogenic parvoviruses, can also be used to express optimized viral polypeptides of the invention as these vectors evoke almost no anti-vector cellular immune response, and produce transgene expression lasting months in most experimental systems.

Retroviruses

Retroviruses are useful for the expression of optimized viral polypeptides of the invention. Unlike adenoviruses, the retroviral genome is based in RNA. When a retrovirus infects a cell, it will introduce its RNA together with several enzymes into the cell. The viral RNA molecules from the retrovirus will produce a double-stranded DNA copy, called a provirus, through a process called reverse transcription. Following transport into the cell nucleus, the proviral DNA is integrated in a host cell chromosome, permanently altering the genome of the transduced cell and any progeny cells that may derive from this cell. The ability to permanently introduce a gene into a cell or organism is the defining characteristic of retroviruses used for gene therapy. Retroviruses include lentiviruses, a family of viruses including human immunodeficiency virus (HIV) that includes several accessory proteins to facilitate viral infection and proviral integration. Current, "third-generation," lentiviral vectors feature total replication incompetence, broad tropism, and increased gene transfer capacity for mammalian cells (see, e.g., Mangeat and and Trono, Human Gene Therapy 16(8): 913 (2005) and Wiznerowicz and Trono, Trends Biotechnol. 23(1):42 (2005), each herein incorporated by reference).

Other Viral Vectors

Besides adenoviral and retroviral vectors, other viral vectors and techniques are known in the art that can be used to express optimized viral polypeptides of the invention in a cell (e.g., a blood cell, such as a lymphocyte) or subject (e.g., a human). Theses viruses include Poxviruses (e.g., vaccinia virus and modified vaccinia virus Ankara or (MVA); see, e.g., U.S. Pat. Nos. 4,603,112 and 5,762,938, each incorporated by reference herein), Herpesviruses, Togaviruses (e.g., Venezuelan Equine Encephalitis virus; see, e.g., U.S. Pat. No. 5,643,576, incorporated by reference herein), Picornaviruses (e.g., poliovirus; see, e.g., U.S. Pat. No. 5,639,649, incorporated by reference herein), Baculoviruses, and others described by Wattanapitayakul and Bauer (*Biomed. Pharmacother.* 54:487 (2000), incorporated by reference herein).
Other Expression Vectors: Naked DNA and Oligonucleotides Naked DNA or oligonucleotides encoding one or more optimized viral polypeptides of the invention can also be used to express these polypeptides in a cell (e.g., a blood cell, such as a lymphocyte) or subject (e.g., a human). See, e.g., Cohen, *Science* 259:1691-1692 (1993); Fynan et al., *Proc. Natl. Acad. Sci. USA,* 90:11478 (1993); and Wolff et al., *BioTechniques* 11:474485 (1991), each herein incorporated by reference. This is the simplest method of non-viral transfection. Efficient methods for delivery of naked DNA exist such as electroporation and the use of a "gene gun," which shoots DNA-coated gold particles into a cell using high pressure gas and carrier particles (e.g., gold).
Lipoplexes and Polyplexes To improve the delivery of an nucleic acid encoding an optimized viral polypeptide of the invention into a cell or subject, lipoplexes (e.g., liposomes) and polyplexes can be used to protect the vector DNA from undesirable degradation during the transfection process. Plasmid DNA can be covered with lipids in an organized structure like a micelle or a liposome. When the organized structure is complexed with DNA it is called a lipoplex. There are three types of lipids, anionic (negatively-charged), neutral, or cationic (positively-charged). Lipoplexes that utilize cationic lipids have proven utility for gene transfer. Cationic lipids, due to their positive charge, naturally complex with the negatively-charged DNA. Also as a result of their charge they interact with the cell membrane, endocytosis of the lipoplex occurs, and the DNA is released into the cytoplasm. The cationic lipids also protect against degradation of the DNA by the cell.

Complexes of polymers with DNA are called polyplexes. Most polyplexes consist of cationic polymers and their production is regulated by ionic interactions. One large difference between the methods of action of polyplexes and lipoplexes is that polyplexes cannot release their DNA load into the cytoplasm, so to this end, co-transfection with endosome-lytic agents (to lyse the endosome that is made during endocytosis) such as inactivated adenovirus must occur. However, this is not always the case; polymers such as polyethylenimine have their own method of endosome disruption as does chitosan and trimethylchitosan.

Exemplary cationic lipids and polymers that can be used in combination with an nucleic acid encoding an optimized viral polypeptide of the invention to form lipoplexes, or polyplexes include, but are not limited to, polyethylenimine, lipofectin, lipofectamine, polylysine, chitosan, trimethylchitosan, and alginate.
Hybrid Methods Several hybrid methods of gene transfer combine two or more techniques. Virosomes, for example, combine lipoplexes (e.g., liposomes) with an inactivated virus. This approach has been shown to result in more efficient gene transfer in respiratory epithelial cells than either viral or liposomal methods alone. Other methods involve mixing other viral vectors with cationic lipids or hybridising viruses. Each of these methods can be used to facilitate transfer of an nucleic acid encoding optimized viral polypeptides of the invention into a cell (e.g., a blood cell, such as a lymphocyte) or subject (e.g., a human).
Dendrimers Dendrimers may be also be used to transfer an nucleic acid encoding an optimized viral polypeptide of the invention into a cell (e.g., a blood cell, such as a lymphocyte) or subject (e.g., a human). A dendrimer is a highly branched macromolecule with a spherical shape. The surface of the particle may be functionalized in many ways, and many of the properties of the resulting construct are determined by its surface. In particular it is possible to construct a cationic dendrimer (i.e. one with a positive surface charge). When in the presence of genetic material such as DNA or RNA, charge complimentarity leads to a temporary association of the nucleic acid with the cationic dendrimer. On reaching its destination the dendrimer-nucleic acid complex is then taken into the cell via endocytosis.
In Vivo Administration The invention also features in vivo methods for immunizing a subject (e.g., a human) with a vaccine of the invention. In one embodiment, one or more vaccines of the invention can be directly administered to a subject to elicit a protective or therapeutic immune response (e.g., a cellular or humoral immune response) against a virus (e.g., HIV-1). Alternatively, a vector encoding one or more optimized viral polypeptides of the invention, as described above, can be directly administered to a subject to prevent or treat a viral infection. A vector (e.g., a viral vector) that efficiently transfects or transduces one or more cells in vivo can elicit a broad, durable, and potent immune response in the treated subject. Upon transfer of the nucleic acid component of the expression vector into a host cell (e.g., a blood cell, such as a lymphocyte), the host cell produces and displays or secretes the vaccine of the invention, which then serves to activate components of the immune system such as antigen-presenting cells (APCs), T cells, and B cells, resulting in the establishment of immunity.
Pharmaceutical Compositions The invention features the vaccines, vectors, and optimized viral polypeptides of the invention in combination with one or more pharmaceutically acceptable excipients, diluents, buffers, or other acceptable carriers. The formulation of a vaccine, vector, or optimized viral polypeptides will employ or allow expression of an effective amount of the optimized viral polypeptide immunogen. That is, there will be included an amount of antigen which will cause the treated subject (e.g., a human) to produce a specific and sufficient immunological response so as to impart protection to the subject from subsequent exposure to a virus (e.g., HIV-1) or to treat an existing viral infection. For example, a formulation of a vaccine of the invention can allow for the expression of an amount of antigen which will cause the subject to produce a broad and specific cellular immune response. A subject treated with a vaccine, vector, or optimized viral polypeptide of the invention can also produce anti-viral antibodies (e.g., neutralizing antibodies) which can confer a protective or therapeutic benefit to the subject. A vaccine, vector, or optimized viral polypeptide of the invention can be directly administered to a subject, either alone or in combination with any pharmaceutically acceptable carrier, salt or adjuvant known in the art.

Pharmaceutically acceptable salts may include non-toxic acid addition salts or metal complexes that are commonly used in the pharmaceutical industry. Examples of acid addition salts include organic acids such as acetic, lactic, pamoic, maleic, citric, malic, ascorbic, succinic, benzoic, palmitic, suberic, salicylic, tartaric, methanesulfonic, toluenesulfonic, or trifluoroacetic acids or the like; polymeric acids such as tannic acid, carboxymethyl cellulose, or the like; and inorganic acids such as hydrochloric acid, hydrobromic acid, sulfuric acid phosphoric acid, or the like. Metal complexes include zinc, iron, and the like. One exemplary pharmaceutically acceptable carrier is physiological saline. Other physiologically acceptable carriers and their formulations are known to one skilled in the art and described, for example, in *Remington's Pharmaceutical Sciences*, (18th edition), ed. A. Gennaro, 1990, Mack Publishing Company, Easton, Pa.

Pharmaceutical formulations of a prophylactically or therapeutically effective amount of a vaccine, vector, or optimized viral polypeptide of the invention can be administered orally, parenterally (e.g., intramuscular, intraperitoneal, intravenous, or subcutaneous injection, inhalation, intradermally, optical drops, or implant), nasally, vaginally, rectally, sublingually, or topically, in admixture with a pharmaceutically acceptable carrier adapted for the route of administration. The concentration of a vaccine, vector, or optimized viral polypeptide of the invention in the formulation can vary from about 0.1-100 wt. %.

Formulations for parenteral administration of compositions containing a vaccine, vector, or optimized viral polypeptide of the invention include sterile aqueous or non-aqueous solutions, suspensions, or emulsions. Examples of suitable vehicles include propylene glycol, polyethylene glycol, vegetable oils, gelatin, hydrogenated naphalenes, and injectable organic esters, such as ethyl oleate. Such formulations may also contain adjuvants, such as preserving, wetting, emulsifying, and dispersing agents. Biocompatible, biodegradable lactide polymer, lactide/glycolide copolymer, or polyoxyethylene-polyoxypropylene copolymers may be used to control the release of the compounds. Other potentially useful parenteral delivery systems for compositions containing a vaccine, vector, or optimized viral polypeptide of the invention include ethylene-vinyl acetate copolymer particles, osmotic pumps, implantable infusion systems, and liposomes.

Liquid formulations can be sterilized by, for example, filtration through a bacteria-retaining filter, by incorporating sterilizing agents into the compositions, or by irradiating or heating the compositions. Alternatively, they can also be manufactured in the form of sterile, solid compositions, which can be dissolved in sterile water or some other sterile injectable medium immediately before use.

Compositions containing vaccine, vector, or optimized viral polypeptide of the invention for rectal or vaginal administration are preferably suppositories which may contain, in addition to active substances, excipients such as coca butter or a suppository wax. Compositions for nasal or sublingual administration are also prepared with standard excipients known in the art. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops or spray, or as a gel.

The amount of active ingredient in the compositions of the invention can be varied. One skilled in the art will appreciate that the exact individual dosages may be adjusted somewhat depending upon a variety of factors, including the peptide being administered, the time of administration, the route of administration, the nature of the formulation, the rate of excretion, the nature of the subject's conditions, and the age, weight, health, and gender of the patient. In addition, the severity of the condition treated by the vaccine, vector, or optimized viral polypeptide will also have an impact on the dosage level. Generally, dosage levels of between 0.1 µg/kg to 100 mg/kg of body weight are administered daily as a single dose or divided into multiple doses. Preferably, the general dosage range is between 250 µg/kg to 5.0 mg/kg of body weight per day. Wide variations in the needed dosage are to be expected in view of the differing efficiencies of the various routes of administration. For instance, oral administration generally would be expected to require higher dosage levels than administration by intravenous injection. Variations in these dosage levels can be adjusted using standard empirical routines for optimization, which are well known in the art. In general, the precise prophylactically or therapeutically effective dosage can be determined by the attending clinician in consideration of the above-identified factors.

The amount of a vaccine, vector, or optimized viral polypeptide of the invention present in each dose given to a patient is selected with regard to consideration of the patient's age, weight, sex, general physical condition and the like. The amount of a vaccine, vector, or optimized viral polypeptide required to induce an immune response (e.g., a cellular immune response) or produce an exogenous effect in the patient without significant adverse side effects varies depending upon the pharmaceutical composition employed and the optional presence of an adjuvant. Initial doses can be optionally followed by repeated boosts, where desirable. The method can involve chronically administering the vaccine, vector, or optimized viral polypeptide of the invention. For therapeutic use or prophylactic use, repeated dosages of the immunizing vaccine, vector, or optimized viral polypeptide can be desirable, such as a yearly booster or a booster at other intervals. The dosage administered will, of course, vary depending upon known factors such as the pharmacodynamic characteristics of the particular vaccine, vector, or optimized viral polypeptide, and its mode and route of administration; age, health, and weight of the recipient; nature and extent of symptoms, kind of concurrent treatment, frequency of treatment, and the effect desired. A vaccine, vector, or optimized viral polypeptide of the invention can be administered in chronic treatments for subjects at risk of acute infection due to needle sticks or maternal infection. A dosage frequency for such "acute" infections may range from daily dosages to once or twice a week i.v. or i.m., for a duration of about 6 weeks. The vaccine, vector, or optimized viral polypeptide can also be employed in chronic treatments for infected patients, or patients with advanced infection with a virus (e.g., HIV-1). In infected patients, the frequency of chronic administration can range from daily dosages to once or twice a week i.v. or i.m., and may depend upon the half-life of immunogen present in the vaccine, vector, or optimized viral polypeptide of the invention.

Adjuvants

A vaccine of the invention used to vaccinate a mammal (e.g., a human) in need thereof against a virus can be administered concurrent with or in series with one or more pharmaceutically acceptable adjuvants to increase the immunogenicity of the vaccine. Adjuvants approved for human use include aluminum salts (alum). These adjuvants have been useful for some vaccines including hepatitis B, diphtheria, polio, rabies, and influenza. Other useful adjuvants include Complete Freund's Adjuvant (CFA), Incomplete Freund's Adjuvant (IFA), muramyl dipeptide (MDP), synthetic analogues of MDP, N-acetylmuramyl-L-alanyl-D-isoglutamyl-L-alanine-2-[1,2-dipalmitoyl-s-gly-cero-3-(hydroxyphosphoryloxy)]ethylamide (MTP-PE) and compositions containing a metabolizable oil and an emulsifying agent, wherein the oil and emulsifying agent are present in the form of an oil-in-water emulsion having oil droplets substantially all of which are less than one micron in diameter.

Kits

The invention provides kits that include a pharmaceutical composition containing a vaccine, vector, or optimized viral polypeptide of the invention, and a pharmaceutically-acceptable carrier, in a therapeutically effective amount for preventing or treating a viral infection. The kits include instructions to allow a clinician (e.g., a physician or nurse) to administer the composition contained therein.

Preferably, the kits include multiple packages of the single-dose pharmaceutical composition(s) containing an effective amount of a vaccine, vector, or optimized viral polypeptide of the invention. Optionally, instruments or devices necessary for administering the pharmaceutical composition(s) may be included in the kits. For instance, a kit of this invention may provide one or more pre-filled syringes containing an effective amount of a vaccine, vector, or optimized viral polypeptide of the invention. Furthermore, the kits may also include additional components such as instructions or administration schedules for a patient infected with or at risk of being infected with a virus to use the pharmaceutical composition(s) containing a vaccine, vector, or optimized viral polypeptide of the invention.

It will be apparent to those skilled in the art that various modifications and variations can be made in the compositions, methods, and kits of the present invention without departing from the spirit or scope of the invention. Thus, it is intended that the present invention cover the modifications and variations of this invention provided they come within the scope of the appended claims and their equivalents.

EXAMPLES

The present invention is illustrated by the following examples, which are in no way intended to be limiting of the invention.

Example 1

The mosaic antigen Gag, Pol, Nef, and Env sequences (SEQ ID NOS:1-8) were constructed using the genetic algorithm discussed above. These sequences were then modified to make them practical for vaccine development by eliminating cleavage/fusion activity in Env (SEQ ID NOS: 9-11), eliminating catalytic activity in Pol (SEQ ID NOS: 12-14), eliminating myristylation sites in Nef (SEQ ID NOS:16-18), and constructing fusion constructs including GagNef, GagPol, or GagPolNef (SEQ ID NOS:19-29). The comparator optimal natural clade C genes are also depicted (SEQ ID NOS:30-36).

Example 2

Twenty rhesus monkeys were immunized with $3\times10^{10}$ vp rAd26 vectors expressing Gag, Pol, and Env genes from M consensus (Group 1), 2-valent M mosaic (Group 2), or optimal natural clade C (Group 3) sequences. The M consensus sequences represent synthetic sequences that represent the single best "average" of circulating viruses worldwide. The 2-valent M mosaic sequences are described above. The optimal natural clade C sequences are naturally occurring sequences from actual clade C HIV-1 viruses that are the most "consensus-like" in character. Cellular immune breadth was assessed by evaluating the number of responding peptides from the global potential T cell epitope (PTE) peptide set. The PTE peptides represent >85% of global HIV-1 sequences and are freely available from the NIH.

The results show that the novel 2-valent M mosaic sequences dramatically outperformed these other two leading antigen concepts. As shown in Table 1, the 2-valent M mosaic antigens elicited significantly increased breadth of Gag-specific, Env-specific, Pol-specific, and total T lymphocyte responses as compared with M consensus antigens and optimal natural clade C antigens. (Mean represents the average # epitopes in each group of monkeys; SEM represents the standard error of the mean).

TABLE 1

Mosaic HIV-1 Gag/Pol/Env Antigens Expand Breadth Against Global PTE Peptides in Rhesus Monkeys

| Breadth | Group I: M Consensus | | Group II: 2-valent M Mosaic | | Group III: Natural Clade C | |
|---|---|---|---|---|---|---|
| | Mean | SEM | Mean | SEM | Mean | SEM |
| Gag | 2.0 | 0.4 | 7.7 | 0.9 | 2.2 | 0.5 |
| Env | 2.0 | 0.4 | 4.0 | 0.6 | 1.6 | 0.5 |
| Pol | 2.7 | 0.5 | 8.1 | 1.4 | 2.4 | 0.5 |
| Total | 6.7 | 0.7 | 19.9 | 1.9 | 6.1 | 1.1 |

Example 3

Macaque monkeys were immunized IM with $3\times10^{10}$ vp rAd26 vectors expressing Gag, Pol, and Env genes from M consensus (Group 1; n=7), 2-valent M mosaic (Group 2; n=7), or optimal natural clade C (Group 3; n=6) sequences described in Example 2. Cellular immune breadth was assessed by evaluating the number of responding peptides from the global potential T cell epitope (PTE) peptide set.

As a readout, we assessed the CD4/CD8 IFNγ Elispot responses to pooled PTE peptides (magnitude). The epitopes were comprehensively mapped using 15 mer PTE peptides to assess the number of positives (positives were defined as 55 spot forming cells (SFC) per $10^6$ PBMC and 4× background). Pooled sets of overlapping peptides spanning 5 Gag proteins were also tested to compare responses to a set of complete proteins.

The results show that the 2-valent M mosaic sequences dramatically outperformed the other two leading antigen concepts (Mcon and OptC).

Example 4

We used modeling to validate our observation that T cell responses increase as a result of the mosaic vaccine. We fit Poisson regression models that predicted the number of reactive peptides as a function of vaccine, polypeptide, and T cell type and then did a stepwise elimination of interactions. We observed that, although the mosaic vaccine produced a highly significant enhancement in the number of positive PTE responses, it did so more-or-less uniformly across all polyproteins and T-cell types. Thus, one may predict the number of peptides having a positive effect in an animal by combining contributions that depend, separately, on the type of T-cell, the polypeptide, and the vaccine the animal received.

These models also included random effects to account for animal-to-animal variation. This is a precaution designed to make for more credible p-values, by properly apportioning the predictive power of the model.

We observed the following effects:

a) There are many more CD8 responses than CD4 responses, by a factor of 4.37, $p<2\times10^{-16}$;

b) There are fewer responses in gp160 than in gag or pol, by a factor of 0.54, p=0.000830, and no significant difference between gag and pol (even when normalized by sequence length as poi is twice as long as Gag and so has more opportunity to react); and c) The mosaic vaccine generates significantly more positive responses than Mcon (by a factor of 3.6, $p=6.26\times10^{-11}$) while OptC generates fewer, though the Mcon-OptC difference is not significant.

Example 5

If one considers just the minimal number of responses elicited by a vaccine and detected by PTE peptides, so that all peptide that overlap by ≥8 amino acids regardless of variation are counted just 1 time, the mosaic vaccines still generate a greater number of responses to distinct regions. For CD8, counting each overlapping peptide set just once:
Statistical summary:
Mos2>Mcon~OptC (Mcon shows a trend for more response than OptC)
Wilcoxon p-value for Mos2 compared to Mcon: p-value=0.0009992
Wilcoxon p-value for Mcon compared to Optimal C: p-value=0.2351
Summary of the Groups:

| Vaccine | Min. | 1stQu. | Median | Mean | 3rdQu. | Max. |
| --- | --- | --- | --- | --- | --- | --- |
| Mos2.cd8 | 7 | 7.5 | 8 | 9.4 | 11 | 14 |
| Mcon.cd8 | 0 | 3 | 3 | 3.3 | 4 | 6 |
| OptC.cd8 | 0 | 1 | 1.5 | 2 | 4.25 | 5 |

For CD4, counting each overlapping peptide set just once (there is very little overlap in CD4, so this is almost the same as the first count).
Statistical Summary:
Mos2>>Mcon~OptC (Mcon shows a trend for more response than OptC)
Wilcoxon p-value for Mos2 compared to Mcon: p-value=0.00198
Wilcoxon p-value for Mcon compared to Optimal C: 0.099
Summary of the Groups:

| Vaccine | Min. | 1stQu. | Median | Mean | 3rdQu. | Max. |
| --- | --- | --- | --- | --- | --- | --- |
| Mos2.cd4 | 2 | 2.5 | 3 | 3.4 | 4.5 | 5 |
| Mcon.cd4 | 0 | 1 | 1 | 1.3 | 2 | 2 |
| OptC.cd4 | 0 | 0 | 0.5 | 0.67 | 1 | 2 |

Example 6

Poisson Regression Counting Each Overlapping Peptide Set Just Once

Using overlapping PTE peptides, we determined the following, which are in broad agreement with the results discussed in Example 4 above, where each positive PTE response counted separately:

a) There are many more CD8 responses than CD4 responses, by a factor of about 2.8, $p\approx1\times10^{-7}$;

b) The mosaic vaccine generates significantly more positive responses than Mcon (by a factor of 2.84, $p\approx4.3\times10^{-7}$), while OptC generates fewer, though the Mcon-OptC difference is not significant; and c) There are more responses to Pol than to Gag and more to Gag than gp160, but only the Pol-gp160 difference, a factor of about 2, was significant, p<0.001.

Example 7

The following table is a tally of the total responses to Gag, Pol, and Env responses to the three vaccines in the 7 animals vaccinated with 2 Mosaic (Mos2) or Mcon, and the 6 animals vaccinated with the Optimal Natural C clade (OptC):

| | CD8 | | | CD4 | | |
| --- | --- | --- | --- | --- | --- | --- |
| | Env | Gag | Pol | Env | Gag | Pol |
| 2Mos | 13 | 20 | 33 | 3 | 10 | 11 |
| ConM | 8 | 7 | 8 | 2 | 3 | 4 |
| OptC | 4 | 5 | 5 | 1 | 2 | 1 |

The OptC vaccine yielded an average response across all monkeys that was slightly less than the CD8+ T cell response per protein. The Mcon vaccine exhibited ~1 response per protein. Only with Mos2 do we observe a difference in the proteins, where Env typically has fewer responses than either Gag or Pol.

Each of the proteins in the Mos2 vaccine elicited many responses and contributed to the overall response. The relative length of the consensus proteins after the modifications to inactivate pol and the deletion of the cleavage and fusion domain in Env was: 671 amino acids of Env, 851 of Pol, 498 of Gag (1.35:1.7:1).
Summary
Breadth: The 2 mosaic vaccines elicit T cell responses that are capable of recognizing many more epitope-regions than the M consensus or a single optimal natural strain.

Depth: The diversity of the PTE peptides recognized suggests both forms in the 2 mosaics are eliciting different T cell responses to the variant peptides, increasing the cross-reactive potential.

Example 8

Mosaic HIV-1 vaccines of the invention expand the breadth and depth of cellular immune responses in Rhesus monkeys. We constructed mosaic HIV-1 Gag, Pol, and Env antigens that optimized PTE coverage of HIV-1 M group sequences, which include all major HIV-1 clades and recombinant lineages in the Los Alamos HIV-1 sequence database. A 2-valent mosaic strategy was utilized to balance the competing issues of theoretical coverage and practical utility. 2-valent mosaic HIV-1 Gag, Pol, and Env antigens substantially expanded the breadth and magnitude (depth) of epitope-specific CD8+ and CD4+ T lymphocyte responses in rhesus monkeys, relative to the immune response observed using consensus and natural sequence HIV-1 antigens in rhesus monkeys.

We immunized 27 outbred rhesus monkeys with a single injection of recombinant adenovirus serotype 26 (rAd26) vectors expressing the following antigens: (i) 2-valent mosaic (N=7), (ii) M consensus (N=7), (iii) 2-valent combined clade B and clade C (N=7), or (iv) optimal natural clade C (N=6) HIV-1 Gag, Pol, and Env antigens. A total dose of $3\times10^{10}$ viral particles of rAd26 vectors expressing these antigens was administered once i.m. to each animal. The optimal clade C antigens were the natural strain sequences selected to provide maximal PTE coverage of clade C sequences in the Los Alamos HIV-1 sequence database (discussed in the Materials and Methods below). We assessed the breadth and magnitude (depth) of vaccine-elicited HIV-1-specific T lymphocyte responses by IFN-γ ELISPOT assays at week 4 following immunization utilizing pools and subpools of peptides that included all PTEs found in at least 15% of HIV-1 M group sequences. All individual peptide responses were resolved, and cell-depleted IFN-γ ELISPOT assays were performed to determine if reactive peptides represented CD8+ or CD4+ T lymphocyte epitopes.

The total number of Gag-, Pol-, and Env-specific cellular immune responses to PTE peptides elicited by the mosaic antigens was 3.8-fold higher than the number of responses induced by the consensus or natural sequence antigens (FIG. 19A; $P=1\times10-11$, comparing the mosaic with the consensus antigens, the next highest group, based on a Poisson regression model). There were 4.4-fold more CD8+ than CD4+ T lymphocyte responses ($P<10-11$) and fewer responses to Env than to Gag or Pol ($P<0.0007$). The median number of CD8+ T lymphocyte responses was highest for the mosaic vaccine, followed by the consensus, the combined B+C, and the natural clade C vaccines (medians of 16, 5, 3, and 2 responses per animal in each group, respectively). Although there were fewer CD4+ T lymphocyte responses overall, the same relative pattern emerged with the highest number of CD4+ T lymphocyte responses to the mosaic vaccine, followed by the consensus, the combined B+C, and the natural clade C vaccines (medians of 4, 1, 1, and 0.5 responses per animal in each group, respectively). The numbers of CD8+ and CD4+ T lymphocyte responses elicited by the consensus, the combined B+C, and the natural clade C vaccines were not statistically distinguishable.

PTE peptides include multiple overlapping sequences that reflect naturally occurring HIV-1 sequence polymorphisms, and thus the PTE peptide responses encompass both the recognition of a particular epitope (breadth) and the cross-recognition of variants of that epitope (depth). We performed a conservative analysis of breadth by assessing the number of reactive epitopic regions per monkey in which all reactive PTE peptides that overlapped by 8 or more amino acids were counted as one event. In this conservative analysis, we still observed that the mosaic antigens elicited 3.1-fold increased numbers of Gag, Pol, and Env reactive epitopic regions as compared with the consensus antigens or natural sequence antigens (FIG. 19B; $P=1.6\times10-7$, Poisson regression). Epitopic regions exhibited some clustering across animals, as evidenced by regions of high epitope density (FIGS. 20A-20C and FIGS. 21A-21C). Complete alignments of all positive peptides organized by response regions are shown in FIG. 22.

These data show that the mosaic antigens substantially increased the breadth of cellular immune responses as compared with M consensus and natural clade C antigens. The 2-valent mosaic antigens also proved superior to the 2-valent combination of clade B and clade C antigens (FIGS. 19A and 19B), indicating that the enhanced breadth was due to the mosaic sequence design and did not simply reflect the use of two distinct antigenic sequences per protein. To determine if the increased breadth induced by mosaic antigens compromised the potency of the responses, we assessed the magnitude of all individual CD8+ and CD4+ T lymphocyte responses. The magnitude of these responses proved comparable among all groups (FIG. 23; $P=0.58$ and $P=0.99$, respectively, two-sided Kolmogorov-Smirnov tests). Thus, mosaic antigens expanded cellular immune breadth without compromising the magnitude of individual epitope-specific responses, indicating that antigenic competition and immunodominance constraints did not limit the immunogenicity of the mosaic antigens in this study.

We next characterized the depth of the cellular immune responses elicited by the various vaccine regimens. We defined depth as the number of simultaneously elicited variant PTE peptides for a particular epitopic region. Inducing responses to multiple common epitope variants may increase immunologic coverage of infecting virus sequences, block common escape routes in vivo, or force the virus down tertiary escape routes that incur high fitness costs. The consensus and natural sequence antigens elicited responses that were characterized by a high degree of sequence identity between the vaccine sequences and the reactive PTE peptides, as exemplified by the responses in monkey 366 that received the natural clade C antigens (FIG. 24A; see also FIG. 22). In contrast, the mosaic antigens elicited responses that were characterized by multiple reactive PTE peptides in particular epitopic regions. These peptides represented common variants and often reflected the polymorphisms contained in the mosaic vaccine sequences, as exemplified by the responses in monkey 361 (FIG. 24B; see also FIG. 22). A summary of all epitope-specific responses in these animals demonstrates that the mosaic antigens increased the frequency of cellular immune responses to peptides with two or more targeted variants as compared with the consensus or natural sequence antigens (FIG. 24C; $P=0.001$, Wilcoxon rank-sum test comparing the mosaic with the consensus antigens, the next highest group).

To complement the analysis utilizing PTE peptides, we also assessed the breadth of cellular immune responses in the vaccinated monkeys with traditional overlapping peptides covering 5 different Gag sequences: clade C DU422, clade C ZM651, consensus C, consensus A, and consensus B. Cellular immune breadth was determined by assessing reactivity to subpools of 10 overlapping peptides spanning each Gag sequence. The mosaic antigens elicited greater breadth of T lymphocyte responses as compared with the consensus or natural sequence antigens against all Gag sequences that were tested (FIG. 25; $P=1\times10^{-7}$, binomial regression). Thus, the mosaic antigens augmented cellular immune breadth not only to PTE peptides but also to actual Gag peptides from clades A, B, and C. The mosaic antigens even proved superior to the optimal natural clade C antigens for inducing responses against clade C Gag peptides. Moreover, the mosaic antigens elicited comparable responses to Gag peptides from multiple clades, whereas the natural clade C antigens exhibited diminished responses to clade A and clade B Gag peptides (FIG. 25).

To assess the durability of these observations, we boosted the monkeys that received the mosaic, consensus, and optimal natural clade C antigens at week 40 with a total dose of $3\times10^{10}$ viral particles of the heterologous vector rAd5HVR48 expressing HIV-1 Gag, Pol, and Env antigens that matched the sequences utilized in the initial immunization. Cellular immune breadth was determined by assessing reactivity to subpools of 10 PTE peptides at week 4 (post-prime) and at week 44 (post-boost). The majority of CD8+ and CD4+ T lymphocyte responses that were observed after the priming immunization expanded following the boost (FIG. 26A, red and blue lines), and a number of new responses were also detected (FIG. 26A, red and blue dots). At week 44, the magnitude of individual cellular immune responses proved comparable among groups (FIG. 26A). The number of subpool responses elicited by the mosaic antigens (median 27 responses per animal), however, remained substantially higher than the number of subpool responses induced by the consensus antigens (median 11 responses per animal) or the optimal natural clade C antigens (median 10 responses per animal) following the boost immunization (FIG. 26B). Both before and after the boost, there were more responses per animal elicited by the mosaic vaccine than by the consensus or natural clade C vaccines (P<0.001, Wilcoxon rank-sum tests for all pairwise comparisons).

We also measured Env-specific humoral immune responses following the boost immunization by ELISAs (FIG. 26C) and luciferase-based pseudovirus neutralization assays (FIG. 26D). All groups exhibited comparable ELISA titers to clade C gp140 and comparable neutralizing antibody (NAb) responses to the tier 1 clade C virus MW965.26. The mosaic antigens elicited slightly higher Nab responses to the tier 1 clade B virus SF162.LS as compared with the consensus or natural clade C antigens (P=0.02, Wilcoxon rank-sum test), although we did not detect any NAb responses to tier 2 viruses in any group.

Our data demonstrate that mosaic HIV-1 Gag, Pol, and Env antigens augmented both the breadth and depth of epitope-specific cellular immune responses as compared with consensus or natural sequence antigens in rhesus monkeys, in good agreement with theoretical predictions (FIG. 27). The striking results with mosaic antigens in this study may have reflected the fact that rAd26 vectors are particularly efficient at eliciting CD8+ T lymphocyte responses as well as the fact that mosaic antigens appear particularly effective at augmenting CD8+ T lymphocyte breadth (FIGS. 19A and 19B). We also observed enhanced CD4+ T lymphocyte breadth with mosaic antigens, although there were substantially lower numbers of these responses.

The breadth of Gag-specific cellular immune responses has been shown to be critical for SIV control in rhesus monkeys and for HIV-1 control in humans. Moreover, in the phase 2b STEP study, the rAd5-based HIV-1 vaccine candidate expressing natural clade B Gag, Pol, and Nef antigens elicited only a limited breadth of HIV-1-specific cellular immune responses, and no vaccine benefit was observed. Vaccinees in the STEP study developed a median of only 2-3 epitope-specific T lymphocyte responses, including a median of only 1 epitope-specific response to Gag, and this very narrow breadth of cellular immune responses likely provided insufficient immunologic coverage of the diversity of infecting viruses. Viral escape from CD8+ T lymphocytes has also been reported to occur rapidly during acute HIV-1 infection, and thus vaccine-elicited cellular immune responses against common epitope variants may also prove critical. Taken together, these studies emphasize the need to develop HIV-1 vaccine strategies that augment cellular immune breadth and depth.

Since we evaluated mosaic HIV-1 antigens in the present study, we were unable to assess the protective efficacy of these vaccine regimens against SIV challenges. However, we have previously reported that the breadth of SIV-specific cellular immune responses elicited by rAd vectors correlated with protective efficacy against SIV challenges in rhesus monkeys (Liu et al., Nature 457:87, 2009). We have also shown that cellular immune responses against variant epitopes can block SIV mutational evolution in rhesus monkeys in vivo (Barouch et al., Nat. Immunol. 6:247, 2005), suggesting the biologic relevance of expanding cellular immune depth. Modeling the protective efficacy of mosaic vaccines against SIV challenges in nonhuman primates has intrinsic limitations, since the observed diversity of SIV and HIV-1 M group sequences differs substantially and is influenced by different underlying biology. For example, CD8+ T lymphocyte selection pressure in natural hosts such as sooty mangabees appears substantially less than that in humans. Thus, the further evaluation of mosaic antigens as candidate HIV-1 vaccines can be benefited by clinical trials.

In summary, we demonstrate that 2-valent mosaic HIV-1 Gag, Pol, and Env antigens substantially expanded cellular immune breadth and depth in rhesus monkeys. These findings have major implications for HIV-1 vaccine development, since global virus diversity and viral escape from cellular immune responses represent critical hurdles in the development of a T cell-based HIV-1 vaccine. A 2-valent cocktail of mosaic antigens is also practical and potentially feasible for clinical development. Increasing the valency of mosaic antigens may further improve coverage. Finally, the mosaic antigen strategy is generalizable and could be utilized for other genetically diverse pathogens in addition to HIV-1.

Materials and Methods

Antigen design and vector production. 2-valent mosaic Gag, Pol, and Env antigens were constructed to provide optimal coverage of HIV-1 M group sequences in the Los Alamos HIV-1 sequence database essentially as described (1, 2). Optimal natural clade C antigens were selected to be the sequences that provide optimal PTE coverage of clade C sequences in the Los Alamos HIV-1 sequence database (C.IN.-.70177 Gag, C.ZA.04.04ZASK208B1 Pol, C.SN.90.90SE_364 Env). Clade B antigens were selected to be near-consensus or consensus sequences (B.CAM-1 Gag, B.IIIB Pol, B.Con Env) and were used to complement the optimal clade C antigens for the 2-valent clade B+C vaccine approach. Pol antigens contained RT and IN without PR and included point mutations to eliminate catalytic activity as described (Priddy et al., Clinical infectious diseases 46:1769, 2008). Env gp140 antigens contained point mutations to eliminate cleavage and fusion activity. Vaccine sequences are depicted in FIG. 27. Recombinant, replication-incompetent adenovirus serotype 26 (rAd26) and hexon-chimeric rAd5HVR48 vectors expressing these antigens were grown in PER.55K cells and purified by double CsCl gradient sedimentation essentially as described (Abbink et al., J. Virol. 81:4654, 2007, and Roberts et al., Nature 441:239, 2006).

Animals and immunizations. 27 outbred rhesus monkeys that did not express the MHC class I allele Mamu-A*01 were housed at New England Primate Research Center (NEPRC), Southborough, Mass. Immunizations involved $3 \times 10^{10}$ viral particles rAd26 or rAd5HVR48 vectors expressing mosaic, M consensus, clade B+clade C, or optimal natural clade C HIV-1 Gag, Pol, and Env antigens delivered as 1 ml injections i.m. in both quadriceps muscles at weeks 0 and 40. All animal studies were approved by our Institutional Animal Care and Use Committees (IACUC).

IFN-γ ELISPOT assays. HIV-1-specific cellular immune responses in vaccinated monkeys were assessed by interferon-γ (IFN-γ) ELISPOT assays essentially as described (Roberts et al., Nature 441:239, 2006, and Liu et al., Nature 457:87, 2009). HIV-1 Gag, Pol, and Env potential T cell epitope (PTE) peptides that included all PTEs found in at least 15% of HIV-1 M group sequences as well as HIV-1 Gag peptides from clade C DU422, clade C ZM651, consensus C, consensus A, and consensus B strains were obtained from the NIH AIDS Research and Reference Reagent Program. 96-well multiscreen plates (Millipore) were coated overnight with 100 μl/well of 10 μg/ml anti-human IFN-γ (BD Biosciences) in endotoxin-free Dulbecco's PBS (D-PBS). The plates were then washed three times with D-PBS containing 0.25% Tween-20 (D-PBS/Tween), blocked for 2 h with D-PBS containing 5% FBS at 37° C., washed three times with D-PBS/Tween, rinsed with RPMI 1640 containing 10% FBS to remove the Tween-20, and incubated with 2 μg/ml each peptide and $2 \times 10^5$ PBMC in triplicate in 100 μl reaction volumes. Following an 18 h incubation at 37° C., the plates were washed nine times with PBS/Tween and once with distilled water. The plates were then incubated with 2 μg/ml biotinylated anti-human IFN-γ (BD Biosciences) for 2 h at room temperature, washed six times with PBS/Tween, and incubated for 2 h with a 1:500 dilution of streptavidin-alkaline phosphatase (Southern Biotechnology Associates). Following five washes with PBS/Tween and one with PBS, the plates were developed with nitro blue tetrazolium/5-bromo-4-chloro-3-indolyl-phosphate chromogen (Pierce), stopped by washing with tap water, air dried, and read using an ELISPOT reader (Cellular Technology Ltd). Spot-forming cells (SFC) per $10^6$ PBMC were calculated. Media backgrounds were typically <15 SFC per $10^6$ PBMC. Positive responses were defined as >55 SFC per $10^6$ PBMC and >4-fold background.

Epitope mapping. Comprehensive CD8+ and CD4+ T lymphocyte epitope mapping was performed utilizing Gag, Pol, and Env PTE peptides that were obtained from the NIH AIDS Research and Reference Reagent Program. IFN-γ ELISPOT assays were conducted at week 4 following immunization initially with complete peptide pools as well as with subpools containing 10 PTE peptides. All peptide subpools with positive responses were deconvoluted, and epitopes were confirmed with individual 15 amino acid PTE peptides. Cell-depleted TFN-γ ELISPOT assays were then performed to determine if reactive peptides represented CD8+ or CD4+ T lymphocyte epitopes. Partial epitope mapping utilizing PTE subpools was also performed 4 weeks following the boost immunization at week 44. All borderline responses were retested and only considered positive if confirmed. Partial epitope mapping utilizing subpools containing 10 overlapping Gag peptides was also performed to assess breadth to HIV-1 Gag from various clades.

Humoral immune assays. Env-specific humoral immune responses were evaluated by direct ELISAs utilizing HIV-1 clade C Env gp140 and luciferase-based pseudovirus neutralization assays essentially as described (Montefiori, *Evaluating neutralizing antibodies against HIV, SIV and SHIV in luciferase reporter gene assays. Current Protocols in Immunology*, Coligan, Kruisbeek, Margulies, Shevach, Strober, and Coico, Ed. (John Wiley & Sons, 2004, pp. 1-15).

Statistical analyses. All statistical analyses were done using the package R (Team, *Foundation for Statistical Computing*, Vienna, Austria, 2009). To analyze the breadth of cellular immune responses to mapped PTE peptides (FIG. 19A), we fit Poisson regression models that predicted the number of reactive peptides as a function of vaccine group, antigen (Gag, Pol, Env), and lymphocyte subpopulation (CD4, CD8). Our models included random effects to accommodate animal-to-animal variation and were fit with the lme4 library (Pinheiro, Springer, New York (2000)) of the package R. The data fit the models well (dispersion parameter 1.0), and there were no significant interactions among the three explanatory factors. For example, the 3.8-fold enhancement in the number of PTE peptides recognized by monkeys that received the mosaic antigens as compared to those that received the consensus or natural sequence antigens (FIG. 19A) applied equally to PTEs from Gag, Pol, and Env and held for responses by CD8+ as well as CD4+ T lymphocytes. The analysis of the number of reactive epitopic regions (FIG. 19B) also included Poisson regression models with random effects and again fit well (dispersion parameter 0.87) without any significant interactions. Comparisons of the magnitude of CD8+ and CD4+ T lymphocyte responses (FIG. 23) were performed utilizing 2-sided Kolmogorov-Smirnov tests. Non-parametric tests to compare the breadth and depth of responses per monkey between different vaccines were also performed (FIGS. 19A and 24C). We initially employed Kruskal-Wallis tests to determine if there was a difference among the 4 vaccine groups. In each case this was highly significant, and we then assessed all pairwise comparisons between the 4 vaccine groups using Wilcoxon rank-sum tests. In each of these comparisons, the mosaic vaccine elicited significantly more responses per monkey than the other 3 vaccines. To analyze the breadth of responses to HIV-1 Gag from various clades (FIG. 25), we fit the data to binomial regression models. These models used the vaccine group as an explanatory variable and included random effects to account for animal-to-animal and strain-to-strain variation. The data were slightly underdispersed, but the animals that received the mosaic vaccine still elicited a significantly larger number of responses. PTE coverage assessment was performed using tools available at the Los Alamos HIV-1 sequence database.

| SEQUENCE APPENDIX |
|---|
| I. 2-VALENT M MOSAIC ENV GP160, GAG, POL, NEF SEQUENCES |
| MOSAIC ENV1 GP160 (AA SEQUENCE) |
| SEQ ID NO: 1 |
| MRVTGIRKNYQHLWRWGTMLLGILMICSAAGKLWVTVYYGVPVWKEATT |
| TLFCASDAKAYDTEVHNVWATHACVPTDPNPQEVVLENVTENFNMWKNN |
| MVEQMHEDIISLWDQSLKPCVKLTPLCVTLNCTDDVRNVTNNATNTNSS |
| WGEPMEKGEIKNCSFNITTSIRNKVQKQYALFYKLDVVPIDNDSNNTNY |
| RLISCNTSVITQACPKVSFEPIPIHYCAPAGFAILKCNDKKFNGTGPCT |
| NVSTVQCTHGIRPVVSTQLLLNGSLAEEEVVIRSENFTNNAKTIMVQLN |
| VSVEINCTRPNNNTRKSIHIGPGRAFYTAGDIIGDIRQAHCNISRANWN |
| NTLRQIVEKLGKQFGNNKTIVFNHSSGGDPEIVMHSFNCGGEFFYCNST |
| KLFNSTWTWNNSTWNNTKRSNDTEEHITLPCRIKQIINMWQEVGKAMYA |
| PPIRGQIRCSSNITGLLLTRDGGNDTSGTEIFRPGGGDMRDNWRSELYK |
| YKVVKIEPLGVAPTKAKRRVVQREKRAVGIGAVFLGFLGAAGSTMGAAS |
| MTLTVQARLLLSGIVQQQNNLLRAIEAQQHLLQLTVWGIKQLQARVLAV |
| ERYLKDQQLLGIWGCSGKLICTTTVPWNASWSNKSLDKIWNNMTWMEWE |
| REINNYTSLIYTLIEESQNQQEKNEQELLELDKWASLWNWFDISNWLWY |
| IKIFIMIVGGLVGLRIVFAVLSIVNRVRQGYSPLSFQTRLPAPRGPDRP |
| EGIEEEGGERDRDRSVRLVDGFLVLIWDDLQSLCLFSYHRLRDLLLIVE |
| LLGRRGWEALKYWWNLLQYWSQELKNSAISLLNATAVAVAEGTDRVIEA |
| LQRACRAILHIPRRIRQGLERLLL |

SEQUENCE APPENDIX

MOSAIC ENV2 GP160 (AA SEQUENCE)
SEQ ID NO: 2
MRVRGIQRNWPQWWIWGILGFWMIIICRVMGNLWVTVYYGVPVWKEAKT
TLFCASDAKAYEKEVHNVWATHACVPTDPNPQEMVLENVTENFNMWKND
MVDQMHEDIIRLWDQSLKPCVKLTPLCVTLECRNVRNVSSNGTYNIIHN
ETYKEMKNCSFNATTVVEDRKQKVHALFYRLDIVPLDENNSSEKSSENS
SEYYRLINCNTSAITQACPKVSFDPIPTHYCAPAGYAILKCNNKTFNGT
GPCNNVSTVQCTHGIKPVVSTQLLLNGSLAEEEIIIRSENLTNNAKTII
VHLNETVNITCTRPNNNTRKSIRIGPGQTFYATGDIIGDIRQAHCNLSR
DGWNKTLQGVKKKLAEHFPNKTINFTSSSGGDLEITTHSFNCRGEFFYC
NTSGLFNGTYMPNGTNSNSSSNITLPCRIKQIINMWQEVGRAMYAPPIA
GNITCRSNITGLLLTRDGGSNNGVPNDTETFRPGGGDMRNNWRSELYKY
KVVEVKPLGVAPTEAKRRVVEREKRAVGIGAVFLGILGAAGSTMGAASI
TLTVQARQLLSGIVQQQSNLLRAIEAQQHMLQLTVWGIKQLQTRVLAIE
RYLQDQQLLGLWGCSGKLICTTAVPWNTSWSNKSQTDIWDNMTWMQWDK
EIGNYTGEIYRLLEESQNQQEKNEKDLLALDSWKNLWNWFDITNWLWYI
KIFIMIVGGLIGLRIILGVLSIVRRVRQGYSPLSFQTLTPNPRGLDRLG
RIEEEGGEQDRDRSIRLVNGFLALAWDDLRSLCLFSYHQLRDFILIVAR
AVELLGRSSLRGLQRGWEALKYLGNLVQYWGLELKKGAISLLDTIAIAV
AEGTDRIIELIQSICRAIRNIPRRIRQGFEASLL

MOSAIC GAG1 (AA SEQUENCE)
SEQ ID NO: 3
MGARASVLSGGELDRWEKIRLRPGGKKKYRLKHIVWASRELERFAVNPG
LLETSEGCRQILGQLQPSLQTGSEELRSLYNTVATLYCVHQRIEIKDTK
EALEKIEEEQNKSKKKAQQAAADTGNSSQVSQNYPIVQNIQGQMVHQAI
SPRTLNAWVKVVEEKAFSPEVIPMFSALSEGATPQDLNTMLNTVGGHQA
AMQMLKETINEEAAEWDRVHPVHAGPIAPGQMREPRGSDIAGTTSTLQE
QIGWMTNNPPIPVGEIYKRWIILGLNKIVRMYSPVSILDIRQGPKEPFR
DYVDREYKTLRAEQASQDVKNWMTETLLVQNANPDCKTILKALGPAATL
EEMMTACQGVGGPGHKARVLAEAMSQVTNSATIMMQRGNERNQRKTVKC
FNCGKEGHIAKNCRAPRKKGCWKCGKEGHQMKDCTERQANFLGKIWPSN
KGRPGNFLQNRPEPTAPPEESERFGEETTTPSQKQEPIDKEMYPLASLK
SLEGNDPSSQ

MOSAIC GAG2 (AA SEQUENCE)
SEQ ID NO: 4
MGARASILRGGKLDKWEKIRLRPGGKKHYMLKHLVWASRELERFALNPG
LLETSEGCKQIIKQLQPALQTGTEELRSLENTVATLYCVHAEIEVRDTK
EALDKIEEEQNKSQQKTQQAKEADGKVSQNYPIVQNLQGQMVHQPISPR
TLNAWVKVIEEKAFSPEVIPMFTALSEGATPQDLNTMLNTVGGHQAAMQ
MLKDTINEEAAEWDRLHPVHAGPVAPGQMREPRGSDIAGTTSNLQEQIA
WMTSNPPIPVGDIYKRWIILGLNKIVRMYSPTSILDIKQGPKEPERDYV
DRFEKTLRAEQATQDVKNWMTDTLLVQNANPDCKTILRALGPGATLEEM

MTACQGVGGPSHKARVLAEAMSQTNSTILMQRSNFKGSKRIVKCFNCGK
EGHIARNCRAPRKKGCWKCGKEGHQMKDCTERQANFLGKIWPSHKGRPG
NFLQSRPEPTAPPAESFRFEETTPAPKQEPKDREPLTSLRSLFGSDPLS
Q

MOSAIC POL1 (AA SEQUENCE)
SEQ ID NO: 5
FFRENLAFQQGEAREFPSEQTRANSPTSRELQVRGDNPHSEAGAERQGT
LNFPQITLWQRPLVSIKVGGQIREALLDTGADDTVLEDINLPGKWKPKM
IGGIGGFIKVRQYDQILIEICGKKAIGTVLVGPTPVNIIGRNMLTQLGC
TLNEFISPIETVPVKLKPGMDGPRVKQWPLTEEKIKALTAICEEMEKEG
KITKIGPENPYNTPVFAIKKKDSTKWRKLVDFRELNKRTQDFWEVQLGI
PHFAGLKKKKSVTVLDVGDAYFSVPLDEGFRKYTAFTIPSTNNETPGIR
YQYNVLPQGWKGSPAIFQCSMTRILEPFRAKNPEIVIYQYMDDLYVGSD
LEIGQHRAKIEELREHLLKWGFTTPDKKHQKEPPFLWMGYELHPDKWTV
QPIQLPEKDSWTVNDIQKLVGKLNWASQTYPGIKVRQLCKLLRGAKALT
DIVPLTEEAELELAENREILKEPVHGVYYDPSKDLIAEIQKQGHDQWTY
QIYQEPFKNLKTGKYAKMRTAHTNDVKQLTEAVQKIAMESIVIWGKTPK
FRLPIQKETWETWWTDYWQATWIPEWEEVNTPPLVKLWYQLEKDPIAGV
ETFYVDGAANRETKLGKAGYVTDRGRQKIVSLTETTNQKTELQAIYLAL
QDSGSEVNIVTDSQYALGIIQAQPDKSESELVNQIIEQLIKKERVYLSW
VPAHKGIGGNEQVDKLVSSGIRKVLELDGIDKAQEEHEKYHSNWRAMAS
DFNLPPVVAKEIVASCDQCQLKGEAMHGQVDCSPGIWQLDCTHLEGKII
LVAVHVASGYIEAEVIPAETGQETAYFILKLAGRWPVKVIHTDNGSNFT
SAAVKAACWWAGIQQEFGIPYNPQSQGVVESMNKELKKIIGQVRDQAEH
LKTAVQMAVFIHNFKRKGGIGGYSAGERIIDIIATDIQTKELQKQIIKI
QNFRVYYRDSRDPIWKGPAKLLWKGEGAVVIQDNSDIKVVPRRKVKIIK
DYGKQMAGADCVAGRQDED

MOSAIC POL2 (AA SEQUENCE)
SEQ ID NO: 6
FFRENLAFPQGKAREFSSEQTRANSPTRRELQVWGRDNNSLSEAGADRQ
GTVSFSFPQITLWQRPLVTIKIGGQLKEALLDTGADDTVLEEMNLPGRW
KPKMIGGIGGFIKVRQYDQIPIEICGHKAIGTVLVGPTPVNIIGRNLLT
QIGCTLNFPISPIETVPVKLKPGMDGPKVKQWPLTEEKIKALVEICTEM
EKEGKISKIGPENPYNTPIFAIKKKDSTKWRKLVDFRELNKRTQDFWEV
QLGIPHPAGLKKKKSVTVLDVGDAYFSVPLDEDFRKYTAFTIPSINNET
PGIRYQYNVLPQGWKGSPAIFQSSMTKILEPFRKQNPDIVIYQYMDDLY
VGSDLEIGQHRTKIEELRQHLLRWGFTTPDKKHQKEPPFLWMGYELHPD
KWTVQPIVLPEKDSWTVNDIQKLVGKLNWASQIYAGIKVKQLCKLLRGT
KALTEVVPLTEEAELELAENREILKEPVHGVYYDPSKDLIAEIQKQGGG
QWTYQIYQEPFKNLKTGKYARMRGAHTNDVKQLTEAVQKIATESIVIWG

SEQUENCE APPENDIX

KTPKFKLPIQKETWEAWWTEYWQATWIPEWEFVNTPPLVKLWYQLEKEP
IVGAETFYVDGAANRETKLGKAGYVTDRGRQKVVSLTDTTNQKTELQAI
HLALQDSGLEVNIVTDSQYALGIIQAQPDKSESELVSQIIEQLIKKEKV
YLAWVPAHKGIGGNEQVDKLVSRGIRKVLELDGIDKAQEEHEKYHSNWR
AMASEFNLPPIVAKEIVASCDKCQLKGEAIHGQVDCSPGIWQLDCTHLE
GKVILVAVHVASGYIEAEVIPAETGQETAYFLLKLAGRWPVKTIHTDNG
SNFTSATVKAACWWAGIKQEFGIPYNPQSQGVVESINKELKKIIGQVRD
QAEHLKTAVQMAVFIHNFKRKGGIGEYSAGERIVDIIASDIQTKELQKQ
ITKIQNFRVYYRDSRDPLWKGPAKLLWKGEGAVVIQDNSDIKVVPRRKA
KIIRDYGKQMAGDDCVASRQDED

MOSAIC NEF1 (AA SEQUENCE)

SEQ ID NO: 7

MGGKWSKSSVVGWPAIRERMRRAEPAADGVGAVSRDLEKHGAITSSNTA
ANNADCAWLEAQEEEEVGFPVRPQVPLRPMTYKGALDLSHFLKEKGGLE
GLIYSQKRQDILDLWVYHTQGYFPDWQNYTPGPGIRYPLTFGWCFKLVP
VEPEKIEEANEGENNSLLHPMSQHGMDDPEKEVLMWKFDSRLAFHHMAR
ELHPEYYKDC

MOSAIC NEF2 (AA SEQUENCE)

SEQ ID NO: 8

MGGKWSKSSIVGWPAVRERIRRAEPAAEGVGAASQDLDKYGALTSSNTA
ATNADCAWLEAQEDEEVGFPVKPQVPLRPMTYKAAFDLSFFLKEKGGLD
GLIYSKKRQEILDLWVYNTQGFFPDWQNYTPGPGVRYPLTFGWCFKLVP
VDPREVEEANKGENNCLLHPMNLHGMDDPEREVLVWRFDSRLAFHHMAR
EKHPEYYKNC

II. 2-VALENT M MOSAIC ENV GP140 SEQUENCES (CLEAVAGE/FUSION-DEFECTIVE)

MOSAIC ENV1 GP140 (AA SEQUENCE)

SEQ ID NO: 9

MRVTGIRKNYQHLWRWGTMLLGILMICSAAGKLWVTVYYGVPVWKEATTT
LFCASDAKAYDTEVHNVWATHACVPTDPNPQEVVLENVTENFNMWKNNMV
EQMHEDIISLWDQSLKPCVKLTPLCVTLNCTDDVRNVTNNATNTNSSWGE
PMEKGEIKNCSFNITTSIRNKVQKQYALFYKLDVVPIDNDSNNTNYRLIS
CNTSVITQACPKVSFEPIPIHYCAPAGFAILKCNDKKENGTGPCTNVSTV
QCTHGIRPVVSTQLLLNGSLAEEEVVIRSENFTNNAKTIMVQLNVSVEIN
CTRPNNNTRKSIHIGPGRAFYTAGDIIGDIRQAHCNISRANWNNTLRQIV
EKLGKQFGNNKTIVFNHSSGGDPEIVMHSFNCGGEFFYCNSTKLFNSTWT
WNNSTWNNTKRSNDTEEHITLPCRIKQIINMWQEVGKAMYAPPIRGQIRC
SSNITGLLLTRDGGNDTSGTEIFRPGGGDMRDNWRSELYKYKVVKIEPLG
VAPTKAKRRVVQSEKSAVGIGAVFLGFLGAAGSTMGAASMTLTVQARLLL
SGIVQQQNNLLRAIEAQQHLLQLTVWGIKQLQARVLAVERYLKDQQLLGI
WGCSGKLICTTTVPWNASWSNKSLDKIWNNMTWMEWEREINNYTSLIYTL
IEESQNQQEKNEQELLELDKWASLWNWFDISNWLW

MOSAIC ENV2 GP140 (AA SEQUENCE)

SEQ ID NO: 10

MRVRGIQRNWPQWWIWGILGFWMIIICRVMGNLWVTVYYGVPVWKEAKTT
LFCASDAKAYEKEVHNVWATHACVPTDPNPQEMVLENVTENFNMWKNDMV
DQMHEDIIRLWDQSLKPCVKLTPLCVTLECRNVRNVSSNGTYNIIHNETY
KEMKNCSFNATTVVEDRKQKVHALFYRLDIVPLDENNSSEKSSENSSEYY
RLINCNTSAITQACPKVSFDPIPIHYCAPAGYAILKCNNKTENGTGPCNN
VSTVQCTHGIKPVVSTQLLLNGSLAEEEIIIRSENLTNNAKTIIVHLNET
VNITCTRPNNNTRKSIRIGPGQTFYATGDIIGDIRQAHCNLSRDGWNKTL
QGVKKKLAEHFPNKTINFTSSSGGDLEITTHSENCRGEFFYCNTSGLENG
TYMPNGTNSNSSSNITLPCRIKQIINMWQEVGRAMYAPPIAGNITCRSNI
TGLLLTRDGGSNNGVPNDTETFRPGGGDMRNNWRSELYKYKVVEVKPLGV
APTEAKRRVVESEKSAVGIGAVFLGILGAAGSTMGAASITLTVQARQLLS
GIVQQQSNLLRAIEAQQHMLQLTVWGIKQLQTRVLATERYLQDQQLLGLW
GCSGKLIGTTAVPWNTSWSNKSQTDIWDNMTWMQWDKEIGNYTGEIYRLL
EESQNQQEKNEKDLLALDSWKNLWNWFDITNWLW

MOS3 ENV GP140 (AA SEQUENCE)
678 AA

SEQ ID NO: 11

MRVKGIRKNYQHLWKWGTMLLGLMLMICSAAEQLWVTVYYGVPVWRDAETT
LFCASDAKAYERENHNIWATHACVPTDPNPQEIVLENVTEEFNMWKNDMV
EQMHTDIISLWDESLKPCVKLAPLCVTLNCTNANLNCTNDNCNRTVDKMR
EEIKNCSFNMTTELRDKKQKVYALFYKLDIVPIEKNSSEYRLINCNTSTI
TQACPKVTFEPIPIHYCTPAGFAILKCKDKKENGTGPCKNVSTVQCTHGI
KPVISTQLLLNGSLAEGEHIRSENITNNAKTIIVQLNESVVINCTRPGNN
TRKSVRIGPGQAFYATGEIIGDIRQAYCNISRAKWNNTLKQIVTKLKEQF
KNKTIVFNQSSGGDPEITTHSENCGGEFFYCNTTQLENSTWNSNSTWNDT
TGSVTEGNDTITLPCRIKQIVNMWQRVGQAMYAPPIEGNITCKSNITGLL
LVRDGGNINRTNETFRPGGGNMKDNWRSELYKYKVVEIKPLGVAPTRAKR
RVVESEKSAVGLGAVFLGELGTAGSTMGAASLTLTVQARQVLSGIVQQQS
NLLKAIEAQQHLLKLTVWGIKQLQARILAVERYLRDQQLLGIWGCSGKLI
CTTNVPWNSSWSNKSQEEIWNNMTWMQWDREISNYTDTIYRLLEDSQNQQ
EKNEQDLLALDKWASLWNVVFSITNVVLW

III. 2-VALENT M MOSAIC POL SEQUENCES (EXTENSIVELY INACTIVATED, PR-DELETED, 9 A INACTIVATION MUTATIONS TO ELIMINATE CATALYTIC ACTIVITY)

MOSAIC POL1 (AA SEQUENCE)

SEQ ID NO: 12

MAPISPIETVPVKLKPGMDGPRVKQWPLTEEKIKALTAICEEMEKEGKIT
KIGPENPYNTPVFAIKKKDSTKWRKLVDFRELNKRTQDFWEVQLGIPHPA
GLKKKKSVTVLAVGDAYFSVPLDEGFRKYTAFTIPSTNNETPGIRYQYNV
LPQGWKGSPAIFQCSMTRILEPFRAKNPEIVIYQYMAALYVGSDLEIGQH
RAKIEELREHLLKWGETTPDKKHQKEPPFLWMGYELHPDKWTVQPIQLPE

SEQUENCE APPENDIX

KDSWTVNDIQKLVGKLNWASQIYPGIKVRQLCKLLRGAKALTDIVPLTEE
AELELAENREILKEPVHCVYYDPSKDLIAEIQKQGHDQWTYQIYQEPFKN
LKTGKYAKMRTAHTNDVKQLTEAVQKIAMESIVIWGKTPKERLPIQKETW
ETWWTDYWQATWIPEWEEVNTPPLVKLWYQLEKDPIAGVETFYVAGAANR
ETKLGKAGYVTDRGRQKIVSLTETTNQKTALQAIYLALQDSGSEVNIVTA
SQYALGIIQAPDKSESELVNQIIEELIKKERVYLSWVPAHKGIGGNEQV
DKLVSSGIRKVLELDGIDKAQEEHEKYHSNWRAMASDFNLPPVVAKEIVA
SCDQCQLKGEAMHGQVDCSPGIWQLACTHLEGKIILVAVHVASGYIEAEV
IPAETGQETAYFILKLAGRWPVKVIHTANGSNFTSAAVKAACWWAGIQQE
FGIPYNPQSQGVVASMNKELKKIIGQVRDQAEHLKTAVQMAVFIHNFKRK
GGIGGYSAGERIIDIIATDIQTKELQKQIIKIQNFRVYYRDSRDPIWKGP
AKLLWKGEGAVVIQDNSDIKVVPRRKVKIIKDYGKQMAGADCVAGRQDED

MOSAIC POL2 (AA SEQUENCE)

SEQ ID NO: 13

MAPISPIETVPVKLKPGMDGPKVKQWPLTEEKIKALVEICTEMEKEGKIS
KIGPENPYNTPIFAIKKKDSTKWRKLVDFRELNKRTQDFWEVQLGIPHPA
GLKKKKSVTVLAVGDAYFSVPLDEDFRKYTAFTIPSINNETPGIRYQYNV
LPQGWKGSPAIFQSSMTKILEPERKQNPDIVIYQYMAALYVGSDLEIGQH
RTKIEELRQHLLRWGFTTPDKKHQKEPPFLWMGYELHPDKWTVQPIVLPE
KDSWTVNDIQKLVGKLNWASQIYAGIKVKQLCKLLRGTKALTEVVPLTEE
AELELAENREILKEPVHGVYYDPSKDLIAEIQKQGQGQWTYQIYQEPFKN
LKTGKYARMRGAHTNDVKQLTEAVQKIATESIVIWGKTPKFKLPIQKETW
EAWWTEYWQATWIPEWEEVNTPPLVKLWYQLEKEPIVGAETFYVAGAANR
ETKLGKAGYVTDRGRQKVVSLTDTTNQKTALQAIHLALQDSGLEVNIVTA
SQYALGIIQAPDKSESELVSQIIEQLIKKEKVYLAWVPAHKGIGCNEQV
DKLVSRGIRKVLFLDGIDKAQEEHEKYHSNWRAMASEFNLPPIVAKEIVA
SCDKGQLKGEAIHGQVDCSPGIWQLACTHLEGKVILVAVHVASGYIEREV
IPAETGQETAYFLLKLAGRWPVKTIHTANGSNFTSATVKAACWWAGIKQE
FGIPYNPQSQGVVASINKELKKIIGQVRDQAEHLKTAVQMAVFIHNFKRK
GGIGEYSAGERIVDIIASDIQTKELQKQITKIQNFRVYYRDSRDPLWKGP
AKLLWKGEGAVVIQDNSDIKVVPRRKAKIIRDYGKQMAGDDCVASRQDED

MOS3 POL V3 (AA SEQUENCE)
851 AA

SEQ ID NO: 14

MAPISPIDTVPVTLKPGMDGPKIKQWPLTEEKIKALTEICTEMEKEGKIS
RIGPENPYNTPVFAIKKKNSTRWRKLVDFRELNKKTQDFWEVQLGIPHPA
GLKKKRSVTVLAVGDAYFSVPLDKDFRKYTAFTIPSVNNETPGVRYQYNV
LPQGWKGSPAIFQCSMTKILEPPFRAQNPEIVIYQYVAALYVGSDLEIEQH
RTKIEELRAHLLSWGFTTPDKKHQREPPFLWMGYELHPDRWTVQPIELPE
KESWTVNDIQKLVGKLNWASQIYPGIKVKQLCRLLRGAKALTEVIELTKE
AELELAENREILREPVHGVYYDPSKDLVAEIQKQGQDQWTYQIYQEPYKN

LKTGKYARKRSAHTNDVRQLTEAVQKIALESIVIWGKIPKFRLPIQRETW
ETWWTEYWQATWIPDWEFVNTPPLVKLWYQLEKEPIAGAETFYVAGASNR
ETKIGKAGYVTDKGRQKVVSLTETTNQKAALQAIQLALQDSGPEVNIVTA
SQYVLGIIQAPDRSESELVNQIIEELIKKEKVYLSWVPAHKGIGGNEQV
DKLVSAGIRKILFLDGIDKAQEEHERYHSNWRTMASDFNLPPIVAKEIVA
NCDKCQLKGEAMHGQVDCSPGMWQLACTHLEGKIIIVAVHVASGYMEAEV
IPAETGQETAYYILKLAGRWPVKVVHTANGSNFTSTTVKAACWWANVTQE
FGIPYNPQSQGVIASMNKELKKIIGQVREQAEHLKTAVQMAVLIHNFKRR
GGIGGYSAGERIVDIIATDIQTRELQKQIIKIQNFRVYFRDSRDPVWKGP
AKLLWKGEGAVVIQDNSEIKVVPRRKVKTTRDYGKQMAGDDCVAGRQDED
Q

IV. 2-VALENT M MOSAIC GAG SEQUENCE

MOS3 GAG (AA SEQUENCE)
508 AA

SEQ ID NO: 15

MGARASVLSGGKLDAWEKIRLRPGGKKKYKLKHIVWASRELDRFALNPGL
LETAEGCQQIIEQLQPALQTGSEELKSLYNTVAVLYCVHQRIDVKDTKEA
LDKIEEIQNKSKQKTQQAAADTGSSSKVSQNYPIVQNAQGQMVHQALSPR
TLNAWVKVVEEKGFNPEVIPMFSALAEGATEQDLNMMLNIVGGHQAAMQI
LKDTINEEAADWDRLHPVHAGPIPPGQMREPRGSDIAGTTSTPQEQIGWM
TSNPPVPVGEIYKRWIIMGLNKIVRMYSPVSILDIKQGPKESFRDYVDRF
FKVLRAEQATQEVKNWMTETLLIQNANPDCKSILRALGPGASLEEMMTAC
QGVGGPSHKARILAEAMSQANNTNIMMQRGNFKGQKRIKCFNCGKEGHLA
RNCRAPRKRGCWKCGREGHQMKDCNERQANFLGKIWPSSKGRPGNFPQSR
PEPTAPLEPTAPPAEPTAPPAESFGFGEEITPSPKQEQKDREPLTSLKSL
FGSDPLLQ

V. 2-VALENT M MOSAIC NEF SEQUENCES (POSITION 2 G TO A TO DELETE MYRISTYLATION SITE

MOS1 NEF
(206 AA)

SEQ ID NO: 16

MAGKWSKSSVVGWPAIRERMRRAEPAADGVGAVSRDLEKHGAITSSNTAA
NNADCAWLEAQEEEEVGFPVRPQVPLRPMTYKGALDLSHFLKEKGGLEGL
IYSQKRQDILDLWVYHTQGYFPDWQNYTPGPGIRYPLTFGWCFKLVPVEP
EKIEEANEGENNSLLHPMSQHGMDDREKEVLMWKEDSRLAFHHMARELHP
EYYKDC

MOS2 NEF
(206 AA)-POSITION 2 G TO A TO DELETE
MYRISTYLATION SITE

SEQ ID NO: 17

MAGKWSKSSIVGWPAVRERIRRAEPAAEGVGAASQDLDKYGALTSSNTAA
TNADCAWLEAQEDEEVGFPVKPQVPLRPMTYKAAFDLSFFLKEKGGLDGL
IYSKKRQEILDLWVYNTQGFFPDWQNYTPGPGVRYPLTFGWCFKLVPVDP

SEQUENCE APPENDIX

REVEEANKGENNCLLHPMNLHGMDDPEREVLVWRFDSRLAFHHMAREKHP
EYYKNC

MOS3 NEF
(208 AA)
SEQ ID NO: 18

MAGKWSKRSVVGWPAVRERMRRTEPAAEGVGAVSQDLDKHGALTSSNTAH
NNADCAWLQAQEEEEVGFPVRPQVPVRPMTYKAAVDLSHFLKEKGGLEG
LIHSQKRQEILDLWVYHTQGFFPDWHNYTPGPGTRFPLTEGWCYKLVPVD
PKEVEEANEGENNCLLHPMSQHGMEDEDREVLKWKFDSSLARRHMARELH
PEFYKDCL

VI. 2-VALENT M MOSAIC GAGNEF FUSION SEQUENCES

MOSAIC GAGNEF1 (AA SEQUENCE)
SEQ ID NO: 19

MGARASVLSGGELDRWEKIRLRPGGKKKYRLKHIVWASRELERFAVNPGL
LETSEGCRQILGQLQPSLQTGSEELRSLYNTVATLYCVHQRIEIKDTKEA
LEKIEEEQNKSKKKAQQAAADTGNSSQVSQNYPIVQNIQGQMVHQAISPR
TLNAWVKVVEEKAFSPEVIPMFSALSEGATPQDLNTMLNTVGGHQAAMQM
LKETINEEAAEWDRVHPVHAGPIAPGQMREPRGSDTAGTTSTLQEQIGWM
TNNPPIPVGEIYKRWIILGLNKIVRMYSPVSILDIRQGPKEPFRDYVDRF
YKTLRAEQASQDVKNWMTETLLVQNANPDCKTILKALGPAATLEEMMTAC
QGVGGPGHKARVLAEAMSQVTNSATIMMQRGNFRNQRKTVKCFNCGKEGH
IAKNCRAPRKKGCWKCGKEGHQMKDCTERQANFLGKIWPSNKGRPGNFLQ
NRPEPTAPPEESFRFGEETTTPSQKQEPIDKEMYPLASLKSLFGNDPSSQ
AGKWSKSSVVGWPAIRERMRRAEPAADGVGAVSRDLEKHGAITSSNTAAN
NADCAWLEAQEEEEVGFPVRPQVPLRPMTYKGALDLSHFLKEKGGLEGLI
YSQKRQDILDLWVYHTQGYFPDWQNYTPGPGIRYPLTFGWCFKLVPVEPE
KIEEANEGENNSLLHPMSQHGMDDPEKEVLMWKFDSRLAFHHMARELHPE
YYKDC

MOSAIC GAGNEF2 (AA SEQUENCE)
SEQ ID NO: 20

MGARASILRGGKLDKWEKIRLRPGGKKHYMLKHLVWASRELERFALNPGL
LETSEGCKQIIKQLQPALQTGTEELRSLENTVATLYCVHAEIEVRDTKEA
LDKIEEEQNKSQQKTQQAKEADGKVSQNYPIVQNLQGQMVHQPISPRTLN
AWVKVIEEKAFSPEVIPMFTALSEGATPQDLNTMLNTVGGHQAAMQMLKD
TINEEAAEWDRLHPVHAGPVAPGQMREPRGSDIAGTTSNLQEQIAWMTSN
PPIPVGDIYKRWITLGLNKIVRMYSPTSILDIKQGPKEPFRDYVDRFFKT
LRAEQATQDVKNWMTDTLLVQNANPDCKTILRALGPGATLEEMMTACQGV
GGPSHKARVLAEAMSQTNSTILMQRSNFKGSKRIVKCFNCGKEGHIARNC
RAPRKKGCWKCGKEGHQMKDCTERQANFLGKIWPSHKGRPGNFLQSRPEP
TAPPAESERFEETTPAPKQEPKDREPLTSLRSLFGSDPLSQAGKWSKSSI
VGWPAVRERIRRAEPAAEGVGAASQDLDKYGALTSSNTAATNADCAWLEA
QEDEEVGFPVKPQVPLRPMTYKAAFDLSFELKEKGGLDGLIYSKKRQEIL

DLWVYNTQGFFPDWQNYTPGPGVRYPLTFGWCFKLVPVDPREVEEANKGE
NNCLLHPMNLHGMDDPEREVLVWRFDSRLAFHHMAREKHPEYYKNC

VII. 2-VALENT M MOSAIC GAGPOL FUSION SEQUENCES (VERSION 3; POL EXTENSIVELY INACTIVATED, PR-DELETED, 9 A INACTIVATION MUTATIONS TO ELIMINATE CATALYTIC ACTIVITY)

MOSAIC GAGPOL1 V3 (AA SEQUENCE)
SEQ ID NO: 21

MGARASVLSGGELDRWEKIRLRPGGKKKYRLKHIVWASRELERFAVNPGL
LETSEGCRQILGQLQPSLQTGSEELRSLYNTVATLYCVHQRIEIKDTKEA
LEKIEEEQNKSKKKAQQAAADTGNSSQVSQNYPIVQNIQGQMVHQAISPR
TLNAWVKVVEEKAFSPEVIPMFSALSEGATPQDLNTMLNTVGGHQAAMQM
LKETINEEAAEWDRVHPVHAGPIAPGQMREPRGSDIAGTTSTLQEQIGWM
TNNPPIPVGEIYKRWIILGLNKIVRMYSPVSILDIRQGPKEPFRDYVDRF
YKTLRAEQASQDVKNWMTETLLVQNANPDCKTILKALGPAATLEEMMTAC
QGVGGPGHKARVLAEAMSQVTNSATIMMQRGNFRNQRKTVKCFNCGKEGH
IAKNCRAPRKKGCWKCGKEGHQMKDCTERQANFLGKIWPSNKGRPGNFLQ
NRPEPTAPPEESFRFGEETTTPSQKQEPIDKEMYPLASLKSLFGNDPSSQ
MAPISPIETVPVKLKPGMDGPRVKQWPLTEEKIKALTAICEEMEKEGKIT
KIGPENPYNTPVFAIKKKDSTKWRKLVDFRELNKRTQDFWEVQLGIPHPA
GLKKKKSVTVLAVGDAYFSVPLDEGFRKYTAFTIPSTNNETPGIRYQYNV
LPQGWKGSPAIFQCSMTRILEFFRAKNPEIVIYQYMAALYVGSDLEIGQH
RAKIEELREHLLKWGFTTPDKKHQKEPPFLWMGYELHPDKWTVQPIQLPE
KDSWTVNDIQKLVGKLNWASQTYPGIKVRQLCKLLRGAKALTDIVPLTEE
AELELAENREILKEPVHGVYYDPSKDLIAEIQKQGHDQWTYQIYQEPFKN
LKTGKYAKMRTAHTNDVKQLTEAVQNIAMESIVIWGKTPKFRLPIQKETW
ETWWTDYWQATWIPEWEEVNTPPLVKLWYQLEKDPIAGVETFYVAGAANR
ETKLGKAGYVTDRGRQKIVSLTETTNQKTALQAIYLALQDSGSEVNIVTA
SQYALGIIQAQPDKSESELVNQIIEQLIKKERVYLSWVPAHKGIGGNEQV
DKLVSSGIRKVLELDGIDKAQEEHEKYHSNWRAMASDFNLPPVVAKEIVA
SCDQCQLKGEAMHGQVDCSPGIWQLACTHLEGKIILVAVHVASGYIEAEV
IPAETGQETAYFILKLAGRWPVKVIHTANGSNFTSAAVKAACWWAGIQQE
FGIPYNPQSQGVVASMNKELKKIIGQVRDQAEHLKTAVQMAVEIHNEKRK
GGIGGYSAGERIIDIIATDIQTKELQKQIIKIQNFRVYYRDSRDPIWKGP
AKLLWKGEGAVVIQDNSDIKVVPRRKVKIIKDYGKQMAGADCVAGRQDED

MOSAIC GAGPOL2 V3 (AA SEQUENCE)
SEQ ID NO: 22

MGARASILRGGKLDKWEKIRLRPGGKKHYMLKHLVWASRELERFALNPGL
LETSEGCKQIIKQLQPALQTGTEELRSLENTVATLYCVHAEIEVRDTKEA
LDKIEEEQNKSQQKTQQAKEADGKVSQNYPIVQNLQGQMVHQPISPRTLN
AWVKVIEEKAFSPEVIPMFTALSEGATPQDLNTMLNTVGGHQAAMQMLKD
TINEEAAEWDRLHPVHAGPVAPGQMREPRGSDIAGTTSNLQEQIAWMTSN

SEQUENCE APPENDIX

PPIPVGDIYKRWIILGLNKIVRMYSPTSILDIKQGPKEPERDYVDRFEKT
LRAEQATQDVKNWMTDTLLVQNANPDCKTILRALGPGATLEEMMTAGQGV
GGPSHKARVLAEAMSQTNSTILMQRSNFKGSKRIVKCFNCGKEGHIARNC
RAPRKKGCWKCGKEGHQMKDCTERQANFLGKIWPSHKGRPGNFLQSRPEP
TAPPAESFRFEETTPAPKQEPKDREPLTSLRSLFGSDPLSQMAPISPIET
VPVKLKPGMDGPKVKQWPLTEEKIKALVEICTEMEKEGKISKIGPENPYN
TPIFAIKKKDSTKWRKLVDFRELNKRTQDFWEVQLGIPHPAGLKKKKSVT
VLAVGDAYFSVPLDEDFRKYTAFTIPSINNETPGIRYQYNVLPQGWKGSP
AIFQSSMTKILEPERKQNPDIVIYQYMAALYVGSDLEIGQHRTKIEELRQ
HLLRWGETTPDKKHQKEPPFLWMGYELHPDKWTVQPIVLPEKDSWTVNDI
QKLVGKLNWASQIYAGIKVKQLCKLLRGTKALTEVVPLTEEAELELAENR
EILKEPVHGVYYDPSKDLIAEIQKGQGQWTYQIYQEPFKNLKTGKYARM
RGAHTNDVKQLTEAVQKIATESIVIWGKTPKFKLPIQKETWEAWWTEYWQ
ATWIPEWEFVNTPPLVKLWYQLEKEPIVGAETFYVAGAANRETKLGKAGY
VTDRGRQKVVSLTDTTNQKTALQAIHLALQDSGLEVNIVTASQYALGIIQ
AQPDKSESELVSQIIEQLIKKEKVYLAWVPAHKGIGGNEQVDKLVSRGIR
KVLFLDGIDKAQEEKEYHSNWRAMASEFNLPPIVAKEIVASCDKCQLKG
EAIHGQVDCSPGIWQLACTHLEGKVILAVHVASGYIEAEVIPAETGQET
AYELLKLAGRWPVKTIHTANGSNFTSATVKAACWWAGIKQEFGIPYNPQS
QGVVASINKELKKIIGQVRDQAEHLKTAVQMAVFIHNFKRKGGIGEYSAG
ERIVDIIASDIQTKELQKQITKIQNFRVYYRDSRDPLWKGPAKLLWKGEG
AVVIQDNSDIKVVPRRKAKIIRDYGKQMAGDDCVASRQDED

MOS3 GAG-POL V3 (AA SEQUENCES)
1359 aa-GAG-POL FUSION WITH COMPLETE GAG AND
MODIFIED POL
SEQ ID NO: 23
MGARASVLSGGKLDAWEKIRLPGGKKKYKLKHIVWASRELDRFALNPGL
LETAEGCQQIIEQLQPALQTGSEELKSLYNTVAVLYCVHQRIDVKDTKEA
LDKIEEIQNKSKQKTQQAAADTGSSSKVSQNYPIVQNAQGQMVEQALSPR
TLNAWVKVVEEKGENPEVIPMFSALAEGATPQDLNMMLNIVGGHQAAMQI
LKDTINEEAADWDRLHPVHAGPIPPGQMREPRGSDIAGTTSTPQEQIGWM
TSNPPVPVGEIYKRWIIMGLNKIVRMYSPVSILDIKQGPKESFRDYVDRF
FKVLRAEQATQEVKNWMTEILLIQNANPDCKSILRALGPGASLEEMMTAC
QGVGGPSHKARILAEAMSQANNTNIMMQRGNFKGQKRIKCFNCGKEGHLA
RNCRAPRKRGCWECGREGHQMKDCNERQANFLGKIWPSSKGRPGNFPQSR
PEPTAPLEPTAPPAEPTAPPAESEGFGEEITPSPKQEQKDREPLTSLKSL
FGSDPLLQMAPISPIDTVPVTLKPGMDGPKIKQWPLTEEKIKALTEICTE
MEKEGKISPIGPENPYNTPVFAIKKKNSTRWRKLVDFRELNKKTQDFWEV
QLGIPHPAGLKKKRSVTVLAVGDAYESVPLDKDFRKYTAFTIPSVNNETP
GVRYWNVLPQGWKGSPAIFQCSMTKILEPFRAQNPEIVIYQYVAALYVGS

DLEIEQHRTKIEELRAHLLSWGFTTPDKKHQREPPFLWMGYELHPDRWTV
QPIELPEKESWTVNDIQKLVGKLNWASQIYPGIKVKQLCRLLRGAKALTE
VIPLTKEAELELAENREILREPVHGVYYDPSKDLVAEIQKGQGDQWTYQI
YYQEPKNLKTGKYARKRSAHTNDVRQLTEAVQKIALESIVIWGKIPKFRL
FIQRETWETWWTEYWQATWIPDWEFVNTPPLVKLWYQLEKEPIAGAETFY
VAGASNRETKIGKAGYVTDKGRQKVVSLTETTNQKAALQAIQLALQDSGP
EVNIVTASQYVLGIIQAQPDRSESELVNQIIEELIKKEKVYLSWVPAHKG
IGGNEQVDKLVSAGIRKILFLDGIDKAQEEHERYHSNWRTMASDENLPPI
VAKEIVANCDKCQLKGEAMEGQVDCSEGMWQLACTHLEGKIIIVAVHVAS
GYMEAEVIPAETGQETAYYILKLAGRWPVKVVHTANGSNFTSTTVKAACW
WANVTQEFGIPYNPQSQGVLASMNKELKKIIGQVREQAEHLKTAVQMAVL
IHNFKRRCGIGGYSAGERIVDIIATDIQTRELQKQIIKIQNFRVYFRDSR
DPVWKGPAKLLWKGEGAVVIQDNSEIKVVPRRKVKIIRDYGKQMAGDDCV
AGRQDEDQ

VIII. 2-VALENT M MOSAIC GAGPOL FUSION SEQUENCES (VERSION 4; POL MINIMALLY INACTIVATED, COMPLETE PR-RT-IN)

MOSAIC GAGPOL1 V4 (AA SEQUENCE)
SEQ ID NO: 24
MGARASVLSGGELDRWEKIRLRPGGKKKYRLKHIVWASRELERFAVNPGL
LETSEGC
RQILGQLQPSLQTGSEELRSLYNTVATLYCVHQRIEIKDTKEALEKIEEE
QNKSKKKAQQAAADTGNSSQVSQNYPIVQNIQGQMVHQAISPRTLNAWVK
VVEEKAFSPEVIPMFSALSEGATPQDLNTMLNTVGGHQAAMQMLKETINE
EAAEWDRVHPVHAGPIAPGQMREPRGSDIAGTTSTLQEQIGWMTNNPPIP
VGEIYKRWIIGLNKIVRMYSPVSILDIRQGPKEPFRDYVDRFYKTLRAE
QASQDVKNWMTETLLVQNANPDCKTILKALGPAATLEEMMTACQGVGGPG
HKARVLAEAMSQVTNSATIMMQRGNFRNQRKTVKCFNCGKEGHIAKNCRA
PRKKGCWKCGKEGHQMKDCTERQANFLGKIWPSNKGRPGNFLQNRPEPTA
PPEESFRFGEETTTPSQKQEPIDKEMYPLASLKSLFGNDPSSQRENLAFQ
QGEAREFPSEQTRANSPTSRELQVRGDNPHSEAGAERQGTLNFPQITLWQ
RPLVSIKVGGQIREALLATGADDTVLEDINLPGKWKPKMIGGICGFIKVG
QYDQILIEICGKKAIGTVLVGPTPVNIIGRNMLTQLGCTLNFPISPIETV
PVKLKPGMDGPRVKQWPLTEEKIKALTAICEEMEKEGKITKIGPENPYNT
PVFAIKKKDSTKWRKLVDFRELNKRTQDFWEVQLGIPHPAGLKKKKSVTV
LDVGDAYFSVPLDEGFRKYTAFTIPSTNNETPGIRYQYNVLPQGWKGSPA
IFQCSMTRILEPFRAKNPEIVIYQYMDHLYVGSDLEIGQHRAKIEELREH
LLKWGETTPDKKHQKEPPFLWMGYELHPDKWTVQPIQLPEKDSWTVNDIQ
KLVGKLNWASQIYPGIKVRQLCKLLRGAKALTDIVPLTEEAELELAENRE
ILKEPVHGVYYDPSKDLIAEIQKGHDQWTYQIYQEPFKNLKTGKYAKMR
TAHTNDVKQLTEAVQKIAMESIVIWGKTPKERLPIQKETWETWWTDYWQA
TWIPEWEEVNTPPLVKLWYQLEKDPIAGVETFYVDGAANRETKLGKAGYV

SEQUENCE APPENDIX

TDRGRQKIVSLTETTNQKTELQATYLALQDSGSEVNIVTDSYALGIIQA

QPDKSESELVNQIIEQLIKKERVYLSWVPAHKGIGGNEQVDKLVSSGIRK

VLELDGIDKAQEEHEKYHSNWRAMASDFNLPPVVAKEIVASCDQCQLKGE

AMHGQVDCSPGIWQLACTHLEGKIILVAVHVASGYIEAEVIPAETGQETA

YEILKLAGRWPVKVIHTDNGSNFTSAAVKAACWWAGIQQEFGIPYNPQSQ

GVVESMNKELKKIIGQVRDQAEHLKTAVQMAVFIHNFKRKGGIGGYSAGE

RIIDIIATDIQTKELQKQIIKIQNFRVYYRDSRDPIWKGPAKLLWKEGA

VVIQDNSDIKVVPRRKVKIIKDYGKQMAGADCVAGRQDED

MOSAIC GAGPOL2 V4 (AA SEQUENCE)
SEQ ID NO: 25

MGARASILRGGKLDKWEKIRLRPGGKKHYMLKHLVWASRELERFALNPGL

LETSEGCKQIIKQLQPALQTGEELRSLFNTVATLYCVHAEIEVRDTKEA

LDKIEEEQNKSQQKTQQAKEADGKVSQNYPIVQNLQGQMVHQPISPRTLN

AWVKVIEEKAFSPEVIPMFTALSEGATPQDLNTMLNTVGGHQAAMQMLKD

TINEEAAEWDRLHPVHAGPVAPGQMREPRGSDIAGTTSNLQEQIAWMTSN

PPIPVGDIYKRWIILGLNKIVRMYSPTSILDIKQGPKEPERDYVDRFFKT

LRAEQATQDVKNWMTDTLLVQNANPDCKTILRALGPGATLEEMMTACQGV

GGPSHKARVLAEAMSQTNSTILMQRSNFKGSKRIVKCFNCGKEGHIARNC

RAPRKKGCWKCGKEGHQMKDCTERQANFLGKIWPSHKGRPGNFLQSRPEP

TAPPAESERFEETTPAPKQEPKDREPLTSLRSLEGSDPLSQRENLAFPQG

KAREFSSEQTRANSPTRRELQVWGRDNNSLSEAGADRQGTVSFSFPQITL

WQRPLVTIKIGGQLKEALLATGADDTVLEEMNLPGRWKPKMIGGIGGFIK

VGQYDQIPIEICGHKAIGTVLVGPTPVNIIGRNLLTQIGCTLNFPISPIE

TVPVKLKPGMDGPKVKQWPLTEEKIKALVETCTEMEKEGKISKIGPENPY

NTPIFAIKKKDSTKWRKLVDFRELNKRTQDFWEVQLGIPHPAGLKKKKSV

TVLDVGDAYFSVPLDEDFRKYTAFTIPSINNETPGIRYQYNVLPQGWKGS

PAIFQSSMTKILEPERKQNPDIVIYQYMDHLYVGSDLEIGQHRTKIEELR

QHLLRWGETTPDKKHQKEPPFLWMGYELHPDKWTVQPIVLPEKDSWTVND

IQKLVGKLNWASQIYAGIKVKQLCKLLRGTKALTEVVPLTEEAELELAEN

REILKEPVHGVYYDPSKDLIAEIQKQGQGQWTYQIYQEPFKNLKTGKYAR

MRGAHTNDVKQLTEAVQKIATESIVIWGKTPKFKLPIQKETWEAWWTEYW

QATWIPEWEEVNTPPLVKLWYQLEKEPIVGAETFYVDGAANRETKLGKAG

YVTDRGRQKVVSLTDTTNQKTELQAIHLALQDSGLEVNIVTDSQYALGII

QAQPDKSESELVSQIIEQLIKKEKVYLAWVPAHKGIGGNEQVDKLVSRGI

RKVLFLDGIDKAQEEHEKYHSNWRAMASEFNLPPIVAKEIVASCDKCQLK

GEAIHGQVDCSPGIWQLACTHLEGKVILVAVHVASGYIEAEVIPAETGQE

TAYELLKLAGRWPVKTIHTDNGSNFTSATVKAACWWAGIKQEFGIPYNPQ

SQGVVESINKELKKIIGQVRDQAEHLKTAVQMAVFIHNFKRKGGIGEYSA

GERIVDIIASDIQTKELQKQIITKIQNERVYYRDSRDPLWKGPAKLLWKGE

GAVVIQDNSDIKVVPRRKAKIIRDYGKQMAGDDCVASRQDED

IX. 2-VALENT M MOSAIC GAGPOL FUSION SEQUENCES
(VERSION 5; POL MINIMALLY INACTIVATED, PR-DELETED)

MOSAIC GAGPOL1 V5 (AA SEQUENCE)
SEQ ID NO: 26

MGARASVLSGGELDRWEKIRLRPGGKKKYRLKHIVWASRELERFAVNPGL

LETSEGCRQILGQLQPSLQTGSEELRSLYNTVATLYCVHQRIEIKDTKEA

LEKIEEEQNKSKKKAQQAAADTGNSSQVSQNYPIVQNIQGQMVHQAISPR

TLNAWVKVVEEKAFSPEVIPMFSALSEGATPQDLNTMLNTVGGHQAAMQM

LKETINEEAAEWDRVHRVHAGPIAPGQMREPRGSDIAGTTSTLQEQIGWM

TNNPPIPVGEIYKRWIILGLNKIVRMYSPVSILDIRQGPKEPERDYVDRE

YKTLRAEQASQDVKNWMTETLLVQNANPDCKTILKALGPAATLEEMMTAC

QGVGGPGHKARVLAEAMSQVTNSATIMMQRGNFRNQRKTVKCFNCGKEGH

IAKNCRAPRKKGCWKCGKEGHQMKDCTERQANFLGKIWPSNKGRPGNFLQ

NRPEPTAPPEESFRFGEETTTPSQKQEPIDKEMYPLASLKSLFGNDPSSQ

MAPISPIETVPVKLKPGMDGPRVKQWPLTEEKIKALTAICEEMEKEGKIT

KIGPENPYNTPVFAIKKKDSTKWRKLVDERELNKRTQDFWEVQLGIPHPA

GLKKKKSVTVLDVGDAYFSVPLDEGFRKYTAFTIPSTNNETPGIRYQYNV

LPQGWKGSPAIFQCSMTRILEPFRAKNPEIVIYQYMDHLYVGSDLEIGQH

RAKIEELREHLLKWGFTTPDKKHQKEPPFLWMGYELHPDKWTVQPIQLPE

KDSWTVNDIQKLVGKLNWASQIYPGIKVRQLCKLLRGAKALTDIVPLTEE

AELELAENREILKEPVHGVYYDPSKDLIAEIQKQGHDQWTYQIYQEPFKN

LKTGKYRKMRTAHTNDVKQLTEAVQKIAMESIVIWGKTPKFRLPIQKETW

ETWWTDYWQATWIPEWEFVNTPPLVELWYQLEKDPIAGVETFYVDGAANR

ETKLGKAGYVTDRGRQKIVSLTETTNQKTELQAIYLALQDSGSEVNIVTD

SQYALGIIQAQPDKSESELVNQIIEQLIKKERVYLSWVPAHKGIGGNEQV

DKLVSSGIRKVLFLDGIDKAQEEHEKYHSNWRAMASDFNLPPVVAKEIVA

SCDQCQLKGEAMHGQVDCSPGIWQLACTHLEGKIILVAVHVASGYIEAEV

IPAETGQETAYFILKLAGRWPVKVIHTDNGSNFTSAAVKAACWWAGIQQE

FGIPYNPQSQGVVESMNKELKKIIGQVRDQAEHLKTAVQMAVFIHNFKRK

GGIGGYSAGERIIDITATDIQTKELQKQIIKIQNFRVYYRDSRDPIWKGP

AKLLWKEGAVVIQDNSDIKVVPRRKVKIIKDYGKQMAGADCVAGRQDED

MOSAIC GAGPOL2 V5 (AA SEQUENCE)
SEQ ID NO: 27

MGARASILRGGKLDKWEKIRLRPGGKKHYMLKHLVWASRELERFALNPGL

LETSEGCKQIIKQLQPALQTGEELRSLFNTVATLYCVHAEIEVRDTKEA

LDKIEEEQNKSQQKTQQAKEADGKVSQNYPIVQNLQGQMVHQPISPRTLN

AWVKVIEEKAFSPEVIPMFTALSEGATPQDLNTMLNTVGGHQAAMQMLKD

TINEEAAEWDRLHPVHAGPVAPGQMREPRGSDIAGTTSNLQEQIAWMTSN

SEQUENCE APPENDIX

PPIPVGDIYKRWIILGLNKIVRMYSPTSILDIKQGPKEPERDYVDRFFKT
LRAEQATQDVKNWMTDTLLVQNANPDCKTILRALGPGATLEEMMTACQGV
GGPSHKARVLAEAMSQTNSTILMQRSNFKGSKRIVKCFNCGKEGHIARNC
RAPRKKGCWKCGKEGHQMKDCTERQANFLGKIWPSHKGRPGNFLQSRPEP
TAPPAESFRFEETTPAPKQEPKDREPLTSLRSLFGSDPLSQMAPISPIET
VPVKLKPGMDGPKVKQWPLTEEKIKALVEICTEMEKEGKISKIGPENPYN
TPIFAIKKKDSTKWRKLVDFRELNKRTQDFWEVQLGIPHPAGLKKKKSVT
VLDVGDAYFSVPLDEDFRKYTAFTIPSINNETPGIRYQYNVLPQGWKGSP
AIFQSSMTKILEPFRKQNPDIVIYQYMDHLYVGSDLEIGQHRTKIEELRQ
HLLRWGFTTPDKKHQKEPPFLWMGYELHPDKWTVQPIVLPEKDSWTVNDI
QKLVGKLNWASQIYAGIKVKQLCKLLRGTKALTEVVPLTEEAELELAENR
EILKERVHGVYYDPSKDLIAEIQKQGQGQWTYQIYQEPFKNLKTGKYARM
RGAHTNDVKQLTEAVQKIATESIVIWGKTPKFKLPIQKETWEAWWTEYWQ
ATWIPEWEFVNTPPLVKLWYQLEKEPIVGAETFYVDGAANRETKLGKAGY
VTDRGRQKVVSLTDTTNQKTELQAIELALQDSGLEVNIVTDSQYALGIIQ
AQPDKSESELVSQIIEQLIKKEKVYLAWVPAHKGIGGNEQVDKLVSRGIR
KVLFLDGIDKAQEEHEKYHSNWRAMASEFNLPPIVAKEIVASCDKCQLKG
EAIHGQVDCSPGIWQLACTHLEGKVILVAVHVASGYIEAEVIPAETGQET
AYELLKLAGRWPVKTIHTDNGSNFTSATVKAACWWAGIKQEFGIPYNPQS
QGVVESINKELKKIIGQVRDQAEHLKTAVQMAVFIHNFKRKGGIGEYSAG
ERIVDITASDIQTKELQKQITKIQNFRVYYRDSRDPLWKGPAKLLWKGEG
AVVIQDNSDIKVVPRRKAKIIRDYGKQMAGDDCVASRQDED

X. 2-VALENT M MOSAIC GAGPOLNEF FUSION SEQUENCES
(POL EXTENSIVELY INACTIVATED, PR-DELETED)

MOSAIC GAGPOLNEF1 (AA SEQUENCE)
SEQ ID NO: 28
MGARASVLSGGELDRWEKIRLRPGGKKKYRLKHIVWASRELERFAVNPGL
LETSEGCRQILGQLQPSLQTGSEELRSLYNTVATLYCVHQRIEIKDTKEA
LEKIEEEQNKSKKKAQQAAADTGNSSQVSQNYPIVQNIQGQMVHQAISPR
TLNAWVKVVEEKAFSPEVIPMFSALSEGATPQDLNTMLNTVGGHQAAMQM
LKETINEEAAEWDRVHPVHAGPIAPGQMREPRGSDIAGTTSTLQEQIGWM
TNNPPIPVGEIYKRWIILGLNKIVRMYSPVSILDIRQGPKEPERDYVDRF
YKTLRAEQASQDVKNWMTETLLVQNANPDCKTILKALGPAATLEEMMTAC
QGVGGPGHKARVLAEAMSQVTNSATIMMQRGNFRNQRKTVKCFNCGKEGH
IAKNCRAPRKKGCWKCGKEGHQMKDCTERQANFLGKIWPSNKGRPGNFLQ
NRPEPTAPPEESFRFGEETTTPSQKQEPIDKEMYPLASLKSLFGNDPSSQ
MAPISPIETVPVKLKPGMDGPRVKQWPLTEEKIKALTAICEEMEKEGKIT
KIGPENPYNTPVFAIKKKDSTKWRKLVDFRELNKRTQDFWEVQLGIPHPA
GLKKKKSVTVLAVGDAYFSVPLDEGFRKYTAFTIPSTNNETPGIRYQYNV
LPQGWKGSPAIFQCSMTRILEPFRAKNPEIVIYQYMAALYVGSDLEIGQH

RAKIEELREHLLKWGFTTPDKKHQKEPPFLWMGYELHPDKWTVQPIQLPE
KDSWTVNDIQKLVGKLNWASQIYPGIKVRQLCKLLRGAKALTDIVPLTEE
AELELAENREILKEPVHGVYYDPSKDLIAEIQKQGHDQWTYQIYQEPFKN
LKTGKYAKMRTAHTNDVKQLTEAVQKIAMESIVIWGKTPKFRLPIQKETW
ETWWTDYWQATWIPEWEFVNTPPLVKLWYQLEKDPIAGVETFYVAGAANR
ETKLGKAGYVTDRGRQKIVSLTETTNQKTALQAIYLALQDSGSEVNIVTA
SQYALGIIQAQPDKSESELVNQIIEQLIKKERVYLSWVPAHKGIGGNEQV
DKLVSSGIRKVLFLDGIDKAQEEHEKYHSNWRAMASDFNLPPVVAKEIVA
SCDQCQLKGEAMHGQVDCSPGIWQLACTHLEGKIILVAVHVASGYIEAEV
IPAETGQETAYFILKLAGRWPVKVIHTANGSNFTSAAVKAACWWAGIQQE
FGIPYNPQSQGVVASMNKELKKIIGQVRDQAEHLKTAVQMAVFIHNFKRK
GGIGGYSAGERIIDIIATDIQTKELQKQIIKIQNFRVYYRDSRDPIWKGP
AKLLWKGEGAVVIQDNSDIKVVPRRKVKIIKDYGKQMAGADCVAGRQDED
MAGKWSKSSVVGWPAIRERMRRAEPAADGVGAVSRDLEKHGAITSSNTAA
NNADCAWLEAQEEEEVGFPVRPQVPLRPMTYKGALDLSHFLKEKGGLEGL
IYSQKRQDILDLWVYHTQGYFPDWQNYTPGPGIRYPLTFGWCFKLVPVEP
ERIEEANEGENNSLLHPMSQHGMDDPEKEVLMWKFDSRLAFHHMARELHP
EYYKDC

MOSAIC GAGPOLNEF2 (AA SEQUENCE)
SEQ ID NO: 29
MGARASILRGGKLDKWEKIRLRPGGKKHYMLKHLVWASRELERFALNPGL
LETSEGCKQIIKQLQPALQTGTEELRSLFNTVATLYCVHAEIEVRDTKEA
LDKIEEEQNKSQQKTQQAKEADGKVSQNYPIVQNLQGQMVHQPISPRTLN
AWVKVIEEKAFSPEVIPMFTALSEGATPQDLNTMLNTVGGHQAAMQMLKD
TINEEAAEWDRLHPVHAGPVAPGQMREPRGSDIAGTTSNLQEQIAWMTSN
PPIPVGDIYKRWIILGLNKIVRMYSPTSILDIKQGPKEPKFRDYVDRFFKT
LRAEQATQDVKNWMTDTLLVQNANPDCKTILRALGPGATLEEMMTACQGV
GGPSHKARVLAEAMSQTNSTILMQRSNFKGSKRIVKCFNCGKEGHIARNC
RAPRKKGCWKCGKEGHQMKDCTERQANFLGKIWPSHKGRPGNFLQSRPEP
TAPPAESFRFEETTPAPKQEPKDREPLTSLRSLFGSDPLSQMAPISPIET
VPVKLKPGMDGPKVKQWPLTEEKIKALVFICTEMEKEGKISKIGPENPYN
TPIFAIKKKDSTKWRKLVDFRELNKRTQDFWEVQLGIPHPAGLKKKKSVT
VLAVGDAYFSVPLDEDFRKYTAFTIPSINNETPGIRYQYNVLPQGWKGSP
AIFQSSMTKILEPFRKQNPDIVIYQYMAALYVGSDLEIGQHRTKIEELRQ
HLLRWGFTTPDKKHQKEPPFLWMGYELHPDKWTVQPIVLPEKDSWTVNDI
QKLVGKLNWASQIYAGIKVKQLCKLLRGTKALTEVVPLTEEAELELAENR
EILKEPVHGVYYDPSKDLIAEIQKQGQGQWTYQIYQEPFKNLKTGKYARM
RGAHTNDVKQLTEAVQKIATESIVIWGKTPKFKLPIQKETWEAWWTEYWQ
ATWIPEWEFVNTPPLVKLWYQLEKEPIVGAETFYVAGAANRETKLGKAGY

SEQUENCE APPENDIX

VTDRGRQKVVSLTDTTNQKTALQAIHLALQDSGLEVNIVTASQYALGIIQ

AQPDKSESELVSQIIEQLIKKEKVYLAWVPAHKGIGGNEQVDKLVSRGIR

KVLFLDGIDKAQEEHEKYHSNWRAMASEFNLPPIVAKEIVASCDKCQLKG

EATHGQVDCSPGIWQLACTHLEGKVILVAVHVASGYIEAEVIPAETGQET

AYFLLKLAGRWPVKTIHTANGSNFTSATVKAACWWAGIKQEFGIPYNPQS

QGVVASINKELKKIIGQVRDQAEHLKTAVQMAVFIHNFKRKGGIGEYSAG

ERIVDIIASDIQTKELQKQITKIQNFRVYYRDSRDPLWKGPAKLLWKGEG

AVVIQDNSDIKVVPRRKAKIIRDYGKQMAGDDCVASRQDEDMAGKWSKSS

IVGWPAVRERIRRAEPAAEGVAASQDLDKYGALTSSNTAATNADCAWLE

AQEDEEVGFPVKPQVPLRPMTYKAAFDLSFELKEKGGLDGLIYSKKRQEI

LDLWVYNTQGFFPDWQNYTPGPGVRYPLTFGWCFKLVPVDPREVEEANKG

ENNCLLHPMNLHGMDDPEREVLVWRFDSRLAFHHMAREKHPEYYKNC

XI. OPTIMAL CLADE C ENV GP160, GAG, POL, NEF SEQUENCES

OPTIMAL CLADE C ENV GP160 (SN90.90.SE364)
(AA SEQUENCE)
SEQ ID NO: 30

MRVTGMLRNCQPWWIWGILGEWMLLIYNVGGNLWVTVYYGVPVWKEAKTT

LFCASDAKAYEKEVHNVWATHACVPTDPNPQEMVLENVTEYFNMWKNDMV

DQMHEDIISLWDQSLKPCVKLTPLCVTLNCRNVTTSNNATSNDNPNGEIK

NCSFNITTELRDKRRNEYALFYRLDIVPLSGSKNSSNSSEYRLINCNTSA

ITQACPKVSFDPIPIHYCAPAGYAILKCNNKTFNGTGPCNNVSTVQCTHG

IKPVVSTQLLLNGSLAEGEIIIRSENLTNNAKTIIVHLNESIEIVCARPN

NNTRKSMRIGPGQTFYATGDIIGDIRQAHCNISGNWNATLEKVKGKLQEH

FPGKNISFEPSSGGDLEITTHSFNCRGEFFYCDTSKLFNGTTHTANSSIT

IQCRIKQIINMWQGVGRAIYAPPIAGNITCKSNITGLLLTRDGGTLNNDT

EKFRPGGGDMRDNWRSELYKYKVVEIKPLGIAPTKAKRRVVEREKRAVGI

GAVFLGELGAAGSTMGAASITLTVQARQLLSGIVQQQSNLLRAIEAQQHM

LQLTVWGIKQLQTRVLAIERYLKDQQLLGIWGCSGKIICTTAVPWNTSWS

NKSLEDIWDNMTWMQWDREINNYTSIIYSLLEESQNQQEKNEKDLLALDS

WNNLWNWFNITKWLWYIKIFIMIVGGLIGLRIIFAVLSIVNRVRQGYSPL

SFQTLIPNPRGPDRLGRIEEEGGEQDRDRSIRLVNGFLAIAWDDLRSLCL

FSYRRLRDFILIVARAVELLIQRGWETLKYLGSL?QYWGLELKKSAISLL

DTIAITVAEGTDRIIELVQRICRAISNIPRRIRQGFEAALQ

OPTIMAL CLADE C GAG (IN.70177) (AA SEQUENCE)

SEQ ID NO: 31

MGARASILRGGKLDKWEKIRLRPGGKKHYMLKHLVWASRELERFALNPGL

LETSEGCKQILKQLQPALQTGTEELRSLYNTVATLYCVHAGIEVRDTKEA

LDKIEEEQNKGQQKTQQAKGADGKVSQNYPIVQNLQGQMVHQAISPRTLN

AWVKVIEEKAFSPEVIPMFTALSEGATPQDLNTMLNTVGGHQAAMQMLKD

TINEEAAEWDRLHRVHAGPIAPGQMREPRGSDIAGTTSTLQEQIAWMTNN

PPVPVGDIYKRWIILGLNKIVRMYSPVSILDIKQGPKEPERDYVDRFFKT

-continued

SEQUENCE APPENDIX

LRAEQATQDVKNWMTDTLLVQNANPDCKTILRALGPGATLEEMMTACQGV

GGPSHKARVLAEAMSQTGSTIMMQRSNFKGSKRIVKCFNCGKEGHIARNC

RAPRKKGCWKCGKEGHQMKDCTERQANFLGKIWPSHKGRPGNFLQSRPEP

TAPPAESFRFEETTPAPKQELKDREPLTSLKSLFGSDPLSQ

OPTIMAL CLADE C POL (ZA.04.04ZASK208B1)
(AA SEQUENCE)

SEQ ID NO: 32

FFRENLAFQQGEAREEPSEQARANSPTSREFQVRUDNPCSEAGVKGQGTL

NFPQITLWQRPLVSIKVGGQVKEALLDTGADDTVLEEINLPGKWKPKMIG

GIGGFIKVRQYDQILIEICGKKAIGTVLVGPTPVNIIGRNMLTQLGCTLN

FPISPIETVPVKLKPGMDGPKIKQWPLTEEKIKALMAICEEMEKEGKITK

IGPENPYNTPIFAIKKKDSTKWRKLVDFRELNKRTQDFWEVQLGIPHPAG

LKKKKSVTVLDVGDAYFSVPLDESFRKYTAFTIPSINNETPGIRYQYNVL

PQGWKGSPAIFQSSMTKILEPFRAKNPEIVIYQYMDDLYVGSDLEIGQHR

AKIEELREHLLRWGFTTPDKKHQKEPPFLWMGYELHPDKWTVQPIQLPEK

DSWTVNDIQKLVGKLNWASQIYSGIKVRQLCKLLRGAKALTDIVPLTEEA

ELELAENREILKEPVHGVYYDPSKDLIAEIQKQGYDQWTYQIYQEPFKNL

KTGKYAKMRTAHTNDVKQLTEAVQKIALESIVIWGKTPKFRLPIQKETWE

IWWTDYWQATWIPEWEFVNTPPLVKLWYQLEKEPIAGAETFYVDGAANRE

TKIGKAGYVTDKGRQKIVTLTETTNQKTELQATQLALQDSGSEVNIVTDS

QYALGIIQAQPDKSESELVNQIIEQLINKERVYLSWVPAHKGIGGNEQVD

KLVSSGIRKVLFLDGIDKAQEEHEKYHSNWRAMASEFNLPPVVAKEIVAS

CDKCQLKGEAIHGQVDCSPGIWQLDCTHLEGKVILVAVHVASGYMEAEVI

PAETGQETAYYILKLAGRWPVKVIHTDNGSNFTSAAVKAACWWAGIQQEF

GIPYNPQSQGVVESMNKELKKIIGQVRDQAEHLKTAVQMAVFIHNFKRKG

GIGGYSAGERIIDIIATDIQTKELQKQIIKTQNFRVYYRDSRDPIWKGPA

KLLWKGEGAVVIQDNSDIKVVPRRKVKIIKDYGKQMAGADCVAGRQDED

OPTIMAL CLADE C NEF (ZA00.1170MB) (AA SEQUENCE)

SEQ ID NO: 33

MGGKWSKSSIVGWPDVRERMRRTEPAAEGVGAASQDLDKYGALTSSNTTH

NNADCAWLEAQEEGEVGFPVRPQVPLRPMTYKGAFDLSFELKEKGGLDGL

IYSKKRQEILDLWVYHTQGFFPDWQNYTPGPGVRYPLTEGWCFKLVPVDP

REVEEANKGENNCLLHPMSLHGMEDEEREVLKWEFDSSLARRHLARELHP

EYYKDC

XII. OPTIMAL CLADE C ENV GP140 SEQUENCE (CLEAVAGE/FUSION-DEFECTIVE)

OPTIMAL CLADE C ENV GP140 (SN90.90.SE364)
(AA SEQUENCE)

SEQ ID NO: 34

MRVTGMLRNCQPWWIWGILGFWMLLIYNVGGNLWVTVYYGVPVWKEAKTT

LFCASDAKAYEKEVHNVWATHACVPTDPNPQEMVLENVTEYFNMWKNDMV

DQMHEDIISLWDQSLKPCVKLTPLCVTLNCRNVTTSNNATSNDNPNGEIK

NCSFNITTELRDKRRNEYALFYRLDIVPLSGSKNSSNSSEYRLINCNTSA

SEQUENCE APPENDIX

ITQACPKVSFDPIPIHYCAPACYAILKCNNKTENGTGPCNNVSTVQCTHG
IKPVVSTQLLLNGSLAEGEIIIRSENLTNNAKTIIVHLNESIEIVCARPN
NNTRKSMRIGPGQTFYATGDIIGDIRQAHCNISGNWNATLEKVKGKLQEH
FPGKNISFEPSSGGDLEITTHSFNCRGEFFYCDTSKLFNGTTHTANSSIT
IQCRIKQIINMWQGVGRAIYAPPIAGNITCKSNITGLLLTRDGGTLNNDT
EKFRPCGGDMRDNWRSELYKYKVVEIKPLGIAPTKAKRRVVESEKSAVGI
GAVFLGELGAAGSTMGAASITLTVQARQLLSGIVQQQSNLLRAIEAQQHM
LQLTVWGIKQLQTRVLAIERYLKDQQLLGIWGCSGKIICTTAVPWNTSWS

NKSLEDIWDNMTWMQWDREINNYTSIIYSLLEESQNQQEKNEKDLLALDS

WNNLWNWFNITKWLW

XIII. OPTIMAL CLADE C VOL SEQUENCE (EXTENSIVELY INACTIVATED, PR-DELETED)

OPTIMAL CLADE C POL (ZA.04.04ZASK208B1)
(AA SEQUENCE)

SEQ ID NO: 35

MAPISPIETVPVKLKPGMDGPKIKQWPLTEEKIKALMAICEEMEKEGKIT

KIGPENPYNTPIFAIKKKDSTKWRKLVDFRELNKRTQDFWEVQLGIPHPA

GLKKKKSVTVLAVGDAYFSVPLDESFRKYTAFTIPSINNETPGIRYQYNV

LPQGWKGSPAIFQSSMTKILEPFRAKNPEIVIYQYMAALYVGSDLEIGQH

RAKIEELREHLLRWGFTTPDKKHQKEPPFLWMGYELHPDKWTVQPIQLPE

KDSWTVNDIQKLVGKLNWASQIYSGIKVRQLCKLLRGAKALTDIVPLTEE

AELELAENREILKEPVHGVYYDPSKDLIAEIQKQGYDQWTYQIYQEPFKN

LKTGKYAKMRTAHTNDVKQLTEAVQKIALESIVIWGKTPKFRLPIQKETW

EIWWTDYWQATWIPEWEFVNTPPLVKLWYQLEKEPIAGAETFYVAGAANR

ETKIGKAGYVTDKGRQKIVTLTETTNQKTALQAIQLALQDSGSEVNIVTA

SQYALGIIQAQPDKSESELVNQIIEQLINKERVYLSWVPAHKGIGGNEQV

DKLVSSGIRKVLFLDGIDKAQEEHEKYHSNWRAMASEFNLPPVVAKEIVA

SCDKCQLKGEAIHGQVDCSPGIWQLACTHLEGKVILVAVHVASGYMEAEV

IPAETGQETAYYILKLAGRWPVKVIHTANGSNFTSAAVKAACWWAGIQQE

FGIPYNPQSQGVVASMNKELKKIIGQVRDQAEHLKTAVQMAVFIHNFKRK

GGIGGYSAGERIIDIIATDIQTKELQKQIIKIQNFRVYYRDSRDPIWKGP

AKLLWKGEGAVVIQDNSDIKVVPRRKVKIIKDYGKQMAGADCVAGRQDED

XIV. OPTIMAL CLADE C GAGNEF FUSION SEQUENCE

OPTIMAL CLADE C GAGNEF (IN.70177-ZA00.1170MB)
(AA SEQUENCE)

SEQ ID NO: 36

MGARASILRGGKLDKWEKIRLRPGGKKHYMLKHLVWASRELERFALNPGL

LETSEGCKQILKQLQPALQTGTEELRSLYNTVATLYCVHAGIEVRDTKEA

LDKIEEEQNKGQQKTQQAKGADGKVSQNYPIVQNLQGQMVHQAISPRTLN

AWVKVIEEKAFSPEVIPMFTALSEGATPQDLNTMLNTVGGHQAAMQMLKD

TINEEAAEWDRLHPVHAGPIAPGQMREPRGSDIAGTTSTLQEQIAWMTNN

PPVPVGDIYKRWIILGLNKIVRMYSPVSILDIKQGPKEPFRDYVDRFFKT

SEQUENCE APPENDIX

LRAEQATQDVKNWMTDTLLVQNANPDCKTILRALGPGATLEEMMTACQGV

GGPSHKARVLAEAMSQTGSTIMMQRSNFKGSKRIVKCFNCGKEGHIARNC

RAPRKKGCWKCGKEGHQMKDCTERQANFLGKIWPSHKGRPGNFLQSRPEP

TAPPAESFRFEETTPAPKQELKDREPLTSLKSLFGSDPLSQAGKWSKSSI

VGWPDVRERMRRTEPAAEGVGAASQDLDKYGALTSSNTTHNNADCAWLEA

QEEGEVGFPVRPQVPLRPMTYKGAFDLSFFLKEKGGLDGLIYSKKRQEIL

DLWVYHTQGFFPDWQNYTPGPGVRYTLTFGWCFKLVPVDPREVEEANKGE

NNCLLHPMSLHGMEDEEREVLKWEFDSSLARRHLARELHPEYYKDC

XV. CONSENSUS SEQUENCES

M CONSENSUS ENV

SEQ ID NO: 37

MRVRGIQRNCQHLWRWGTLILGMLMICSAAENLWVTVYYGVPVWKEANTT

LFCASDAKAYDTEVHNVWATHACVPTDPNPQEIVLENVTENFNMWKNNMV

EQMHEDIISLWDQSLKPCVKLTPLCVTLNCTNVNVTNTTNNTEEKGEIKN

CSFNITTEIRDKKQKVYALFYRLDVVPIDDNNNNSSNYRLINCNTSAITQ

ACPKVSFEPIPIHYCAPAGFAILKCNDKKENGTGPCKNVSTVQCTHGIKP

VVSTQLLLNGSLAEEEIIIRSENITNNAKTIIVQLNESVEINCTRPNNNT

RKSIRIGPGQAFYATGDIIGDIRQAHCNISGTKWNKTLQQVAKKLREHEN

NKTIIFKPSSGGDLEITTHSENCRGEFFYCNTSGLENSTWIGNGTKNNNN

TNDTITLPCRIKQIINMWQGVGQAMYAPPIEGKITCKSNITGLLLTRDGG

NNNTNETEIFRPGGGDMRDNWRSELYKYKVVKIEPLGVAPTKAKRRVVES

EKSAVGIGAVFLGFLGAAGSTMGAASITLTVQARQLLSGIVQQQSNLLRA

TEAQQHLLQLTVWGIKQLQARVLAVERYLKDQQLLGIWGCSGKLICTTTV

PWNSSWSNKSQDEIWDNMTWMEWEREINNYTDIIYSLIEESQNQQEKNEQ

ELLALDKWASLWNWFDITNWLW

M CONSENSUS GAG

SEQ ID NO: 38

MGARASVLSGGKLDAWEKIRLRPGGKKKYRLKHLVWASRELERFALNPGL

LETSEGCKQIIGQLQPALQTGSEELRSLYNTVATLYCVHQRIEVKDTKEA

LEKIEEEQNKSQQKTQQAADKGNSSKVSQNYPIVQNLQGQMVHQAISPR

TLNAWVKVIEEKAFSPEVIPMFSALSEGATPQDLNTMLNTVGGHQAAMQM

LKDTINEEAAEWDRLHPVHAGPIPPGQMREPRGSDIAGTTSTLQEQIAWM

TSNPPIPVGEIYKRWIILGLNKIVRMYSPVSILDIRQGPKEPFRDYVDRF

EKTLRAEQATQDVKNWMTDTLLVQNANPDCKTILKALGPGATLEEMMTAC

QGVGGPGHKARVLAEAMSQVTNAAIMMQRCNFKGQRRIIKCFNCGKEGHI

ARNCRAPRKKGCWKCGKEGHQMHDCTERQANFLGKIWPSNKGRPGNFLQS

RPEPTAPPAESFGFGEEITPSPKQEPKDKEPPLTSLKSLFGNDPLSQ

M CONSENSUS POL

SEQ ID NO: 39

MAPISPIETVPVKLKPGMDGPKVKQWPLTEEKIKALTEICTEMEKEGKIS

KIGPENPYNTPIFAIKKKDSTKWRKLVDFRELNKRIQDFWEVQLGIPHPA

SEQUENCE APPENDIX

```
GLKKKKSVTVLDVGDAYFSVPLDEDFRKYTAFTIPSINNETPGIRYQYNV

LPQGWKGSPAIFQSSMTKILEPFRTQNPEIVIYQYMDHLYVGSDLEIGQH

RAKIEELREHLLRWGFTTPDKKHQKEPPFLWMGYELHPDKWTVQPIQLPE

KDSWTVNDIQKLVGKLNWASQIYPGIKVKQLCKLLRGAKALTDIVPLTEE

AELELAENREILKEPVHGVYYDPSKDLIAEIQKQGQDQWTYQIYQEPFKN

LKTGKYAKMRSAHTNDVKQLTEAVQKIATESIVIWGKTPKFRLPIQKETW

ETWWTEYWQATWIPEWEFVNTPPLVKLWYQLEKEPIAGAETFYVDGAANR

ETKLGKAGYVTDRGRQKVVSLTETTNQKTELQAIHLALQDSGSEVNIVTD

SQYALGIIQAQPDKSESELVNQIIEQLIKKEKVYLSWVPAHKGIGGNEQV

DKLVSTGIRKVLFLDGIDKAQEEHEKYHSNWRAMASDFNLPPIVAKEIVA

SCDKCQLKGEAMHGQVDCSPGIWQLACTHLEGKIILVAVHVASGYIEAEV

IPAETGQETAYFILKLAGRWPVKVIHTDNGSNFTSAAVKAACWWAGIQQE
```

SEQUENCE APPENDIX

```
FGIEYNPQSQGVVESMNKELKKIIGQVRDQAEHLKTAVQMAVFIHNFKRK

GGIGGYSAGERIIDIIATDIQTKELQKQITKIQNFRVYYRDSRDPIWKGP

AKLLWKGEGAVVIQDNSDIKVVPRRKAKIIRDYGKQMAGDDCVAGRQDED
```

Other Embodiments

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth.

All publications and patent applications mentioned in this specification are herein incorporated by reference to the same extent as if each independent publication or patent application was specifically and individually indicated to be incorporated by reference in their entirety.

What is claimed is:

1. A nucleic acid molecule encoding a polypeptide comprising a sequence at least 99% identical to SEQ ID NO:9.

2. A vector comprising the nucleic acid molecule of claim 1.

3. The vector of claim 2, wherein said vector is an adenoviral vector.

4. The vector of claim 2, wherein said vector is a pox virus vector.

5. The vector of claim 3, wherein said vector is selected from the group consisting of adenovirus serotype 26 (Ad26), adenovirus serotype 34 (Ad34), adenovirus serotype 35 (Ad35), adenovirus serotype 48 (Ad48), and adenovirus serotype 5 HVR48 (Ad5HVR48).

6. The vector of claim 5, wherein said vector is the Ad26 vector.

7. The vector of claim 4, wherein the vector is a modified vaccinia virus Ankara (MVA).

8. A pharmaceutical composition comprising the vector of claim 2 and a pharmaceutically acceptable carrier, excipient, or diluent.

9. The pharmaceutical composition of claim 8, wherein said vector is an adenoviral vector.

10. The pharmaceutical composition of claim 8, wherein the vector is a pox virus vector.

11. The pharmaceutical composition of claim 8, wherein said vector is selected from the group consisting of Ad26, Ad34, Ad35, Ad48, Ad5HVR48, and MVA.

12. The pharmaceutical composition of claim 8, wherein said vector is the Ad26.

13. The pharmaceutical composition of claim 8, wherein said vector is the MVA vector.

14. A kit comprising:
   a) the pharmaceutical composition of claim 8;
   b) instructions for use thereof; and, optionally,
   c) an adjuvant.

15. A method for inducing an HIV-1 specific immune response in a mammal comprising administering to said mammal the nucleic acid of claim 1 or a vector comprising said nucleic acid.

16. The method of claim 15, wherein said nucleic acid or said vector is in a pharmaceutical composition.

17. The method of claim 15, wherein said vector is the Ad26 vector.

18. The method of claim 15, wherein said vector is the MVA vector.

19. The method of claim 15, wherein said mammal is a human.

20. A method of manufacturing the pharmaceutical composition of claim 8, said method comprising combining a vector comprising a nucleic acid molecule encoding a polypeptide comprising a sequence at least 99% identical to SEQ ID NO:9 with a pharmaceutically acceptable carrier, excipient, or diluent.

* * * * *

SEQUENCE LISTING

```
<160> NUMBER OF SEQ ID NOS: 685

<210> SEQ ID NO 1
<211> LENGTH: 857
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Met Arg Val Thr Gly Ile Arg Lys Asn Tyr Gln His Leu Trp Arg Trp
1               5                   10                  15

Gly Thr Met Leu Leu Gly Ile Leu Met Ile Cys Ser Ala Ala Gly Lys
                20                  25                  30

Leu Trp Val Thr Val Tyr Tyr Gly Val Pro Val Trp Lys Glu Ala Thr
            35                  40                  45

Thr Thr Leu Phe Cys Ala Ser Asp Ala Lys Ala Tyr Asp Thr Glu Val
        50                  55                  60

His Asn Val Trp Ala Thr His Ala Cys Val Pro Thr Asp Pro Asn Pro
65                  70                  75                  80

Gln Glu Val Val Leu Glu Asn Val Thr Glu Asn Phe Asn Met Trp Lys
                85                  90                  95

Asn Asn Met Val Glu Gln Met His Glu Asp Ile Ile Ser Leu Trp Asp
                100                 105                 110

Gln Ser Leu Lys Pro Cys Val Lys Leu Thr Pro Leu Cys Val Thr Leu
            115                 120                 125

Asn Cys Thr Asp Asp Val Arg Asn Val Thr Asn Asn Ala Thr Asn Thr
        130                 135                 140

Asn Ser Ser Trp Gly Glu Pro Met Glu Lys Gly Glu Ile Lys Asn Cys
145                 150                 155                 160

Ser Phe Asn Ile Thr Thr Ser Ile Arg Asn Lys Val Gln Lys Gln Tyr
                165                 170                 175

Ala Leu Phe Tyr Lys Leu Asp Val Val Pro Ile Asp Asn Asp Ser Asn
                180                 185                 190
```

```
Asn Thr Asn Tyr Arg Leu Ile Ser Cys Asn Thr Ser Val Ile Thr Gln
            195                 200                 205

Ala Cys Pro Lys Val Ser Phe Glu Pro Ile Pro Ile His Tyr Cys Ala
210                 215                 220

Pro Ala Gly Phe Ala Ile Leu Lys Cys Asn Asp Lys Lys Phe Asn Gly
225                 230                 235                 240

Thr Gly Pro Cys Thr Asn Val Ser Thr Val Gln Cys Thr His Gly Ile
            245                 250                 255

Arg Pro Val Val Ser Thr Gln Leu Leu Leu Asn Gly Ser Leu Ala Glu
                260                 265                 270

Glu Glu Val Val Ile Arg Ser Glu Asn Phe Thr Asn Asn Ala Lys Thr
            275                 280                 285

Ile Met Val Gln Leu Asn Val Ser Val Glu Ile Asn Cys Thr Arg Pro
            290                 295                 300

Asn Asn Asn Thr Arg Lys Ser Ile His Ile Gly Pro Gly Arg Ala Phe
305                 310                 315                 320

Tyr Thr Ala Gly Asp Ile Ile Gly Asp Ile Arg Gln Ala His Cys Asn
                325                 330                 335

Ile Ser Arg Ala Asn Trp Asn Asn Thr Leu Arg Gln Ile Val Glu Lys
            340                 345                 350

Leu Gly Lys Gln Phe Gly Asn Asn Lys Thr Ile Val Phe Asn His Ser
            355                 360                 365

Ser Gly Gly Asp Pro Glu Ile Val Met His Ser Phe Asn Cys Gly Gly
    370                 375                 380

Glu Phe Phe Tyr Cys Asn Ser Thr Lys Leu Phe Asn Ser Thr Trp Thr
385                 390                 395                 400

Trp Asn Asn Ser Thr Trp Asn Asn Thr Lys Arg Ser Asn Asp Thr Glu
                405                 410                 415

Glu His Ile Thr Leu Pro Cys Arg Ile Lys Gln Ile Ile Asn Met Trp
            420                 425                 430

Gln Glu Val Gly Lys Ala Met Tyr Ala Pro Pro Ile Arg Gly Gln Ile
            435                 440                 445

Arg Cys Ser Ser Asn Ile Thr Gly Leu Leu Leu Thr Arg Asp Gly Gly
            450                 455                 460

Asn Asp Thr Ser Gly Thr Glu Ile Phe Arg Pro Gly Gly Gly Asp Met
465                 470                 475                 480

Arg Asp Asn Trp Arg Ser Glu Leu Tyr Lys Tyr Lys Val Val Lys Ile
                485                 490                 495

Glu Pro Leu Gly Val Ala Pro Thr Lys Ala Lys Arg Arg Val Val Gln
            500                 505                 510

Arg Glu Lys Arg Ala Val Gly Ile Gly Ala Val Phe Leu Gly Phe Leu
            515                 520                 525

Gly Ala Ala Gly Ser Thr Met Gly Ala Ala Ser Met Thr Leu Thr Val
    530                 535                 540

Gln Ala Arg Leu Leu Leu Ser Gly Ile Val Gln Gln Asn Asn Leu
545                 550                 555                 560

Leu Arg Ala Ile Glu Ala Gln Gln His Leu Leu Gln Leu Thr Val Trp
                565                 570                 575

Gly Ile Lys Gln Leu Gln Ala Arg Val Leu Ala Val Glu Arg Tyr Leu
            580                 585                 590

Lys Asp Gln Gln Leu Leu Gly Ile Trp Gly Cys Ser Gly Lys Leu Ile
            595                 600                 605
```

```
Cys Thr Thr Val Pro Trp Asn Ala Ser Trp Ser Asn Lys Ser Leu
    610                 615                 620

Asp Lys Ile Trp Asn Asn Met Thr Trp Met Glu Trp Glu Arg Glu Ile
625                 630                 635                 640

Asn Asn Tyr Thr Ser Leu Ile Tyr Thr Leu Ile Glu Glu Ser Gln Asn
                645                 650                 655

Gln Gln Glu Lys Asn Glu Gln Glu Leu Leu Glu Leu Asp Lys Trp Ala
            660                 665                 670

Ser Leu Trp Asn Trp Phe Asp Ile Ser Asn Trp Leu Trp Tyr Ile Lys
                675                 680                 685

Ile Phe Ile Met Ile Val Gly Gly Leu Val Gly Leu Arg Ile Val Phe
690                 695                 700

Ala Val Leu Ser Ile Val Asn Arg Val Arg Gln Gly Tyr Ser Pro Leu
705                 710                 715                 720

Ser Phe Gln Thr Arg Leu Pro Ala Pro Arg Gly Pro Asp Arg Pro Glu
                725                 730                 735

Gly Ile Glu Glu Glu Gly Gly Glu Arg Asp Arg Asp Arg Ser Val Arg
                740                 745                 750

Leu Val Asp Gly Phe Leu Val Leu Ile Trp Asp Asp Leu Gln Ser Leu
                755                 760                 765

Cys Leu Phe Ser Tyr His Arg Leu Arg Asp Leu Leu Leu Ile Val Glu
770                 775                 780

Leu Leu Gly Arg Arg Gly Trp Glu Ala Leu Lys Tyr Trp Trp Asn Leu
785                 790                 795                 800

Leu Gln Tyr Trp Ser Gln Glu Leu Lys Asn Ser Ala Ile Ser Leu Leu
                805                 810                 815

Asn Ala Thr Ala Val Ala Val Ala Glu Gly Thr Asp Arg Val Ile Glu
                820                 825                 830

Ala Leu Gln Arg Ala Cys Arg Ala Ile Leu His Ile Pro Arg Arg Ile
            835                 840                 845

Arg Gln Gly Leu Glu Arg Leu Leu Leu
    850                 855
```

<210> SEQ ID NO 2
<211> LENGTH: 867
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 2

```
Met Arg Val Arg Gly Ile Gln Arg Asn Trp Pro Gln Trp Trp Ile Trp
1               5                   10                  15

Gly Ile Leu Gly Phe Trp Met Ile Ile Cys Arg Val Met Gly Asn
                20                  25                  30

Leu Trp Val Thr Val Tyr Tyr Gly Val Pro Val Trp Lys Glu Ala Lys
            35                  40                  45

Thr Thr Leu Phe Cys Ala Ser Asp Ala Lys Ala Tyr Glu Lys Glu Val
    50                  55                  60

His Asn Val Trp Ala Thr His Ala Cys Val Pro Thr Asp Pro Asn Pro
65                  70                  75                  80

Gln Glu Met Val Leu Glu Asn Val Thr Glu Asn Phe Asn Met Trp Lys
                85                  90                  95

Asn Asp Met Val Asp Gln Met His Glu Asp Ile Ile Arg Leu Trp Asp
            100                 105                 110
```

-continued

```
Gln Ser Leu Lys Pro Cys Val Lys Leu Thr Pro Leu Cys Val Thr Leu
    115                 120                 125
Glu Cys Arg Asn Val Arg Asn Val Ser Ser Asn Gly Thr Tyr Asn Ile
130                 135                 140
Ile His Asn Glu Thr Tyr Lys Glu Met Lys Asn Cys Ser Phe Asn Ala
145                 150                 155                 160
Thr Thr Val Val Glu Asp Arg Lys Gln Lys Val His Ala Leu Phe Tyr
                165                 170                 175
Arg Leu Asp Ile Val Pro Leu Asp Glu Asn Asn Ser Ser Glu Lys Ser
            180                 185                 190
Ser Glu Asn Ser Ser Glu Tyr Tyr Arg Leu Ile Asn Cys Asn Thr Ser
        195                 200                 205
Ala Ile Thr Gln Ala Cys Pro Lys Val Ser Phe Asp Pro Ile Pro Ile
    210                 215                 220
His Tyr Cys Ala Pro Ala Gly Tyr Ala Ile Leu Lys Cys Asn Asn Lys
225                 230                 235                 240
Thr Phe Asn Gly Thr Gly Pro Cys Asn Asn Val Ser Thr Val Gln Cys
                245                 250                 255
Thr His Gly Ile Lys Pro Val Val Ser Thr Gln Leu Leu Leu Asn Gly
            260                 265                 270
Ser Leu Ala Glu Glu Glu Ile Ile Ile Arg Ser Glu Asn Leu Thr Asn
        275                 280                 285
Asn Ala Lys Thr Ile Ile Val His Leu Asn Glu Thr Val Asn Ile Thr
    290                 295                 300
Cys Thr Arg Pro Asn Asn Thr Arg Lys Ser Ile Arg Ile Gly Pro
305                 310                 315                 320
Gly Gln Thr Phe Tyr Ala Thr Gly Asp Ile Ile Gly Asp Ile Arg Gln
                325                 330                 335
Ala His Cys Asn Leu Ser Arg Asp Gly Trp Asn Lys Thr Leu Gln Gly
            340                 345                 350
Val Lys Lys Lys Leu Ala Glu His Phe Pro Asn Lys Thr Ile Asn Phe
        355                 360                 365
Thr Ser Ser Ser Gly Gly Asp Leu Glu Ile Thr Thr His Ser Phe Asn
    370                 375                 380
Cys Arg Gly Glu Phe Phe Tyr Cys Asn Thr Ser Gly Leu Phe Asn Gly
385                 390                 395                 400
Thr Tyr Met Pro Asn Gly Thr Asn Ser Asn Ser Ser Asn Ile Thr
                405                 410                 415
Leu Pro Cys Arg Ile Lys Gln Ile Ile Asn Met Trp Gln Glu Val Gly
            420                 425                 430
Arg Ala Met Tyr Ala Pro Pro Ile Ala Gly Asn Ile Thr Cys Arg Ser
        435                 440                 445
Asn Ile Thr Gly Leu Leu Leu Thr Arg Asp Gly Gly Ser Asn Asn Gly
    450                 455                 460
Val Pro Asn Asp Thr Glu Thr Phe Arg Pro Gly Gly Asp Met Arg
465                 470                 475                 480
Asn Asn Trp Arg Ser Glu Leu Tyr Lys Tyr Lys Val Val Glu Val Lys
                485                 490                 495
Pro Leu Gly Val Ala Pro Thr Glu Ala Lys Arg Arg Val Val Glu Arg
            500                 505                 510
Glu Lys Arg Ala Val Gly Ile Gly Ala Val Phe Leu Gly Ile Leu Gly
        515                 520                 525
```

Ala Ala Gly Ser Thr Met Gly Ala Ala Ser Ile Thr Leu Thr Val Gln
530                535                540

Ala Arg Gln Leu Leu Ser Gly Ile Val Gln Gln Ser Asn Leu Leu
545                550                555                560

Arg Ala Ile Glu Ala Gln Gln His Met Leu Gln Leu Thr Val Trp Gly
                565                570                575

Ile Lys Gln Leu Gln Thr Arg Val Leu Ala Ile Glu Arg Tyr Leu Gln
                580                585                590

Asp Gln Gln Leu Leu Gly Leu Trp Gly Cys Ser Gly Lys Leu Ile Cys
            595                600                605

Thr Thr Ala Val Pro Trp Asn Thr Ser Trp Ser Asn Lys Ser Gln Thr
610                615                620

Asp Ile Trp Asp Asn Met Thr Trp Met Gln Trp Asp Lys Glu Ile Gly
625                630                635                640

Asn Tyr Thr Gly Glu Ile Tyr Arg Leu Leu Glu Ser Gln Asn Gln
                645                650                655

Gln Glu Lys Asn Glu Lys Asp Leu Leu Ala Leu Asp Ser Trp Lys Asn
            660                665                670

Leu Trp Asn Trp Phe Asp Ile Thr Asn Trp Leu Trp Tyr Ile Lys Ile
            675                680                685

Phe Ile Met Ile Val Gly Gly Leu Ile Gly Leu Arg Ile Ile Leu Gly
690                695                700

Val Leu Ser Ile Val Arg Val Arg Gln Gly Tyr Ser Pro Leu Ser
705                710                715                720

Phe Gln Thr Leu Thr Pro Asn Pro Arg Gly Leu Asp Arg Leu Gly Arg
                725                730                735

Ile Glu Glu Glu Gly Gly Glu Gln Asp Arg Asp Arg Ser Ile Arg Leu
            740                745                750

Val Asn Gly Phe Leu Ala Leu Ala Trp Asp Asp Leu Arg Ser Leu Cys
            755                760                765

Leu Phe Ser Tyr His Gln Leu Arg Asp Phe Ile Leu Ile Val Ala Arg
            770                775                780

Ala Val Glu Leu Leu Gly Arg Ser Ser Leu Arg Gly Leu Gln Arg Gly
785                790                795                800

Trp Glu Ala Leu Lys Tyr Leu Gly Asn Leu Val Gln Tyr Trp Gly Leu
                805                810                815

Glu Leu Lys Lys Gly Ala Ile Ser Leu Leu Asp Thr Ile Ala Ile Ala
            820                825                830

Val Ala Glu Gly Thr Asp Arg Ile Ile Glu Leu Ile Gln Ser Ile Cys
            835                840                845

Arg Ala Ile Arg Asn Ile Pro Arg Arg Ile Arg Gln Gly Phe Glu Ala
850                855                860

Ser Leu Leu
865

<210> SEQ ID NO 3
<211> LENGTH: 500
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Met Gly Ala Arg Ala Ser Val Leu Ser Gly Gly Glu Leu Asp Arg Trp
1               5                   10                  15

-continued

Glu Lys Ile Arg Leu Arg Pro Gly Gly Lys Lys Tyr Arg Leu Lys
            20                  25                  30

His Ile Val Trp Ala Ser Arg Glu Leu Glu Arg Phe Ala Val Asn Pro
                35                  40                  45

Gly Leu Leu Glu Thr Ser Glu Gly Cys Arg Gln Ile Leu Gly Gln Leu
 50                  55                  60

Gln Pro Ser Leu Gln Thr Gly Ser Glu Glu Leu Arg Ser Leu Tyr Asn
 65                  70                  75                  80

Thr Val Ala Thr Leu Tyr Cys Val His Gln Arg Ile Glu Ile Lys Asp
                85                  90                  95

Thr Lys Glu Ala Leu Glu Lys Ile Glu Glu Gln Asn Lys Ser Lys
            100                 105                 110

Lys Lys Ala Gln Gln Ala Ala Ala Asp Thr Gly Asn Ser Ser Gln Val
            115                 120                 125

Ser Gln Asn Tyr Pro Ile Val Gln Asn Ile Gln Gly Gln Met Val His
130                 135                 140

Gln Ala Ile Ser Pro Arg Thr Leu Asn Ala Trp Val Lys Val Val Glu
145                 150                 155                 160

Glu Lys Ala Phe Ser Pro Glu Val Ile Pro Met Phe Ser Ala Leu Ser
                165                 170                 175

Glu Gly Ala Thr Pro Gln Asp Leu Asn Thr Met Leu Asn Thr Val Gly
            180                 185                 190

Gly His Gln Ala Ala Met Gln Met Leu Lys Glu Thr Ile Asn Glu Glu
            195                 200                 205

Ala Ala Glu Trp Asp Arg Val His Pro Val His Ala Gly Pro Ile Ala
210                 215                 220

Pro Gly Gln Met Arg Glu Pro Arg Gly Ser Asp Ile Ala Gly Thr Thr
225                 230                 235                 240

Ser Thr Leu Gln Glu Gln Ile Gly Trp Met Thr Asn Asn Pro Pro Ile
                245                 250                 255

Pro Val Gly Glu Ile Tyr Lys Arg Trp Ile Ile Leu Gly Leu Asn Lys
            260                 265                 270

Ile Val Arg Met Tyr Ser Pro Val Ser Ile Leu Asp Ile Arg Gln Gly
            275                 280                 285

Pro Lys Glu Pro Phe Arg Asp Tyr Val Asp Arg Phe Tyr Lys Thr Leu
            290                 295                 300

Arg Ala Glu Gln Ala Ser Gln Asp Val Lys Asn Trp Met Thr Glu Thr
305                 310                 315                 320

Leu Leu Val Gln Asn Ala Asn Pro Asp Cys Lys Thr Ile Leu Lys Ala
                325                 330                 335

Leu Gly Pro Ala Ala Thr Leu Glu Glu Met Met Thr Ala Cys Gln Gly
            340                 345                 350

Val Gly Gly Pro Gly His Lys Ala Arg Val Leu Ala Glu Ala Met Ser
            355                 360                 365

Gln Val Thr Asn Ser Ala Thr Ile Met Met Gln Arg Gly Asn Phe Arg
            370                 375                 380

Asn Gln Arg Lys Thr Val Lys Cys Phe Asn Cys Gly Lys Glu Gly His
385                 390                 395                 400

Ile Ala Lys Asn Cys Arg Ala Pro Arg Lys Gly Cys Trp Lys Cys
                405                 410                 415

Gly Lys Glu Gly His Gln Met Lys Asp Cys Thr Glu Arg Gln Ala Asn
            420                 425                 430

```
Phe Leu Gly Lys Ile Trp Pro Ser Asn Lys Gly Arg Pro Gly Asn Phe
            435                 440                 445

Leu Gln Asn Arg Pro Glu Pro Thr Ala Pro Pro Glu Glu Ser Phe Arg
    450                 455                 460

Phe Gly Glu Glu Thr Thr Thr Pro Ser Gln Lys Gln Glu Pro Ile Asp
465                 470                 475                 480

Lys Glu Met Tyr Pro Leu Ala Ser Leu Lys Ser Leu Phe Gly Asn Asp
                485                 490                 495

Pro Ser Ser Gln
            500

<210> SEQ ID NO 4
<211> LENGTH: 491
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Met Gly Ala Arg Ala Ser Ile Leu Arg Gly Gly Lys Leu Asp Lys Trp
1               5                   10                  15

Glu Lys Ile Arg Leu Arg Pro Gly Gly Lys Lys His Tyr Met Leu Lys
            20                  25                  30

His Leu Val Trp Ala Ser Arg Glu Leu Glu Arg Phe Ala Leu Asn Pro
        35                  40                  45

Gly Leu Leu Glu Thr Ser Glu Gly Cys Lys Gln Ile Ile Lys Gln Leu
    50                  55                  60

Gln Pro Ala Leu Gln Thr Gly Thr Glu Glu Leu Arg Ser Leu Phe Asn
65                  70                  75                  80

Thr Val Ala Thr Leu Tyr Cys Val His Ala Glu Ile Glu Val Arg Asp
                85                  90                  95

Thr Lys Glu Ala Leu Asp Lys Ile Glu Glu Glu Gln Asn Lys Ser Gln
            100                 105                 110

Gln Lys Thr Gln Gln Ala Lys Glu Ala Asp Gly Lys Val Ser Gln Asn
        115                 120                 125

Tyr Pro Ile Val Gln Asn Leu Gln Gly Gln Met Val His Gln Pro Ile
    130                 135                 140

Ser Pro Arg Thr Leu Asn Ala Trp Val Lys Val Ile Glu Glu Lys Ala
145                 150                 155                 160

Phe Ser Pro Glu Val Ile Pro Met Phe Thr Ala Leu Ser Glu Gly Ala
                165                 170                 175

Thr Pro Gln Asp Leu Asn Thr Met Leu Asn Thr Val Gly Gly His Gln
            180                 185                 190

Ala Ala Met Gln Met Leu Lys Asp Thr Ile Asn Glu Glu Ala Ala Glu
        195                 200                 205

Trp Asp Arg Leu His Pro Val His Ala Gly Pro Val Ala Pro Gly Gln
    210                 215                 220

Met Arg Glu Pro Arg Gly Ser Asp Ile Ala Gly Thr Thr Ser Asn Leu
225                 230                 235                 240

Gln Glu Gln Ile Ala Trp Met Thr Ser Asn Pro Pro Ile Pro Val Gly
                245                 250                 255

Asp Ile Tyr Lys Arg Trp Ile Ile Leu Gly Leu Asn Lys Ile Val Arg
            260                 265                 270

Met Tyr Ser Pro Thr Ser Ile Leu Asp Ile Lys Gln Gly Pro Lys Glu
        275                 280                 285
```

```
Pro Phe Arg Asp Tyr Val Asp Arg Phe Phe Lys Thr Leu Arg Ala Glu
        290                 295                 300

Gln Ala Thr Gln Asp Val Lys Asn Trp Met Thr Asp Thr Leu Leu Val
305                 310                 315                 320

Gln Asn Ala Asn Pro Asp Cys Lys Thr Ile Leu Arg Ala Leu Gly Pro
                325                 330                 335

Gly Ala Thr Leu Glu Glu Met Met Thr Ala Cys Gln Gly Val Gly Gly
            340                 345                 350

Pro Ser His Lys Ala Arg Val Leu Ala Glu Ala Met Ser Gln Thr Asn
        355                 360                 365

Ser Thr Ile Leu Met Gln Arg Ser Asn Phe Lys Gly Ser Lys Arg Ile
    370                 375                 380

Val Lys Cys Phe Asn Cys Gly Lys Glu Gly His Ile Ala Arg Asn Cys
385                 390                 395                 400

Arg Ala Pro Arg Lys Lys Gly Cys Trp Lys Cys Gly Lys Glu Gly His
                405                 410                 415

Gln Met Lys Asp Cys Thr Glu Arg Gln Ala Asn Phe Leu Gly Lys Ile
            420                 425                 430

Trp Pro Ser His Lys Gly Arg Pro Gly Asn Phe Leu Gln Ser Arg Pro
        435                 440                 445

Glu Pro Thr Ala Pro Pro Ala Glu Ser Phe Arg Phe Glu Glu Thr Thr
    450                 455                 460

Pro Ala Pro Lys Gln Glu Pro Lys Asp Arg Glu Pro Leu Thr Ser Leu
465                 470                 475                 480

Arg Ser Leu Phe Gly Ser Asp Pro Leu Ser Gln
                485                 490

<210> SEQ ID NO 5
<211> LENGTH: 999
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Phe Phe Arg Glu Asn Leu Ala Phe Gln Gln Gly Glu Ala Arg Glu Phe
1               5                   10                  15

Pro Ser Glu Gln Thr Arg Ala Asn Ser Pro Thr Ser Arg Glu Leu Gln
            20                  25                  30

Val Arg Gly Asp Asn Pro His Ser Glu Ala Gly Ala Glu Arg Gln Gly
        35                  40                  45

Thr Leu Asn Phe Pro Gln Ile Thr Leu Trp Gln Arg Pro Leu Val Ser
    50                  55                  60

Ile Lys Val Gly Gly Gln Ile Arg Glu Ala Leu Leu Asp Thr Gly Ala
65                  70                  75                  80

Asp Asp Thr Val Leu Glu Asp Ile Asn Leu Pro Gly Lys Trp Lys Pro
                85                  90                  95

Lys Met Ile Gly Gly Ile Gly Gly Phe Ile Lys Val Arg Gln Tyr Asp
            100                 105                 110

Gln Ile Leu Ile Glu Ile Cys Gly Lys Lys Ala Ile Gly Thr Val Leu
        115                 120                 125

Val Gly Pro Thr Pro Val Asn Ile Ile Gly Arg Asn Met Leu Thr Gln
    130                 135                 140

Leu Gly Cys Thr Leu Asn Phe Pro Ile Ser Pro Ile Glu Thr Val Pro
```

-continued

```
            145                 150                 155                 160
Val Lys Leu Lys Pro Gly Met Asp Gly Pro Arg Val Lys Gln Trp Pro
                165                 170                 175
Leu Thr Glu Glu Lys Ile Lys Ala Leu Thr Ala Ile Cys Glu Glu Met
            180                 185                 190
Glu Lys Glu Gly Lys Ile Thr Lys Ile Gly Pro Glu Asn Pro Tyr Asn
            195                 200                 205
Thr Pro Val Phe Ala Ile Lys Lys Lys Asp Ser Thr Lys Trp Arg Lys
        210                 215                 220
Leu Val Asp Phe Arg Glu Leu Asn Lys Arg Thr Gln Asp Phe Trp Glu
225                 230                 235                 240
Val Gln Leu Gly Ile Pro His Pro Ala Gly Leu Lys Lys Lys Lys Ser
                245                 250                 255
Val Thr Val Leu Asp Val Gly Asp Ala Tyr Phe Ser Val Pro Leu Asp
            260                 265                 270
Glu Gly Phe Arg Lys Tyr Thr Ala Phe Thr Ile Pro Ser Thr Asn Asn
        275                 280                 285
Glu Thr Pro Gly Ile Arg Tyr Gln Tyr Asn Val Leu Pro Gln Gly Trp
    290                 295                 300
Lys Gly Ser Pro Ala Ile Phe Gln Cys Ser Met Thr Arg Ile Leu Glu
305                 310                 315                 320
Pro Phe Arg Ala Lys Asn Pro Glu Ile Val Ile Tyr Gln Tyr Met Asp
                325                 330                 335
Asp Leu Tyr Val Gly Ser Asp Leu Glu Ile Gly Gln His Arg Ala Lys
            340                 345                 350
Ile Glu Glu Leu Arg Glu His Leu Leu Lys Trp Gly Phe Thr Thr Pro
        355                 360                 365
Asp Lys Lys His Gln Lys Glu Pro Pro Phe Leu Trp Met Gly Tyr Glu
    370                 375                 380
Leu His Pro Asp Lys Trp Thr Val Gln Pro Ile Gln Leu Pro Glu Lys
385                 390                 395                 400
Asp Ser Trp Thr Val Asn Asp Ile Gln Lys Leu Val Gly Lys Leu Asn
                405                 410                 415
Trp Ala Ser Gln Ile Tyr Pro Gly Ile Lys Val Arg Gln Leu Cys Lys
            420                 425                 430
Leu Leu Arg Gly Ala Lys Ala Leu Thr Asp Ile Val Pro Leu Thr Glu
        435                 440                 445
Glu Ala Glu Leu Glu Leu Ala Glu Asn Arg Glu Ile Leu Lys Glu Pro
    450                 455                 460
Val His Gly Val Tyr Tyr Asp Pro Ser Lys Asp Leu Ile Ala Glu Ile
465                 470                 475                 480
Gln Lys Gln Gly His Asp Gln Trp Thr Tyr Gln Ile Tyr Gln Glu Pro
                485                 490                 495
Phe Lys Asn Leu Lys Thr Gly Lys Tyr Ala Lys Met Arg Thr Ala His
            500                 505                 510
Thr Asn Asp Val Lys Gln Leu Thr Glu Ala Val Gln Lys Ile Ala Met
        515                 520                 525
Glu Ser Ile Val Ile Trp Gly Lys Thr Pro Lys Phe Arg Leu Pro Ile
    530                 535                 540
Gln Lys Glu Thr Trp Glu Thr Trp Trp Thr Asp Tyr Trp Gln Ala Thr
545                 550                 555                 560
Trp Ile Pro Glu Trp Glu Phe Val Asn Thr Pro Pro Leu Val Lys Leu
                565                 570                 575
```

```
Trp Tyr Gln Leu Glu Lys Asp Pro Ile Ala Gly Val Glu Thr Phe Tyr
            580                 585                 590

Val Asp Gly Ala Ala Asn Arg Glu Thr Lys Leu Gly Lys Ala Gly Tyr
        595                 600                 605

Val Thr Asp Arg Gly Arg Gln Lys Ile Val Ser Leu Thr Glu Thr Thr
    610                 615                 620

Asn Gln Lys Thr Glu Leu Gln Ala Ile Tyr Leu Ala Leu Gln Asp Ser
625                 630                 635                 640

Gly Ser Glu Val Asn Ile Val Thr Asp Ser Gln Tyr Ala Leu Gly Ile
                645                 650                 655

Ile Gln Ala Gln Pro Asp Lys Ser Glu Ser Glu Leu Val Asn Gln Ile
            660                 665                 670

Ile Glu Gln Leu Ile Lys Lys Glu Arg Val Tyr Leu Ser Trp Val Pro
        675                 680                 685

Ala His Lys Gly Ile Gly Gly Asn Glu Gln Val Asp Lys Leu Val Ser
    690                 695                 700

Ser Gly Ile Arg Lys Val Leu Phe Leu Asp Gly Ile Asp Lys Ala Gln
705                 710                 715                 720

Glu Glu His Glu Lys Tyr His Ser Asn Trp Arg Ala Met Ala Ser Asp
                725                 730                 735

Phe Asn Leu Pro Pro Val Val Ala Lys Glu Ile Val Ala Ser Cys Asp
            740                 745                 750

Gln Cys Gln Leu Lys Gly Glu Ala Met His Gly Gln Val Asp Cys Ser
        755                 760                 765

Pro Gly Ile Trp Gln Leu Asp Cys Thr His Leu Glu Gly Lys Ile Ile
    770                 775                 780

Leu Val Ala Val His Val Ala Ser Gly Tyr Ile Glu Ala Glu Val Ile
785                 790                 795                 800

Pro Ala Glu Thr Gly Gln Glu Thr Ala Tyr Phe Ile Leu Lys Leu Ala
                805                 810                 815

Gly Arg Trp Pro Val Lys Val Ile His Thr Asp Asn Gly Ser Asn Phe
            820                 825                 830

Thr Ser Ala Ala Val Lys Ala Ala Cys Trp Trp Ala Gly Ile Gln Gln
        835                 840                 845

Glu Phe Gly Ile Pro Tyr Asn Pro Gln Ser Gln Gly Val Val Glu Ser
    850                 855                 860

Met Asn Lys Glu Leu Lys Lys Ile Ile Gly Gln Val Arg Asp Gln Ala
865                 870                 875                 880

Glu His Leu Lys Thr Ala Val Gln Met Ala Val Phe Ile His Asn Phe
                885                 890                 895

Lys Arg Lys Gly Gly Ile Gly Gly Tyr Ser Ala Gly Glu Arg Ile Ile
            900                 905                 910

Asp Ile Ile Ala Thr Asp Ile Gln Thr Lys Glu Leu Gln Lys Gln Ile
        915                 920                 925

Ile Lys Ile Gln Asn Phe Arg Val Tyr Tyr Arg Asp Ser Arg Asp Pro
    930                 935                 940

Ile Trp Lys Gly Pro Ala Lys Leu Leu Trp Lys Gly Glu Gly Ala Val
945                 950                 955                 960

Val Ile Gln Asp Asn Ser Asp Ile Lys Val Val Pro Arg Arg Lys Val
                965                 970                 975

Lys Ile Ile Lys Asp Tyr Gly Lys Gln Met Ala Gly Ala Asp Cys Val
            980                 985                 990
```

Ala Gly Arg Gln Asp Glu Asp
        995

<210> SEQ ID NO 6
<211> LENGTH: 1003
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Phe Phe Arg Glu Asn Leu Ala Phe Pro Gln Gly Lys Ala Arg Glu Phe
1               5                   10                  15

Ser Ser Glu Gln Thr Arg Ala Asn Ser Pro Thr Arg Arg Glu Leu Gln
            20                  25                  30

Val Trp Gly Arg Asp Asn Asn Ser Leu Ser Glu Ala Gly Ala Asp Arg
        35                  40                  45

Gln Gly Thr Val Ser Phe Ser Phe Pro Gln Ile Thr Leu Trp Gln Arg
    50                  55                  60

Pro Leu Val Thr Ile Lys Ile Gly Gly Gln Leu Lys Glu Ala Leu Leu
65                  70                  75                  80

Asp Thr Gly Ala Asp Asp Thr Val Leu Glu Glu Met Asn Leu Pro Gly
                85                  90                  95

Arg Trp Lys Pro Lys Met Ile Gly Gly Ile Gly Gly Phe Ile Lys Val
            100                 105                 110

Arg Gln Tyr Asp Gln Ile Pro Ile Glu Ile Cys Gly His Lys Ala Ile
        115                 120                 125

Gly Thr Val Leu Val Gly Pro Thr Pro Val Asn Ile Ile Gly Arg Asn
    130                 135                 140

Leu Leu Thr Gln Ile Gly Cys Thr Leu Asn Phe Pro Ile Ser Pro Ile
145                 150                 155                 160

Glu Thr Val Pro Val Lys Leu Lys Pro Gly Met Asp Gly Pro Lys Val
                165                 170                 175

Lys Gln Trp Pro Leu Thr Glu Glu Lys Ile Lys Ala Leu Val Glu Ile
            180                 185                 190

Cys Thr Glu Met Glu Lys Glu Gly Lys Ile Ser Lys Ile Gly Pro Glu
        195                 200                 205

Asn Pro Tyr Asn Thr Pro Ile Phe Ala Ile Lys Lys Lys Asp Ser Thr
    210                 215                 220

Lys Trp Arg Lys Leu Val Asp Phe Arg Glu Leu Asn Lys Arg Thr Gln
225                 230                 235                 240

Asp Phe Trp Glu Val Gln Leu Gly Ile Pro His Pro Ala Gly Leu Lys
                245                 250                 255

Lys Lys Lys Ser Val Thr Val Leu Asp Val Gly Asp Ala Tyr Phe Ser
            260                 265                 270

Val Pro Leu Asp Glu Asp Phe Arg Lys Tyr Thr Ala Phe Thr Ile Pro
        275                 280                 285

Ser Ile Asn Asn Glu Thr Pro Gly Ile Arg Tyr Gln Tyr Asn Val Leu
    290                 295                 300

Pro Gln Gly Trp Lys Gly Ser Pro Ala Ile Phe Gln Ser Ser Met Thr
305                 310                 315                 320

Lys Ile Leu Glu Pro Phe Arg Lys Gln Asn Pro Asp Ile Val Ile Tyr
                325                 330                 335

Gln Tyr Met Asp Asp Leu Tyr Val Gly Ser Asp Leu Glu Ile Gly Gln
            340                 345                 350

```
His Arg Thr Lys Ile Glu Glu Leu Arg Gln His Leu Arg Trp Gly
            355                 360                 365

Phe Thr Thr Pro Asp Lys Lys His Gln Lys Glu Pro Pro Phe Leu Trp
    370                 375                 380

Met Gly Tyr Glu Leu His Pro Asp Lys Trp Thr Val Gln Pro Ile Val
385                 390                 395                 400

Leu Pro Glu Lys Asp Ser Trp Thr Val Asn Asp Ile Gln Lys Leu Val
                405                 410                 415

Gly Lys Leu Asn Trp Ala Ser Gln Ile Tyr Ala Gly Ile Lys Val Lys
                420                 425                 430

Gln Leu Cys Lys Leu Leu Arg Gly Thr Lys Ala Leu Thr Glu Val Val
            435                 440                 445

Pro Leu Thr Glu Glu Ala Glu Leu Glu Leu Ala Glu Asn Arg Glu Ile
    450                 455                 460

Leu Lys Glu Pro Val His Gly Val Tyr Tyr Asp Pro Ser Lys Asp Leu
465                 470                 475                 480

Ile Ala Glu Ile Gln Lys Gln Gly Gln Gly Gln Trp Thr Tyr Gln Ile
                485                 490                 495

Tyr Gln Glu Pro Phe Lys Asn Leu Lys Thr Gly Lys Tyr Ala Arg Met
            500                 505                 510

Arg Gly Ala His Thr Asn Asp Val Lys Gln Leu Thr Glu Ala Val Gln
            515                 520                 525

Lys Ile Ala Thr Glu Ser Ile Val Ile Trp Gly Lys Thr Pro Lys Phe
            530                 535                 540

Lys Leu Pro Ile Gln Lys Glu Thr Trp Glu Trp Trp Thr Glu Tyr
545                 550                 555                 560

Trp Gln Ala Thr Trp Ile Pro Glu Trp Glu Phe Val Asn Thr Pro Pro
                565                 570                 575

Leu Val Lys Leu Trp Tyr Gln Leu Glu Lys Glu Pro Ile Val Gly Ala
                580                 585                 590

Glu Thr Phe Tyr Val Asp Gly Ala Ala Asn Arg Glu Thr Lys Leu Gly
            595                 600                 605

Lys Ala Gly Tyr Val Thr Asp Arg Gly Arg Gln Lys Val Val Ser Leu
            610                 615                 620

Thr Asp Thr Thr Asn Gln Lys Thr Glu Leu Gln Ala Ile His Leu Ala
625                 630                 635                 640

Leu Gln Asp Ser Gly Leu Glu Val Asn Ile Val Thr Asp Ser Gln Tyr
                645                 650                 655

Ala Leu Gly Ile Ile Gln Ala Gln Pro Asp Lys Ser Glu Ser Glu Leu
            660                 665                 670

Val Ser Gln Ile Ile Glu Gln Leu Ile Lys Lys Glu Lys Val Tyr Leu
            675                 680                 685

Ala Trp Val Pro Ala His Lys Gly Ile Gly Gly Asn Glu Gln Val Asp
            690                 695                 700

Lys Leu Val Ser Arg Gly Ile Arg Lys Val Leu Phe Leu Asp Gly Ile
705                 710                 715                 720

Asp Lys Ala Gln Glu Glu His Glu Lys Tyr His Ser Asn Trp Arg Ala
                725                 730                 735

Met Ala Ser Glu Phe Asn Leu Pro Pro Ile Val Ala Lys Glu Ile Val
                740                 745                 750

Ala Ser Cys Asp Lys Cys Gln Leu Lys Gly Glu Ala Ile His Gly Gln
            755                 760                 765
```

```
Val Asp Cys Ser Pro Gly Ile Trp Gln Leu Asp Cys Thr His Leu Glu
770                 775                 780

Gly Lys Val Ile Leu Val Ala Val His Val Ala Ser Gly Tyr Ile Glu
785                 790                 795                 800

Ala Glu Val Ile Pro Ala Glu Thr Gly Gln Glu Thr Ala Tyr Phe Leu
                805                 810                 815

Leu Lys Leu Ala Gly Arg Trp Pro Val Lys Thr Ile His Thr Asp Asn
                820                 825                 830

Gly Ser Asn Phe Thr Ser Ala Thr Val Lys Ala Ala Cys Trp Trp Ala
                835                 840                 845

Gly Ile Lys Gln Glu Phe Gly Ile Pro Tyr Asn Pro Gln Ser Gln Gly
            850                 855                 860

Val Val Glu Ser Ile Asn Lys Glu Leu Lys Lys Ile Gly Gln Val
865                 870                 875                 880

Arg Asp Gln Ala Glu His Leu Lys Thr Ala Val Gln Met Ala Val Phe
                885                 890                 895

Ile His Asn Phe Lys Arg Lys Gly Gly Ile Gly Glu Tyr Ser Ala Gly
            900                 905                 910

Glu Arg Ile Val Asp Ile Ile Ala Ser Asp Ile Gln Thr Lys Glu Leu
            915                 920                 925

Gln Lys Gln Ile Thr Lys Ile Gln Asn Phe Arg Val Tyr Tyr Arg Asp
            930                 935                 940

Ser Arg Asp Pro Leu Trp Lys Gly Pro Ala Lys Leu Leu Trp Lys Gly
945                 950                 955                 960

Glu Gly Ala Val Val Ile Gln Asp Asn Ser Asp Ile Lys Val Val Pro
                965                 970                 975

Arg Arg Lys Ala Lys Ile Ile Arg Asp Tyr Gly Lys Gln Met Ala Gly
                980                 985                 990

Asp Asp Cys Val Ala Ser Arg Gln  Asp Glu Asp
            995                 1000

<210> SEQ ID NO 7
<211> LENGTH: 206
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Met Gly Gly Lys Trp Ser Lys Ser Ser Val Val Gly Trp Pro Ala Ile
1               5                   10                  15

Arg Glu Arg Met Arg Arg Ala Glu Pro Ala Ala Asp Gly Val Gly Ala
                20                  25                  30

Val Ser Arg Asp Leu Glu Lys His Gly Ala Ile Thr Ser Ser Asn Thr
            35                  40                  45

Ala Ala Asn Asn Ala Asp Cys Ala Trp Leu Glu Ala Gln Glu Glu Glu
        50                  55                  60

Glu Val Gly Phe Pro Val Arg Pro Gln Val Pro Leu Arg Pro Met Thr
65                  70                  75                  80

Tyr Lys Gly Ala Leu Asp Leu Ser His Phe Leu Lys Glu Lys Gly Gly
                85                  90                  95

Leu Glu Gly Leu Ile Tyr Ser Gln Lys Arg Gln Asp Ile Leu Asp Leu
                100                 105                 110

Trp Val Tyr His Thr Gln Gly Tyr Phe Pro Asp Trp Gln Asn Tyr Thr
            115                 120                 125
```

```
Pro Gly Pro Gly Ile Arg Tyr Pro Leu Thr Phe Gly Trp Cys Phe Lys
        130                 135                 140

Leu Val Pro Val Glu Pro Glu Lys Ile Glu Glu Ala Asn Glu Gly Glu
145                 150                 155                 160

Asn Asn Ser Leu Leu His Pro Met Ser Gln His Gly Met Asp Asp Pro
                165                 170                 175

Glu Lys Glu Val Leu Met Trp Lys Phe Asp Ser Arg Leu Ala Phe His
            180                 185                 190

His Met Ala Arg Glu Leu His Pro Glu Tyr Tyr Lys Asp Cys
            195                 200                 205

<210> SEQ ID NO 8
<211> LENGTH: 206
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Met Gly Gly Lys Trp Ser Lys Ser Ser Ile Val Gly Trp Pro Ala Val
1               5                   10                  15

Arg Glu Arg Ile Arg Arg Ala Glu Pro Ala Ala Glu Gly Val Gly Ala
            20                  25                  30

Ala Ser Gln Asp Leu Asp Lys Tyr Gly Ala Leu Thr Ser Ser Asn Thr
        35                  40                  45

Ala Ala Thr Asn Ala Asp Cys Ala Trp Leu Glu Ala Gln Glu Asp Glu
    50                  55                  60

Glu Val Gly Phe Pro Val Lys Pro Gln Val Pro Leu Arg Pro Met Thr
65                  70                  75                  80

Tyr Lys Ala Ala Phe Asp Leu Ser Phe Phe Leu Lys Glu Lys Gly Gly
                85                  90                  95

Leu Asp Gly Leu Ile Tyr Ser Lys Lys Arg Gln Glu Ile Leu Asp Leu
            100                 105                 110

Trp Val Tyr Asn Thr Gln Gly Phe Phe Pro Asp Trp Gln Asn Tyr Thr
        115                 120                 125

Pro Gly Pro Gly Val Arg Tyr Pro Leu Thr Phe Gly Trp Cys Phe Lys
    130                 135                 140

Leu Val Pro Val Asp Pro Arg Glu Val Glu Glu Ala Asn Lys Gly Glu
145                 150                 155                 160

Asn Asn Cys Leu Leu His Pro Met Asn Leu His Gly Met Asp Asp Pro
                165                 170                 175

Glu Arg Glu Val Leu Val Trp Arg Phe Asp Ser Arg Leu Ala Phe His
            180                 185                 190

His Met Ala Arg Glu Lys His Pro Glu Tyr Tyr Lys Asn Cys
            195                 200                 205

<210> SEQ ID NO 9
<211> LENGTH: 685
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Met Arg Val Thr Gly Ile Arg Lys Asn Tyr Gln His Leu Trp Arg Trp
1               5                   10                  15
```

Gly Thr Met Leu Leu Gly Ile Leu Met Ile Cys Ser Ala Ala Gly Lys
            20                  25                  30

Leu Trp Val Thr Val Tyr Tyr Gly Val Pro Val Trp Lys Glu Ala Thr
        35                  40                  45

Thr Thr Leu Phe Cys Ala Ser Asp Ala Lys Ala Tyr Asp Thr Glu Val
    50                  55                  60

His Asn Val Trp Ala Thr His Ala Cys Val Pro Thr Asp Pro Asn Pro
65                  70                  75                  80

Gln Glu Val Val Leu Glu Asn Val Thr Glu Asn Phe Asn Met Trp Lys
                85                  90                  95

Asn Asn Met Val Glu Gln Met His Glu Asp Ile Ile Ser Leu Trp Asp
            100                 105                 110

Gln Ser Leu Lys Pro Cys Val Lys Leu Thr Pro Leu Cys Val Thr Leu
        115                 120                 125

Asn Cys Thr Asp Asp Val Arg Asn Val Thr Asn Ala Thr Asn Thr
130                 135                 140

Asn Ser Ser Trp Gly Glu Pro Met Glu Lys Gly Glu Ile Lys Asn Cys
145                 150                 155                 160

Ser Phe Asn Ile Thr Thr Ser Ile Arg Asn Lys Val Gln Lys Gln Tyr
                165                 170                 175

Ala Leu Phe Tyr Lys Leu Asp Val Val Pro Ile Asp Asn Asp Ser Asn
            180                 185                 190

Asn Thr Asn Tyr Arg Leu Ile Ser Cys Asn Thr Ser Val Ile Thr Gln
        195                 200                 205

Ala Cys Pro Lys Val Ser Phe Glu Pro Ile Pro Ile His Tyr Cys Ala
210                 215                 220

Pro Ala Gly Phe Ala Ile Leu Lys Cys Asn Asp Lys Lys Phe Asn Gly
225                 230                 235                 240

Thr Gly Pro Cys Thr Asn Val Ser Thr Val Gln Cys Thr His Gly Ile
                245                 250                 255

Arg Pro Val Val Ser Thr Gln Leu Leu Leu Asn Gly Ser Leu Ala Glu
            260                 265                 270

Glu Glu Val Val Ile Arg Ser Glu Asn Phe Thr Asn Asn Ala Lys Thr
        275                 280                 285

Ile Met Val Gln Leu Asn Val Ser Val Glu Ile Asn Cys Thr Arg Pro
290                 295                 300

Asn Asn Asn Thr Arg Lys Ser Ile His Ile Gly Pro Gly Arg Ala Phe
305                 310                 315                 320

Tyr Thr Ala Gly Asp Ile Ile Gly Asp Ile Arg Gln Ala His Cys Asn
                325                 330                 335

Ile Ser Arg Ala Asn Trp Asn Asn Thr Leu Arg Gln Ile Val Glu Lys
            340                 345                 350

Leu Gly Lys Gln Phe Gly Asn Asn Lys Thr Ile Val Phe Asn His Ser
        355                 360                 365

Ser Gly Gly Asp Pro Glu Ile Val Met His Ser Phe Asn Cys Gly Gly
370                 375                 380

Glu Phe Phe Tyr Cys Asn Ser Thr Lys Leu Phe Asn Ser Thr Trp Thr
385                 390                 395                 400

Trp Asn Asn Ser Thr Trp Asn Asn Thr Lys Arg Ser Asn Asp Thr Glu
                405                 410                 415

Glu His Ile Thr Leu Pro Cys Arg Ile Lys Gln Ile Ile Asn Met Trp
            420                 425                 430

Gln Glu Val Gly Lys Ala Met Tyr Ala Pro Pro Ile Arg Gly Gln Ile
            435                 440                 445

Arg Cys Ser Ser Asn Ile Thr Gly Leu Leu Thr Arg Asp Gly Gly
    450                 455                 460

Asn Asp Thr Ser Gly Thr Glu Ile Phe Arg Pro Gly Gly Gly Asp Met
465                 470                 475                 480

Arg Asp Asn Trp Arg Ser Glu Leu Tyr Lys Tyr Lys Val Val Lys Ile
                485                 490                 495

Glu Pro Leu Gly Val Ala Pro Thr Lys Ala Lys Arg Arg Val Val Gln
            500                 505                 510

Ser Glu Lys Ser Ala Val Gly Ile Gly Ala Val Phe Leu Gly Phe Leu
        515                 520                 525

Gly Ala Ala Gly Ser Thr Met Gly Ala Ala Ser Met Thr Leu Thr Val
    530                 535                 540

Gln Ala Arg Leu Leu Leu Ser Gly Ile Val Gln Gln Gln Asn Asn Leu
545                 550                 555                 560

Leu Arg Ala Ile Glu Ala Gln Gln His Leu Leu Gln Leu Thr Val Trp
                565                 570                 575

Gly Ile Lys Gln Leu Gln Ala Arg Val Leu Ala Val Glu Arg Tyr Leu
            580                 585                 590

Lys Asp Gln Gln Leu Leu Gly Ile Trp Gly Cys Ser Gly Lys Leu Ile
        595                 600                 605

Cys Thr Thr Thr Val Pro Trp Asn Ala Ser Trp Ser Asn Lys Ser Leu
    610                 615                 620

Asp Lys Ile Trp Asn Asn Met Thr Trp Met Glu Trp Glu Arg Glu Ile
625                 630                 635                 640

Asn Asn Tyr Thr Ser Leu Ile Tyr Thr Leu Ile Glu Glu Ser Gln Asn
                645                 650                 655

Gln Gln Glu Lys Asn Glu Gln Glu Leu Leu Glu Leu Asp Lys Trp Ala
            660                 665                 670

Ser Leu Trp Asn Trp Phe Asp Ile Ser Asn Trp Leu Trp
        675                 680                 685

<210> SEQ ID NO 10
<211> LENGTH: 684
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Met Arg Val Arg Gly Ile Gln Arg Asn Trp Pro Gln Trp Trp Ile Trp
1               5                   10                  15

Gly Ile Leu Gly Phe Trp Met Ile Ile Cys Arg Val Met Gly Asn
            20                  25                  30

Leu Trp Val Thr Val Tyr Tyr Gly Val Pro Val Trp Lys Glu Ala Lys
        35                  40                  45

Thr Thr Leu Phe Cys Ala Ser Asp Ala Lys Ala Tyr Glu Lys Glu Val
    50                  55                  60

His Asn Val Trp Ala Thr His Ala Cys Val Pro Thr Asp Pro Asn Pro
65                  70                  75                  80

Gln Glu Met Val Leu Glu Asn Val Thr Glu Asn Phe Asn Met Trp Lys
                85                  90                  95

Asn Asp Met Val Asp Gln Met His Glu Asp Ile Ile Arg Leu Trp Asp
            100                 105                 110

```
Gln Ser Leu Lys Pro Cys Val Lys Leu Thr Pro Leu Cys Val Thr Leu
    115                 120                 125

Glu Cys Arg Asn Val Arg Asn Val Ser Ser Asn Gly Thr Tyr Asn Ile
    130                 135                 140

Ile His Asn Glu Thr Tyr Lys Glu Met Lys Asn Cys Ser Phe Asn Ala
145                 150                 155                 160

Thr Thr Val Val Glu Asp Arg Lys Gln Lys Val His Ala Leu Phe Tyr
                165                 170                 175

Arg Leu Asp Ile Val Pro Leu Asp Glu Asn Asn Ser Ser Glu Lys Ser
            180                 185                 190

Ser Glu Asn Ser Ser Glu Tyr Tyr Arg Leu Ile Asn Cys Asn Thr Ser
    195                 200                 205

Ala Ile Thr Gln Ala Cys Pro Lys Val Ser Phe Asp Pro Ile Pro Ile
    210                 215                 220

His Tyr Cys Ala Pro Ala Gly Tyr Ala Ile Leu Lys Cys Asn Asn Lys
225                 230                 235                 240

Thr Phe Asn Gly Thr Gly Pro Cys Asn Asn Val Ser Thr Val Gln Cys
                245                 250                 255

Thr His Gly Ile Lys Pro Val Val Ser Thr Gln Leu Leu Leu Asn Gly
            260                 265                 270

Ser Leu Ala Glu Glu Glu Ile Ile Ile Arg Ser Glu Asn Leu Thr Asn
    275                 280                 285

Asn Ala Lys Thr Ile Ile Val His Leu Asn Glu Thr Val Asn Ile Thr
    290                 295                 300

Cys Thr Arg Pro Asn Asn Thr Arg Lys Ser Ile Arg Ile Gly Pro
305                 310                 315                 320

Gly Gln Thr Phe Tyr Ala Thr Gly Asp Ile Ile Gly Asp Ile Arg Gln
                325                 330                 335

Ala His Cys Asn Leu Ser Arg Asp Gly Trp Asn Lys Thr Leu Gln Gly
            340                 345                 350

Val Lys Lys Lys Leu Ala Glu His Phe Pro Asn Lys Thr Ile Asn Phe
    355                 360                 365

Thr Ser Ser Ser Gly Gly Asp Leu Glu Ile Thr Thr His Ser Phe Asn
    370                 375                 380

Cys Arg Gly Glu Phe Phe Tyr Cys Asn Thr Ser Gly Leu Phe Asn Gly
385                 390                 395                 400

Thr Tyr Met Pro Asn Gly Thr Asn Ser Asn Ser Ser Asn Ile Thr
                405                 410                 415

Leu Pro Cys Arg Ile Lys Gln Ile Ile Asn Met Trp Gln Glu Val Gly
            420                 425                 430

Arg Ala Met Tyr Ala Pro Pro Ile Ala Gly Asn Ile Thr Cys Arg Ser
    435                 440                 445

Asn Ile Thr Gly Leu Leu Leu Thr Arg Asp Gly Gly Ser Asn Asn Gly
    450                 455                 460

Val Pro Asn Asp Thr Glu Thr Phe Arg Pro Gly Gly Gly Asp Met Arg
465                 470                 475                 480

Asn Asn Trp Arg Ser Glu Leu Tyr Lys Tyr Lys Val Val Glu Val Lys
                485                 490                 495

Pro Leu Gly Val Ala Pro Thr Glu Ala Lys Arg Arg Val Val Glu Ser
            500                 505                 510

Glu Lys Ser Ala Val Gly Ile Gly Ala Val Phe Leu Gly Ile Leu Gly
    515                 520                 525
```

-continued

```
Ala Ala Gly Ser Thr Met Gly Ala Ala Ser Ile Thr Leu Thr Val Gln
            530                 535                 540

Ala Arg Gln Leu Leu Ser Gly Ile Val Gln Gln Ser Asn Leu Leu
545                 550                 555                 560

Arg Ala Ile Glu Ala Gln Gln His Met Leu Gln Leu Thr Val Trp Gly
                565                 570                 575

Ile Lys Gln Leu Gln Thr Arg Val Leu Ala Ile Glu Arg Tyr Leu Gln
            580                 585                 590

Asp Gln Gln Leu Leu Gly Leu Trp Gly Cys Ser Gly Lys Leu Ile Cys
                595                 600                 605

Thr Thr Ala Val Pro Trp Asn Thr Ser Trp Ser Asn Lys Ser Gln Thr
610                 615                 620

Asp Ile Trp Asp Asn Met Thr Trp Met Gln Trp Asp Lys Glu Ile Gly
625                 630                 635                 640

Asn Tyr Thr Gly Glu Ile Tyr Arg Leu Leu Glu Ser Gln Asn Gln
                645                 650                 655

Gln Glu Lys Asn Glu Lys Asp Leu Leu Ala Leu Asp Ser Trp Lys Asn
                660                 665                 670

Leu Trp Asn Trp Phe Asp Ile Thr Asn Trp Leu Trp
            675                 680
```

<210> SEQ ID NO 11
<211> LENGTH: 678
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

```
Met Arg Val Lys Gly Ile Arg Lys Asn Tyr Gln His Leu Trp Lys Trp
1               5                   10                  15

Gly Thr Met Leu Leu Gly Met Leu Met Ile Cys Ser Ala Ala Glu Gln
            20                  25                  30

Leu Trp Val Thr Val Tyr Tyr Gly Val Pro Val Trp Arg Asp Ala Glu
        35                  40                  45

Thr Thr Leu Phe Cys Ala Ser Asp Ala Lys Ala Tyr Glu Arg Glu Val
    50                  55                  60

His Asn Ile Trp Ala Thr His Ala Cys Val Pro Thr Asp Pro Asn Pro
65                  70                  75                  80

Gln Glu Ile Val Leu Glu Asn Val Thr Glu Glu Phe Asn Met Trp Lys
                85                  90                  95

Asn Asp Met Val Glu Gln Met His Thr Asp Ile Ile Ser Leu Trp Asp
            100                 105                 110

Glu Ser Leu Lys Pro Cys Val Lys Leu Ala Pro Leu Cys Val Thr Leu
        115                 120                 125

Asn Cys Thr Asn Ala Asn Leu Asn Cys Thr Asn Asp Asn Cys Asn Arg
    130                 135                 140

Thr Val Asp Lys Met Arg Glu Glu Ile Lys Asn Cys Ser Phe Asn Met
145                 150                 155                 160

Thr Thr Glu Leu Arg Asp Lys Lys Gln Lys Val Tyr Ala Leu Phe Tyr
                165                 170                 175

Lys Leu Asp Ile Val Pro Ile Glu Lys Asn Ser Ser Glu Tyr Arg Leu
            180                 185                 190

Ile Asn Cys Asn Thr Ser Thr Ile Thr Gln Ala Cys Pro Lys Val Thr
        195                 200                 205
```

```
Phe Glu Pro Ile Pro Ile His Tyr Cys Thr Pro Ala Gly Phe Ala Ile
    210                 215                 220

Leu Lys Cys Lys Asp Lys Phe Asn Gly Thr Gly Pro Cys Lys Asn
225                 230                 235                 240

Val Ser Thr Val Gln Cys Thr His Gly Ile Lys Pro Val Ile Ser Thr
                245                 250                 255

Gln Leu Leu Asn Gly Ser Leu Ala Glu Gly Glu Ile Ile Ile Arg
            260                 265                 270

Ser Glu Asn Ile Thr Asn Asn Ala Lys Thr Ile Ile Val Gln Leu Asn
        275                 280                 285

Glu Ser Val Val Ile Asn Cys Thr Arg Pro Gly Asn Asn Thr Arg Lys
    290                 295                 300

Ser Val Arg Ile Gly Pro Gly Gln Ala Phe Tyr Ala Thr Gly Glu Ile
305                 310                 315                 320

Ile Gly Asp Ile Arg Gln Ala Tyr Cys Asn Ile Ser Arg Ala Lys Trp
                325                 330                 335

Asn Asn Thr Leu Lys Gln Ile Val Thr Lys Leu Lys Glu Gln Phe Lys
            340                 345                 350

Asn Lys Thr Ile Val Phe Asn Gln Ser Ser Gly Gly Asp Pro Glu Ile
        355                 360                 365

Thr Thr His Ser Phe Asn Cys Gly Gly Glu Phe Phe Tyr Cys Asn Thr
    370                 375                 380

Thr Gln Leu Phe Asn Ser Thr Trp Asn Ser Asn Ser Thr Trp Asn Asp
385                 390                 395                 400

Thr Thr Gly Ser Val Thr Glu Gly Asn Asp Thr Ile Thr Leu Pro Cys
                405                 410                 415

Arg Ile Lys Gln Ile Val Asn Met Trp Gln Arg Val Gly Gln Ala Met
            420                 425                 430

Tyr Ala Pro Pro Ile Glu Gly Asn Ile Thr Cys Lys Ser Asn Ile Thr
        435                 440                 445

Gly Leu Leu Leu Val Arg Asp Gly Gly Asn Ile Asn Arg Thr Asn Glu
    450                 455                 460

Thr Phe Arg Pro Gly Gly Gly Asn Met Lys Asp Asn Trp Arg Ser Glu
465                 470                 475                 480

Leu Tyr Lys Tyr Lys Val Val Glu Ile Lys Pro Leu Gly Val Ala Pro
                485                 490                 495

Thr Arg Ala Lys Arg Arg Val Val Glu Ser Glu Lys Ser Ala Val Gly
            500                 505                 510

Leu Gly Ala Val Phe Leu Gly Phe Leu Gly Thr Ala Gly Ser Thr Met
        515                 520                 525

Gly Ala Ala Ser Leu Thr Leu Thr Val Gln Ala Arg Gln Val Leu Ser
    530                 535                 540

Gly Ile Val Gln Gln Ser Asn Leu Leu Lys Ala Ile Glu Ala Gln
545                 550                 555                 560

Gln His Leu Leu Lys Leu Thr Val Trp Gly Ile Lys Gln Leu Gln Ala
                565                 570                 575

Arg Ile Leu Ala Val Glu Arg Tyr Leu Arg Asp Gln Gln Leu Leu Gly
            580                 585                 590

Ile Trp Gly Cys Ser Gly Lys Leu Ile Cys Thr Thr Asn Val Pro Trp
        595                 600                 605

Asn Ser Ser Trp Ser Asn Lys Ser Gln Glu Glu Ile Trp Asn Met
    610                 615                 620
```

```
Thr Trp Met Gln Trp Asp Arg Glu Ile Ser Asn Tyr Thr Asp Thr Ile
625                 630                 635                 640

Tyr Arg Leu Leu Glu Asp Ser Gln Asn Gln Gln Glu Lys Asn Glu Gln
            645                 650                 655

Asp Leu Leu Ala Leu Asp Lys Trp Ala Ser Leu Trp Asn Trp Phe Ser
        660                 665                 670

Ile Thr Asn Trp Leu Trp
        675

<210> SEQ ID NO 12
<211> LENGTH: 850
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Met Ala Pro Ile Ser Pro Ile Glu Thr Val Pro Val Lys Leu Lys Pro
1               5                   10                  15

Gly Met Asp Gly Pro Arg Val Lys Gln Trp Pro Leu Thr Glu Glu Lys
            20                  25                  30

Ile Lys Ala Leu Thr Ala Ile Cys Glu Glu Met Glu Lys Glu Gly Lys
        35                  40                  45

Ile Thr Lys Ile Gly Pro Glu Asn Pro Tyr Asn Thr Pro Val Phe Ala
50                  55                  60

Ile Lys Lys Lys Asp Ser Thr Lys Trp Arg Lys Leu Val Asp Phe Arg
65                  70                  75                  80

Glu Leu Asn Lys Arg Thr Gln Asp Phe Trp Glu Val Gln Leu Gly Ile
                85                  90                  95

Pro His Pro Ala Gly Leu Lys Lys Lys Ser Val Thr Val Leu Ala
            100                 105                 110

Val Gly Asp Ala Tyr Phe Ser Val Pro Leu Asp Glu Gly Phe Arg Lys
        115                 120                 125

Tyr Thr Ala Phe Thr Ile Pro Ser Thr Asn Asn Glu Thr Pro Gly Ile
130                 135                 140

Arg Tyr Gln Tyr Asn Val Leu Pro Gln Gly Trp Lys Gly Ser Pro Ala
145                 150                 155                 160

Ile Phe Gln Cys Ser Met Thr Arg Ile Leu Glu Pro Phe Arg Ala Lys
                165                 170                 175

Asn Pro Glu Ile Val Ile Tyr Gln Tyr Met Ala Ala Leu Tyr Val Gly
            180                 185                 190

Ser Asp Leu Glu Ile Gly Gln His Arg Ala Lys Ile Glu Glu Leu Arg
        195                 200                 205

Glu His Leu Leu Lys Trp Gly Phe Thr Thr Pro Asp Lys Lys His Gln
210                 215                 220

Lys Glu Pro Pro Phe Leu Trp Met Gly Tyr Glu Leu His Pro Asp Lys
225                 230                 235                 240

Trp Thr Val Gln Pro Ile Gln Leu Pro Glu Lys Asp Ser Trp Thr Val
                245                 250                 255

Asn Asp Ile Gln Lys Leu Val Gly Lys Leu Asn Trp Ala Ser Gln Ile
            260                 265                 270

Tyr Pro Gly Ile Lys Val Arg Gln Leu Cys Lys Leu Leu Arg Gly Ala
        275                 280                 285

Lys Ala Leu Thr Asp Ile Val Pro Leu Thr Glu Glu Ala Glu Leu Glu
290                 295                 300
```

```
Leu Ala Glu Asn Arg Glu Ile Leu Lys Glu Pro Val His Gly Val Tyr
305                 310                 315                 320

Tyr Asp Pro Ser Lys Asp Leu Ile Ala Glu Ile Gln Lys Gln Gly His
            325                 330                 335

Asp Gln Trp Thr Tyr Gln Ile Tyr Gln Glu Pro Phe Lys Asn Leu Lys
        340                 345                 350

Thr Gly Lys Tyr Ala Lys Met Arg Thr Ala His Thr Asn Asp Val Lys
    355                 360                 365

Gln Leu Thr Glu Ala Val Gln Lys Ile Ala Met Glu Ser Ile Val Ile
370                 375                 380

Trp Gly Lys Thr Pro Lys Phe Arg Leu Pro Ile Gln Lys Glu Thr Trp
385                 390                 395                 400

Glu Thr Trp Trp Thr Asp Tyr Trp Gln Ala Thr Trp Ile Pro Glu Trp
                405                 410                 415

Glu Phe Val Asn Thr Pro Pro Leu Val Lys Leu Trp Tyr Gln Leu Glu
            420                 425                 430

Lys Asp Pro Ile Ala Gly Val Glu Thr Phe Tyr Val Ala Gly Ala Ala
        435                 440                 445

Asn Arg Glu Thr Lys Leu Gly Lys Ala Gly Tyr Val Thr Asp Arg Gly
    450                 455                 460

Arg Gln Lys Ile Val Ser Leu Thr Glu Thr Thr Asn Gln Lys Thr Ala
465                 470                 475                 480

Leu Gln Ala Ile Tyr Leu Ala Leu Gln Asp Ser Gly Ser Glu Val Asn
                485                 490                 495

Ile Val Thr Ala Ser Gln Tyr Ala Leu Gly Ile Ile Gln Ala Gln Pro
            500                 505                 510

Asp Lys Ser Glu Ser Glu Leu Val Asn Gln Ile Ile Glu Gln Leu Ile
        515                 520                 525

Lys Lys Glu Arg Val Tyr Leu Ser Trp Val Pro Ala His Lys Gly Ile
    530                 535                 540

Gly Gly Asn Glu Gln Val Asp Lys Leu Val Ser Ser Gly Ile Arg Lys
545                 550                 555                 560

Val Leu Phe Leu Asp Gly Ile Asp Lys Ala Gln Glu Glu His Glu Lys
                565                 570                 575

Tyr His Ser Asn Trp Arg Ala Met Ala Ser Asp Phe Asn Leu Pro Pro
            580                 585                 590

Val Val Ala Lys Glu Ile Val Ala Ser Cys Asp Gln Cys Gln Leu Lys
        595                 600                 605

Gly Glu Ala Met His Gly Gln Val Asp Cys Ser Pro Gly Ile Trp Gln
    610                 615                 620

Leu Ala Cys Thr His Leu Glu Gly Lys Ile Ile Leu Val Ala Val His
625                 630                 635                 640

Val Ala Ser Gly Tyr Ile Glu Ala Glu Val Ile Pro Ala Glu Thr Gly
                645                 650                 655

Gln Glu Thr Ala Tyr Phe Ile Leu Lys Leu Ala Gly Arg Trp Pro Val
            660                 665                 670

Lys Val Ile His Thr Ala Asn Gly Ser Asn Phe Thr Ser Ala Ala Val
        675                 680                 685

Lys Ala Ala Cys Trp Trp Ala Gly Ile Gln Gln Glu Phe Gly Ile Pro
    690                 695                 700

Tyr Asn Pro Gln Ser Gln Gly Val Val Ala Ser Met Asn Lys Glu Leu
705                 710                 715                 720
```

```
Lys Lys Ile Ile Gly Gln Val Arg Asp Gln Ala Glu His Leu Lys Thr
                725                 730                 735
Ala Val Gln Met Ala Val Phe Ile His Asn Phe Lys Arg Lys Gly Gly
            740                 745                 750
Ile Gly Gly Tyr Ser Ala Gly Glu Arg Ile Ile Asp Ile Ile Ala Thr
        755                 760                 765
Asp Ile Gln Thr Lys Glu Leu Gln Lys Gln Ile Ile Lys Ile Gln Asn
    770                 775                 780
Phe Arg Val Tyr Tyr Arg Asp Ser Arg Asp Pro Ile Trp Lys Gly Pro
785                 790                 795                 800
Ala Lys Leu Leu Trp Lys Gly Glu Gly Ala Val Val Ile Gln Asp Asn
            805                 810                 815
Ser Asp Ile Lys Val Val Pro Arg Arg Lys Val Lys Ile Ile Lys Asp
        820                 825                 830
Tyr Gly Lys Gln Met Ala Gly Ala Asp Cys Val Ala Gly Arg Gln Asp
    835                 840                 845
Glu Asp
    850

<210> SEQ ID NO 13
<211> LENGTH: 850
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Met Ala Pro Ile Ser Pro Ile Glu Thr Val Pro Val Lys Leu Lys Pro
1               5                   10                  15
Gly Met Asp Gly Pro Lys Val Lys Gln Trp Pro Leu Thr Glu Glu Lys
            20                  25                  30
Ile Lys Ala Leu Val Glu Ile Cys Thr Glu Met Glu Lys Glu Gly Lys
        35                  40                  45
Ile Ser Lys Ile Gly Pro Glu Asn Pro Tyr Asn Thr Pro Ile Phe Ala
    50                  55                  60
Ile Lys Lys Lys Asp Ser Thr Lys Trp Arg Lys Leu Val Asp Phe Arg
65                  70                  75                  80
Glu Leu Asn Lys Arg Thr Gln Asp Phe Trp Glu Val Gln Leu Gly Ile
            85                  90                  95
Pro His Pro Ala Gly Leu Lys Lys Lys Lys Ser Val Thr Val Leu Ala
        100                 105                 110
Val Gly Asp Ala Tyr Phe Ser Val Pro Leu Asp Glu Asp Phe Arg Lys
    115                 120                 125
Tyr Thr Ala Phe Thr Ile Pro Ser Ile Asn Asn Glu Thr Pro Gly Ile
    130                 135                 140
Arg Tyr Gln Tyr Asn Val Leu Pro Gln Gly Trp Lys Gly Ser Pro Ala
145                 150                 155                 160
Ile Phe Gln Ser Ser Met Thr Lys Ile Leu Glu Pro Phe Arg Lys Gln
                165                 170                 175
Asn Pro Asp Ile Val Ile Tyr Gln Tyr Met Ala Ala Leu Tyr Val Gly
            180                 185                 190
Ser Asp Leu Glu Ile Gly Gln His Arg Thr Lys Ile Glu Glu Leu Arg
        195                 200                 205
Gln His Leu Leu Arg Trp Gly Phe Thr Thr Pro Asp Lys Lys His Gln
    210                 215                 220
```

-continued

```
Lys Glu Pro Pro Phe Leu Trp Met Gly Tyr Glu Leu His Pro Asp Lys
225                 230                 235                 240

Trp Thr Val Gln Pro Ile Val Leu Pro Glu Lys Asp Ser Trp Thr Val
            245                 250                 255

Asn Asp Ile Gln Lys Leu Val Gly Lys Leu Asn Trp Ala Ser Gln Ile
        260                 265                 270

Tyr Ala Gly Ile Lys Val Lys Gln Leu Cys Lys Leu Leu Arg Gly Thr
    275                 280                 285

Lys Ala Leu Thr Glu Val Val Pro Leu Thr Glu Glu Ala Glu Leu Glu
290                 295                 300

Leu Ala Glu Asn Arg Glu Ile Leu Lys Glu Pro Val His Gly Val Tyr
305                 310                 315                 320

Tyr Asp Pro Ser Lys Asp Leu Ile Ala Glu Ile Gln Lys Gln Gly Gln
            325                 330                 335

Gly Gln Trp Thr Tyr Gln Ile Tyr Gln Glu Pro Phe Lys Asn Leu Lys
        340                 345                 350

Thr Gly Lys Tyr Ala Arg Met Arg Gly Ala His Thr Asn Asp Val Lys
    355                 360                 365

Gln Leu Thr Glu Ala Val Gln Lys Ile Ala Thr Glu Ser Ile Val Ile
370                 375                 380

Trp Gly Lys Thr Pro Lys Phe Lys Leu Pro Ile Gln Lys Glu Thr Trp
385                 390                 395                 400

Glu Ala Trp Trp Thr Glu Tyr Trp Gln Ala Thr Trp Ile Pro Glu Trp
            405                 410                 415

Glu Phe Val Asn Thr Pro Pro Leu Val Lys Leu Trp Tyr Gln Leu Glu
        420                 425                 430

Lys Glu Pro Ile Val Gly Ala Glu Thr Phe Tyr Val Ala Gly Ala Ala
    435                 440                 445

Asn Arg Glu Thr Lys Leu Gly Lys Ala Gly Tyr Val Thr Asp Arg Gly
450                 455                 460

Arg Gln Lys Val Val Ser Leu Thr Asp Thr Thr Asn Gln Lys Thr Ala
465                 470                 475                 480

Leu Gln Ala Ile His Leu Ala Leu Gln Asp Ser Gly Leu Glu Val Asn
            485                 490                 495

Ile Val Thr Ala Ser Gln Tyr Ala Leu Gly Ile Ile Gln Ala Gln Pro
        500                 505                 510

Asp Lys Ser Glu Ser Glu Leu Val Ser Gln Ile Ile Glu Gln Leu Ile
    515                 520                 525

Lys Lys Glu Lys Val Tyr Leu Ala Trp Val Pro Ala His Lys Gly Ile
530                 535                 540

Gly Gly Asn Glu Gln Val Asp Lys Leu Val Ser Arg Gly Ile Arg Lys
545                 550                 555                 560

Val Leu Phe Leu Asp Gly Ile Asp Lys Ala Gln Glu Glu His Glu Lys
            565                 570                 575

Tyr His Ser Asn Trp Arg Ala Met Ala Ser Glu Phe Asn Leu Pro Pro
        580                 585                 590

Ile Val Ala Lys Glu Ile Val Ala Ser Cys Asp Lys Cys Gln Leu Lys
    595                 600                 605

Gly Glu Ala Ile His Gly Gln Val Asp Cys Ser Pro Gly Ile Trp Gln
610                 615                 620

Leu Ala Cys Thr His Leu Glu Gly Lys Val Ile Leu Val Ala Val His
625                 630                 635                 640
```

```
Val Ala Ser Gly Tyr Ile Glu Ala Glu Val Ile Pro Ala Glu Thr Gly
                645                 650                 655

Gln Glu Thr Ala Tyr Phe Leu Leu Lys Leu Ala Gly Arg Trp Pro Val
            660                 665                 670

Lys Thr Ile His Thr Ala Asn Gly Ser Asn Phe Thr Ser Ala Thr Val
        675                 680                 685

Lys Ala Ala Cys Trp Trp Ala Gly Ile Lys Gln Glu Phe Gly Ile Pro
    690                 695                 700

Tyr Asn Pro Gln Ser Gln Gly Val Val Ala Ser Ile Asn Lys Glu Leu
705                 710                 715                 720

Lys Lys Ile Ile Gly Gln Val Arg Asp Gln Ala Glu His Leu Lys Thr
                725                 730                 735

Ala Val Gln Met Ala Val Phe Ile His Asn Phe Lys Arg Lys Gly Gly
            740                 745                 750

Ile Gly Glu Tyr Ser Ala Gly Glu Arg Ile Val Asp Ile Ile Ala Ser
        755                 760                 765

Asp Ile Gln Thr Lys Glu Leu Gln Lys Gln Ile Thr Lys Ile Gln Asn
    770                 775                 780

Phe Arg Val Tyr Tyr Arg Asp Ser Arg Asp Pro Leu Trp Lys Gly Pro
785                 790                 795                 800

Ala Lys Leu Leu Trp Lys Gly Glu Gly Ala Val Val Ile Gln Asp Asn
                805                 810                 815

Ser Asp Ile Lys Val Val Pro Arg Arg Lys Ala Lys Ile Ile Arg Asp
            820                 825                 830

Tyr Gly Lys Gln Met Ala Gly Asp Asp Cys Val Ala Ser Arg Gln Asp
        835                 840                 845

Glu Asp
    850

<210> SEQ ID NO 14
<211> LENGTH: 851
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Met Ala Pro Ile Ser Pro Ile Asp Thr Val Pro Val Thr Leu Lys Pro
1               5                   10                  15

Gly Met Asp Gly Pro Lys Ile Lys Gln Trp Pro Leu Thr Glu Glu Lys
            20                  25                  30

Ile Lys Ala Leu Thr Glu Ile Cys Thr Glu Met Glu Lys Glu Gly Lys
        35                  40                  45

Ile Ser Arg Ile Gly Pro Glu Asn Pro Tyr Asn Thr Pro Val Phe Ala
    50                  55                  60

Ile Lys Lys Lys Asn Ser Thr Arg Trp Arg Lys Leu Val Asp Phe Arg
65                  70                  75                  80

Glu Leu Asn Lys Lys Thr Gln Asp Phe Trp Glu Val Gln Leu Gly Ile
                85                  90                  95

Pro His Pro Ala Gly Leu Lys Lys Lys Arg Ser Val Thr Val Leu Ala
            100                 105                 110

Val Gly Asp Ala Tyr Phe Ser Val Pro Leu Asp Lys Asp Phe Arg Lys
        115                 120                 125

Tyr Thr Ala Phe Thr Ile Pro Ser Val Asn Asn Glu Thr Pro Gly Val
    130                 135                 140
```

```
Arg Tyr Gln Tyr Asn Val Leu Pro Gln Gly Trp Lys Gly Ser Pro Ala
145                 150                 155                 160

Ile Phe Gln Cys Ser Met Thr Lys Ile Leu Glu Pro Phe Arg Ala Gln
                165                 170                 175

Asn Pro Glu Ile Val Ile Tyr Gln Tyr Val Ala Ala Leu Tyr Val Gly
            180                 185                 190

Ser Asp Leu Glu Ile Glu Gln His Arg Thr Lys Ile Glu Glu Leu Arg
        195                 200                 205

Ala His Leu Leu Ser Trp Gly Phe Thr Thr Pro Asp Lys Lys His Gln
    210                 215                 220

Arg Glu Pro Pro Phe Leu Trp Met Gly Tyr Glu Leu His Pro Asp Arg
225                 230                 235                 240

Trp Thr Val Gln Pro Ile Glu Leu Pro Glu Lys Glu Ser Trp Thr Val
                245                 250                 255

Asn Asp Ile Gln Lys Leu Val Gly Lys Leu Asn Trp Ala Ser Gln Ile
            260                 265                 270

Tyr Pro Gly Ile Lys Val Lys Gln Leu Cys Arg Leu Leu Arg Gly Ala
        275                 280                 285

Lys Ala Leu Thr Glu Val Ile Pro Leu Thr Lys Glu Ala Glu Leu Glu
290                 295                 300

Leu Ala Glu Asn Arg Glu Ile Leu Arg Glu Pro Val His Gly Val Tyr
305                 310                 315                 320

Tyr Asp Pro Ser Lys Asp Leu Val Ala Glu Ile Gln Lys Gln Gly Gln
                325                 330                 335

Asp Gln Trp Thr Tyr Gln Ile Tyr Gln Glu Pro Tyr Lys Asn Leu Lys
            340                 345                 350

Thr Gly Lys Tyr Ala Arg Lys Arg Ser Ala His Thr Asn Asp Val Arg
        355                 360                 365

Gln Leu Thr Glu Ala Val Gln Lys Ile Ala Leu Glu Ser Ile Val Ile
    370                 375                 380

Trp Gly Lys Ile Pro Lys Phe Arg Leu Pro Ile Gln Arg Glu Thr Trp
385                 390                 395                 400

Glu Thr Trp Trp Thr Glu Tyr Trp Gln Ala Thr Trp Ile Pro Asp Trp
                405                 410                 415

Glu Phe Val Asn Thr Pro Pro Leu Val Lys Leu Trp Tyr Gln Leu Glu
            420                 425                 430

Lys Glu Pro Ile Ala Gly Ala Glu Thr Phe Tyr Val Ala Gly Ala Ser
        435                 440                 445

Asn Arg Glu Thr Lys Ile Gly Lys Ala Gly Tyr Val Thr Asp Lys Gly
    450                 455                 460

Arg Gln Lys Val Val Ser Leu Thr Glu Thr Thr Asn Gln Lys Ala Ala
465                 470                 475                 480

Leu Gln Ala Ile Gln Leu Ala Leu Gln Asp Ser Gly Pro Glu Val Asn
                485                 490                 495

Ile Val Thr Ala Ser Gln Tyr Val Leu Gly Ile Ile Gln Ala Gln Pro
            500                 505                 510

Asp Arg Ser Glu Ser Glu Leu Val Asn Gln Ile Ile Glu Glu Leu Ile
        515                 520                 525

Lys Lys Glu Lys Val Tyr Leu Ser Trp Val Pro Ala His Lys Gly Ile
    530                 535                 540

Gly Gly Asn Glu Gln Val Asp Lys Leu Val Ser Ala Gly Ile Arg Lys
545                 550                 555                 560
```

-continued

Ile Leu Phe Leu Asp Gly Ile Asp Lys Ala Gln Glu Glu His Glu Arg
                565                 570                 575

Tyr His Ser Asn Trp Arg Thr Met Ala Ser Asp Phe Asn Leu Pro Pro
            580                 585                 590

Ile Val Ala Lys Glu Ile Val Ala Asn Cys Asp Lys Cys Gln Leu Lys
        595                 600                 605

Gly Glu Ala Met His Gly Gln Val Asp Cys Ser Pro Gly Met Trp Gln
    610                 615                 620

Leu Ala Cys Thr His Leu Glu Gly Lys Ile Ile Val Ala Val His
625                 630                 635                 640

Val Ala Ser Gly Tyr Met Glu Ala Glu Val Ile Pro Ala Glu Thr Gly
                645                 650                 655

Gln Glu Thr Ala Tyr Tyr Ile Leu Lys Leu Ala Gly Arg Trp Pro Val
            660                 665                 670

Lys Val His Thr Ala Asn Gly Ser Asn Phe Thr Ser Thr Thr Val
        675                 680                 685

Lys Ala Ala Cys Trp Trp Ala Asn Val Thr Gln Glu Phe Gly Ile Pro
    690                 695                 700

Tyr Asn Pro Gln Ser Gln Gly Val Ile Ala Ser Met Asn Lys Glu Leu
705                 710                 715                 720

Lys Lys Ile Ile Gly Gln Val Arg Glu Gln Ala Glu His Leu Lys Thr
                725                 730                 735

Ala Val Gln Met Ala Val Leu Ile His Asn Phe Lys Arg Arg Gly Gly
            740                 745                 750

Ile Gly Gly Tyr Ser Ala Gly Glu Arg Ile Val Asp Ile Ile Ala Thr
        755                 760                 765

Asp Ile Gln Thr Arg Glu Leu Gln Lys Gln Ile Ile Lys Ile Gln Asn
    770                 775                 780

Phe Arg Val Tyr Phe Arg Asp Ser Arg Asp Pro Val Trp Lys Gly Pro
785                 790                 795                 800

Ala Lys Leu Leu Trp Lys Gly Glu Gly Ala Val Val Ile Gln Asp Asn
                805                 810                 815

Ser Glu Ile Lys Val Val Pro Arg Arg Lys Val Lys Ile Ile Arg Asp
            820                 825                 830

Tyr Gly Lys Gln Met Ala Gly Asp Asp Cys Val Ala Gly Arg Gln Asp
        835                 840                 845

Glu Asp Gln
    850

<210> SEQ ID NO 15
<211> LENGTH: 508
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Met Gly Ala Arg Ala Ser Val Leu Ser Gly Gly Lys Leu Asp Ala Trp
1               5                   10                  15

Glu Lys Ile Arg Leu Arg Pro Gly Gly Lys Lys Lys Tyr Lys Leu Lys
            20                  25                  30

His Ile Val Trp Ala Ser Arg Glu Leu Asp Arg Phe Ala Leu Asn Pro
        35                  40                  45

Gly Leu Leu Glu Thr Ala Glu Gly Cys Gln Gln Ile Ile Glu Gln Leu
    50                  55                  60

-continued

```
Gln Pro Ala Leu Gln Thr Gly Ser Glu Glu Leu Lys Ser Leu Tyr Asn
 65                  70                  75                  80

Thr Val Ala Val Leu Tyr Cys Val His Gln Arg Ile Asp Val Lys Asp
                 85                  90                  95

Thr Lys Glu Ala Leu Asp Lys Ile Glu Glu Ile Gln Asn Lys Ser Lys
            100                 105                 110

Gln Lys Thr Gln Gln Ala Ala Ala Asp Thr Gly Ser Ser Ser Lys Val
        115                 120                 125

Ser Gln Asn Tyr Pro Ile Val Gln Asn Ala Gln Gly Gln Met Val His
130                 135                 140

Gln Ala Leu Ser Pro Arg Thr Leu Asn Ala Trp Val Lys Val Val Glu
145                 150                 155                 160

Glu Lys Gly Phe Asn Pro Glu Val Ile Pro Met Phe Ser Ala Leu Ala
                165                 170                 175

Glu Gly Ala Thr Pro Gln Asp Leu Asn Met Met Leu Asn Ile Val Gly
            180                 185                 190

Gly His Gln Ala Ala Met Gln Ile Leu Lys Asp Thr Ile Asn Glu Glu
        195                 200                 205

Ala Ala Asp Trp Asp Arg Leu His Pro Val His Ala Gly Pro Ile Pro
210                 215                 220

Pro Gly Gln Met Arg Glu Pro Arg Gly Ser Asp Ile Ala Gly Thr Thr
225                 230                 235                 240

Ser Thr Pro Gln Glu Gln Ile Gly Trp Met Thr Ser Asn Pro Pro Val
                245                 250                 255

Pro Val Gly Glu Ile Tyr Lys Arg Trp Ile Ile Met Gly Leu Asn Lys
            260                 265                 270

Ile Val Arg Met Tyr Ser Pro Val Ser Ile Leu Asp Ile Lys Gln Gly
        275                 280                 285

Pro Lys Glu Ser Phe Arg Asp Tyr Val Asp Arg Phe Phe Lys Val Leu
290                 295                 300

Arg Ala Glu Gln Ala Thr Gln Glu Val Lys Asn Trp Met Thr Glu Thr
305                 310                 315                 320

Leu Leu Ile Gln Asn Ala Asn Pro Asp Cys Lys Ser Ile Leu Arg Ala
                325                 330                 335

Leu Gly Pro Gly Ala Ser Leu Glu Glu Met Met Thr Ala Cys Gln Gly
            340                 345                 350

Val Gly Gly Pro Ser His Lys Ala Arg Ile Leu Ala Glu Ala Met Ser
        355                 360                 365

Gln Ala Asn Asn Thr Asn Ile Met Met Gln Arg Gly Asn Phe Lys Gly
370                 375                 380

Gln Lys Arg Ile Lys Cys Phe Asn Cys Gly Lys Glu Gly His Leu Ala
385                 390                 395                 400

Arg Asn Cys Arg Ala Pro Arg Lys Arg Gly Cys Trp Lys Cys Gly Arg
                405                 410                 415

Glu Gly His Gln Met Lys Asp Cys Asn Glu Arg Gln Ala Asn Phe Leu
            420                 425                 430

Gly Lys Ile Trp Pro Ser Ser Lys Gly Arg Pro Gly Asn Phe Pro Gln
        435                 440                 445

Ser Arg Pro Glu Pro Thr Ala Pro Leu Glu Pro Thr Ala Pro Pro Ala
450                 455                 460

Glu Pro Thr Ala Pro Pro Ala Glu Ser Phe Gly Phe Gly Glu Glu Ile
465                 470                 475                 480
```

```
Thr Pro Ser Pro Lys Gln Glu Gln Lys Asp Arg Glu Pro Leu Thr Ser
            485                 490                 495

Leu Lys Ser Leu Phe Gly Ser Asp Pro Leu Leu Gln
            500                 505

<210> SEQ ID NO 16
<211> LENGTH: 206
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Met Ala Gly Lys Trp Ser Lys Ser Ser Val Val Gly Trp Pro Ala Ile
1               5                   10                  15

Arg Glu Arg Met Arg Arg Ala Glu Pro Ala Ala Asp Gly Val Gly Ala
                20                  25                  30

Val Ser Arg Asp Leu Glu Lys His Gly Ala Ile Thr Ser Ser Asn Thr
            35                  40                  45

Ala Ala Asn Asn Ala Asp Cys Ala Trp Leu Glu Ala Gln Glu Glu Glu
        50                  55                  60

Glu Val Gly Phe Pro Val Arg Pro Gln Val Pro Leu Arg Pro Met Thr
65                  70                  75                  80

Tyr Lys Gly Ala Leu Asp Leu Ser His Phe Leu Lys Glu Lys Gly Gly
                85                  90                  95

Leu Glu Gly Leu Ile Tyr Ser Gln Lys Arg Gln Asp Ile Leu Asp Leu
                100                 105                 110

Trp Val Tyr His Thr Gln Gly Tyr Phe Pro Asp Trp Gln Asn Tyr Thr
            115                 120                 125

Pro Gly Pro Gly Ile Arg Tyr Pro Leu Thr Phe Gly Trp Cys Phe Lys
        130                 135                 140

Leu Val Pro Val Glu Pro Glu Lys Ile Glu Glu Ala Asn Glu Gly Glu
145                 150                 155                 160

Asn Asn Ser Leu Leu His Pro Met Ser Gln His Gly Met Asp Asp Pro
                165                 170                 175

Glu Lys Glu Val Leu Met Trp Lys Phe Asp Ser Arg Leu Ala Phe His
                180                 185                 190

His Met Ala Arg Glu Leu His Pro Glu Tyr Tyr Lys Asp Cys
            195                 200                 205

<210> SEQ ID NO 17
<211> LENGTH: 206
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Met Ala Gly Lys Trp Ser Lys Ser Ser Ile Val Gly Trp Pro Ala Val
1               5                   10                  15

Arg Glu Arg Ile Arg Arg Ala Glu Pro Ala Ala Glu Gly Val Gly Ala
                20                  25                  30

Ala Ser Gln Asp Leu Asp Lys Tyr Gly Ala Leu Thr Ser Ser Asn Thr
            35                  40                  45

Ala Ala Thr Asn Ala Asp Cys Ala Trp Leu Glu Ala Gln Glu Asp Glu
        50                  55                  60
```

```
Glu Val Gly Phe Pro Val Lys Pro Gln Val Pro Leu Arg Pro Met Thr
 65                  70                  75                  80

Tyr Lys Ala Ala Phe Asp Leu Ser Phe Leu Lys Glu Lys Gly Gly
                 85                  90                  95

Leu Asp Gly Leu Ile Tyr Ser Lys Lys Arg Gln Glu Ile Leu Asp Leu
            100                 105                 110

Trp Val Tyr Asn Thr Gln Gly Phe Phe Pro Asp Trp Gln Asn Tyr Thr
            115                 120                 125

Pro Gly Pro Gly Val Arg Tyr Pro Leu Thr Phe Gly Trp Cys Phe Lys
            130                 135                 140

Leu Val Pro Val Asp Pro Arg Glu Val Glu Glu Ala Asn Lys Gly Glu
145                 150                 155                 160

Asn Asn Cys Leu Leu His Pro Met Asn Leu His Gly Met Asp Asp Pro
                165                 170                 175

Glu Arg Glu Val Leu Val Trp Arg Phe Asp Ser Arg Leu Ala Phe His
            180                 185                 190

His Met Ala Arg Glu Lys His Pro Glu Tyr Tyr Lys Asn Cys
            195                 200                 205

<210> SEQ ID NO 18
<211> LENGTH: 208
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Met Ala Gly Lys Trp Ser Lys Arg Ser Val Gly Trp Pro Ala Val
  1               5                  10                  15

Arg Glu Arg Met Arg Arg Thr Glu Pro Ala Ala Glu Gly Val Gly Ala
                 20                  25                  30

Val Ser Gln Asp Leu Asp Lys His Gly Ala Leu Thr Ser Ser Asn Thr
             35                  40                  45

Ala His Asn Asn Ala Asp Cys Ala Trp Leu Gln Ala Gln Glu Glu Glu
         50                  55                  60

Glu Glu Val Gly Phe Pro Val Arg Pro Gln Val Pro Val Arg Pro Met
 65                  70                  75                  80

Thr Tyr Lys Ala Ala Val Asp Leu Ser His Phe Leu Lys Glu Lys Gly
                 85                  90                  95

Gly Leu Glu Gly Leu Ile His Ser Gln Lys Arg Gln Glu Ile Leu Asp
            100                 105                 110

Leu Trp Val Tyr His Thr Gln Gly Phe Phe Pro Asp Trp His Asn Tyr
            115                 120                 125

Thr Pro Gly Pro Gly Thr Arg Phe Pro Leu Thr Phe Gly Trp Cys Tyr
            130                 135                 140

Lys Leu Val Pro Val Asp Pro Lys Glu Val Glu Glu Ala Asn Glu Gly
145                 150                 155                 160

Glu Asn Asn Cys Leu Leu His Pro Met Ser Gln His Gly Met Glu Asp
                165                 170                 175

Glu Asp Arg Glu Val Leu Lys Trp Lys Phe Asp Ser Ser Leu Ala Arg
            180                 185                 190

Arg His Met Ala Arg Glu Leu His Pro Glu Phe Tyr Lys Asp Cys Leu
            195                 200                 205

<210> SEQ ID NO 19
```

```
<211> LENGTH: 705
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19
```

| Met | Gly | Ala | Arg | Ala | Ser | Val | Leu | Ser | Gly | Gly | Glu | Leu | Asp | Arg | Trp |
|---|---|---|---|---|---|---|---|---|---|---|---|---|---|---|---|
| 1 | | | | 5 | | | | | 10 | | | | | 15 | |

| Glu | Lys | Ile | Arg | Leu | Arg | Pro | Gly | Gly | Lys | Lys | Tyr | Arg | Leu | Lys |
|---|---|---|---|---|---|---|---|---|---|---|---|---|---|---|
| | | | 20 | | | | | 25 | | | | | 30 | |

| His | Ile | Val | Trp | Ala | Ser | Arg | Glu | Leu | Glu | Arg | Phe | Ala | Val | Asn | Pro |
|---|---|---|---|---|---|---|---|---|---|---|---|---|---|---|---|
| | | | 35 | | | | | 40 | | | | | 45 | | |

| Gly | Leu | Leu | Glu | Thr | Ser | Glu | Gly | Cys | Arg | Gln | Ile | Leu | Gly | Gln | Leu |
|---|---|---|---|---|---|---|---|---|---|---|---|---|---|---|---|
| | 50 | | | | | 55 | | | | | 60 | | | | |

| Gln | Pro | Ser | Leu | Gln | Thr | Gly | Ser | Glu | Glu | Leu | Arg | Ser | Leu | Tyr | Asn |
|---|---|---|---|---|---|---|---|---|---|---|---|---|---|---|---|
| 65 | | | | | 70 | | | | | 75 | | | | | 80 |

| Thr | Val | Ala | Thr | Leu | Tyr | Cys | Val | His | Gln | Arg | Ile | Glu | Ile | Lys | Asp |
|---|---|---|---|---|---|---|---|---|---|---|---|---|---|---|---|
| | | | | 85 | | | | | 90 | | | | | 95 | |

| Thr | Lys | Glu | Ala | Leu | Glu | Lys | Ile | Glu | Glu | Gln | Asn | Lys | Ser | Lys |
|---|---|---|---|---|---|---|---|---|---|---|---|---|---|---|
| | | | 100 | | | | | 105 | | | | | 110 | |

| Lys | Lys | Ala | Gln | Gln | Ala | Ala | Ala | Asp | Thr | Gly | Asn | Ser | Ser | Gln | Val |
|---|---|---|---|---|---|---|---|---|---|---|---|---|---|---|---|
| | | 115 | | | | | 120 | | | | | 125 | | | |

| Ser | Gln | Asn | Tyr | Pro | Ile | Val | Gln | Asn | Ile | Gln | Gly | Gln | Met | Val | His |
|---|---|---|---|---|---|---|---|---|---|---|---|---|---|---|---|
| | 130 | | | | | 135 | | | | | 140 | | | | |

| Gln | Ala | Ile | Ser | Pro | Arg | Thr | Leu | Asn | Ala | Trp | Val | Lys | Val | Val | Glu |
|---|---|---|---|---|---|---|---|---|---|---|---|---|---|---|---|
| 145 | | | | | 150 | | | | | 155 | | | | | 160 |

| Glu | Lys | Ala | Phe | Ser | Pro | Glu | Val | Ile | Pro | Met | Phe | Ser | Ala | Leu | Ser |
|---|---|---|---|---|---|---|---|---|---|---|---|---|---|---|---|
| | | | | 165 | | | | | 170 | | | | | 175 | |

| Glu | Gly | Ala | Thr | Pro | Gln | Asp | Leu | Asn | Thr | Met | Leu | Asn | Thr | Val | Gly |
|---|---|---|---|---|---|---|---|---|---|---|---|---|---|---|---|
| | | | 180 | | | | | 185 | | | | | 190 | | |

| Gly | His | Gln | Ala | Ala | Met | Gln | Met | Leu | Lys | Glu | Thr | Ile | Asn | Glu | Glu |
|---|---|---|---|---|---|---|---|---|---|---|---|---|---|---|---|
| | | | 195 | | | | | 200 | | | | | 205 | | |

| Ala | Ala | Glu | Trp | Asp | Arg | Val | His | Pro | Val | His | Ala | Gly | Pro | Ile | Ala |
|---|---|---|---|---|---|---|---|---|---|---|---|---|---|---|---|
| 210 | | | | | 215 | | | | | 220 | | | | | |

| Pro | Gly | Gln | Met | Arg | Glu | Pro | Arg | Gly | Ser | Asp | Ile | Ala | Gly | Thr | Thr |
|---|---|---|---|---|---|---|---|---|---|---|---|---|---|---|---|
| 225 | | | | | 230 | | | | | 235 | | | | | 240 |

| Ser | Thr | Leu | Gln | Glu | Gln | Ile | Gly | Trp | Met | Thr | Asn | Asn | Pro | Pro | Ile |
|---|---|---|---|---|---|---|---|---|---|---|---|---|---|---|---|
| | | | | 245 | | | | | 250 | | | | | 255 | |

| Pro | Val | Gly | Glu | Ile | Tyr | Lys | Arg | Trp | Ile | Ile | Leu | Gly | Leu | Asn | Lys |
|---|---|---|---|---|---|---|---|---|---|---|---|---|---|---|---|
| | | | 260 | | | | | 265 | | | | | 270 | | |

| Ile | Val | Arg | Met | Tyr | Ser | Pro | Val | Ser | Ile | Leu | Asp | Ile | Arg | Gln | Gly |
|---|---|---|---|---|---|---|---|---|---|---|---|---|---|---|---|
| | | | 275 | | | | | 280 | | | | | 285 | | |

| Pro | Lys | Glu | Pro | Phe | Arg | Asp | Tyr | Val | Asp | Arg | Phe | Tyr | Lys | Thr | Leu |
|---|---|---|---|---|---|---|---|---|---|---|---|---|---|---|---|
| | 290 | | | | | 295 | | | | | 300 | | | | |

| Arg | Ala | Glu | Gln | Ala | Ser | Gln | Asp | Val | Lys | Asn | Trp | Met | Thr | Glu | Thr |
|---|---|---|---|---|---|---|---|---|---|---|---|---|---|---|---|
| 305 | | | | | 310 | | | | | 315 | | | | | 320 |

| Leu | Leu | Val | Gln | Asn | Ala | Asn | Pro | Asp | Cys | Lys | Thr | Ile | Leu | Lys | Ala |
|---|---|---|---|---|---|---|---|---|---|---|---|---|---|---|---|
| | | | | 325 | | | | | 330 | | | | | 335 | |

| Leu | Gly | Pro | Ala | Ala | Thr | Leu | Glu | Glu | Met | Met | Thr | Ala | Cys | Gln | Gly |
|---|---|---|---|---|---|---|---|---|---|---|---|---|---|---|---|
| | | | 340 | | | | | 345 | | | | | 350 | | |

| Val | Gly | Gly | Pro | Gly | His | Lys | Ala | Arg | Val | Leu | Ala | Glu | Ala | Met | Ser |
|---|---|---|---|---|---|---|---|---|---|---|---|---|---|---|---|
| | | 355 | | | | | 360 | | | | | 365 | | | |

| Gln | Val | Thr | Asn | Ser | Ala | Thr | Ile | Met | Met | Gln | Arg | Gly | Asn | Phe | Arg |
|---|---|---|---|---|---|---|---|---|---|---|---|---|---|---|---|

```
                    370                 375                 380
Asn Gln Arg Lys Thr Val Lys Cys Phe Asn Cys Gly Lys Glu Gly His
385                 390                 395                 400

Ile Ala Lys Asn Cys Arg Ala Pro Arg Lys Lys Gly Cys Trp Lys Cys
                405                 410                 415

Gly Lys Glu Gly His Gln Met Lys Asp Cys Thr Glu Arg Gln Ala Asn
            420                 425                 430

Phe Leu Gly Lys Ile Trp Pro Ser Asn Lys Gly Arg Pro Gly Asn Phe
        435                 440                 445

Leu Gln Asn Arg Pro Glu Pro Thr Ala Pro Glu Glu Ser Phe Arg
    450                 455                 460

Phe Gly Glu Glu Thr Thr Thr Pro Ser Gln Lys Gln Glu Pro Ile Asp
465                 470                 475                 480

Lys Glu Met Tyr Pro Leu Ala Ser Leu Lys Ser Leu Phe Gly Asn Asp
                485                 490                 495

Pro Ser Ser Gln Ala Gly Lys Trp Ser Lys Ser Ser Val Val Gly Trp
            500                 505                 510

Pro Ala Ile Arg Glu Arg Met Arg Arg Ala Glu Pro Ala Ala Asp Gly
        515                 520                 525

Val Gly Ala Val Ser Arg Asp Leu Glu Lys His Gly Ala Ile Thr Ser
    530                 535                 540

Ser Asn Thr Ala Ala Asn Asn Ala Asp Cys Ala Trp Leu Glu Ala Gln
545                 550                 555                 560

Glu Glu Glu Glu Val Gly Phe Pro Val Arg Pro Gln Val Pro Leu Arg
                565                 570                 575

Pro Met Thr Tyr Lys Gly Ala Leu Asp Leu Ser His Phe Leu Lys Glu
            580                 585                 590

Lys Gly Gly Leu Glu Gly Leu Ile Tyr Ser Gln Lys Arg Gln Asp Ile
        595                 600                 605

Leu Asp Leu Trp Val Tyr His Thr Gln Gly Tyr Phe Pro Asp Trp Gln
    610                 615                 620

Asn Tyr Thr Pro Gly Pro Gly Ile Arg Tyr Pro Leu Thr Phe Gly Trp
625                 630                 635                 640

Cys Phe Lys Leu Val Pro Val Glu Pro Glu Lys Ile Glu Glu Ala Asn
                645                 650                 655

Glu Gly Glu Asn Asn Ser Leu Leu His Pro Met Ser Gln His Gly Met
            660                 665                 670

Asp Asp Pro Glu Lys Glu Val Leu Met Trp Lys Phe Asp Ser Arg Leu
        675                 680                 685

Ala Phe His His Met Ala Arg Glu Leu His Pro Glu Tyr Tyr Lys Asp
    690                 695                 700
Cys
705

<210> SEQ ID NO 20
<211> LENGTH: 696
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Met Gly Ala Arg Ala Ser Ile Leu Arg Gly Gly Lys Leu Asp Lys Trp
1               5                   10                  15
```

-continued

```
Glu Lys Ile Arg Leu Arg Pro Gly Gly Lys Lys His Tyr Met Leu Lys
         20                  25                  30
His Leu Val Trp Ala Ser Arg Glu Leu Glu Arg Phe Ala Leu Asn Pro
             35                  40                  45
Gly Leu Leu Glu Thr Ser Glu Gly Cys Lys Gln Ile Ile Lys Gln Leu
 50                  55                  60
Gln Pro Ala Leu Gln Thr Gly Thr Glu Glu Leu Arg Ser Leu Phe Asn
 65                  70                  75                  80
Thr Val Ala Thr Leu Tyr Cys Val His Ala Glu Ile Glu Val Arg Asp
                 85                  90                  95
Thr Lys Glu Ala Leu Asp Lys Ile Glu Glu Gln Asn Lys Ser Gln
             100                 105                 110
Gln Lys Thr Gln Gln Ala Lys Glu Ala Asp Gly Lys Val Ser Gln Asn
         115                 120                 125
Tyr Pro Ile Val Gln Asn Leu Gln Gly Gln Met Val His Gln Pro Ile
130                 135                 140
Ser Pro Arg Thr Leu Asn Ala Trp Val Lys Val Ile Glu Glu Lys Ala
145                 150                 155                 160
Phe Ser Pro Glu Val Ile Pro Met Phe Thr Ala Leu Ser Glu Gly Ala
                 165                 170                 175
Thr Pro Gln Asp Leu Asn Thr Met Leu Asn Thr Val Gly Gly His Gln
             180                 185                 190
Ala Ala Met Gln Met Leu Lys Asp Thr Ile Asn Glu Glu Ala Ala Glu
         195                 200                 205
Trp Asp Arg Leu His Pro Val His Ala Gly Pro Val Ala Pro Gly Gln
210                 215                 220
Met Arg Glu Pro Arg Gly Ser Asp Ile Ala Gly Thr Thr Ser Asn Leu
225                 230                 235                 240
Gln Glu Gln Ile Ala Trp Met Thr Ser Asn Pro Pro Ile Pro Val Gly
                 245                 250                 255
Asp Ile Tyr Lys Arg Trp Ile Ile Leu Gly Leu Asn Lys Ile Val Arg
             260                 265                 270
Met Tyr Ser Pro Thr Ser Ile Leu Asp Ile Lys Gln Gly Pro Lys Glu
         275                 280                 285
Pro Phe Arg Asp Tyr Val Asp Arg Phe Phe Lys Thr Leu Arg Ala Glu
290                 295                 300
Gln Ala Thr Gln Asp Val Lys Asn Trp Met Thr Asp Thr Leu Leu Val
305                 310                 315                 320
Gln Asn Ala Asn Pro Asp Cys Lys Thr Ile Leu Arg Ala Leu Gly Pro
                 325                 330                 335
Gly Ala Thr Leu Glu Glu Met Met Thr Ala Cys Gln Gly Val Gly Gly
             340                 345                 350
Pro Ser His Lys Ala Arg Val Leu Ala Glu Ala Met Ser Gln Thr Asn
         355                 360                 365
Ser Thr Ile Leu Met Gln Arg Ser Asn Phe Lys Gly Ser Lys Arg Ile
370                 375                 380
Val Lys Cys Phe Asn Cys Gly Lys Glu Gly His Ile Ala Arg Asn Cys
385                 390                 395                 400
Arg Ala Pro Arg Lys Lys Gly Cys Trp Lys Cys Gly Lys Glu Gly His
                 405                 410                 415
Gln Met Lys Asp Cys Thr Glu Arg Gln Ala Asn Phe Leu Gly Lys Ile
             420                 425                 430
Trp Pro Ser His Lys Gly Arg Pro Gly Asn Phe Leu Gln Ser Arg Pro
```

```
                       435                 440                 445
Glu Pro Thr Ala Pro Ala Glu Ser Phe Arg Phe Glu Thr Thr
450                 455                 460

Pro Ala Pro Lys Gln Glu Pro Lys Asp Arg Glu Pro Leu Thr Ser Leu
465                 470                 475                 480

Arg Ser Leu Phe Gly Ser Asp Pro Leu Ser Gln Ala Gly Lys Trp Ser
                485                 490                 495

Lys Ser Ser Ile Val Gly Trp Pro Ala Val Arg Glu Arg Ile Arg Arg
            500                 505                 510

Ala Glu Pro Ala Glu Gly Val Gly Ala Ala Ser Gln Asp Leu Asp
        515                 520                 525

Lys Tyr Gly Ala Leu Thr Ser Ser Asn Thr Ala Thr Asn Ala Asp
530                 535                 540

Cys Ala Trp Leu Glu Ala Gln Glu Asp Glu Val Gly Phe Pro Val
545                 550                 555                 560

Lys Pro Gln Val Pro Leu Arg Pro Met Thr Tyr Lys Ala Ala Phe Asp
                565                 570                 575

Leu Ser Phe Phe Leu Lys Glu Lys Gly Gly Leu Asp Gly Leu Ile Tyr
            580                 585                 590

Ser Lys Lys Arg Gln Glu Ile Leu Asp Leu Trp Val Tyr Asn Thr Gln
        595                 600                 605

Gly Phe Phe Pro Asp Trp Gln Asn Tyr Thr Pro Gly Pro Gly Val Arg
610                 615                 620

Tyr Pro Leu Thr Phe Gly Trp Cys Phe Lys Leu Val Pro Val Asp Pro
625                 630                 635                 640

Arg Glu Val Glu Glu Ala Asn Lys Gly Glu Asn Asn Cys Leu Leu His
                645                 650                 655

Pro Met Asn Leu His Gly Met Asp Asp Pro Glu Arg Glu Val Leu Val
            660                 665                 670

Trp Arg Phe Asp Ser Arg Leu Ala Phe His His Met Ala Arg Glu Lys
        675                 680                 685

His Pro Glu Tyr Tyr Lys Asn Cys
    690                 695

<210> SEQ ID NO 21
<211> LENGTH: 1350
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Met Gly Ala Arg Ala Ser Val Leu Ser Gly Gly Glu Leu Asp Arg Trp
1               5                   10                  15

Glu Lys Ile Arg Leu Arg Pro Gly Gly Lys Lys Tyr Arg Leu Lys
            20                  25                  30

His Ile Val Trp Ala Ser Arg Glu Leu Glu Arg Phe Ala Val Asn Pro
        35                  40                  45

Gly Leu Leu Glu Thr Ser Glu Gly Cys Arg Gln Ile Leu Gly Gln Leu
    50                  55                  60

Gln Pro Ser Leu Gln Thr Gly Ser Glu Glu Leu Arg Ser Leu Tyr Asn
65                  70                  75                  80

Thr Val Ala Thr Leu Tyr Cys Val His Gln Arg Ile Glu Ile Lys Asp
                85                  90                  95
```

-continued

```
Thr Lys Glu Ala Leu Glu Lys Ile Glu Glu Gln Asn Lys Ser Lys
             100                 105                 110
Lys Lys Ala Gln Gln Ala Ala Asp Thr Gly Asn Ser Ser Gln Val
         115                 120                 125
Ser Gln Asn Tyr Pro Ile Val Gln Asn Ile Gln Gly Gln Met Val His
     130                 135                 140
Gln Ala Ile Ser Pro Arg Thr Leu Asn Ala Trp Val Lys Val Val Glu
145                 150                 155                 160
Glu Lys Ala Phe Ser Pro Glu Val Ile Pro Met Phe Ser Ala Leu Ser
                 165                 170                 175
Glu Gly Ala Thr Pro Gln Asp Leu Asn Thr Met Leu Asn Thr Val Gly
             180                 185                 190
Gly His Gln Ala Ala Met Gln Met Leu Lys Glu Thr Ile Asn Glu Glu
         195                 200                 205
Ala Ala Glu Trp Asp Arg Val His Pro Val His Ala Gly Pro Ile Ala
     210                 215                 220
Pro Gly Gln Met Arg Glu Pro Arg Gly Ser Asp Ile Ala Gly Thr Thr
225                 230                 235                 240
Ser Thr Leu Gln Glu Gln Ile Gly Trp Met Thr Asn Asn Pro Pro Ile
                 245                 250                 255
Pro Val Gly Glu Ile Tyr Lys Arg Trp Ile Ile Leu Gly Leu Asn Lys
             260                 265                 270
Ile Val Arg Met Tyr Ser Pro Val Ser Ile Leu Asp Ile Arg Gln Gly
         275                 280                 285
Pro Lys Glu Pro Phe Arg Asp Tyr Val Asp Arg Phe Tyr Lys Thr Leu
     290                 295                 300
Arg Ala Glu Gln Ala Ser Gln Asp Val Lys Asn Trp Met Thr Glu Thr
305                 310                 315                 320
Leu Leu Val Gln Asn Ala Asn Pro Asp Cys Lys Thr Ile Leu Lys Ala
                 325                 330                 335
Leu Gly Pro Ala Ala Thr Leu Glu Glu Met Met Thr Ala Cys Gln Gly
             340                 345                 350
Val Gly Gly Pro Gly His Lys Ala Arg Val Leu Ala Glu Ala Met Ser
         355                 360                 365
Gln Val Thr Asn Ser Ala Thr Ile Met Met Gln Arg Gly Asn Phe Arg
     370                 375                 380
Asn Gln Arg Lys Thr Val Lys Cys Phe Asn Cys Gly Lys Glu Gly His
385                 390                 395                 400
Ile Ala Lys Asn Cys Arg Ala Pro Arg Lys Lys Gly Cys Trp Lys Cys
                 405                 410                 415
Gly Lys Glu Gly His Gln Met Lys Asp Cys Thr Glu Arg Gln Ala Asn
             420                 425                 430
Phe Leu Gly Lys Ile Trp Pro Ser Asn Lys Gly Arg Pro Gly Asn Phe
         435                 440                 445
Leu Gln Asn Arg Pro Glu Pro Thr Ala Pro Pro Glu Glu Ser Phe Arg
     450                 455                 460
Phe Gly Glu Glu Thr Thr Thr Pro Ser Gln Lys Gln Glu Pro Ile Asp
465                 470                 475                 480
Lys Glu Met Tyr Pro Leu Ala Ser Leu Lys Ser Leu Phe Gly Asn Asp
                 485                 490                 495
Pro Ser Ser Gln Met Ala Pro Ile Ser Pro Ile Glu Thr Val Pro Val
             500                 505                 510
Lys Leu Lys Pro Gly Met Asp Gly Pro Arg Val Lys Gln Trp Pro Leu
```

```
                515                 520                 525
Thr Glu Glu Lys Ile Lys Ala Leu Thr Ala Ile Cys Glu Glu Met Glu
    530                 535                 540

Lys Glu Gly Lys Ile Thr Lys Ile Gly Pro Glu Asn Pro Tyr Asn Thr
545                 550                 555                 560

Pro Val Phe Ala Ile Lys Lys Lys Asp Ser Thr Lys Trp Arg Lys Leu
                565                 570                 575

Val Asp Phe Arg Glu Leu Asn Lys Arg Thr Gln Asp Phe Trp Glu Val
            580                 585                 590

Gln Leu Gly Ile Pro His Pro Ala Gly Leu Lys Lys Lys Lys Ser Val
        595                 600                 605

Thr Val Leu Ala Val Gly Asp Ala Tyr Phe Ser Val Pro Leu Asp Glu
    610                 615                 620

Gly Phe Arg Lys Tyr Thr Ala Phe Thr Ile Pro Ser Thr Asn Asn Glu
625                 630                 635                 640

Thr Pro Gly Ile Arg Tyr Gln Tyr Asn Val Leu Pro Gln Gly Trp Lys
                645                 650                 655

Gly Ser Pro Ala Ile Phe Gln Cys Ser Met Thr Arg Ile Leu Glu Pro
            660                 665                 670

Phe Arg Ala Lys Asn Pro Glu Ile Val Ile Tyr Gln Tyr Met Ala Ala
        675                 680                 685

Leu Tyr Val Gly Ser Asp Leu Glu Ile Gly Gln His Arg Ala Lys Ile
    690                 695                 700

Glu Glu Leu Arg Glu His Leu Leu Lys Trp Gly Phe Thr Thr Pro Asp
705                 710                 715                 720

Lys Lys His Gln Lys Glu Pro Pro Phe Leu Trp Met Gly Tyr Glu Leu
                725                 730                 735

His Pro Asp Lys Trp Thr Val Gln Pro Ile Gln Leu Pro Glu Lys Asp
            740                 745                 750

Ser Trp Thr Val Asn Asp Ile Gln Lys Leu Val Gly Lys Leu Asn Trp
        755                 760                 765

Ala Ser Gln Ile Tyr Pro Gly Ile Lys Val Arg Gln Leu Cys Lys Leu
    770                 775                 780

Leu Arg Gly Ala Lys Ala Leu Thr Asp Ile Val Pro Leu Thr Glu Glu
785                 790                 795                 800

Ala Glu Leu Glu Leu Ala Glu Asn Arg Glu Ile Leu Lys Glu Pro Val
                805                 810                 815

His Gly Val Tyr Tyr Asp Pro Ser Lys Asp Leu Ile Ala Glu Ile Gln
            820                 825                 830

Lys Gln Gly His Asp Gln Trp Thr Tyr Gln Ile Tyr Gln Glu Pro Phe
        835                 840                 845

Lys Asn Leu Lys Thr Gly Lys Tyr Ala Lys Met Arg Thr Ala His Thr
    850                 855                 860

Asn Asp Val Lys Gln Leu Thr Glu Ala Val Gln Lys Ile Ala Met Glu
865                 870                 875                 880

Ser Ile Val Ile Trp Gly Lys Thr Pro Lys Phe Arg Leu Pro Ile Gln
                885                 890                 895

Lys Glu Thr Trp Glu Thr Trp Trp Thr Asp Tyr Trp Gln Ala Thr Trp
            900                 905                 910

Ile Pro Glu Trp Glu Phe Val Asn Thr Pro Pro Leu Val Lys Leu Trp
        915                 920                 925

Tyr Gln Leu Glu Lys Asp Pro Ile Ala Gly Val Glu Thr Phe Tyr Val
    930                 935                 940
```

```
Ala Gly Ala Ala Asn Arg Glu Thr Lys Leu Gly Lys Ala Gly Tyr Val
945                 950                 955                 960

Thr Asp Arg Gly Arg Gln Lys Ile Val Ser Leu Thr Glu Thr Thr Asn
                965                 970                 975

Gln Lys Thr Ala Leu Gln Ala Ile Tyr Leu Ala Leu Gln Asp Ser Gly
            980                 985                 990

Ser Glu Val Asn Ile Val Thr Ala Ser Gln Tyr Ala Leu Gly Ile Ile
        995                 1000                1005

Gln Ala Gln Pro Asp Lys Ser Glu Ser Glu Leu Val Asn Gln Ile
    1010                1015                1020

Ile Glu Gln Leu Ile Lys Lys Glu Arg Val Tyr Leu Ser Trp Val
    1025                1030                1035

Pro Ala His Lys Gly Ile Gly Gly Asn Glu Gln Val Asp Lys Leu
    1040                1045                1050

Val Ser Ser Gly Ile Arg Lys Val Leu Phe Leu Asp Gly Ile Asp
    1055                1060                1065

Lys Ala Gln Glu Glu His Glu Lys Tyr His Ser Asn Trp Arg Ala
    1070                1075                1080

Met Ala Ser Asp Phe Asn Leu Pro Pro Val Val Ala Lys Glu Ile
    1085                1090                1095

Val Ala Ser Cys Asp Gln Cys Gln Leu Lys Gly Glu Ala Met His
    1100                1105                1110

Gly Gln Val Asp Cys Ser Pro Gly Ile Trp Gln Leu Ala Cys Thr
    1115                1120                1125

His Leu Glu Gly Lys Ile Ile Leu Val Ala Val His Val Ala Ser
    1130                1135                1140

Gly Tyr Ile Glu Ala Glu Val Ile Pro Ala Glu Thr Gly Gln Glu
    1145                1150                1155

Thr Ala Tyr Phe Ile Leu Lys Leu Ala Gly Arg Trp Pro Val Lys
    1160                1165                1170

Val Ile His Thr Ala Asn Gly Ser Asn Phe Thr Ser Ala Ala Val
    1175                1180                1185

Lys Ala Ala Cys Trp Trp Ala Gly Ile Gln Gln Glu Phe Gly Ile
    1190                1195                1200

Pro Tyr Asn Pro Gln Ser Gln Gly Val Val Ala Ser Met Asn Lys
    1205                1210                1215

Glu Leu Lys Lys Ile Ile Gly Gln Val Arg Asp Gln Ala Glu His
    1220                1225                1230

Leu Lys Thr Ala Val Gln Met Ala Val Phe Ile His Asn Phe Lys
    1235                1240                1245

Arg Lys Gly Gly Ile Gly Gly Tyr Ser Ala Gly Glu Arg Ile Ile
    1250                1255                1260

Asp Ile Ile Ala Thr Asp Ile Gln Thr Lys Glu Leu Gln Lys Gln
    1265                1270                1275

Ile Ile Lys Ile Gln Asn Phe Arg Val Tyr Tyr Arg Asp Ser Arg
    1280                1285                1290

Asp Pro Ile Trp Lys Gly Pro Ala Lys Leu Leu Trp Lys Gly Glu
    1295                1300                1305

Gly Ala Val Val Ile Gln Asp Asn Ser Asp Ile Lys Val Val Pro
    1310                1315                1320

Arg Arg Lys Val Lys Ile Ile Lys Asp Tyr Gly Lys Gln Met Ala
    1325                1330                1335
```

```
Gly Ala Asp Cys Val Ala Gly Arg Gln Asp Glu Asp
    1340                1345                1350
```

<210> SEQ ID NO 22
<211> LENGTH: 1341
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

```
Met Gly Ala Arg Ala Ser Ile Leu Arg Gly Gly Lys Leu Asp Lys Trp
1               5                   10                  15

Glu Lys Ile Arg Leu Arg Pro Gly Gly Lys Lys His Tyr Met Leu Lys
            20                  25                  30

His Leu Val Trp Ala Ser Arg Glu Leu Glu Arg Phe Ala Leu Asn Pro
        35                  40                  45

Gly Leu Leu Glu Thr Ser Glu Gly Cys Lys Gln Ile Ile Lys Gln Leu
    50                  55                  60

Gln Pro Ala Leu Gln Thr Gly Thr Glu Glu Leu Arg Ser Leu Phe Asn
65                  70                  75                  80

Thr Val Ala Thr Leu Tyr Cys Val His Ala Glu Ile Glu Val Arg Asp
                85                  90                  95

Thr Lys Glu Ala Leu Asp Lys Ile Glu Glu Gln Asn Lys Ser Gln
            100                 105                 110

Gln Lys Thr Gln Gln Ala Lys Glu Ala Asp Gly Lys Val Ser Gln Asn
        115                 120                 125

Tyr Pro Ile Val Gln Asn Leu Gln Gly Gln Met Val His Gln Pro Ile
    130                 135                 140

Ser Pro Arg Thr Leu Asn Ala Trp Val Lys Val Ile Glu Glu Lys Ala
145                 150                 155                 160

Phe Ser Pro Glu Val Ile Pro Met Phe Thr Ala Leu Ser Glu Gly Ala
                165                 170                 175

Thr Pro Gln Asp Leu Asn Thr Met Leu Asn Thr Val Gly Gly His Gln
            180                 185                 190

Ala Ala Met Gln Met Leu Lys Asp Thr Ile Asn Glu Glu Ala Ala Glu
        195                 200                 205

Trp Asp Arg Leu His Pro Val His Ala Gly Pro Val Ala Pro Gly Gln
    210                 215                 220

Met Arg Glu Pro Arg Gly Ser Asp Ile Ala Gly Thr Thr Ser Asn Leu
225                 230                 235                 240

Gln Glu Gln Ile Ala Trp Met Thr Ser Asn Pro Pro Ile Pro Val Gly
                245                 250                 255

Asp Ile Tyr Lys Arg Trp Ile Ile Leu Gly Leu Asn Lys Ile Val Arg
            260                 265                 270

Met Tyr Ser Pro Thr Ser Ile Leu Asp Ile Lys Gln Gly Pro Lys Glu
        275                 280                 285

Pro Phe Arg Asp Tyr Val Asp Arg Phe Phe Lys Thr Leu Arg Ala Glu
    290                 295                 300

Gln Ala Thr Gln Asp Val Lys Asn Trp Met Thr Asp Thr Leu Leu Val
305                 310                 315                 320

Gln Asn Ala Asn Pro Asp Cys Lys Thr Ile Leu Arg Ala Leu Gly Pro
                325                 330                 335

Gly Ala Thr Leu Glu Glu Met Met Thr Ala Cys Gln Gly Val Gly Gly
            340                 345                 350
```

```
Pro Ser His Lys Ala Arg Val Leu Ala Glu Ala Met Ser Gln Thr Asn
    355                 360                 365

Ser Thr Ile Leu Met Gln Arg Ser Asn Phe Lys Gly Ser Lys Arg Ile
370                 375                 380

Val Lys Cys Phe Asn Cys Gly Lys Glu Gly His Ile Ala Arg Asn Cys
385                 390                 395                 400

Arg Ala Pro Arg Lys Gly Cys Trp Lys Cys Gly Lys Glu Gly His
                405                 410                 415

Gln Met Lys Asp Cys Thr Glu Arg Gln Ala Asn Phe Leu Gly Lys Ile
                420                 425                 430

Trp Pro Ser His Lys Gly Arg Pro Gly Asn Phe Leu Gln Ser Arg Pro
            435                 440                 445

Glu Pro Thr Ala Pro Pro Ala Glu Ser Phe Arg Phe Glu Glu Thr Thr
            450                 455                 460

Pro Ala Pro Lys Gln Glu Pro Lys Asp Arg Glu Pro Leu Thr Ser Leu
465                 470                 475                 480

Arg Ser Leu Phe Gly Ser Asp Pro Leu Ser Gln Met Ala Pro Ile Ser
                485                 490                 495

Pro Ile Glu Thr Val Pro Val Lys Leu Lys Pro Gly Met Asp Gly Pro
                500                 505                 510

Lys Val Lys Gln Trp Pro Leu Thr Glu Glu Lys Ile Lys Ala Leu Val
            515                 520                 525

Glu Ile Cys Thr Glu Met Glu Lys Glu Gly Lys Ile Ser Lys Ile Gly
            530                 535                 540

Pro Glu Asn Pro Tyr Asn Thr Pro Ile Phe Ala Ile Lys Lys Lys Asp
545                 550                 555                 560

Ser Thr Lys Trp Arg Lys Leu Val Asp Phe Arg Glu Leu Asn Lys Arg
                565                 570                 575

Thr Gln Asp Phe Trp Glu Val Gln Leu Gly Ile Pro His Pro Ala Gly
                580                 585                 590

Leu Lys Lys Lys Lys Ser Val Thr Val Leu Ala Val Gly Asp Ala Tyr
            595                 600                 605

Phe Ser Val Pro Leu Asp Glu Asp Phe Arg Lys Tyr Thr Ala Phe Thr
            610                 615                 620

Ile Pro Ser Ile Asn Asn Glu Thr Pro Gly Ile Arg Tyr Gln Tyr Asn
625                 630                 635                 640

Val Leu Pro Gln Gly Trp Lys Gly Ser Pro Ala Ile Phe Gln Ser Ser
                645                 650                 655

Met Thr Lys Ile Leu Glu Pro Phe Arg Lys Gln Asn Pro Asp Ile Val
                660                 665                 670

Ile Tyr Gln Tyr Met Ala Ala Leu Tyr Val Gly Ser Asp Leu Glu Ile
            675                 680                 685

Gly Gln His Arg Thr Lys Ile Glu Glu Leu Arg Gln His Leu Leu Arg
            690                 695                 700

Trp Gly Phe Thr Thr Pro Asp Lys Lys His Gln Lys Glu Pro Pro Phe
705                 710                 715                 720

Leu Trp Met Gly Tyr Glu Leu His Pro Asp Lys Trp Thr Val Gln Pro
                725                 730                 735

Ile Val Leu Pro Glu Lys Asp Ser Trp Thr Val Asn Asp Ile Gln Lys
                740                 745                 750

Leu Val Gly Lys Leu Asn Trp Ala Ser Gln Ile Tyr Ala Gly Ile Lys
            755                 760                 765
```

-continued

Val Lys Gln Leu Cys Lys Leu Leu Arg Gly Thr Lys Ala Leu Thr Glu
770             775                 780

Val Val Pro Leu Thr Glu Glu Ala Glu Leu Glu Leu Ala Glu Asn Arg
785             790                 795                 800

Glu Ile Leu Lys Glu Pro Val His Gly Val Tyr Tyr Asp Pro Ser Lys
                805                 810                 815

Asp Leu Ile Ala Glu Ile Gln Lys Gln Gly Gln Gly Gln Trp Thr Tyr
                820                 825                 830

Gln Ile Tyr Gln Glu Pro Phe Lys Asn Leu Lys Thr Gly Lys Tyr Ala
                835                 840                 845

Arg Met Arg Gly Ala His Thr Asn Asp Val Lys Gln Leu Thr Glu Ala
850                 855                 860

Val Gln Lys Ile Ala Thr Glu Ser Ile Val Ile Trp Gly Lys Thr Pro
865                 870                 875                 880

Lys Phe Lys Leu Pro Ile Gln Lys Glu Thr Trp Glu Ala Trp Trp Thr
                885                 890                 895

Glu Tyr Trp Gln Ala Thr Trp Ile Pro Glu Trp Glu Phe Val Asn Thr
                900                 905                 910

Pro Pro Leu Val Lys Leu Trp Tyr Gln Leu Glu Lys Glu Pro Ile Val
                915                 920                 925

Gly Ala Glu Thr Phe Tyr Val Ala Gly Ala Ala Asn Arg Glu Thr Lys
930                 935                 940

Leu Gly Lys Ala Gly Tyr Val Thr Asp Arg Gly Arg Gln Lys Val Val
945                 950                 955                 960

Ser Leu Thr Asp Thr Thr Asn Gln Lys Thr Ala Leu Gln Ala Ile His
                965                 970                 975

Leu Ala Leu Gln Asp Ser Gly Leu Glu Val Asn Ile Val Thr Ala Ser
                980                 985                 990

Gln Tyr Ala Leu Gly Ile Ile Gln Ala Gln Pro Asp Lys Ser Glu Ser
                995                 1000                1005

Glu Leu Val Ser Gln Ile Ile Glu Gln Leu Ile Lys Lys Glu Lys
                1010                1015                1020

Val Tyr Leu Ala Trp Val Pro Ala His Lys Gly Ile Gly Gly Asn
                1025                1030                1035

Glu Gln Val Asp Lys Leu Val Ser Arg Gly Ile Arg Lys Val Leu
                1040                1045                1050

Phe Leu Asp Gly Ile Asp Lys Ala Gln Glu Glu His Glu Lys Tyr
                1055                1060                1065

His Ser Asn Trp Arg Ala Met Ala Ser Glu Phe Asn Leu Pro Pro
                1070                1075                1080

Ile Val Ala Lys Glu Ile Val Ala Ser Cys Asp Lys Cys Gln Leu
                1085                1090                1095

Lys Gly Glu Ala Ile His Gly Gln Val Asp Cys Ser Pro Gly Ile
                1100                1105                1110

Trp Gln Leu Ala Cys Thr His Leu Glu Gly Lys Val Ile Leu Val
                1115                1120                1125

Ala Val His Val Ala Ser Gly Tyr Ile Glu Ala Glu Val Ile Pro
                1130                1135                1140

Ala Glu Thr Gly Gln Glu Thr Ala Tyr Phe Leu Leu Lys Leu Ala
                1145                1150                1155

Gly Arg Trp Pro Val Lys Thr Ile His Thr Ala Asn Gly Ser Asn
                1160                1165                1170

Phe Thr Ser Ala Thr Val Lys Ala Ala Cys Trp Trp Ala Gly Ile

```
                1175                1180                1185

Lys Gln Glu Phe Gly Ile Pro Tyr Asn Pro Gln Ser Gln Gly Val
            1190                1195                1200

Val Ala Ser Ile Asn Lys Glu Leu Lys Lys Ile Ile Gly Gln Val
            1205                1210                1215

Arg Asp Gln Ala Glu His Leu Lys Thr Ala Val Gln Met Ala Val
            1220                1225                1230

Phe Ile His Asn Phe Lys Arg Lys Gly Ile Gly Glu Tyr Ser
            1235                1240                1245

Ala Gly Glu Arg Ile Val Asp Ile Ile Ala Ser Asp Ile Gln Thr
            1250                1255                1260

Lys Glu Leu Gln Lys Gln Ile Thr Lys Ile Gln Asn Phe Arg Val
            1265                1270                1275

Tyr Tyr Arg Asp Ser Arg Asp Pro Leu Trp Lys Gly Pro Ala Lys
            1280                1285                1290

Leu Leu Trp Lys Gly Glu Gly Ala Val Val Ile Gln Asp Asn Ser
            1295                1300                1305

Asp Ile Lys Val Val Pro Arg Arg Lys Ala Lys Ile Ile Arg Asp
            1310                1315                1320

Tyr Gly Lys Gln Met Ala Gly Asp Asp Cys Val Ala Ser Arg Gln
            1325                1330                1335

Asp Glu Asp
    1340

<210> SEQ ID NO 23
<211> LENGTH: 1359
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Met Gly Ala Arg Ala Ser Val Leu Ser Gly Gly Lys Leu Asp Ala Trp
1               5                   10                  15

Glu Lys Ile Arg Leu Arg Pro Gly Gly Lys Lys Tyr Lys Leu Lys
            20                  25                  30

His Ile Val Trp Ala Ser Arg Glu Leu Asp Arg Phe Ala Leu Asn Pro
        35                  40                  45

Gly Leu Leu Glu Thr Ala Glu Gly Cys Gln Gln Ile Ile Glu Gln Leu
    50                  55                  60

Gln Pro Ala Leu Gln Thr Gly Ser Glu Glu Leu Lys Ser Leu Tyr Asn
65                  70                  75                  80

Thr Val Ala Val Leu Tyr Cys Val His Gln Arg Ile Asp Val Lys Asp
                85                  90                  95

Thr Lys Glu Ala Leu Asp Lys Ile Glu Glu Ile Gln Asn Lys Ser Lys
            100                 105                 110

Gln Lys Thr Gln Gln Ala Ala Ala Asp Thr Gly Ser Ser Ser Lys Val
        115                 120                 125

Ser Gln Asn Tyr Pro Ile Val Gln Asn Ala Gln Gly Gln Met Val His
    130                 135                 140

Gln Ala Leu Ser Pro Arg Thr Leu Asn Ala Trp Val Lys Val Val Glu
145                 150                 155                 160

Glu Lys Gly Phe Asn Pro Glu Val Ile Pro Met Phe Ser Ala Leu Ala
                165                 170                 175
```

-continued

Glu Gly Ala Thr Pro Gln Asp Leu Asn Met Met Leu Asn Ile Val Gly
                180                 185                 190

Gly His Gln Ala Ala Met Gln Ile Leu Lys Asp Thr Ile Asn Glu Glu
            195                 200                 205

Ala Ala Asp Trp Asp Arg Leu His Pro Val His Ala Gly Pro Ile Pro
        210                 215                 220

Pro Gly Gln Met Arg Glu Pro Arg Gly Ser Asp Ile Ala Gly Thr Thr
225                 230                 235                 240

Ser Thr Pro Gln Glu Gln Ile Gly Trp Met Thr Ser Asn Pro Pro Val
                245                 250                 255

Pro Val Gly Glu Ile Tyr Lys Arg Trp Ile Ile Met Gly Leu Asn Lys
            260                 265                 270

Ile Val Arg Met Tyr Ser Pro Val Ser Ile Leu Asp Ile Lys Gln Gly
        275                 280                 285

Pro Lys Glu Ser Phe Arg Asp Tyr Val Asp Arg Phe Phe Lys Val Leu
    290                 295                 300

Arg Ala Glu Gln Ala Thr Gln Glu Val Lys Asn Trp Met Thr Glu Thr
305                 310                 315                 320

Leu Leu Ile Gln Asn Ala Asn Pro Asp Cys Lys Ser Ile Leu Arg Ala
                325                 330                 335

Leu Gly Pro Gly Ala Ser Leu Glu Glu Met Met Thr Ala Cys Gln Gly
            340                 345                 350

Val Gly Gly Pro Ser His Lys Ala Arg Ile Leu Ala Glu Ala Met Ser
        355                 360                 365

Gln Ala Asn Asn Thr Asn Ile Met Met Gln Arg Gly Asn Phe Lys Gly
    370                 375                 380

Gln Lys Arg Ile Lys Cys Phe Asn Cys Gly Lys Glu Gly His Leu Ala
385                 390                 395                 400

Arg Asn Cys Arg Ala Pro Arg Lys Arg Gly Cys Trp Lys Cys Gly Arg
                405                 410                 415

Glu Gly His Gln Met Lys Asp Cys Asn Glu Arg Gln Ala Asn Phe Leu
            420                 425                 430

Gly Lys Ile Trp Pro Ser Ser Lys Gly Arg Pro Gly Asn Phe Pro Gln
        435                 440                 445

Ser Arg Pro Glu Pro Thr Ala Pro Leu Glu Pro Thr Ala Pro Pro Ala
    450                 455                 460

Glu Pro Thr Ala Pro Pro Ala Glu Ser Phe Gly Phe Gly Glu Glu Ile
465                 470                 475                 480

Thr Pro Ser Pro Lys Gln Glu Gln Lys Asp Arg Glu Pro Leu Thr Ser
                485                 490                 495

Leu Lys Ser Leu Phe Gly Ser Asp Pro Leu Leu Gln Met Ala Pro Ile
            500                 505                 510

Ser Pro Ile Asp Thr Val Pro Val Thr Leu Lys Pro Gly Met Asp Gly
        515                 520                 525

Pro Lys Ile Lys Gln Trp Pro Leu Thr Glu Glu Lys Ile Lys Ala Leu
    530                 535                 540

Thr Glu Ile Cys Thr Glu Met Glu Lys Glu Gly Lys Ile Ser Arg Ile
545                 550                 555                 560

Gly Pro Glu Asn Pro Tyr Asn Thr Pro Val Phe Ala Ile Lys Lys Lys
                565                 570                 575

Asn Ser Thr Arg Trp Arg Lys Leu Val Asp Phe Arg Glu Leu Asn Lys
            580                 585                 590

Lys Thr Gln Asp Phe Trp Glu Val Gln Leu Gly Ile Pro His Pro Ala

```
                595                 600                 605
Gly Leu Lys Lys Lys Arg Ser Val Thr Val Leu Ala Val Gly Asp Ala
    610                 615                 620

Tyr Phe Ser Val Pro Leu Asp Lys Asp Phe Arg Lys Tyr Thr Ala Phe
625                 630                 635                 640

Thr Ile Pro Ser Val Asn Asn Glu Thr Pro Gly Val Arg Tyr Gln Tyr
                645                 650                 655

Asn Val Leu Pro Gln Gly Trp Lys Gly Ser Pro Ala Ile Phe Gln Cys
            660                 665                 670

Ser Met Thr Lys Ile Leu Glu Pro Phe Arg Ala Gln Asn Pro Glu Ile
        675                 680                 685

Val Ile Tyr Gln Tyr Val Ala Ala Leu Tyr Val Gly Ser Asp Leu Glu
    690                 695                 700

Ile Glu Gln His Arg Thr Lys Ile Glu Leu Arg Ala His Leu Leu
705                 710                 715                 720

Ser Trp Gly Phe Thr Thr Pro Asp Lys Lys His Gln Arg Glu Pro Pro
                725                 730                 735

Phe Leu Trp Met Gly Tyr Glu Leu His Pro Asp Arg Trp Thr Val Gln
            740                 745                 750

Pro Ile Glu Leu Pro Glu Lys Glu Ser Trp Thr Val Asn Asp Ile Gln
        755                 760                 765

Lys Leu Val Gly Lys Leu Asn Trp Ala Ser Gln Ile Tyr Pro Gly Ile
    770                 775                 780

Lys Val Lys Gln Leu Cys Arg Leu Leu Arg Gly Ala Lys Ala Leu Thr
785                 790                 795                 800

Glu Val Ile Pro Leu Thr Lys Glu Ala Glu Leu Glu Leu Ala Glu Asn
                805                 810                 815

Arg Glu Ile Leu Arg Glu Pro Val His Gly Val Tyr Tyr Asp Pro Ser
            820                 825                 830

Lys Asp Leu Val Ala Glu Ile Gln Lys Gln Gly Gln Asp Gln Trp Thr
        835                 840                 845

Tyr Gln Ile Tyr Gln Glu Pro Tyr Lys Asn Leu Lys Thr Gly Lys Tyr
    850                 855                 860

Ala Arg Lys Arg Ser Ala His Thr Asn Asp Val Arg Gln Leu Thr Glu
865                 870                 875                 880

Ala Val Gln Lys Ile Ala Leu Glu Ser Ile Val Ile Trp Gly Lys Ile
                885                 890                 895

Pro Lys Phe Arg Leu Pro Ile Gln Arg Glu Thr Trp Glu Thr Trp Trp
            900                 905                 910

Thr Glu Tyr Trp Gln Ala Thr Trp Ile Pro Asp Trp Glu Phe Val Asn
        915                 920                 925

Thr Pro Pro Leu Val Lys Leu Trp Tyr Gln Leu Glu Lys Glu Pro Ile
    930                 935                 940

Ala Gly Ala Glu Thr Phe Tyr Val Ala Gly Ala Ser Asn Arg Glu Thr
945                 950                 955                 960

Lys Ile Gly Lys Ala Gly Tyr Val Thr Asp Lys Gly Arg Gln Lys Val
                965                 970                 975

Val Ser Leu Thr Glu Thr Thr Asn Gln Lys Ala Ala Leu Gln Ala Ile
            980                 985                 990

Gln Leu Ala Leu Gln Asp Ser Gly  Pro Glu Val Asn Ile  Val Thr Ala
        995                 1000                1005

Ser Gln  Tyr Val Leu Gly Ile  Ile Gln Ala Gln Pro  Asp Arg Ser
    1010                1015                1020
```

Glu Ser Glu Leu Val Asn Gln Ile Ile Glu Glu Leu Ile Lys Lys
1025                1030                1035

Glu Lys Val Tyr Leu Ser Trp Val Pro Ala His Lys Gly Ile Gly
    1040                1045                1050

Gly Asn Glu Gln Val Asp Lys Leu Val Ser Ala Gly Ile Arg Lys
    1055                1060                1065

Ile Leu Phe Leu Asp Gly Ile Asp Lys Ala Gln Glu Glu His Glu
    1070                1075                1080

Arg Tyr His Ser Asn Trp Arg Thr Met Ala Ser Asp Phe Asn Leu
    1085                1090                1095

Pro Pro Ile Val Ala Lys Glu Ile Val Ala Asn Cys Asp Lys Cys
    1100                1105                1110

Gln Leu Lys Gly Glu Ala Met His Gly Gln Val Asp Cys Ser Pro
    1115                1120                1125

Gly Met Trp Gln Leu Ala Cys Thr His Leu Glu Gly Lys Ile Ile
    1130                1135                1140

Ile Val Ala Val His Val Ala Ser Gly Tyr Met Glu Ala Glu Val
    1145                1150                1155

Ile Pro Ala Glu Thr Gly Gln Glu Thr Ala Tyr Tyr Ile Leu Lys
    1160                1165                1170

Leu Ala Gly Arg Trp Pro Val Lys Val Val His Thr Ala Asn Gly
    1175                1180                1185

Ser Asn Phe Thr Ser Thr Thr Val Lys Ala Ala Cys Trp Trp Ala
    1190                1195                1200

Asn Val Thr Gln Glu Phe Gly Ile Pro Tyr Asn Pro Gln Ser Gln
    1205                1210                1215

Gly Val Ile Ala Ser Met Asn Lys Glu Leu Lys Lys Ile Ile Gly
    1220                1225                1230

Gln Val Arg Glu Gln Ala Glu His Leu Lys Thr Ala Val Gln Met
    1235                1240                1245

Ala Val Leu Ile His Asn Phe Lys Arg Arg Gly Gly Ile Gly Gly
    1250                1255                1260

Tyr Ser Ala Gly Glu Arg Ile Val Asp Ile Ile Ala Thr Asp Ile
    1265                1270                1275

Gln Thr Arg Glu Leu Gln Lys Gln Ile Ile Lys Ile Gln Asn Phe
    1280                1285                1290

Arg Val Tyr Phe Arg Asp Ser Arg Asp Pro Val Trp Lys Gly Pro
    1295                1300                1305

Ala Lys Leu Leu Trp Lys Gly Glu Gly Ala Val Val Ile Gln Asp
    1310                1315                1320

Asn Ser Glu Ile Lys Val Val Pro Arg Arg Lys Val Lys Ile Ile
    1325                1330                1335

Arg Asp Tyr Gly Lys Gln Met Ala Gly Asp Asp Cys Val Ala Gly
    1340                1345                1350

Arg Gln Asp Glu Asp Gln
    1355

<210> SEQ ID NO 24
<211> LENGTH: 1497
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 24

Met Gly Ala Arg Ala Ser Val Leu Ser Gly Gly Glu Leu Asp Arg Trp
1               5                   10                  15

Glu Lys Ile Arg Leu Arg Pro Gly Gly Lys Lys Tyr Arg Leu Lys
            20                  25                  30

His Ile Val Trp Ala Ser Arg Glu Leu Glu Arg Phe Ala Val Asn Pro
            35                  40                  45

Gly Leu Leu Glu Thr Ser Glu Gly Cys Arg Gln Ile Leu Gly Gln Leu
    50                  55                  60

Gln Pro Ser Leu Gln Thr Gly Ser Glu Glu Leu Arg Ser Leu Tyr Asn
65                  70                  75                  80

Thr Val Ala Thr Leu Tyr Cys Val His Gln Arg Ile Glu Ile Lys Asp
                85                  90                  95

Thr Lys Glu Ala Leu Glu Lys Ile Glu Glu Gln Asn Lys Ser Lys
            100                 105                 110

Lys Lys Ala Gln Gln Ala Ala Asp Thr Gly Asn Ser Ser Gln Val
            115                 120                 125

Ser Gln Asn Tyr Pro Ile Val Gln Asn Ile Gln Gly Gln Met Val His
    130                 135                 140

Gln Ala Ile Ser Pro Arg Thr Leu Asn Ala Trp Val Lys Val Val Glu
145                 150                 155                 160

Glu Lys Ala Phe Ser Pro Glu Val Ile Pro Met Phe Ser Ala Leu Ser
                165                 170                 175

Glu Gly Ala Thr Pro Gln Asp Leu Asn Thr Met Leu Asn Thr Val Gly
            180                 185                 190

Gly His Gln Ala Ala Met Gln Met Leu Lys Glu Thr Ile Asn Glu Glu
    195                 200                 205

Ala Ala Glu Trp Asp Arg Val His Pro Val His Ala Gly Pro Ile Ala
210                 215                 220

Pro Gly Gln Met Arg Glu Pro Arg Gly Ser Asp Ile Ala Gly Thr Thr
225                 230                 235                 240

Ser Thr Leu Gln Glu Gln Ile Gly Trp Met Thr Asn Asn Pro Pro Ile
                245                 250                 255

Pro Val Gly Glu Ile Tyr Lys Arg Trp Ile Ile Leu Gly Leu Asn Lys
            260                 265                 270

Ile Val Arg Met Tyr Ser Pro Val Ser Ile Leu Asp Ile Arg Gln Gly
        275                 280                 285

Pro Lys Glu Pro Phe Arg Asp Tyr Val Asp Arg Phe Tyr Lys Thr Leu
    290                 295                 300

Arg Ala Glu Gln Ala Ser Gln Asp Val Lys Asn Trp Met Thr Glu Thr
305                 310                 315                 320

Leu Leu Val Gln Asn Ala Asn Pro Asp Cys Lys Thr Ile Leu Lys Ala
                325                 330                 335

Leu Gly Pro Ala Ala Thr Leu Glu Glu Met Met Thr Ala Cys Gln Gly
            340                 345                 350

Val Gly Gly Pro Gly His Lys Ala Arg Val Leu Ala Glu Ala Met Ser
        355                 360                 365

Gln Val Thr Asn Ser Ala Thr Ile Met Met Gln Arg Gly Asn Phe Arg
    370                 375                 380

Asn Gln Arg Lys Thr Val Lys Cys Phe Asn Cys Gly Lys Glu Gly His
385                 390                 395                 400

Ile Ala Lys Asn Cys Arg Ala Pro Arg Lys Lys Gly Cys Trp Lys Cys
                405                 410                 415
```

```
Gly Lys Glu Gly His Gln Met Lys Asp Cys Thr Arg Gln Ala Asn
            420                 425                 430

Phe Leu Gly Lys Ile Trp Pro Ser Asn Lys Gly Arg Pro Gly Asn Phe
            435                 440                 445

Leu Gln Asn Arg Pro Glu Pro Thr Ala Pro Pro Glu Glu Ser Phe Arg
450                 455                 460

Phe Gly Glu Glu Thr Thr Thr Pro Ser Gln Lys Gln Glu Pro Ile Asp
465                 470                 475                 480

Lys Glu Met Tyr Pro Leu Ala Ser Leu Lys Ser Leu Phe Gly Asn Asp
                485                 490                 495

Pro Ser Ser Gln Arg Glu Asn Leu Ala Phe Gln Gln Gly Glu Ala Arg
                500                 505                 510

Glu Phe Pro Ser Glu Gln Thr Arg Ala Asn Ser Pro Thr Ser Arg Glu
            515                 520                 525

Leu Gln Val Arg Gly Asp Asn Pro His Ser Glu Ala Gly Ala Glu Arg
            530                 535                 540

Gln Gly Thr Leu Asn Phe Pro Gln Ile Thr Leu Trp Gln Arg Pro Leu
545                 550                 555                 560

Val Ser Ile Lys Val Gly Gly Gln Ile Arg Glu Ala Leu Leu Ala Thr
                565                 570                 575

Gly Ala Asp Asp Thr Val Leu Glu Asp Ile Asn Leu Pro Gly Lys Trp
                580                 585                 590

Lys Pro Lys Met Ile Gly Gly Ile Gly Gly Phe Ile Lys Val Gly Gln
            595                 600                 605

Tyr Asp Gln Ile Leu Ile Glu Ile Cys Gly Lys Lys Ala Ile Gly Thr
            610                 615                 620

Val Leu Val Gly Pro Thr Pro Val Asn Ile Ile Gly Arg Asn Met Leu
625                 630                 635                 640

Thr Gln Leu Gly Cys Thr Leu Asn Phe Pro Ile Ser Pro Ile Glu Thr
                645                 650                 655

Val Pro Val Lys Leu Lys Pro Gly Met Asp Gly Pro Arg Val Lys Gln
                660                 665                 670

Trp Pro Leu Thr Glu Glu Lys Ile Lys Ala Leu Thr Ala Ile Cys Glu
            675                 680                 685

Glu Met Glu Lys Glu Gly Lys Ile Thr Lys Ile Gly Pro Glu Asn Pro
690                 695                 700

Tyr Asn Thr Pro Val Phe Ala Ile Lys Lys Lys Asp Ser Thr Lys Trp
705                 710                 715                 720

Arg Lys Leu Val Asp Phe Arg Glu Leu Asn Lys Arg Thr Gln Asp Phe
                725                 730                 735

Trp Glu Val Gln Leu Gly Ile Pro His Pro Ala Gly Leu Lys Lys Lys
            740                 745                 750

Lys Ser Val Thr Val Leu Asp Val Gly Asp Ala Tyr Phe Ser Val Pro
            755                 760                 765

Leu Asp Glu Gly Phe Arg Lys Tyr Thr Ala Phe Thr Ile Pro Ser Thr
770                 775                 780

Asn Asn Glu Thr Pro Gly Ile Arg Tyr Gln Tyr Asn Val Leu Pro Gln
785                 790                 795                 800

Gly Trp Lys Gly Ser Pro Ala Ile Phe Gln Cys Ser Met Thr Arg Ile
                805                 810                 815

Leu Glu Pro Phe Arg Ala Lys Asn Pro Glu Ile Val Ile Tyr Gln Tyr
                820                 825                 830
```

```
Met Asp His Leu Tyr Val Gly Ser Asp Leu Glu Ile Gly Gln His Arg
            835                 840                 845

Ala Lys Ile Glu Glu Leu Arg Glu His Leu Leu Lys Trp Gly Phe Thr
    850                 855                 860

Thr Pro Asp Lys Lys His Gln Lys Glu Pro Pro Phe Leu Trp Met Gly
865                 870                 875                 880

Tyr Glu Leu His Pro Asp Lys Trp Thr Val Gln Pro Ile Gln Leu Pro
                885                 890                 895

Glu Lys Asp Ser Trp Thr Val Asn Asp Ile Gln Lys Leu Val Gly Lys
            900                 905                 910

Leu Asn Trp Ala Ser Gln Ile Tyr Pro Gly Ile Lys Val Arg Gln Leu
        915                 920                 925

Cys Lys Leu Leu Arg Gly Ala Lys Ala Leu Thr Asp Ile Val Pro Leu
930                 935                 940

Thr Glu Glu Ala Glu Leu Glu Leu Ala Glu Asn Arg Glu Ile Leu Lys
945                 950                 955                 960

Glu Pro Val His Gly Val Tyr Tyr Asp Pro Ser Lys Asp Leu Ile Ala
                965                 970                 975

Glu Ile Gln Lys Gln Gly His Asp Gln Trp Thr Tyr Gln Ile Tyr Gln
            980                 985                 990

Glu Pro Phe Lys Asn Leu Lys Thr Gly Lys Tyr Ala Lys Met Arg Thr
        995                 1000                1005

Ala His Thr Asn Asp Val Lys Gln Leu Thr Glu Ala Val Gln Lys
    1010                1015                1020

Ile Ala Met Glu Ser Ile Val Ile Trp Gly Lys Thr Pro Lys Phe
    1025                1030                1035

Arg Leu Pro Ile Gln Lys Glu Thr Trp Glu Thr Trp Trp Thr Asp
    1040                1045                1050

Tyr Trp Gln Ala Thr Trp Ile Pro Glu Trp Glu Phe Val Asn Thr
    1055                1060                1065

Pro Pro Leu Val Lys Leu Trp Tyr Gln Leu Glu Lys Asp Pro Ile
    1070                1075                1080

Ala Gly Val Glu Thr Phe Tyr Val Asp Gly Ala Ala Asn Arg Glu
    1085                1090                1095

Thr Lys Leu Gly Lys Ala Gly Tyr Val Thr Asp Arg Gly Arg Gln
    1100                1105                1110

Lys Ile Val Ser Leu Thr Glu Thr Thr Asn Gln Lys Thr Glu Leu
    1115                1120                1125

Gln Ala Ile Tyr Leu Ala Leu Gln Asp Ser Gly Ser Glu Val Asn
    1130                1135                1140

Ile Val Thr Asp Ser Gln Tyr Ala Leu Gly Ile Ile Gln Ala Gln
    1145                1150                1155

Pro Asp Lys Ser Glu Ser Glu Leu Val Asn Gln Ile Ile Glu Gln
    1160                1165                1170

Leu Ile Lys Lys Glu Arg Val Tyr Leu Ser Trp Val Pro Ala His
    1175                1180                1185

Lys Gly Ile Gly Gly Asn Glu Gln Val Asp Lys Leu Val Ser Ser
    1190                1195                1200

Gly Ile Arg Lys Val Leu Phe Leu Asp Gly Ile Asp Lys Ala Gln
    1205                1210                1215

Glu Glu His Glu Lys Tyr His Ser Asn Trp Arg Ala Met Ala Ser
    1220                1225                1230

Asp Phe Asn Leu Pro Pro Val Val Ala Lys Glu Ile Val Ala Ser
```

```
                    1235                1240                1245

Cys Asp Gln Cys Gln Leu Lys Gly Glu Ala Met His Gly Gln Val
        1250                1255                1260

Asp Cys Ser Pro Gly Ile Trp Gln Leu Ala Cys Thr His Leu Glu
        1265                1270                1275

Gly Lys Ile Ile Leu Val Ala Val His Val Ala Ser Gly Tyr Ile
        1280                1285                1290

Glu Ala Glu Val Ile Pro Ala Glu Thr Gly Gln Glu Thr Ala Tyr
        1295                1300                1305

Phe Ile Leu Lys Leu Ala Gly Arg Trp Pro Val Lys Val Ile His
        1310                1315                1320

Thr Asp Asn Gly Ser Asn Phe Thr Ser Ala Ala Val Lys Ala Ala
        1325                1330                1335

Cys Trp Trp Ala Gly Ile Gln Gln Glu Phe Gly Ile Pro Tyr Asn
        1340                1345                1350

Pro Gln Ser Gln Gly Val Val Glu Ser Met Asn Lys Glu Leu Lys
        1355                1360                1365

Lys Ile Ile Gly Gln Val Arg Asp Gln Ala Glu His Leu Lys Thr
        1370                1375                1380

Ala Val Gln Met Ala Val Phe Ile His Asn Phe Lys Arg Lys Gly
        1385                1390                1395

Gly Ile Gly Gly Tyr Ser Ala Gly Glu Arg Ile Ile Asp Ile Ile
        1400                1405                1410

Ala Thr Asp Ile Gln Thr Lys Glu Leu Gln Lys Gln Ile Ile Lys
        1415                1420                1425

Ile Gln Asn Phe Arg Val Tyr Tyr Arg Asp Ser Arg Asp Pro Ile
        1430                1435                1440

Trp Lys Gly Pro Ala Lys Leu Leu Trp Lys Gly Glu Gly Ala Val
        1445                1450                1455

Val Ile Gln Asp Asn Ser Asp Ile Lys Val Val Pro Arg Arg Lys
        1460                1465                1470

Val Lys Ile Ile Lys Asp Tyr Gly Lys Gln Met Ala Gly Ala Asp
        1475                1480                1485

Cys Val Ala Gly Arg Gln Asp Glu Asp
        1490                1495

<210> SEQ ID NO 25
<211> LENGTH: 1492
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Met Gly Ala Arg Ala Ser Ile Leu Arg Gly Gly Lys Leu Asp Lys Trp
1               5                   10                  15

Glu Lys Ile Arg Leu Arg Pro Gly Gly Lys Lys His Tyr Met Leu Lys
                20                  25                  30

His Leu Val Trp Ala Ser Arg Glu Leu Glu Arg Phe Ala Leu Asn Pro
            35                  40                  45

Gly Leu Leu Glu Thr Ser Glu Gly Cys Lys Gln Ile Ile Lys Gln Leu
        50                  55                  60

Gln Pro Ala Leu Gln Thr Gly Thr Glu Glu Leu Arg Ser Leu Phe Asn
65                  70                  75                  80
```

```
Thr Val Ala Thr Leu Tyr Cys Val His Ala Glu Ile Glu Val Arg Asp
                    85                  90                  95

Thr Lys Glu Ala Leu Asp Lys Ile Glu Glu Gln Asn Lys Ser Gln
            100                 105                 110

Gln Lys Thr Gln Gln Ala Lys Glu Ala Asp Gly Lys Val Ser Gln Asn
        115                 120                 125

Tyr Pro Ile Val Gln Asn Leu Gln Gly Gln Met Val His Gln Pro Ile
    130                 135                 140

Ser Pro Arg Thr Leu Asn Ala Trp Val Lys Val Ile Glu Glu Lys Ala
145                 150                 155                 160

Phe Ser Pro Glu Val Ile Pro Met Phe Thr Ala Leu Ser Glu Gly Ala
                165                 170                 175

Thr Pro Gln Asp Leu Asn Thr Met Leu Asn Thr Val Gly Gly His Gln
            180                 185                 190

Ala Ala Met Gln Met Leu Lys Asp Thr Ile Asn Glu Glu Ala Ala Glu
        195                 200                 205

Trp Asp Arg Leu His Pro Val His Ala Gly Pro Val Ala Pro Gly Gln
    210                 215                 220

Met Arg Glu Pro Arg Gly Ser Asp Ile Ala Gly Thr Thr Ser Asn Leu
225                 230                 235                 240

Gln Glu Gln Ile Ala Trp Met Thr Ser Asn Pro Pro Ile Pro Val Gly
                245                 250                 255

Asp Ile Tyr Lys Arg Trp Ile Ile Leu Gly Leu Asn Lys Ile Val Arg
            260                 265                 270

Met Tyr Ser Pro Thr Ser Ile Leu Asp Ile Lys Gln Gly Pro Lys Glu
        275                 280                 285

Pro Phe Arg Asp Tyr Val Asp Arg Phe Phe Lys Thr Leu Arg Ala Glu
    290                 295                 300

Gln Ala Thr Gln Asp Val Lys Asn Trp Met Thr Asp Thr Leu Leu Val
305                 310                 315                 320

Gln Asn Ala Asn Pro Asp Cys Lys Thr Ile Leu Arg Ala Leu Gly Pro
                325                 330                 335

Gly Ala Thr Leu Glu Glu Met Met Thr Ala Cys Gln Gly Val Gly Gly
            340                 345                 350

Pro Ser His Lys Ala Arg Val Leu Ala Glu Ala Met Ser Gln Thr Asn
        355                 360                 365

Ser Thr Ile Leu Met Gln Arg Ser Asn Phe Lys Gly Ser Lys Arg Ile
    370                 375                 380

Val Lys Cys Phe Asn Cys Gly Lys Glu Gly His Ile Ala Arg Asn Cys
385                 390                 395                 400

Arg Ala Pro Arg Lys Lys Gly Cys Trp Lys Cys Gly Lys Glu Gly His
                405                 410                 415

Gln Met Lys Asp Cys Thr Glu Arg Gln Ala Asn Phe Leu Gly Lys Ile
            420                 425                 430

Trp Pro Ser His Lys Gly Arg Pro Gly Asn Phe Leu Gln Ser Arg Pro
        435                 440                 445

Glu Pro Thr Ala Pro Ala Glu Ser Phe Arg Phe Glu Glu Thr Thr
    450                 455                 460

Pro Ala Pro Lys Gln Glu Pro Lys Asp Arg Glu Pro Leu Thr Ser Leu
465                 470                 475                 480

Arg Ser Leu Phe Gly Ser Asp Pro Leu Ser Gln Arg Glu Asn Leu Ala
                485                 490                 495

Phe Pro Gln Gly Lys Ala Arg Glu Phe Ser Ser Glu Gln Thr Arg Ala
```

```
                500                     505                     510
Asn Ser Pro Thr Arg Arg Glu Leu Gln Val Trp Gly Arg Asp Asn Asn
            515                     520                     525

Ser Leu Ser Glu Ala Gly Ala Asp Arg Gln Gly Thr Val Ser Phe Ser
530                     535                     540

Phe Pro Gln Ile Thr Leu Trp Gln Arg Pro Leu Val Thr Ile Lys Ile
545                     550                     555                     560

Gly Gly Gln Leu Lys Glu Ala Leu Leu Ala Thr Gly Ala Asp Asp Thr
                565                     570                     575

Val Leu Glu Glu Met Asn Leu Pro Gly Arg Trp Lys Pro Lys Met Ile
            580                     585                     590

Gly Gly Ile Gly Gly Phe Ile Lys Val Gly Gln Tyr Asp Gln Ile Pro
        595                     600                     605

Ile Glu Ile Cys Gly His Lys Ala Ile Gly Thr Val Leu Val Gly Pro
610                     615                     620

Thr Pro Val Asn Ile Ile Gly Arg Asn Leu Leu Thr Gln Ile Gly Cys
625                     630                     635                     640

Thr Leu Asn Phe Pro Ile Ser Pro Ile Glu Thr Val Pro Val Lys Leu
            645                     650                     655

Lys Pro Gly Met Asp Gly Pro Lys Val Lys Gln Trp Pro Leu Thr Glu
                660                     665                     670

Glu Lys Ile Lys Ala Leu Val Glu Ile Cys Thr Glu Met Glu Lys Glu
        675                     680                     685

Gly Lys Ile Ser Lys Ile Gly Pro Glu Asn Pro Tyr Asn Thr Pro Ile
    690                     695                     700

Phe Ala Ile Lys Lys Lys Asp Ser Thr Lys Trp Arg Lys Leu Val Asp
705                     710                     715                     720

Phe Arg Glu Leu Asn Lys Arg Thr Gln Asp Phe Trp Glu Val Gln Leu
            725                     730                     735

Gly Ile Pro His Pro Ala Gly Leu Lys Lys Lys Lys Ser Val Thr Val
                740                     745                     750

Leu Asp Val Gly Asp Ala Tyr Phe Ser Val Pro Leu Asp Glu Asp Phe
        755                     760                     765

Arg Lys Tyr Thr Ala Phe Thr Ile Pro Ser Ile Asn Asn Glu Thr Pro
    770                     775                     780

Gly Ile Arg Tyr Gln Tyr Asn Val Leu Pro Gln Gly Trp Lys Gly Ser
785                     790                     795                     800

Pro Ala Ile Phe Gln Ser Ser Met Thr Lys Ile Leu Glu Pro Phe Arg
            805                     810                     815

Lys Gln Asn Pro Asp Ile Val Ile Tyr Gln Tyr Met Asp His Leu Tyr
                820                     825                     830

Val Gly Ser Asp Leu Glu Ile Gly Gln His Arg Thr Lys Ile Glu Glu
        835                     840                     845

Leu Arg Gln His Leu Leu Arg Trp Gly Phe Thr Thr Pro Asp Lys Lys
    850                     855                     860

His Gln Lys Glu Pro Pro Phe Leu Trp Met Gly Tyr Glu Leu His Pro
865                     870                     875                     880

Asp Lys Trp Thr Val Gln Pro Ile Val Leu Pro Glu Lys Asp Ser Trp
            885                     890                     895

Thr Val Asn Asp Ile Gln Lys Leu Val Gly Lys Leu Asn Trp Ala Ser
                900                     905                     910

Gln Ile Tyr Ala Gly Ile Lys Val Lys Gln Leu Cys Lys Leu Leu Arg
        915                     920                     925
```

```
Gly Thr Lys Ala Leu Thr Glu Val Val Pro Leu Thr Glu Ala Glu
        930                 935                 940

Leu Glu Leu Ala Glu Asn Arg Glu Ile Leu Lys Glu Pro Val His Gly
945                 950                 955                 960

Val Tyr Tyr Asp Pro Ser Lys Asp Leu Ile Ala Glu Ile Gln Lys Gln
                965                 970                 975

Gly Gln Gly Gln Trp Thr Tyr Gln Ile Tyr Gln Glu Pro Phe Lys Asn
            980                 985                 990

Leu Lys Thr Gly Lys Tyr Ala Arg Met Arg Gly Ala His Thr Asn Asp
        995                 1000                1005

Val Lys Gln Leu Thr Glu Ala Val Gln Lys Ile Ala Thr Glu Ser
    1010                1015                1020

Ile Val Ile Trp Gly Lys Thr Pro Lys Phe Lys Leu Pro Ile Gln
    1025                1030                1035

Lys Glu Thr Trp Glu Ala Trp Trp Thr Glu Tyr Trp Gln Ala Thr
    1040                1045                1050

Trp Ile Pro Glu Trp Glu Phe Val Asn Thr Pro Pro Leu Val Lys
    1055                1060                1065

Leu Trp Tyr Gln Leu Glu Lys Glu Pro Ile Val Gly Ala Glu Thr
    1070                1075                1080

Phe Tyr Val Asp Gly Ala Ala Asn Arg Glu Thr Lys Leu Gly Lys
    1085                1090                1095

Ala Gly Tyr Val Thr Asp Arg Gly Arg Gln Lys Val Val Ser Leu
    1100                1105                1110

Thr Asp Thr Thr Asn Gln Lys Thr Glu Leu Gln Ala Ile His Leu
    1115                1120                1125

Ala Leu Gln Asp Ser Gly Leu Glu Val Asn Ile Val Thr Asp Ser
    1130                1135                1140

Gln Tyr Ala Leu Gly Ile Ile Gln Ala Gln Pro Asp Lys Ser Glu
    1145                1150                1155

Ser Glu Leu Val Ser Gln Ile Ile Glu Gln Leu Ile Lys Lys Glu
    1160                1165                1170

Lys Val Tyr Leu Ala Trp Val Pro Ala His Lys Gly Ile Gly Gly
    1175                1180                1185

Asn Glu Gln Val Asp Lys Leu Val Ser Arg Gly Ile Arg Lys Val
    1190                1195                1200

Leu Phe Leu Asp Gly Ile Asp Lys Ala Gln Glu Glu His Glu Lys
    1205                1210                1215

Tyr His Ser Asn Trp Arg Ala Met Ala Ser Glu Phe Asn Leu Pro
    1220                1225                1230

Pro Ile Val Ala Lys Glu Ile Val Ala Ser Cys Asp Lys Cys Gln
    1235                1240                1245

Leu Lys Gly Glu Ala Ile His Gly Gln Val Asp Cys Ser Pro Gly
    1250                1255                1260

Ile Trp Gln Leu Ala Cys Thr His Leu Glu Gly Lys Val Ile Leu
    1265                1270                1275

Val Ala Val His Val Ala Ser Gly Tyr Ile Glu Ala Glu Val Ile
    1280                1285                1290

Pro Ala Glu Thr Gly Gln Glu Thr Ala Tyr Phe Leu Leu Lys Leu
    1295                1300                1305

Ala Gly Arg Trp Pro Val Lys Thr Ile His Thr Asp Asn Gly Ser
    1310                1315                1320
```

-continued

```
Asn Phe Thr Ser Ala Thr Val Lys Ala Ala Cys Trp Trp Ala Gly
    1325                1330                1335

Ile Lys Gln Glu Phe Gly Ile Pro Tyr Asn Pro Gln Ser Gln Gly
    1340                1345                1350

Val Val Glu Ser Ile Asn Lys Glu Leu Lys Lys Ile Ile Gly Gln
    1355                1360                1365

Val Arg Asp Gln Ala Glu His Leu Lys Thr Ala Val Gln Met Ala
    1370                1375                1380

Val Phe Ile His Asn Phe Lys Arg Lys Gly Gly Ile Gly Glu Tyr
    1385                1390                1395

Ser Ala Gly Glu Arg Ile Val Asp Ile Ile Ala Ser Asp Ile Gln
    1400                1405                1410

Thr Lys Glu Leu Gln Lys Gln Ile Thr Lys Ile Gln Asn Phe Arg
    1415                1420                1425

Val Tyr Tyr Arg Asp Ser Arg Asp Pro Leu Trp Lys Gly Pro Ala
    1430                1435                1440

Lys Leu Leu Trp Lys Gly Glu Gly Ala Val Val Ile Gln Asp Asn
    1445                1450                1455

Ser Asp Ile Lys Val Val Pro Arg Arg Lys Ala Lys Ile Ile Arg
    1460                1465                1470

Asp Tyr Gly Lys Gln Met Ala Gly Asp Asp Cys Val Ala Ser Arg
    1475                1480                1485

Gln Asp Glu Asp
    1490

<210> SEQ ID NO 26
<211> LENGTH: 1350
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Met Gly Ala Arg Ala Ser Val Leu Ser Gly Gly Glu Leu Asp Arg Trp
1               5                   10                  15

Glu Lys Ile Arg Leu Arg Pro Gly Gly Lys Lys Tyr Arg Leu Lys
            20                  25                  30

His Ile Val Trp Ala Ser Arg Glu Leu Glu Arg Phe Ala Val Asn Pro
            35                  40                  45

Gly Leu Leu Glu Thr Ser Glu Gly Cys Arg Gln Ile Leu Gly Gln Leu
    50                  55                  60

Gln Pro Ser Leu Gln Thr Gly Ser Glu Glu Leu Arg Ser Leu Tyr Asn
65                  70                  75                  80

Thr Val Ala Thr Leu Tyr Cys Val His Gln Arg Ile Glu Ile Lys Asp
                85                  90                  95

Thr Lys Glu Ala Leu Glu Lys Ile Glu Glu Glu Gln Asn Lys Ser Lys
            100                 105                 110

Lys Lys Ala Gln Gln Ala Ala Ala Asp Thr Gly Asn Ser Ser Gln Val
        115                 120                 125

Ser Gln Asn Tyr Pro Ile Val Gln Asn Ile Gln Gly Gln Met Val His
    130                 135                 140

Gln Ala Ile Ser Pro Arg Thr Leu Asn Ala Trp Val Lys Val Val Glu
145                 150                 155                 160

Glu Lys Ala Phe Ser Pro Glu Val Ile Pro Met Phe Ser Ala Leu Ser
                165                 170                 175
```

```
Glu Gly Ala Thr Pro Gln Asp Leu Asn Thr Met Leu Asn Thr Val Gly
            180                 185                 190

Gly His Gln Ala Ala Met Gln Met Leu Lys Glu Thr Ile Asn Glu Glu
            195                 200                 205

Ala Ala Glu Trp Asp Arg Val His Pro Val His Ala Gly Pro Ile Ala
            210                 215                 220

Pro Gly Gln Met Arg Glu Pro Arg Gly Ser Asp Ile Ala Gly Thr Thr
225                 230                 235                 240

Ser Thr Leu Gln Glu Gln Ile Gly Trp Met Thr Asn Asn Pro Pro Ile
            245                 250                 255

Pro Val Gly Glu Ile Tyr Lys Arg Trp Ile Ile Leu Gly Leu Asn Lys
            260                 265                 270

Ile Val Arg Met Tyr Ser Pro Val Ser Ile Leu Asp Ile Arg Gln Gly
            275                 280                 285

Pro Lys Glu Pro Phe Arg Asp Tyr Val Asp Arg Phe Tyr Lys Thr Leu
            290                 295                 300

Arg Ala Glu Gln Ala Ser Gln Asp Val Lys Asn Trp Met Thr Glu Thr
305                 310                 315                 320

Leu Leu Val Gln Asn Ala Asn Pro Asp Cys Lys Thr Ile Leu Lys Ala
            325                 330                 335

Leu Gly Pro Ala Ala Thr Leu Glu Glu Met Met Thr Ala Cys Gln Gly
            340                 345                 350

Val Gly Gly Pro Gly His Lys Ala Arg Val Leu Ala Glu Ala Met Ser
            355                 360                 365

Gln Val Thr Asn Ser Ala Thr Ile Met Met Gln Arg Gly Asn Phe Arg
            370                 375                 380

Asn Gln Arg Lys Thr Val Lys Cys Phe Asn Cys Gly Lys Glu Gly His
385                 390                 395                 400

Ile Ala Lys Asn Cys Arg Ala Pro Arg Lys Lys Gly Cys Trp Lys Cys
            405                 410                 415

Gly Lys Glu Gly His Gln Met Lys Asp Cys Thr Glu Arg Gln Ala Asn
            420                 425                 430

Phe Leu Gly Lys Ile Trp Pro Ser Asn Lys Gly Arg Pro Gly Asn Phe
            435                 440                 445

Leu Gln Asn Arg Pro Glu Pro Thr Ala Pro Pro Glu Glu Ser Phe Arg
            450                 455                 460

Phe Gly Glu Glu Thr Thr Thr Pro Ser Gln Lys Gln Glu Pro Ile Asp
465                 470                 475                 480

Lys Glu Met Tyr Pro Leu Ala Ser Leu Lys Ser Leu Phe Gly Asn Asp
            485                 490                 495

Pro Ser Ser Gln Met Ala Pro Ile Ser Pro Ile Glu Thr Val Pro Val
            500                 505                 510

Lys Leu Lys Pro Gly Met Asp Gly Pro Arg Val Lys Gln Trp Pro Leu
            515                 520                 525

Thr Glu Glu Lys Ile Lys Ala Leu Thr Ala Ile Cys Glu Glu Met Glu
            530                 535                 540

Lys Glu Gly Lys Ile Thr Lys Ile Gly Pro Glu Asn Pro Tyr Asn Thr
545                 550                 555                 560

Pro Val Phe Ala Ile Lys Lys Asp Ser Thr Lys Trp Arg Lys Leu
            565                 570                 575

Val Asp Phe Arg Glu Leu Asn Lys Arg Thr Gln Asp Phe Trp Glu Val
            580                 585                 590
```

```
Gln Leu Gly Ile Pro His Pro Ala Gly Leu Lys Lys Lys Ser Val
                595                 600                 605

Thr Val Leu Asp Val Gly Asp Ala Tyr Phe Ser Val Pro Leu Asp Glu
    610                 615                 620

Gly Phe Arg Lys Tyr Thr Ala Phe Thr Ile Pro Ser Thr Asn Asn Glu
625                 630                 635                 640

Thr Pro Gly Ile Arg Tyr Gln Tyr Asn Val Leu Pro Gln Gly Trp Lys
                645                 650                 655

Gly Ser Pro Ala Ile Phe Gln Cys Ser Met Thr Arg Ile Leu Glu Pro
                660                 665                 670

Phe Arg Ala Lys Asn Pro Glu Ile Val Ile Tyr Gln Tyr Met Asp His
                675                 680                 685

Leu Tyr Val Gly Ser Asp Leu Glu Ile Gly Gln His Arg Ala Lys Ile
                690                 695                 700

Glu Glu Leu Arg Glu His Leu Leu Lys Trp Gly Phe Thr Thr Pro Asp
705                 710                 715                 720

Lys Lys His Gln Lys Glu Pro Pro Phe Leu Trp Met Gly Tyr Glu Leu
                725                 730                 735

His Pro Asp Lys Trp Thr Val Gln Pro Ile Gln Leu Pro Glu Lys Asp
                740                 745                 750

Ser Trp Thr Val Asn Asp Ile Gln Lys Leu Val Gly Lys Leu Asn Trp
                755                 760                 765

Ala Ser Gln Ile Tyr Pro Gly Ile Lys Val Arg Gln Leu Cys Lys Leu
                770                 775                 780

Leu Arg Gly Ala Lys Ala Leu Thr Asp Ile Val Pro Leu Thr Glu Glu
785                 790                 795                 800

Ala Glu Leu Glu Leu Ala Glu Asn Arg Glu Ile Leu Lys Glu Pro Val
                805                 810                 815

His Gly Val Tyr Tyr Asp Pro Ser Lys Asp Leu Ile Ala Glu Ile Gln
                820                 825                 830

Lys Gln Gly His Asp Gln Trp Thr Tyr Gln Ile Tyr Gln Glu Pro Phe
                835                 840                 845

Lys Asn Leu Lys Thr Gly Lys Tyr Ala Lys Met Arg Thr Ala His Thr
850                 855                 860

Asn Asp Val Lys Gln Leu Thr Glu Ala Val Gln Lys Ile Ala Met Glu
865                 870                 875                 880

Ser Ile Val Ile Trp Gly Lys Thr Pro Lys Phe Arg Leu Pro Ile Gln
                885                 890                 895

Lys Glu Thr Trp Glu Thr Trp Trp Thr Asp Tyr Trp Gln Ala Thr Trp
                900                 905                 910

Ile Pro Glu Trp Glu Phe Val Asn Thr Pro Pro Leu Val Lys Leu Trp
                915                 920                 925

Tyr Gln Leu Glu Lys Asp Pro Ile Ala Gly Val Glu Thr Phe Tyr Val
                930                 935                 940

Asp Gly Ala Ala Asn Arg Glu Thr Lys Leu Gly Lys Ala Gly Tyr Val
945                 950                 955                 960

Thr Asp Arg Gly Arg Gln Lys Ile Val Ser Leu Thr Glu Thr Thr Asn
                965                 970                 975

Gln Lys Thr Glu Leu Gln Ala Ile Tyr Leu Ala Leu Gln Asp Ser Gly
                980                 985                 990

Ser Glu Val Asn Ile Val Thr Asp Ser Gln Tyr Ala Leu Gly Ile Ile
                995                 1000                1005

Gln Ala Gln Pro Asp Lys Ser Glu Ser Glu Leu Val Asn Gln Ile
```

```
                    1010                1015                1020

Ile Glu Gln Leu Ile Lys Lys Glu Arg Val Tyr Leu Ser Trp Val
    1025                1030                1035

Pro Ala His Lys Gly Ile Gly Gly Asn Glu Gln Val Asp Lys Leu
    1040                1045                1050

Val Ser Ser Gly Ile Arg Lys Val Leu Phe Leu Asp Gly Ile Asp
    1055                1060                1065

Lys Ala Gln Glu Glu His Glu Lys Tyr His Ser Asn Trp Arg Ala
    1070                1075                1080

Met Ala Ser Asp Phe Asn Leu Pro Pro Val Val Ala Lys Glu Ile
    1085                1090                1095

Val Ala Ser Cys Asp Gln Cys Gln Leu Lys Gly Glu Ala Met His
    1100                1105                1110

Gly Gln Val Asp Cys Ser Pro Gly Ile Trp Gln Leu Ala Cys Thr
    1115                1120                1125

His Leu Glu Gly Lys Ile Ile Leu Val Ala Val His Val Ala Ser
    1130                1135                1140

Gly Tyr Ile Glu Ala Glu Val Ile Pro Ala Glu Thr Gly Gln Glu
    1145                1150                1155

Thr Ala Tyr Phe Ile Leu Lys Leu Ala Gly Arg Trp Pro Val Lys
    1160                1165                1170

Val Ile His Thr Asp Asn Gly Ser Asn Phe Thr Ser Ala Ala Val
    1175                1180                1185

Lys Ala Ala Cys Trp Trp Ala Gly Ile Gln Gln Glu Phe Gly Ile
    1190                1195                1200

Pro Tyr Asn Pro Gln Ser Gln Gly Val Val Glu Ser Met Asn Lys
    1205                1210                1215

Glu Leu Lys Lys Ile Ile Gly Gln Val Arg Asp Gln Ala Glu His
    1220                1225                1230

Leu Lys Thr Ala Val Gln Met Ala Val Phe Ile His Asn Phe Lys
    1235                1240                1245

Arg Lys Gly Gly Ile Gly Gly Tyr Ser Ala Gly Glu Arg Ile Ile
    1250                1255                1260

Asp Ile Ile Ala Thr Asp Ile Gln Thr Lys Glu Leu Gln Lys Gln
    1265                1270                1275

Ile Ile Lys Ile Gln Asn Phe Arg Val Tyr Tyr Arg Asp Ser Arg
    1280                1285                1290

Asp Pro Ile Trp Lys Gly Pro Ala Lys Leu Leu Trp Lys Gly Glu
    1295                1300                1305

Gly Ala Val Val Ile Gln Asp Asn Ser Asp Ile Lys Val Val Pro
    1310                1315                1320

Arg Arg Lys Val Lys Ile Ile Lys Asp Tyr Gly Lys Gln Met Ala
    1325                1330                1335

Gly Ala Asp Cys Val Ala Gly Arg Gln Asp Glu Asp
    1340                1345                1350

<210> SEQ ID NO 27
<211> LENGTH: 1341
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27
```

```
Met Gly Ala Arg Ala Ser Ile Leu Arg Gly Gly Lys Leu Asp Lys Trp
 1               5                  10                 15
Glu Lys Ile Arg Leu Arg Pro Gly Gly Lys Lys His Tyr Met Leu Lys
             20                 25                 30
His Leu Val Trp Ala Ser Arg Glu Leu Glu Arg Phe Ala Leu Asn Pro
         35                 40                 45
Gly Leu Leu Glu Thr Ser Glu Gly Cys Lys Gln Ile Ile Lys Gln Leu
     50                 55                 60
Gln Pro Ala Leu Gln Thr Gly Thr Glu Glu Leu Arg Ser Leu Phe Asn
65                 70                 75                 80
Thr Val Ala Thr Leu Tyr Cys Val His Ala Glu Ile Glu Val Arg Asp
                 85                 90                 95
Thr Lys Glu Ala Leu Asp Lys Ile Glu Glu Glu Gln Asn Lys Ser Gln
             100                105                110
Gln Lys Thr Gln Gln Ala Lys Glu Ala Asp Gly Lys Val Ser Gln Asn
         115                120                125
Tyr Pro Ile Val Gln Asn Leu Gln Gly Gln Met Val His Gln Pro Ile
     130                135                140
Ser Pro Arg Thr Leu Asn Ala Trp Val Lys Val Ile Glu Glu Lys Ala
145                150                155                160
Phe Ser Pro Glu Val Ile Pro Met Phe Thr Ala Leu Ser Glu Gly Ala
                 165                170                175
Thr Pro Gln Asp Leu Asn Thr Met Leu Asn Thr Val Gly Gly His Gln
             180                185                190
Ala Ala Met Gln Met Leu Lys Asp Thr Ile Asn Glu Glu Ala Ala Glu
         195                200                205
Trp Asp Arg Leu His Pro Val His Ala Gly Pro Val Ala Pro Gly Gln
     210                215                220
Met Arg Glu Pro Arg Gly Ser Asp Ile Ala Gly Thr Thr Ser Asn Leu
225                230                235                240
Gln Glu Gln Ile Ala Trp Met Thr Ser Asn Pro Pro Ile Pro Val Gly
                 245                250                255
Asp Ile Tyr Lys Arg Trp Ile Ile Leu Gly Leu Asn Lys Ile Val Arg
             260                265                270
Met Tyr Ser Pro Thr Ser Ile Leu Asp Ile Lys Gln Gly Pro Lys Glu
         275                280                285
Pro Phe Arg Asp Tyr Val Asp Arg Phe Phe Lys Thr Leu Arg Ala Glu
     290                295                300
Gln Ala Thr Gln Asp Val Lys Asn Trp Met Thr Asp Thr Leu Leu Val
305                310                315                320
Gln Asn Ala Asn Pro Asp Cys Lys Thr Ile Leu Arg Ala Leu Gly Pro
                 325                330                335
Gly Ala Thr Leu Glu Glu Met Met Thr Ala Cys Gln Gly Val Gly Gly
             340                345                350
Pro Ser His Lys Ala Arg Val Leu Ala Glu Ala Met Ser Gln Thr Asn
         355                360                365
Ser Thr Ile Leu Met Gln Arg Ser Asn Phe Lys Gly Ser Lys Arg Ile
     370                375                380
Val Lys Cys Phe Asn Cys Gly Lys Glu Gly His Ile Ala Arg Asn Cys
385                390                395                400
Arg Ala Pro Arg Lys Lys Gly Cys Trp Lys Cys Gly Lys Glu Gly His
                 405                410                415
Gln Met Lys Asp Cys Thr Glu Arg Gln Ala Asn Phe Leu Gly Lys Ile
```

```
                420             425             430
Trp Pro Ser His Lys Gly Arg Pro Gly Asn Phe Leu Gln Ser Arg Pro
            435             440             445
Glu Pro Thr Ala Pro Ala Glu Ser Phe Arg Phe Glu Thr Thr
    450             455             460
Pro Ala Pro Lys Gln Glu Pro Lys Asp Arg Glu Pro Leu Thr Ser Leu
465             470             475             480
Arg Ser Leu Phe Gly Ser Asp Pro Leu Ser Gln Met Ala Pro Ile Ser
                485             490             495
Pro Ile Glu Thr Val Pro Val Lys Leu Lys Pro Gly Met Asp Gly Pro
            500             505             510
Lys Val Lys Gln Trp Pro Leu Thr Glu Glu Lys Ile Lys Ala Leu Val
            515             520             525
Glu Ile Cys Thr Glu Met Glu Lys Glu Gly Lys Ile Ser Lys Ile Gly
            530             535             540
Pro Glu Asn Pro Tyr Asn Thr Pro Ile Phe Ala Ile Lys Lys Lys Asp
545             550             555             560
Ser Thr Lys Trp Arg Lys Leu Val Asp Phe Arg Glu Leu Asn Lys Arg
                565             570             575
Thr Gln Asp Phe Trp Glu Val Gln Leu Gly Ile Pro His Pro Ala Gly
            580             585             590
Leu Lys Lys Lys Lys Ser Val Thr Val Leu Asp Val Gly Asp Ala Tyr
            595             600             605
Phe Ser Val Pro Leu Asp Glu Asp Phe Arg Lys Tyr Thr Ala Phe Thr
            610             615             620
Ile Pro Ser Ile Asn Asn Glu Thr Pro Gly Ile Arg Tyr Gln Tyr Asn
625             630             635             640
Val Leu Pro Gln Gly Trp Lys Gly Ser Pro Ala Ile Phe Gln Ser Ser
                645             650             655
Met Thr Lys Ile Leu Glu Pro Phe Arg Lys Gln Asn Pro Asp Ile Val
            660             665             670
Ile Tyr Gln Tyr Met Asp His Leu Tyr Val Gly Ser Asp Leu Glu Ile
            675             680             685
Gly Gln His Arg Thr Lys Ile Glu Glu Leu Arg Gln His Leu Leu Arg
            690             695             700
Trp Gly Phe Thr Thr Pro Asp Lys Lys His Gln Lys Glu Pro Pro Phe
705             710             715             720
Leu Trp Met Gly Tyr Glu Leu His Pro Asp Lys Trp Thr Val Gln Pro
                725             730             735
Ile Val Leu Pro Glu Lys Asp Ser Trp Thr Val Asn Asp Ile Gln Lys
            740             745             750
Leu Val Gly Lys Leu Asn Trp Ala Ser Gln Ile Tyr Ala Gly Ile Lys
            755             760             765
Val Lys Gln Leu Cys Lys Leu Leu Arg Gly Thr Lys Ala Leu Thr Glu
            770             775             780
Val Val Pro Leu Thr Glu Glu Ala Glu Leu Glu Leu Ala Glu Asn Arg
785             790             795             800
Glu Ile Leu Lys Glu Pro Val His Gly Val Tyr Tyr Asp Pro Ser Lys
                805             810             815
Asp Leu Ile Ala Glu Ile Gln Lys Gln Gly Gln Gly Gln Trp Thr Tyr
            820             825             830
Gln Ile Tyr Gln Glu Pro Phe Lys Asn Leu Lys Thr Gly Lys Tyr Ala
            835             840             845
```

-continued

```
Arg Met Arg Gly Ala His Thr Asn Asp Val Lys Gln Leu Thr Glu Ala
    850                 855                 860
Val Gln Lys Ile Ala Thr Glu Ser Ile Val Ile Trp Gly Lys Thr Pro
865                 870                 875                 880
Lys Phe Lys Leu Pro Ile Gln Lys Glu Thr Trp Glu Ala Trp Trp Thr
                885                 890                 895
Glu Tyr Trp Gln Ala Thr Trp Ile Pro Glu Trp Glu Phe Val Asn Thr
                900                 905                 910
Pro Pro Leu Val Lys Leu Trp Tyr Gln Leu Glu Lys Glu Pro Ile Val
        915                 920                 925
Gly Ala Glu Thr Phe Tyr Val Asp Gly Ala Ala Asn Arg Glu Thr Lys
    930                 935                 940
Leu Gly Lys Ala Gly Tyr Val Thr Asp Arg Gly Arg Gln Lys Val Val
945                 950                 955                 960
Ser Leu Thr Asp Thr Thr Asn Gln Lys Thr Glu Leu Gln Ala Ile His
                965                 970                 975
Leu Ala Leu Gln Asp Ser Gly Leu Glu Val Asn Ile Val Thr Asp Ser
                980                 985                 990
Gln Tyr Ala Leu Gly Ile Ile Gln Ala Gln Pro Asp Lys Ser Glu Ser
        995                 1000                1005
Glu Leu Val Ser Gln Ile Ile Glu Gln Leu Ile Lys Lys Glu Lys
        1010                1015                1020
Val Tyr Leu Ala Trp Val Pro Ala His Lys Gly Ile Gly Gly Asn
        1025                1030                1035
Glu Gln Val Asp Lys Leu Val Ser Arg Gly Ile Arg Lys Val Leu
        1040                1045                1050
Phe Leu Asp Gly Ile Asp Lys Ala Gln Glu Glu His Glu Lys Tyr
        1055                1060                1065
His Ser Asn Trp Arg Ala Met Ala Ser Glu Phe Asn Leu Pro Pro
        1070                1075                1080
Ile Val Ala Lys Glu Ile Val Ala Ser Cys Asp Lys Cys Gln Leu
        1085                1090                1095
Lys Gly Glu Ala Ile His Gly Gln Val Asp Cys Ser Pro Gly Ile
        1100                1105                1110
Trp Gln Leu Ala Cys Thr His Leu Glu Gly Lys Val Ile Leu Val
        1115                1120                1125
Ala Val His Val Ala Ser Gly Tyr Ile Glu Ala Glu Val Ile Pro
        1130                1135                1140
Ala Glu Thr Gly Gln Glu Thr Ala Tyr Phe Leu Leu Lys Leu Ala
        1145                1150                1155
Gly Arg Trp Pro Val Lys Thr Ile His Thr Asp Asn Gly Ser Asn
        1160                1165                1170
Phe Thr Ser Ala Thr Val Lys Ala Ala Cys Trp Trp Ala Gly Ile
        1175                1180                1185
Lys Gln Glu Phe Gly Ile Pro Tyr Asn Pro Gln Ser Gln Gly Val
        1190                1195                1200
Val Glu Ser Ile Asn Lys Glu Leu Lys Lys Ile Ile Gly Gln Val
        1205                1210                1215
Arg Asp Gln Ala Glu His Leu Lys Thr Ala Val Gln Met Ala Val
        1220                1225                1230
Phe Ile His Asn Phe Lys Arg Lys Gly Gly Ile Gly Glu Tyr Ser
        1235                1240                1245
```

Ala Gly Glu Arg Ile Val Asp Ile Ile Ala Ser Asp Ile Gln Thr
    1250            1255            1260

Lys Glu Leu Gln Lys Gln Ile Thr Lys Ile Gln Asn Phe Arg Val
    1265            1270            1275

Tyr Tyr Arg Asp Ser Arg Asp Pro Leu Trp Lys Gly Pro Ala Lys
    1280            1285            1290

Leu Leu Trp Lys Gly Glu Gly Ala Val Val Ile Gln Asp Asn Ser
    1295            1300            1305

Asp Ile Lys Val Val Pro Arg Arg Lys Ala Lys Ile Ile Arg Asp
    1310            1315            1320

Tyr Gly Lys Gln Met Ala Gly Asp Asp Cys Val Ala Ser Arg Gln
    1325            1330            1335

Asp Glu Asp
    1340

<210> SEQ ID NO 28
<211> LENGTH: 1556
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Met Gly Ala Arg Ala Ser Val Leu Ser Gly Gly Glu Leu Asp Arg Trp
1               5                   10                  15

Glu Lys Ile Arg Leu Arg Pro Gly Gly Lys Lys Tyr Arg Leu Lys
            20                  25                  30

His Ile Val Trp Ala Ser Arg Glu Leu Glu Arg Phe Ala Val Asn Pro
                35                  40                  45

Gly Leu Leu Glu Thr Ser Glu Gly Cys Arg Gln Ile Leu Gly Gln Leu
    50                  55                  60

Gln Pro Ser Leu Gln Thr Gly Ser Glu Glu Leu Arg Ser Leu Tyr Asn
65                  70                  75                  80

Thr Val Ala Thr Leu Tyr Cys Val His Gln Arg Ile Glu Ile Lys Asp
                85                  90                  95

Thr Lys Glu Ala Leu Glu Lys Ile Glu Glu Glu Gln Asn Lys Ser Lys
            100                 105                 110

Lys Lys Ala Gln Gln Ala Ala Ala Asp Thr Gly Asn Ser Ser Gln Val
        115                 120                 125

Ser Gln Asn Tyr Pro Ile Val Gln Asn Ile Gln Gly Gln Met Val His
    130                 135                 140

Gln Ala Ile Ser Pro Arg Thr Leu Asn Ala Trp Val Lys Val Val Glu
145                 150                 155                 160

Glu Lys Ala Phe Ser Pro Glu Val Ile Pro Met Phe Ser Ala Leu Ser
                165                 170                 175

Glu Gly Ala Thr Pro Gln Asp Leu Asn Thr Met Leu Asn Thr Val Gly
            180                 185                 190

Gly His Gln Ala Ala Met Gln Met Leu Lys Glu Thr Ile Asn Glu Glu
        195                 200                 205

Ala Ala Glu Trp Asp Arg Val His Pro Val His Ala Gly Pro Ile Ala
    210                 215                 220

Pro Gly Gln Met Arg Glu Pro Arg Gly Ser Asp Ile Ala Gly Thr Thr
225                 230                 235                 240

Ser Thr Leu Gln Glu Gln Ile Gly Trp Met Thr Asn Asn Pro Pro Ile
                245                 250                 255

```
Pro Val Gly Glu Ile Tyr Lys Arg Trp Ile Ile Leu Gly Leu Asn Lys
        260                 265                 270

Ile Val Arg Met Tyr Ser Pro Val Ser Ile Leu Asp Ile Arg Gln Gly
            275                 280                 285

Pro Lys Glu Pro Phe Arg Asp Tyr Val Asp Arg Phe Tyr Lys Thr Leu
    290                 295                 300

Arg Ala Glu Gln Ala Ser Gln Asp Val Lys Asn Trp Met Thr Glu Thr
305                 310                 315                 320

Leu Leu Val Gln Asn Ala Asn Pro Asp Cys Lys Thr Ile Leu Lys Ala
                325                 330                 335

Leu Gly Pro Ala Ala Thr Leu Glu Glu Met Met Thr Ala Cys Gln Gly
            340                 345                 350

Val Gly Gly Pro Gly His Lys Ala Arg Val Leu Ala Glu Ala Met Ser
        355                 360                 365

Gln Val Thr Asn Ser Ala Thr Ile Met Met Gln Arg Gly Asn Phe Arg
    370                 375                 380

Asn Gln Arg Lys Thr Val Lys Cys Phe Asn Cys Gly Lys Glu Gly His
385                 390                 395                 400

Ile Ala Lys Asn Cys Arg Ala Pro Arg Lys Lys Gly Cys Trp Lys Cys
                405                 410                 415

Gly Lys Glu Gly His Gln Met Lys Asp Cys Thr Glu Arg Gln Ala Asn
            420                 425                 430

Phe Leu Gly Lys Ile Trp Pro Ser Asn Lys Gly Arg Pro Gly Asn Phe
        435                 440                 445

Leu Gln Asn Arg Pro Glu Pro Thr Ala Pro Glu Glu Ser Phe Arg
    450                 455                 460

Phe Gly Glu Glu Thr Thr Thr Pro Ser Gln Lys Gln Glu Pro Ile Asp
465                 470                 475                 480

Lys Glu Met Tyr Pro Leu Ala Ser Leu Lys Ser Leu Phe Gly Asn Asp
                485                 490                 495

Pro Ser Ser Gln Met Ala Pro Ile Ser Pro Ile Glu Thr Val Pro Val
            500                 505                 510

Lys Leu Lys Pro Gly Met Asp Gly Pro Arg Val Lys Gln Trp Pro Leu
        515                 520                 525

Thr Glu Glu Lys Ile Lys Ala Leu Thr Ala Ile Cys Glu Glu Met Glu
    530                 535                 540

Lys Glu Gly Lys Ile Thr Lys Ile Gly Pro Glu Asn Pro Tyr Asn Thr
545                 550                 555                 560

Pro Val Phe Ala Ile Lys Lys Lys Asp Ser Thr Lys Trp Arg Lys Leu
                565                 570                 575

Val Asp Phe Arg Glu Leu Asn Lys Arg Thr Gln Asp Phe Trp Glu Val
            580                 585                 590

Gln Leu Gly Ile Pro His Pro Ala Gly Leu Lys Lys Lys Lys Ser Val
        595                 600                 605

Thr Val Leu Ala Val Gly Asp Ala Tyr Phe Ser Val Pro Leu Asp Glu
    610                 615                 620

Gly Phe Arg Lys Tyr Thr Ala Phe Thr Ile Pro Ser Thr Asn Asn Glu
625                 630                 635                 640

Thr Pro Gly Ile Arg Tyr Gln Tyr Asn Val Leu Pro Gln Gly Trp Lys
                645                 650                 655

Gly Ser Pro Ala Ile Phe Gln Cys Ser Met Thr Arg Ile Leu Glu Pro
            660                 665                 670
```

```
Phe Arg Ala Lys Asn Pro Glu Ile Val Ile Tyr Gln Tyr Met Ala Ala
            675                 680                 685

Leu Tyr Val Gly Ser Asp Leu Glu Ile Gly Gln His Arg Ala Lys Ile
        690                 695                 700

Glu Glu Leu Arg Glu His Leu Leu Lys Trp Gly Phe Thr Thr Pro Asp
705                 710                 715                 720

Lys Lys His Gln Lys Glu Pro Pro Phe Leu Trp Met Gly Tyr Glu Leu
                725                 730                 735

His Pro Asp Lys Trp Thr Val Gln Pro Ile Gln Leu Pro Glu Lys Asp
            740                 745                 750

Ser Trp Thr Val Asn Asp Ile Gln Lys Leu Val Gly Lys Leu Asn Trp
        755                 760                 765

Ala Ser Gln Ile Tyr Pro Gly Ile Lys Val Arg Gln Leu Cys Lys Leu
        770                 775                 780

Leu Arg Gly Ala Lys Ala Leu Thr Asp Ile Val Pro Leu Thr Glu Glu
785                 790                 795                 800

Ala Glu Leu Glu Leu Ala Glu Asn Arg Glu Ile Leu Lys Glu Pro Val
                805                 810                 815

His Gly Val Tyr Tyr Asp Pro Ser Lys Asp Leu Ile Ala Glu Ile Gln
            820                 825                 830

Lys Gln Gly His Asp Gln Trp Thr Tyr Gln Ile Tyr Gln Glu Pro Phe
        835                 840                 845

Lys Asn Leu Lys Thr Gly Lys Tyr Ala Lys Met Arg Thr Ala His Thr
        850                 855                 860

Asn Asp Val Lys Gln Leu Thr Glu Ala Val Gln Lys Ile Ala Met Glu
865                 870                 875                 880

Ser Ile Val Ile Trp Gly Lys Thr Pro Lys Phe Arg Leu Pro Ile Gln
                885                 890                 895

Lys Glu Thr Trp Glu Thr Trp Trp Thr Asp Tyr Trp Gln Ala Thr Trp
            900                 905                 910

Ile Pro Glu Trp Glu Phe Val Asn Thr Pro Leu Val Lys Leu Trp
        915                 920                 925

Tyr Gln Leu Glu Lys Asp Pro Ile Ala Gly Val Glu Thr Phe Tyr Val
        930                 935                 940

Ala Gly Ala Ala Asn Arg Glu Thr Lys Leu Gly Lys Ala Gly Tyr Val
945                 950                 955                 960

Thr Asp Arg Gly Arg Gln Lys Ile Val Ser Leu Thr Glu Thr Thr Asn
                965                 970                 975

Gln Lys Thr Ala Leu Gln Ala Ile Tyr Leu Ala Leu Gln Asp Ser Gly
            980                 985                 990

Ser Glu Val Asn Ile Val Thr Ala Ser Gln Tyr Ala Leu Gly Ile Ile
        995                 1000                1005

Gln Ala Gln Pro Asp Lys Ser Glu Ser Glu Leu Val Asn Gln Ile
     1010               1015                1020

Ile Glu Gln Leu Ile Lys Lys Glu Arg Val Tyr Leu Ser Trp Val
     1025               1030                1035

Pro Ala His Lys Gly Ile Gly Gly Asn Glu Gln Val Asp Lys Leu
     1040               1045                1050

Val Ser Ser Gly Ile Arg Lys Val Leu Phe Leu Asp Gly Ile Asp
     1055               1060                1065

Lys Ala Gln Glu Glu His Glu Lys Tyr His Ser Asn Trp Arg Ala
     1070               1075                1080

Met Ala Ser Asp Phe Asn Leu Pro Pro Val Val Ala Lys Glu Ile
```

```
                   1085                1090                1095

Val Ala Ser Cys Asp Gln Cys Gln Leu Lys Gly Glu Ala Met His
                1100                1105                1110

Gly Gln Val Asp Cys Ser Pro Gly Ile Trp Gln Leu Ala Cys Thr
                1115                1120                1125

His Leu Glu Gly Lys Ile Ile Leu Val Ala Val His Val Ala Ser
                1130                1135                1140

Gly Tyr Ile Glu Ala Glu Val Ile Pro Ala Glu Thr Gly Gln Glu
                1145                1150                1155

Thr Ala Tyr Phe Ile Leu Lys Leu Ala Gly Arg Trp Pro Val Lys
                1160                1165                1170

Val Ile His Thr Ala Asn Gly Ser Asn Phe Thr Ser Ala Ala Val
                1175                1180                1185

Lys Ala Ala Cys Trp Trp Ala Gly Ile Gln Gln Glu Phe Gly Ile
                1190                1195                1200

Pro Tyr Asn Pro Gln Ser Gln Gly Val Val Ala Ser Met Asn Lys
                1205                1210                1215

Glu Leu Lys Lys Ile Ile Gly Gln Val Arg Asp Gln Ala Glu His
                1220                1225                1230

Leu Lys Thr Ala Val Gln Met Ala Val Phe Ile His Asn Phe Lys
                1235                1240                1245

Arg Lys Gly Gly Ile Gly Gly Tyr Ser Ala Gly Glu Arg Ile Ile
                1250                1255                1260

Asp Ile Ile Ala Thr Asp Ile Gln Thr Lys Glu Leu Gln Lys Gln
                1265                1270                1275

Ile Ile Lys Ile Gln Asn Phe Arg Val Tyr Tyr Arg Asp Ser Arg
                1280                1285                1290

Asp Pro Ile Trp Lys Gly Pro Ala Lys Leu Leu Trp Lys Gly Glu
                1295                1300                1305

Gly Ala Val Val Ile Gln Asp Asn Ser Asp Ile Lys Val Val Pro
                1310                1315                1320

Arg Arg Lys Val Lys Ile Ile Lys Asp Tyr Gly Lys Gln Met Ala
                1325                1330                1335

Gly Ala Asp Cys Val Ala Gly Arg Gln Asp Glu Asp Met Ala Gly
                1340                1345                1350

Lys Trp Ser Lys Ser Ser Val Val Gly Trp Pro Ala Ile Arg Glu
                1355                1360                1365

Arg Met Arg Arg Ala Glu Pro Ala Ala Asp Gly Val Gly Ala Val
                1370                1375                1380

Ser Arg Asp Leu Glu Lys His Gly Ala Ile Thr Ser Ser Asn Thr
                1385                1390                1395

Ala Ala Asn Asn Ala Asp Cys Ala Trp Leu Glu Ala Gln Glu Glu
                1400                1405                1410

Glu Glu Val Gly Phe Pro Val Arg Pro Gln Val Pro Leu Arg Pro
                1415                1420                1425

Met Thr Tyr Lys Gly Ala Leu Asp Leu Ser His Phe Leu Lys Glu
                1430                1435                1440

Lys Gly Gly Leu Glu Gly Leu Ile Tyr Ser Gln Lys Arg Gln Asp
                1445                1450                1455

Ile Leu Asp Leu Trp Val Tyr His Thr Gln Gly Tyr Phe Pro Asp
                1460                1465                1470

Trp Gln Asn Tyr Thr Pro Gly Pro Gly Ile Arg Tyr Pro Leu Thr
                1475                1480                1485
```

Phe Gly Trp Cys Phe Lys Leu Val Pro Val Glu Pro Glu Lys Ile
    1490                1495                1500

Glu Glu Ala Asn Glu Gly Glu Asn Asn Ser Leu Leu His Pro Met
    1505                1510                1515

Ser Gln His Gly Met Asp Asp Pro Glu Lys Glu Val Leu Met Trp
    1520                1525                1530

Lys Phe Asp Ser Arg Leu Ala Phe His His Met Ala Arg Glu Leu
    1535                1540                1545

His Pro Glu Tyr Tyr Lys Asp Cys
    1550                1555

<210> SEQ ID NO 29
<211> LENGTH: 1547
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Met Gly Ala Arg Ala Ser Ile Leu Arg Gly Gly Lys Leu Asp Lys Trp
1               5                   10                  15

Glu Lys Ile Arg Leu Arg Pro Gly Gly Lys Lys His Tyr Met Leu Lys
                20                  25                  30

His Leu Val Trp Ala Ser Arg Glu Leu Glu Arg Phe Ala Leu Asn Pro
            35                  40                  45

Gly Leu Leu Glu Thr Ser Glu Gly Cys Lys Gln Ile Ile Lys Gln Leu
        50                  55                  60

Gln Pro Ala Leu Gln Thr Gly Thr Glu Glu Leu Arg Ser Leu Phe Asn
65                  70                  75                  80

Thr Val Ala Thr Leu Tyr Cys Val His Ala Glu Ile Glu Val Arg Asp
                85                  90                  95

Thr Lys Glu Ala Leu Asp Lys Ile Glu Glu Glu Gln Asn Lys Ser Gln
            100                 105                 110

Gln Lys Thr Gln Gln Ala Lys Glu Ala Asp Gly Lys Val Ser Gln Asn
        115                 120                 125

Tyr Pro Ile Val Gln Asn Leu Gln Gly Gln Met Val His Gln Pro Ile
    130                 135                 140

Ser Pro Arg Thr Leu Asn Ala Trp Val Lys Val Ile Glu Glu Lys Ala
145                 150                 155                 160

Phe Ser Pro Glu Val Ile Pro Met Phe Thr Ala Leu Ser Glu Gly Ala
                165                 170                 175

Thr Pro Gln Asp Leu Asn Thr Met Leu Asn Thr Val Gly Gly His Gln
            180                 185                 190

Ala Ala Met Gln Met Leu Lys Asp Thr Ile Asn Glu Glu Ala Ala Glu
        195                 200                 205

Trp Asp Arg Leu His Pro Val His Ala Gly Pro Val Ala Pro Gly Gln
    210                 215                 220

Met Arg Glu Pro Arg Gly Ser Asp Ile Ala Gly Thr Thr Ser Asn Leu
225                 230                 235                 240

Gln Glu Gln Ile Ala Trp Met Thr Ser Asn Pro Pro Ile Pro Val Gly
                245                 250                 255

Asp Ile Tyr Lys Arg Trp Ile Ile Leu Gly Leu Asn Lys Ile Val Arg
            260                 265                 270

Met Tyr Ser Pro Thr Ser Ile Leu Asp Ile Lys Gln Gly Pro Lys Glu

-continued

```
             275                 280                 285
Pro Phe Arg Asp Tyr Val Asp Arg Phe Phe Lys Thr Leu Arg Ala Glu
290                 295                 300
Gln Ala Thr Gln Asp Val Lys Asn Trp Met Thr Asp Thr Leu Leu Val
305                 310                 315                 320
Gln Asn Ala Asn Pro Asp Cys Lys Thr Ile Leu Arg Ala Leu Gly Pro
                325                 330                 335
Gly Ala Thr Leu Glu Glu Met Met Thr Ala Cys Gln Gly Val Gly Gly
                340                 345                 350
Pro Ser His Lys Ala Arg Val Leu Ala Glu Ala Met Ser Gln Thr Asn
                355                 360                 365
Ser Thr Ile Leu Met Gln Arg Ser Asn Phe Lys Gly Ser Lys Arg Ile
370                 375                 380
Val Lys Cys Phe Asn Cys Gly Lys Glu Gly His Ile Ala Arg Asn Cys
385                 390                 395                 400
Arg Ala Pro Arg Lys Lys Gly Cys Trp Lys Cys Gly Lys Glu Gly His
                405                 410                 415
Gln Met Lys Asp Cys Thr Glu Arg Gln Ala Asn Phe Leu Gly Lys Ile
                420                 425                 430
Trp Pro Ser His Lys Gly Arg Pro Gly Asn Phe Leu Gln Ser Arg Pro
                435                 440                 445
Glu Pro Thr Ala Pro Pro Ala Glu Ser Phe Arg Phe Glu Glu Thr Thr
450                 455                 460
Pro Ala Pro Lys Gln Glu Pro Lys Asp Arg Glu Pro Leu Thr Ser Leu
465                 470                 475                 480
Arg Ser Leu Phe Gly Ser Asp Pro Leu Ser Gln Met Ala Pro Ile Ser
                485                 490                 495
Pro Ile Glu Thr Val Pro Val Lys Leu Lys Pro Gly Met Asp Gly Pro
                500                 505                 510
Lys Val Lys Gln Trp Pro Leu Thr Glu Glu Lys Ile Lys Ala Leu Val
                515                 520                 525
Glu Ile Cys Thr Glu Met Glu Lys Glu Gly Lys Ile Ser Lys Ile Gly
                530                 535                 540
Pro Glu Asn Pro Tyr Asn Thr Pro Ile Phe Ala Ile Lys Lys Lys Asp
545                 550                 555                 560
Ser Thr Lys Trp Arg Lys Leu Val Asp Phe Arg Glu Leu Asn Lys Arg
                565                 570                 575
Thr Gln Asp Phe Trp Glu Val Gln Leu Gly Ile Pro His Pro Ala Gly
                580                 585                 590
Leu Lys Lys Lys Lys Ser Val Thr Val Leu Ala Val Gly Asp Ala Tyr
                595                 600                 605
Phe Ser Val Pro Leu Asp Glu Asp Phe Arg Lys Tyr Thr Ala Phe Thr
                610                 615                 620
Ile Pro Ser Ile Asn Asn Glu Thr Pro Gly Ile Arg Tyr Gln Tyr Asn
625                 630                 635                 640
Val Leu Pro Gln Gly Trp Lys Gly Ser Pro Ala Ile Phe Gln Ser Ser
                645                 650                 655
Met Thr Lys Ile Leu Glu Pro Phe Arg Lys Gln Asn Pro Asp Ile Val
                660                 665                 670
Ile Tyr Gln Tyr Met Ala Ala Leu Tyr Val Gly Ser Asp Leu Glu Ile
                675                 680                 685
Gly Gln His Arg Thr Lys Ile Glu Glu Leu Arg Gln His Leu Leu Arg
                690                 695                 700
```

```
Trp Gly Phe Thr Thr Pro Asp Lys Lys His Gln Lys Glu Pro Pro Phe
705                 710                 715                 720

Leu Trp Met Gly Tyr Glu Leu His Pro Asp Lys Trp Thr Val Gln Pro
            725                 730                 735

Ile Val Leu Pro Glu Lys Asp Ser Trp Thr Val Asn Asp Ile Gln Lys
                740                 745                 750

Leu Val Gly Lys Leu Asn Trp Ala Ser Gln Ile Tyr Ala Gly Ile Lys
            755                 760                 765

Val Lys Gln Leu Cys Lys Leu Arg Gly Thr Lys Ala Leu Thr Glu
770                 775                 780

Val Val Pro Leu Thr Glu Ala Glu Leu Glu Leu Ala Glu Asn Arg
785                 790                 795                 800

Glu Ile Leu Lys Glu Pro Val His Gly Val Tyr Tyr Asp Pro Ser Lys
                805                 810                 815

Asp Leu Ile Ala Glu Ile Gln Lys Gln Gly Gln Gly Gln Trp Thr Tyr
            820                 825                 830

Gln Ile Tyr Gln Glu Pro Phe Lys Asn Leu Lys Thr Gly Lys Tyr Ala
            835                 840                 845

Arg Met Arg Gly Ala His Thr Asn Asp Val Lys Gln Leu Thr Glu Ala
850                 855                 860

Val Gln Lys Ile Ala Thr Glu Ser Ile Val Ile Trp Gly Lys Thr Pro
865                 870                 875                 880

Lys Phe Lys Leu Pro Ile Gln Lys Glu Thr Trp Glu Ala Trp Trp Thr
                885                 890                 895

Glu Tyr Trp Gln Ala Thr Trp Ile Pro Glu Trp Glu Phe Val Asn Thr
            900                 905                 910

Pro Pro Leu Val Lys Leu Trp Tyr Gln Leu Glu Lys Glu Pro Ile Val
            915                 920                 925

Gly Ala Glu Thr Phe Tyr Val Ala Gly Ala Ala Asn Arg Glu Thr Lys
930                 935                 940

Leu Gly Lys Ala Gly Tyr Val Thr Asp Arg Gly Arg Gln Lys Val Val
945                 950                 955                 960

Ser Leu Thr Asp Thr Thr Asn Gln Lys Thr Ala Leu Gln Ala Ile His
                965                 970                 975

Leu Ala Leu Gln Asp Ser Gly Leu Glu Val Asn Ile Val Thr Ala Ser
            980                 985                 990

Gln Tyr Ala Leu Gly Ile Ile Gln Ala Gln Pro Asp Lys Ser Glu Ser
            995                 1000                1005

Glu Leu Val Ser Gln Ile Ile Glu Gln Leu Ile Lys Lys Glu Lys
    1010                1015                1020

Val Tyr Leu Ala Trp Val Pro Ala His Lys Gly Ile Gly Gly Asn
    1025                1030                1035

Glu Gln Val Asp Lys Leu Val Ser Arg Gly Ile Arg Lys Val Leu
    1040                1045                1050

Phe Leu Asp Gly Ile Asp Lys Ala Gln Glu Glu His Glu Lys Tyr
    1055                1060                1065

His Ser Asn Trp Arg Ala Met Ala Ser Glu Phe Asn Leu Pro Pro
    1070                1075                1080

Ile Val Ala Lys Glu Ile Val Ala Ser Cys Asp Lys Cys Gln Leu
    1085                1090                1095

Lys Gly Glu Ala Ile His Gly Gln Val Asp Cys Ser Pro Gly Ile
    1100                1105                1110
```

```
Trp Gln Leu Ala Cys Thr His Leu Glu Gly Lys Val Ile Leu Val
    1115                1120                1125

Ala Val His Val Ala Ser Gly Tyr Ile Glu Ala Glu Val Ile Pro
    1130                1135                1140

Ala Glu Thr Gly Gln Glu Thr Ala Tyr Phe Leu Leu Lys Leu Ala
    1145                1150                1155

Gly Arg Trp Pro Val Lys Thr Ile His Thr Ala Asn Gly Ser Asn
    1160                1165                1170

Phe Thr Ser Ala Thr Val Lys Ala Ala Cys Trp Trp Ala Gly Ile
    1175                1180                1185

Lys Gln Glu Phe Gly Ile Pro Tyr Asn Pro Gln Ser Gln Gly Val
    1190                1195                1200

Val Ala Ser Ile Asn Lys Glu Leu Lys Lys Ile Gly Gln Val
    1205                1210                1215

Arg Asp Gln Ala Glu His Leu Lys Thr Ala Val Gln Met Ala Val
    1220                1225                1230

Phe Ile His Asn Phe Lys Arg Lys Gly Gly Ile Gly Glu Tyr Ser
    1235                1240                1245

Ala Gly Glu Arg Ile Val Asp Ile Ile Ala Ser Asp Ile Gln Thr
    1250                1255                1260

Lys Glu Leu Gln Lys Gln Ile Thr Lys Ile Gln Asn Phe Arg Val
    1265                1270                1275

Tyr Tyr Arg Asp Ser Arg Asp Pro Leu Trp Lys Gly Pro Ala Lys
    1280                1285                1290

Leu Leu Trp Lys Gly Glu Gly Ala Val Val Ile Gln Asp Asn Ser
    1295                1300                1305

Asp Ile Lys Val Val Pro Arg Arg Lys Ala Lys Ile Ile Arg Asp
    1310                1315                1320

Tyr Gly Lys Gln Met Ala Gly Asp Asp Cys Val Ala Ser Arg Gln
    1325                1330                1335

Asp Glu Asp Met Ala Gly Lys Trp Ser Lys Ser Ser Ile Val Gly
    1340                1345                1350

Trp Pro Ala Val Arg Glu Arg Ile Arg Arg Ala Glu Pro Ala Ala
    1355                1360                1365

Glu Gly Val Gly Ala Ala Ser Gln Asp Leu Asp Lys Tyr Gly Ala
    1370                1375                1380

Leu Thr Ser Ser Asn Thr Ala Ala Thr Asn Ala Asp Cys Ala Trp
    1385                1390                1395

Leu Glu Ala Gln Glu Asp Glu Glu Val Gly Phe Pro Val Lys Pro
    1400                1405                1410

Gln Val Pro Leu Arg Pro Met Thr Tyr Lys Ala Ala Phe Asp Leu
    1415                1420                1425

Ser Phe Phe Leu Lys Glu Lys Gly Gly Leu Asp Gly Leu Ile Tyr
    1430                1435                1440

Ser Lys Lys Arg Gln Glu Ile Leu Asp Leu Trp Val Tyr Asn Thr
    1445                1450                1455

Gln Gly Phe Phe Pro Asp Trp Gln Asn Tyr Thr Pro Gly Pro Gly
    1460                1465                1470

Val Arg Tyr Pro Leu Thr Phe Gly Trp Cys Phe Lys Leu Val Pro
    1475                1480                1485

Val Asp Pro Arg Glu Val Glu Glu Ala Asn Lys Gly Glu Asn Asn
    1490                1495                1500

Cys Leu Leu His Pro Met Asn Leu His Gly Met Asp Asp Pro Glu
```

```
                  1505                1510                1515

Arg Glu Val Leu Val Trp Arg Phe Asp Ser Arg Leu Ala Phe His
        1520                1525                1530

His Met Ala Arg Glu Lys His Pro Glu Tyr Tyr Lys Asn Cys
    1535                1540                1545

<210> SEQ ID NO 30
<211> LENGTH: 841
<212> TYPE: PRT
<213> ORGANISM: Human immunodeficiency virus
<220> FEATURE:
<221> NAME/KEY: MOD_RES
<222> LOCATION: (785)..(785)
<223> OTHER INFORMATION: Any amino acid

<400> SEQUENCE: 30

Met Arg Val Thr Gly Met Leu Arg Asn Cys Gln Pro Trp Trp Ile Trp
1               5                   10                  15

Gly Ile Leu Gly Phe Trp Met Leu Leu Ile Tyr Asn Val Gly Gly Asn
            20                  25                  30

Leu Trp Val Thr Val Tyr Tyr Gly Val Pro Val Trp Lys Glu Ala Lys
        35                  40                  45

Thr Thr Leu Phe Cys Ala Ser Asp Ala Lys Ala Tyr Glu Lys Glu Val
    50                  55                  60

His Asn Val Trp Ala Thr His Ala Cys Val Pro Thr Asp Pro Asn Pro
65                  70                  75                  80

Gln Glu Met Val Leu Glu Asn Val Thr Glu Tyr Phe Asn Met Trp Lys
                85                  90                  95

Asn Asp Met Val Asp Gln Met His Glu Asp Ile Ile Ser Leu Trp Asp
            100                 105                 110

Gln Ser Leu Lys Pro Cys Val Lys Leu Thr Pro Leu Cys Val Thr Leu
        115                 120                 125

Asn Cys Arg Asn Val Thr Thr Ser Asn Asn Ala Thr Ser Asn Asp Asn
    130                 135                 140

Pro Asn Gly Glu Ile Lys Asn Cys Ser Phe Asn Ile Thr Thr Glu Leu
145                 150                 155                 160

Arg Asp Lys Arg Arg Asn Glu Tyr Ala Leu Phe Tyr Arg Leu Asp Ile
                165                 170                 175

Val Pro Leu Ser Gly Ser Lys Asn Ser Ser Asn Ser Ser Glu Tyr Arg
            180                 185                 190

Leu Ile Asn Cys Asn Thr Ser Ala Ile Thr Gln Ala Cys Pro Lys Val
        195                 200                 205

Ser Phe Asp Pro Ile Pro Ile His Tyr Cys Ala Pro Ala Gly Tyr Ala
    210                 215                 220

Ile Leu Lys Cys Asn Asn Lys Thr Phe Asn Gly Thr Gly Pro Cys Asn
225                 230                 235                 240

Asn Val Ser Thr Val Gln Cys Thr His Gly Ile Lys Pro Val Val Ser
                245                 250                 255

Thr Gln Leu Leu Leu Asn Gly Ser Leu Ala Glu Gly Glu Ile Ile Ile
            260                 265                 270

Arg Ser Glu Asn Leu Thr Asn Asn Ala Lys Thr Ile Ile Val His Leu
        275                 280                 285

Asn Glu Ser Ile Glu Ile Val Cys Ala Arg Pro Asn Asn Asn Thr Arg
    290                 295                 300

Lys Ser Met Arg Ile Gly Pro Gly Gln Thr Phe Tyr Ala Thr Gly Asp
305                 310                 315                 320
```

-continued

Ile Ile Gly Asp Ile Arg Gln Ala His Cys Asn Ile Ser Gly Asn Trp
            325                 330                 335

Asn Ala Thr Leu Glu Lys Val Lys Gly Lys Leu Gln Glu His Phe Pro
            340                 345                 350

Gly Lys Asn Ile Ser Phe Glu Pro Ser Ser Gly Gly Asp Leu Glu Ile
            355                 360                 365

Thr Thr His Ser Phe Asn Cys Arg Gly Glu Phe Phe Tyr Cys Asp Thr
    370                 375                 380

Ser Lys Leu Phe Asn Gly Thr Thr His Thr Ala Asn Ser Ser Ile Thr
385                 390                 395                 400

Ile Gln Cys Arg Ile Lys Gln Ile Ile Asn Met Trp Gln Gly Val Gly
                405                 410                 415

Arg Ala Ile Tyr Ala Pro Pro Ile Ala Gly Asn Ile Thr Cys Lys Ser
                420                 425                 430

Asn Ile Thr Gly Leu Leu Leu Thr Arg Asp Gly Gly Thr Leu Asn Asn
            435                 440                 445

Asp Thr Glu Lys Phe Arg Pro Gly Gly Gly Asp Met Arg Asp Asn Trp
    450                 455                 460

Arg Ser Glu Leu Tyr Lys Tyr Lys Val Val Glu Ile Lys Pro Leu Gly
465                 470                 475                 480

Ile Ala Pro Thr Lys Ala Lys Arg Arg Val Val Glu Arg Glu Lys Arg
                485                 490                 495

Ala Val Gly Ile Gly Ala Val Phe Leu Gly Phe Leu Gly Ala Ala Gly
                500                 505                 510

Ser Thr Met Gly Ala Ala Ser Ile Thr Leu Thr Val Gln Ala Arg Gln
            515                 520                 525

Leu Leu Ser Gly Ile Val Gln Gln Gln Ser Asn Leu Leu Arg Ala Ile
            530                 535                 540

Glu Ala Gln Gln His Met Leu Gln Leu Thr Val Trp Gly Ile Lys Gln
545                 550                 555                 560

Leu Gln Thr Arg Val Leu Ala Ile Glu Arg Tyr Leu Lys Asp Gln Gln
                565                 570                 575

Leu Leu Gly Ile Trp Gly Cys Ser Gly Lys Ile Ile Cys Thr Thr Ala
            580                 585                 590

Val Pro Trp Asn Thr Ser Trp Ser Asn Lys Ser Leu Glu Asp Ile Trp
            595                 600                 605

Asp Asn Met Thr Trp Met Gln Trp Asp Arg Glu Ile Asn Asn Tyr Thr
            610                 615                 620

Ser Ile Ile Tyr Ser Leu Leu Glu Glu Ser Gln Asn Gln Gln Glu Lys
625                 630                 635                 640

Asn Glu Lys Asp Leu Leu Ala Leu Asp Ser Trp Asn Asn Leu Trp Asn
                645                 650                 655

Trp Phe Asn Ile Thr Lys Trp Leu Trp Tyr Ile Lys Ile Phe Ile Met
                660                 665                 670

Ile Val Gly Gly Leu Ile Gly Leu Arg Ile Ile Phe Ala Val Leu Ser
            675                 680                 685

Ile Val Asn Arg Val Arg Gln Gly Tyr Ser Pro Leu Ser Phe Gln Thr
            690                 695                 700

Leu Ile Pro Asn Pro Arg Gly Pro Asp Arg Leu Gly Arg Ile Glu Glu
705                 710                 715                 720

Glu Gly Gly Glu Gln Asp Arg Asp Arg Ser Ile Arg Leu Val Asn Gly
                725                 730                 735

```
Phe Leu Ala Ile Ala Trp Asp Asp Leu Arg Ser Leu Cys Leu Phe Ser
                740                 745                 750

Tyr Arg Arg Leu Arg Asp Phe Ile Leu Ile Val Ala Arg Ala Val Glu
        755                 760                 765

Leu Leu Ile Gln Arg Gly Trp Glu Thr Leu Lys Tyr Leu Gly Ser Leu
    770                 775                 780

Xaa Gln Tyr Trp Gly Leu Glu Leu Lys Lys Ser Ala Ile Ser Leu Leu
785                 790                 795                 800

Asp Thr Ile Ala Ile Thr Val Ala Glu Gly Thr Asp Arg Ile Ile Glu
                805                 810                 815

Leu Val Gln Arg Ile Cys Arg Ala Ile Ser Asn Ile Pro Arg Arg Ile
        820                 825                 830

Arg Gln Gly Phe Glu Ala Ala Leu Gln
        835                 840

<210> SEQ ID NO 31
<211> LENGTH: 491
<212> TYPE: PRT
<213> ORGANISM: Human immunodeficiency virus

<400> SEQUENCE: 31

Met Gly Ala Arg Ala Ser Ile Leu Arg Gly Gly Lys Leu Asp Lys Trp
1               5                   10                  15

Glu Lys Ile Arg Leu Arg Pro Gly Gly Lys Lys His Tyr Met Leu Lys
            20                  25                  30

His Leu Val Trp Ala Ser Arg Glu Leu Glu Arg Phe Ala Leu Asn Pro
        35                  40                  45

Gly Leu Leu Glu Thr Ser Glu Gly Cys Lys Gln Ile Leu Lys Gln Leu
    50                  55                  60

Gln Pro Ala Leu Gln Thr Gly Thr Glu Gly Leu Arg Ser Leu Tyr Asn
65                  70                  75                  80

Thr Val Ala Thr Leu Tyr Cys Val His Ala Gly Ile Glu Val Arg Asp
                85                  90                  95

Thr Lys Glu Ala Leu Asp Lys Ile Glu Glu Glu Gln Asn Lys Gly Gln
            100                 105                 110

Gln Lys Thr Gln Gln Ala Lys Gly Ala Asp Gly Lys Val Ser Gln Asn
        115                 120                 125

Tyr Pro Ile Val Gln Asn Leu Gln Gly Gln Met Val His Gln Ala Ile
    130                 135                 140

Ser Pro Arg Thr Leu Asn Ala Trp Val Lys Val Ile Glu Glu Lys Ala
145                 150                 155                 160

Phe Ser Pro Glu Val Ile Pro Met Phe Thr Ala Leu Ser Glu Gly Ala
                165                 170                 175

Thr Pro Gln Asp Leu Asn Thr Met Leu Asn Thr Val Gly Gly His Gln
            180                 185                 190

Ala Ala Met Gln Met Leu Lys Asp Thr Ile Asn Glu Glu Ala Ala Glu
        195                 200                 205

Trp Asp Arg Leu His Pro Val His Ala Gly Pro Ile Ala Pro Gly Gln
    210                 215                 220

Met Arg Glu Pro Arg Gly Ser Asp Ile Ala Gly Thr Thr Ser Thr Leu
225                 230                 235                 240

Gln Glu Gln Ile Ala Trp Met Thr Asn Asn Pro Pro Val Pro Val Gly
                245                 250                 255

Asp Ile Tyr Lys Arg Trp Ile Ile Leu Gly Leu Asn Lys Ile Val Arg
            260                 265                 270
```

```
Met Tyr Ser Pro Val Ser Ile Leu Asp Ile Lys Gln Gly Pro Lys Glu
            275                 280                 285

Pro Phe Arg Asp Tyr Val Asp Arg Phe Phe Lys Thr Leu Arg Ala Glu
290                 295                 300

Gln Ala Thr Gln Asp Val Lys Asn Trp Met Thr Asp Thr Leu Leu Val
305                 310                 315                 320

Gln Asn Ala Asn Pro Asp Cys Lys Thr Ile Leu Arg Ala Leu Gly Pro
                325                 330                 335

Gly Ala Thr Leu Glu Glu Met Met Thr Ala Cys Gln Gly Val Gly Gly
            340                 345                 350

Pro Ser His Lys Ala Arg Val Leu Ala Glu Ala Met Ser Gln Thr Gly
        355                 360                 365

Ser Thr Ile Met Met Gln Arg Ser Asn Phe Lys Gly Ser Lys Arg Ile
    370                 375                 380

Val Lys Cys Phe Asn Cys Gly Lys Glu Gly His Ile Ala Arg Asn Cys
385                 390                 395                 400

Arg Ala Pro Arg Lys Lys Gly Cys Trp Lys Cys Gly Lys Glu Gly His
                405                 410                 415

Gln Met Lys Asp Cys Thr Glu Arg Gln Ala Asn Phe Leu Gly Lys Ile
            420                 425                 430

Trp Pro Ser His Lys Gly Arg Pro Gly Asn Phe Leu Gln Ser Arg Pro
        435                 440                 445

Glu Pro Thr Ala Pro Ala Glu Ser Phe Arg Phe Glu Glu Thr Thr
    450                 455                 460

Pro Ala Pro Lys Gln Glu Leu Lys Asp Arg Glu Pro Leu Thr Ser Leu
465                 470                 475                 480

Lys Ser Leu Phe Gly Ser Asp Pro Leu Ser Gln
                485                 490

<210> SEQ ID NO 32
<211> LENGTH: 999
<212> TYPE: PRT
<213> ORGANISM: Human immunodeficiency virus

<400> SEQUENCE: 32

Phe Phe Arg Glu Asn Leu Ala Phe Gln Gln Gly Glu Ala Arg Glu Phe
1               5                   10                  15

Pro Ser Glu Gln Ala Arg Ala Asn Ser Pro Thr Ser Arg Glu Phe Gln
                20                  25                  30

Val Arg Gly Asp Asn Pro Cys Ser Glu Ala Gly Val Lys Gly Gln Gly
            35                  40                  45

Thr Leu Asn Phe Pro Gln Ile Thr Leu Trp Gln Arg Pro Leu Val Ser
    50                  55                  60

Ile Lys Val Gly Gly Gln Val Lys Glu Ala Leu Leu Asp Thr Gly Ala
65                  70                  75                  80

Asp Asp Thr Val Leu Glu Glu Ile Asn Leu Pro Gly Lys Trp Lys Pro
                85                  90                  95

Lys Met Ile Gly Gly Ile Gly Gly Phe Ile Lys Val Arg Gln Tyr Asp
                100                 105                 110

Gln Ile Leu Ile Glu Ile Cys Gly Lys Lys Ala Ile Gly Thr Val Leu
            115                 120                 125

Val Gly Pro Thr Pro Val Asn Ile Ile Gly Arg Asn Met Leu Thr Gln
    130                 135                 140

Leu Gly Cys Thr Leu Asn Phe Pro Ile Ser Pro Ile Glu Thr Val Pro
```

```
            145                 150                 155                 160
        Val Lys Leu Lys Pro Gly Met Asp Gly Pro Lys Ile Lys Gln Trp Pro
                        165                 170                 175
        Leu Thr Glu Glu Lys Ile Lys Ala Leu Met Ala Ile Cys Glu Glu Met
                        180                 185                 190
        Glu Lys Glu Gly Lys Ile Thr Lys Ile Gly Pro Glu Asn Pro Tyr Asn
                        195                 200                 205
        Thr Pro Ile Phe Ala Ile Lys Lys Lys Asp Ser Thr Lys Trp Arg Lys
                210                 215                 220
        Leu Val Asp Phe Arg Glu Leu Asn Lys Arg Thr Gln Asp Phe Trp Glu
        225                 230                 235                 240
        Val Gln Leu Gly Ile Pro His Pro Ala Gly Leu Lys Lys Lys Lys Ser
                        245                 250                 255
        Val Thr Val Leu Asp Val Gly Asp Ala Tyr Phe Ser Val Pro Leu Asp
                        260                 265                 270
        Glu Ser Phe Arg Lys Tyr Thr Ala Phe Thr Ile Pro Ser Ile Asn Asn
                        275                 280                 285
        Glu Thr Pro Gly Ile Arg Tyr Gln Tyr Asn Val Leu Pro Gln Gly Trp
                290                 295                 300
        Lys Gly Ser Pro Ala Ile Phe Gln Ser Ser Met Thr Lys Ile Leu Glu
        305                 310                 315                 320
        Pro Phe Arg Ala Lys Asn Pro Glu Ile Val Ile Tyr Gln Tyr Met Asp
                        325                 330                 335
        Asp Leu Tyr Val Gly Ser Asp Leu Glu Ile Gly Gln His Arg Ala Lys
                        340                 345                 350
        Ile Glu Glu Leu Arg Glu His Leu Leu Arg Trp Gly Phe Thr Thr Pro
                        355                 360                 365
        Asp Lys Lys His Gln Lys Glu Pro Pro Phe Leu Trp Met Gly Tyr Glu
                        370                 375                 380
        Leu His Pro Asp Lys Trp Thr Val Gln Pro Ile Gln Leu Pro Glu Lys
        385                 390                 395                 400
        Asp Ser Trp Thr Val Asn Asp Ile Gln Lys Leu Val Gly Lys Leu Asn
                        405                 410                 415
        Trp Ala Ser Gln Ile Tyr Ser Gly Ile Lys Val Arg Gln Leu Cys Lys
                        420                 425                 430
        Leu Leu Arg Gly Ala Lys Ala Leu Thr Asp Ile Val Pro Leu Thr Glu
                        435                 440                 445
        Glu Ala Glu Leu Glu Leu Ala Glu Asn Arg Glu Ile Leu Lys Glu Pro
                450                 455                 460
        Val His Gly Val Tyr Tyr Asp Pro Ser Lys Asp Leu Ile Ala Glu Ile
        465                 470                 475                 480
        Gln Lys Gln Gly Tyr Asp Gln Trp Thr Tyr Gln Ile Tyr Gln Glu Pro
                        485                 490                 495
        Phe Lys Asn Leu Lys Thr Gly Lys Tyr Ala Lys Met Arg Thr Ala His
                        500                 505                 510
        Thr Asn Asp Val Lys Gln Leu Thr Glu Ala Val Gln Lys Ile Ala Leu
                        515                 520                 525
        Glu Ser Ile Val Ile Trp Gly Lys Thr Pro Lys Phe Arg Leu Pro Ile
                        530                 535                 540
        Gln Lys Glu Thr Trp Glu Ile Trp Trp Thr Asp Tyr Trp Gln Ala Thr
        545                 550                 555                 560
        Trp Ile Pro Glu Trp Glu Phe Val Asn Thr Pro Pro Leu Val Lys Leu
                        565                 570                 575
```

-continued

Trp Tyr Gln Leu Glu Lys Glu Pro Ile Ala Gly Ala Glu Thr Phe Tyr
          580                 585                 590

Val Asp Gly Ala Ala Asn Arg Glu Thr Lys Ile Gly Lys Ala Gly Tyr
        595                 600                 605

Val Thr Asp Lys Gly Arg Gln Lys Ile Val Thr Leu Thr Glu Thr Thr
    610                 615                 620

Asn Gln Lys Thr Glu Leu Gln Ala Ile Gln Leu Ala Leu Gln Asp Ser
625                 630                 635                 640

Gly Ser Glu Val Asn Ile Val Thr Asp Ser Gln Tyr Ala Leu Gly Ile
                645                 650                 655

Ile Gln Ala Gln Pro Asp Lys Ser Glu Ser Glu Leu Val Asn Gln Ile
        660                 665                 670

Ile Glu Gln Leu Ile Asn Lys Glu Arg Val Tyr Leu Ser Trp Val Pro
    675                 680                 685

Ala His Lys Gly Ile Gly Gly Asn Glu Gln Val Asp Lys Leu Val Ser
    690                 695                 700

Ser Gly Ile Arg Lys Val Leu Phe Leu Asp Gly Ile Asp Lys Ala Gln
705                 710                 715                 720

Glu Glu His Glu Lys Tyr His Ser Asn Trp Arg Ala Met Ala Ser Glu
                725                 730                 735

Phe Asn Leu Pro Pro Val Val Ala Lys Glu Ile Val Ala Ser Cys Asp
            740                 745                 750

Lys Cys Gln Leu Lys Gly Glu Ala Ile His Gly Gln Val Asp Cys Ser
        755                 760                 765

Pro Gly Ile Trp Gln Leu Asp Cys Thr His Leu Glu Gly Lys Val Ile
    770                 775                 780

Leu Val Ala Val His Val Ala Ser Gly Tyr Met Glu Ala Glu Val Ile
785                 790                 795                 800

Pro Ala Glu Thr Gly Gln Glu Thr Ala Tyr Tyr Ile Leu Lys Leu Ala
                805                 810                 815

Gly Arg Trp Pro Val Lys Val Ile His Thr Asp Asn Gly Ser Asn Phe
            820                 825                 830

Thr Ser Ala Ala Val Lys Ala Ala Cys Trp Trp Ala Gly Ile Gln Gln
        835                 840                 845

Glu Phe Gly Ile Pro Tyr Asn Pro Gln Ser Gln Gly Val Val Glu Ser
    850                 855                 860

Met Asn Lys Glu Leu Lys Lys Ile Ile Gly Gln Val Arg Asp Gln Ala
865                 870                 875                 880

Glu His Leu Lys Thr Ala Val Gln Met Ala Val Phe Ile His Asn Phe
                885                 890                 895

Lys Arg Lys Gly Gly Ile Gly Gly Tyr Ser Ala Gly Glu Arg Ile Ile
            900                 905                 910

Asp Ile Ile Ala Thr Asp Ile Gln Thr Lys Glu Leu Gln Lys Gln Ile
        915                 920                 925

Ile Lys Ile Gln Asn Phe Arg Val Tyr Tyr Arg Asp Ser Arg Asp Pro
    930                 935                 940

Ile Trp Lys Gly Pro Ala Lys Leu Leu Trp Lys Gly Glu Gly Ala Val
945                 950                 955                 960

Val Ile Gln Asp Asn Ser Asp Ile Lys Val Val Pro Arg Arg Lys Val
                965                 970                 975

Lys Ile Ile Lys Asp Tyr Gly Lys Gln Met Ala Gly Ala Asp Cys Val
            980                 985                 990

-continued

```
Ala Gly Arg Gln Asp Glu Asp
        995

<210> SEQ ID NO 33
<211> LENGTH: 206
<212> TYPE: PRT
<213> ORGANISM: Human immunodeficiency virus

<400> SEQUENCE: 33

Met Gly Gly Lys Trp Ser Lys Ser Ser Ile Val Gly Trp Pro Asp Val
1               5                   10                  15

Arg Glu Arg Met Arg Arg Thr Glu Pro Ala Ala Glu Gly Val Gly Ala
            20                  25                  30

Ala Ser Gln Asp Leu Asp Lys Tyr Gly Ala Leu Thr Ser Ser Asn Thr
        35                  40                  45

Thr His Asn Asn Ala Asp Cys Ala Trp Leu Glu Ala Gln Glu Glu Gly
    50                  55                  60

Glu Val Gly Phe Pro Val Arg Pro Gln Val Pro Leu Arg Pro Met Thr
65                  70                  75                  80

Tyr Lys Gly Ala Phe Asp Leu Ser Phe Phe Leu Lys Glu Lys Gly Gly
                85                  90                  95

Leu Asp Gly Leu Ile Tyr Ser Lys Lys Arg Gln Glu Ile Leu Asp Leu
            100                 105                 110

Trp Val Tyr His Thr Gln Gly Phe Phe Pro Asp Trp Gln Asn Tyr Thr
        115                 120                 125

Pro Gly Pro Gly Val Arg Tyr Pro Leu Thr Phe Gly Trp Cys Phe Lys
    130                 135                 140

Leu Val Pro Val Asp Pro Arg Glu Val Glu Glu Ala Asn Lys Gly Glu
145                 150                 155                 160

Asn Asn Cys Leu Leu His Pro Met Ser Leu His Gly Met Glu Asp Glu
                165                 170                 175

Glu Arg Glu Val Leu Lys Trp Glu Phe Asp Ser Ser Leu Ala Arg Arg
            180                 185                 190

His Leu Ala Arg Glu Leu His Pro Glu Tyr Tyr Lys Asp Cys
        195                 200                 205

<210> SEQ ID NO 34
<211> LENGTH: 665
<212> TYPE: PRT
<213> ORGANISM: Human immunodeficiency virus

<400> SEQUENCE: 34

Met Arg Val Thr Gly Met Leu Arg Asn Cys Gln Pro Trp Trp Ile Trp
1               5                   10                  15

Gly Ile Leu Gly Phe Trp Met Leu Leu Ile Tyr Asn Val Gly Gly Asn
            20                  25                  30

Leu Trp Val Thr Val Tyr Tyr Gly Val Pro Val Trp Lys Glu Ala Lys
        35                  40                  45

Thr Thr Leu Phe Cys Ala Ser Asp Ala Lys Ala Tyr Glu Lys Glu Val
    50                  55                  60

His Asn Val Trp Ala Thr His Ala Cys Val Pro Thr Asp Pro Asn Pro
65                  70                  75                  80

Gln Glu Met Val Leu Glu Asn Val Thr Glu Tyr Phe Asn Met Trp Lys
                85                  90                  95

Asn Asp Met Val Asp Gln Met His Glu Asp Ile Ile Ser Leu Trp Asp
            100                 105                 110
```

```
Gln Ser Leu Lys Pro Cys Val Lys Leu Thr Pro Leu Cys Val Thr Leu
            115                 120                 125

Asn Cys Arg Asn Val Thr Thr Ser Asn Ala Thr Ser Asn Asp Asn
130                 135                 140

Pro Asn Gly Glu Ile Lys Asn Cys Ser Phe Asn Ile Thr Thr Glu Leu
145                 150                 155                 160

Arg Asp Lys Arg Arg Asn Glu Tyr Ala Leu Phe Tyr Arg Leu Asp Ile
                165                 170                 175

Val Pro Leu Ser Gly Ser Lys Asn Ser Asn Ser Ser Glu Tyr Arg
            180                 185                 190

Leu Ile Asn Cys Asn Thr Ser Ala Ile Thr Gln Ala Cys Pro Lys Val
            195                 200                 205

Ser Phe Asp Pro Ile Pro Ile His Tyr Cys Ala Pro Ala Gly Tyr Ala
210                 215                 220

Ile Leu Lys Cys Asn Asn Lys Thr Phe Asn Gly Thr Gly Pro Cys Asn
225                 230                 235                 240

Asn Val Ser Thr Val Gln Cys Thr His Gly Ile Lys Pro Val Val Ser
                245                 250                 255

Thr Gln Leu Leu Leu Asn Gly Ser Leu Ala Glu Gly Glu Ile Ile Ile
            260                 265                 270

Arg Ser Glu Asn Leu Thr Asn Asn Ala Lys Thr Ile Ile Val His Leu
275                 280                 285

Asn Glu Ser Ile Glu Ile Val Cys Ala Arg Pro Asn Asn Thr Arg
            290                 295                 300

Lys Ser Met Arg Ile Gly Pro Gly Gln Thr Phe Tyr Ala Thr Gly Asp
305                 310                 315                 320

Ile Ile Gly Asp Ile Arg Gln Ala His Cys Asn Ile Ser Gly Asn Trp
                325                 330                 335

Asn Ala Thr Leu Glu Lys Val Lys Gly Lys Leu Gln Glu His Phe Pro
            340                 345                 350

Gly Lys Asn Ile Ser Phe Glu Pro Ser Ser Gly Gly Asp Leu Glu Ile
            355                 360                 365

Thr Thr His Ser Phe Asn Cys Arg Gly Glu Phe Phe Tyr Cys Asp Thr
370                 375                 380

Ser Lys Leu Phe Asn Gly Thr Thr His Thr Ala Asn Ser Ser Ile Thr
385                 390                 395                 400

Ile Gln Cys Arg Ile Lys Gln Ile Ile Asn Met Trp Gln Gly Val Gly
                405                 410                 415

Arg Ala Ile Tyr Ala Pro Pro Ile Ala Gly Asn Ile Thr Cys Lys Ser
            420                 425                 430

Asn Ile Thr Gly Leu Leu Leu Thr Arg Asp Gly Gly Thr Leu Asn Asn
            435                 440                 445

Asp Thr Glu Lys Phe Arg Pro Gly Gly Gly Asp Met Arg Asp Asn Trp
450                 455                 460

Arg Ser Glu Leu Tyr Lys Tyr Lys Val Val Glu Ile Lys Pro Leu Gly
465                 470                 475                 480

Ile Ala Pro Thr Lys Ala Lys Arg Arg Val Val Glu Ser Glu Lys Ser
                485                 490                 495

Ala Val Gly Ile Gly Ala Val Phe Leu Gly Phe Leu Gly Ala Ala Gly
            500                 505                 510

Ser Thr Met Gly Ala Ala Ser Ile Thr Leu Thr Val Gln Ala Arg Gln
            515                 520                 525

Leu Leu Ser Gly Ile Val Gln Gln Gln Ser Asn Leu Leu Arg Ala Ile
```

```
            530                 535                 540
Glu Ala Gln Gln His Met Leu Gln Leu Thr Val Trp Gly Ile Lys Gln
545                 550                 555                 560

Leu Gln Thr Arg Val Leu Ala Ile Glu Arg Tyr Leu Lys Asp Gln Gln
                565                 570                 575

Leu Leu Gly Ile Trp Gly Cys Ser Gly Lys Ile Ile Cys Thr Thr Ala
            580                 585                 590

Val Pro Trp Asn Thr Ser Trp Ser Asn Lys Ser Leu Glu Asp Ile Trp
        595                 600                 605

Asp Asn Met Thr Trp Met Gln Trp Asp Arg Glu Ile Asn Asn Tyr Thr
    610                 615                 620

Ser Ile Ile Tyr Ser Leu Leu Glu Glu Ser Gln Asn Gln Gln Glu Lys
625                 630                 635                 640

Asn Glu Lys Asp Leu Leu Ala Leu Asp Ser Trp Asn Asn Leu Trp Asn
                645                 650                 655

Trp Phe Asn Ile Thr Lys Trp Leu Trp
            660                 665
```

<210> SEQ ID NO 35
<211> LENGTH: 850
<212> TYPE: PRT
<213> ORGANISM: Human immunodeficiency virus

<400> SEQUENCE: 35

```
Met Ala Pro Ile Ser Pro Ile Glu Thr Val Pro Val Lys Leu Lys Pro
1               5                   10                  15

Gly Met Asp Gly Pro Lys Ile Lys Gln Trp Pro Leu Thr Glu Glu Lys
            20                  25                  30

Ile Lys Ala Leu Met Ala Ile Cys Glu Glu Met Glu Lys Glu Gly Lys
        35                  40                  45

Ile Thr Lys Ile Gly Pro Glu Asn Pro Tyr Asn Thr Pro Ile Phe Ala
    50                  55                  60

Ile Lys Lys Lys Asp Ser Thr Lys Trp Arg Lys Leu Val Asp Phe Arg
65                  70                  75                  80

Glu Leu Asn Lys Arg Thr Gln Asp Phe Trp Glu Val Gln Leu Gly Ile
                85                  90                  95

Pro His Pro Ala Gly Leu Lys Lys Lys Ser Val Thr Val Leu Ala
            100                 105                 110

Val Gly Asp Ala Tyr Phe Ser Val Pro Leu Asp Glu Ser Phe Arg Lys
        115                 120                 125

Tyr Thr Ala Phe Thr Ile Pro Ser Ile Asn Asn Glu Thr Pro Gly Ile
    130                 135                 140

Arg Tyr Gln Tyr Asn Val Leu Pro Gln Gly Trp Lys Gly Ser Pro Ala
145                 150                 155                 160

Ile Phe Gln Ser Ser Met Thr Lys Ile Leu Glu Pro Phe Arg Ala Lys
                165                 170                 175

Asn Pro Glu Ile Val Ile Tyr Gln Tyr Met Ala Ala Leu Tyr Val Gly
            180                 185                 190

Ser Asp Leu Glu Ile Gly Gln His Arg Ala Lys Ile Glu Glu Leu Arg
        195                 200                 205

Glu His Leu Leu Arg Trp Gly Phe Thr Thr Pro Asp Lys Lys His Gln
    210                 215                 220

Lys Glu Pro Pro Phe Leu Trp Met Gly Tyr Glu Leu His Pro Asp Lys
225                 230                 235                 240
```

-continued

```
Trp Thr Val Gln Pro Ile Gln Leu Pro Glu Lys Asp Ser Trp Thr Val
            245                 250                 255
Asn Asp Ile Gln Lys Leu Val Gly Lys Leu Asn Trp Ala Ser Gln Ile
        260                 265                 270
Tyr Ser Gly Ile Lys Val Arg Gln Leu Cys Lys Leu Leu Arg Gly Ala
    275                 280                 285
Lys Ala Leu Thr Asp Ile Val Pro Leu Thr Glu Ala Glu Leu Glu
290                 295                 300
Leu Ala Glu Asn Arg Glu Ile Leu Lys Glu Pro Val His Gly Val Tyr
305                 310                 315                 320
Tyr Asp Pro Ser Lys Asp Leu Ile Ala Glu Ile Gln Lys Gln Gly Tyr
                325                 330                 335
Asp Gln Trp Thr Tyr Gln Ile Tyr Gln Glu Pro Phe Lys Asn Leu Lys
            340                 345                 350
Thr Gly Lys Tyr Ala Lys Met Arg Thr Ala His Thr Asn Asp Val Lys
        355                 360                 365
Gln Leu Thr Glu Ala Val Gln Lys Ile Ala Leu Glu Ser Ile Val Ile
    370                 375                 380
Trp Gly Lys Thr Pro Lys Phe Arg Leu Pro Ile Gln Lys Glu Thr Trp
385                 390                 395                 400
Glu Ile Trp Trp Thr Asp Tyr Trp Gln Ala Thr Trp Ile Pro Glu Trp
                405                 410                 415
Glu Phe Val Asn Thr Pro Pro Leu Val Lys Leu Trp Tyr Gln Leu Glu
            420                 425                 430
Lys Glu Pro Ile Ala Gly Ala Glu Thr Phe Tyr Val Ala Gly Ala Ala
        435                 440                 445
Asn Arg Glu Thr Lys Ile Gly Lys Ala Gly Tyr Val Thr Asp Lys Gly
    450                 455                 460
Arg Gln Lys Ile Val Thr Leu Thr Glu Thr Thr Asn Gln Lys Thr Ala
465                 470                 475                 480
Leu Gln Ala Ile Gln Leu Ala Leu Gln Asp Ser Gly Ser Glu Val Asn
                485                 490                 495
Ile Val Thr Ala Ser Gln Tyr Ala Leu Gly Ile Ile Gln Ala Gln Pro
            500                 505                 510
Asp Lys Ser Glu Ser Glu Leu Val Asn Gln Ile Ile Glu Gln Leu Ile
        515                 520                 525
Asn Lys Glu Arg Val Tyr Leu Ser Trp Val Pro Ala His Lys Gly Ile
    530                 535                 540
Gly Gly Asn Glu Gln Val Asp Lys Leu Val Ser Ser Gly Ile Arg Lys
545                 550                 555                 560
Val Leu Phe Leu Asp Gly Ile Asp Lys Ala Gln Glu Glu His Glu Lys
                565                 570                 575
Tyr His Ser Asn Trp Arg Ala Met Ala Ser Glu Phe Asn Leu Pro Pro
            580                 585                 590
Val Val Ala Lys Glu Ile Ala Ser Cys Asp Lys Cys Gln Leu Lys
        595                 600                 605
Gly Glu Ala Ile His Gly Gln Val Asp Cys Ser Pro Gly Ile Trp Gln
    610                 615                 620
Leu Ala Cys Thr His Leu Glu Gly Lys Val Ile Leu Val Ala Val His
625                 630                 635                 640
Val Ala Ser Gly Tyr Met Glu Ala Glu Val Ile Pro Ala Glu Thr Gly
                645                 650                 655
Gln Glu Thr Ala Tyr Tyr Ile Leu Lys Leu Ala Gly Arg Trp Pro Val
```

```
                   660                 665                 670
Lys Val Ile His Thr Ala Asn Gly Ser Asn Phe Thr Ser Ala Ala Val
            675                 680                 685

Lys Ala Ala Cys Trp Trp Ala Gly Ile Gln Gln Glu Phe Gly Ile Pro
            690                 695                 700

Tyr Asn Pro Gln Ser Gln Gly Val Val Ala Ser Met Asn Lys Glu Leu
705                 710                 715                 720

Lys Lys Ile Ile Gly Gln Val Arg Asp Gln Ala Glu His Leu Lys Thr
                725                 730                 735

Ala Val Gln Met Ala Val Phe Ile His Asn Phe Lys Arg Lys Gly Gly
            740                 745                 750

Ile Gly Gly Tyr Ser Ala Gly Glu Arg Ile Ile Asp Ile Ile Ala Thr
            755                 760                 765

Asp Ile Gln Thr Lys Glu Leu Gln Lys Gln Ile Lys Ile Gln Asn
770                 775                 780

Phe Arg Val Tyr Tyr Arg Asp Ser Arg Asp Pro Ile Trp Lys Gly Pro
785                 790                 795                 800

Ala Lys Leu Leu Trp Lys Gly Glu Gly Ala Val Val Ile Gln Asp Asn
                805                 810                 815

Ser Asp Ile Lys Val Val Pro Arg Arg Lys Val Lys Ile Ile Lys Asp
                820                 825                 830

Tyr Gly Lys Gln Met Ala Gly Ala Asp Cys Val Ala Gly Arg Gln Asp
            835                 840                 845

Glu Asp
    850

<210> SEQ ID NO 36
<211> LENGTH: 696
<212> TYPE: PRT
<213> ORGANISM: Human immunodeficiency virus

<400> SEQUENCE: 36

Met Gly Ala Arg Ala Ser Ile Leu Arg Gly Gly Lys Leu Asp Lys Trp
1               5                   10                  15

Glu Lys Ile Arg Leu Arg Pro Gly Gly Lys Lys His Tyr Met Leu Lys
                20                  25                  30

His Leu Val Trp Ala Ser Arg Glu Leu Glu Arg Phe Ala Leu Asn Pro
            35                  40                  45

Gly Leu Leu Glu Thr Ser Glu Gly Cys Lys Gln Ile Leu Lys Gln Leu
        50                  55                  60

Gln Pro Ala Leu Gln Thr Gly Thr Glu Glu Leu Arg Ser Leu Tyr Asn
65                  70                  75                  80

Thr Val Ala Thr Leu Tyr Cys Val His Ala Gly Ile Glu Val Arg Asp
                85                  90                  95

Thr Lys Glu Ala Leu Asp Lys Ile Glu Glu Glu Gln Asn Lys Gly Gln
            100                 105                 110

Gln Lys Thr Gln Gln Ala Lys Gly Ala Asp Gly Lys Val Ser Gln Asn
        115                 120                 125

Tyr Pro Ile Val Gln Asn Leu Gln Gly Gln Met Val His Gln Ala Ile
    130                 135                 140

Ser Pro Arg Thr Leu Asn Ala Trp Val Lys Val Ile Glu Glu Lys Ala
145                 150                 155                 160

Phe Ser Pro Glu Val Ile Pro Met Phe Thr Ala Leu Ser Glu Gly Ala
                165                 170                 175
```

-continued

```
Thr Pro Gln Asp Leu Asn Thr Met Leu Asn Thr Val Gly Gly His Gln
            180                 185                 190

Ala Ala Met Gln Met Leu Lys Asp Thr Ile Asn Glu Glu Ala Ala Glu
        195                 200                 205

Trp Asp Arg Leu His Pro Val His Ala Gly Pro Ile Ala Pro Gly Gln
210                 215                 220

Met Arg Glu Pro Arg Gly Ser Asp Ile Ala Gly Thr Thr Ser Thr Leu
225                 230                 235                 240

Gln Glu Gln Ile Ala Trp Met Thr Asn Asn Pro Pro Val Pro Val Gly
                245                 250                 255

Asp Ile Tyr Lys Arg Trp Ile Ile Leu Gly Leu Asn Lys Ile Val Arg
                260                 265                 270

Met Tyr Ser Pro Val Ser Ile Leu Asp Ile Lys Gln Gly Pro Lys Glu
            275                 280                 285

Pro Phe Arg Asp Tyr Val Asp Arg Phe Phe Lys Thr Leu Arg Ala Glu
        290                 295                 300

Gln Ala Thr Gln Asp Val Lys Asn Trp Met Thr Asp Thr Leu Leu Val
305                 310                 315                 320

Gln Asn Ala Asn Pro Asp Cys Lys Thr Ile Leu Arg Ala Leu Gly Pro
                325                 330                 335

Gly Ala Thr Leu Glu Glu Met Met Thr Ala Cys Gln Gly Val Gly Gly
            340                 345                 350

Pro Ser His Lys Ala Arg Val Leu Ala Glu Ala Met Ser Gln Thr Gly
        355                 360                 365

Ser Thr Ile Met Met Gln Arg Ser Asn Phe Lys Gly Ser Lys Arg Ile
        370                 375                 380

Val Lys Cys Phe Asn Cys Gly Lys Glu Gly His Ile Ala Arg Asn Cys
385                 390                 395                 400

Arg Ala Pro Arg Lys Lys Gly Cys Trp Lys Cys Gly Lys Glu Gly His
                405                 410                 415

Gln Met Lys Asp Cys Thr Glu Arg Gln Ala Asn Phe Leu Gly Lys Ile
            420                 425                 430

Trp Pro Ser His Lys Gly Arg Pro Gly Asn Phe Leu Gln Ser Arg Pro
        435                 440                 445

Glu Pro Thr Ala Pro Pro Ala Glu Ser Phe Arg Phe Glu Glu Thr Thr
        450                 455                 460

Pro Ala Pro Lys Gln Glu Leu Lys Asp Arg Glu Pro Leu Thr Ser Leu
465                 470                 475                 480

Lys Ser Leu Phe Gly Ser Asp Pro Leu Ser Gln Ala Gly Lys Trp Ser
                485                 490                 495

Lys Ser Ser Ile Val Gly Trp Pro Asp Val Arg Glu Arg Met Arg Arg
            500                 505                 510

Thr Glu Pro Ala Ala Glu Gly Val Gly Ala Ala Ser Gln Asp Leu Asp
        515                 520                 525

Lys Tyr Gly Ala Leu Thr Ser Ser Asn Thr Thr His Asn Asn Ala Asp
        530                 535                 540

Cys Ala Trp Leu Glu Ala Gln Glu Glu Gly Glu Val Gly Phe Pro Val
545                 550                 555                 560

Arg Pro Gln Val Pro Leu Arg Pro Met Thr Tyr Lys Gly Ala Phe Asp
                565                 570                 575

Leu Ser Phe Phe Leu Lys Glu Lys Gly Gly Leu Asp Gly Leu Ile Tyr
            580                 585                 590

Ser Lys Lys Arg Gln Glu Ile Leu Asp Leu Trp Val Tyr His Thr Gln
```

```
                595              600              605
Gly Phe Phe Pro Asp Trp Gln Asn Tyr Thr Pro Gly Pro Gly Val Arg
        610              615              620

Tyr Pro Leu Thr Phe Gly Trp Cys Phe Lys Leu Val Pro Val Asp Pro
625              630              635              640

Arg Glu Val Glu Glu Ala Asn Lys Gly Glu Asn Asn Cys Leu Leu His
                645              650              655

Pro Met Ser Leu His Gly Met Glu Asp Glu Glu Arg Glu Val Leu Lys
        660              665              670

Trp Glu Phe Asp Ser Ser Leu Ala Arg Arg His Leu Ala Arg Glu Leu
        675              680              685

His Pro Glu Tyr Tyr Lys Asp Cys
        690              695

<210> SEQ ID NO 37
<211> LENGTH: 672
<212> TYPE: PRT
<213> ORGANISM: Artificial Sequence
<220> FEATURE:
<223> OTHER INFORMATION: Description of Artificial Sequence: Synthetic
      consensus sequence

<400> SEQUENCE: 37

Met Arg Val Arg Gly Ile Gln Arg Asn Cys Gln His Leu Trp Arg Trp
1               5                   10                  15

Gly Thr Leu Ile Leu Gly Met Leu Met Ile Cys Ser Ala Ala Glu Asn
            20                  25                  30

Leu Trp Val Thr Val Tyr Tyr Gly Val Pro Val Trp Lys Glu Ala Asn
        35                  40                  45

Thr Thr Leu Phe Cys Ala Ser Asp Ala Lys Ala Tyr Asp Thr Glu Val
    50                  55                  60

His Asn Val Trp Ala Thr His Ala Cys Val Pro Thr Asp Pro Asn Pro
65                  70                  75                  80

Gln Glu Ile Val Leu Glu Asn Val Thr Glu Asn Phe Asn Met Trp Lys
                85                  90                  95

Asn Asn Met Val Glu Gln Met His Glu Asp Ile Ile Ser Leu Trp Asp
            100                 105                 110

Gln Ser Leu Lys Pro Cys Val Lys Leu Thr Pro Leu Cys Val Thr Leu
        115                 120                 125

Asn Cys Thr Asn Val Asn Val Thr Asn Thr Thr Asn Asn Thr Glu Glu
    130                 135                 140

Lys Gly Glu Ile Lys Asn Cys Ser Phe Asn Ile Thr Thr Glu Ile Arg
145                 150                 155                 160

Asp Lys Lys Gln Lys Val Tyr Ala Leu Phe Tyr Arg Leu Asp Val Val
                165                 170                 175

Pro Ile Asp Asp Asn Asn Asn Ser Ser Asn Tyr Arg Leu Ile Asn
            180                 185                 190

Cys Asn Thr Ser Ala Ile Thr Gln Ala Cys Pro Lys Val Ser Phe Glu
        195                 200                 205

Pro Ile Pro Ile His Tyr Cys Ala Pro Ala Gly Phe Ala Ile Leu Lys
    210                 215                 220

Cys Asn Asp Lys Lys Phe Asn Gly Thr Gly Pro Cys Lys Asn Val Ser
225                 230                 235                 240

Thr Val Gln Cys Thr His Gly Ile Lys Pro Val Val Ser Thr Gln Leu
                245                 250                 255
```

-continued

Leu Leu Asn Gly Ser Leu Ala Glu Glu Ile Ile Ile Arg Ser Glu
            260                 265                 270

Asn Ile Thr Asn Asn Ala Lys Thr Ile Ile Val Gln Leu Asn Glu Ser
        275                 280                 285

Val Glu Ile Asn Cys Thr Arg Pro Asn Asn Asn Thr Arg Lys Ser Ile
    290                 295                 300

Arg Ile Gly Pro Gly Gln Ala Phe Tyr Ala Thr Gly Asp Ile Ile Gly
305                 310                 315                 320

Asp Ile Arg Gln Ala His Cys Asn Ile Ser Gly Thr Lys Trp Asn Lys
                325                 330                 335

Thr Leu Gln Gln Val Ala Lys Lys Leu Arg Glu His Phe Asn Asn Lys
            340                 345                 350

Thr Ile Ile Phe Lys Pro Ser Ser Gly Gly Asp Leu Glu Ile Thr Thr
        355                 360                 365

His Ser Phe Asn Cys Arg Gly Glu Phe Phe Tyr Cys Asn Thr Ser Gly
    370                 375                 380

Leu Phe Asn Ser Thr Trp Ile Gly Asn Gly Thr Lys Asn Asn Asn
385                 390                 395                 400

Thr Asn Asp Thr Ile Thr Leu Pro Cys Arg Ile Lys Gln Ile Ile Asn
                405                 410                 415

Met Trp Gln Gly Val Gly Gln Ala Met Tyr Ala Pro Pro Ile Glu Gly
            420                 425                 430

Lys Ile Thr Cys Lys Ser Asn Ile Thr Gly Leu Leu Leu Thr Arg Asp
        435                 440                 445

Gly Gly Asn Asn Asn Thr Asn Glu Thr Glu Ile Phe Arg Pro Gly Gly
    450                 455                 460

Gly Asp Met Arg Asp Asn Trp Arg Ser Glu Leu Tyr Lys Tyr Lys Val
465                 470                 475                 480

Val Lys Ile Glu Pro Leu Gly Val Ala Pro Thr Lys Ala Lys Arg Arg
                485                 490                 495

Val Val Glu Ser Glu Lys Ser Ala Val Gly Ile Gly Ala Val Phe Leu
            500                 505                 510

Gly Phe Leu Gly Ala Ala Gly Ser Thr Met Gly Ala Ala Ser Ile Thr
        515                 520                 525

Leu Thr Val Gln Ala Arg Gln Leu Leu Ser Gly Ile Val Gln Gln Gln
    530                 535                 540

Ser Asn Leu Leu Arg Ala Ile Glu Ala Gln Gln His Leu Leu Gln Leu
545                 550                 555                 560

Thr Val Trp Gly Ile Lys Gln Leu Gln Ala Arg Val Leu Ala Val Glu
                565                 570                 575

Arg Tyr Leu Lys Asp Gln Gln Leu Leu Gly Ile Trp Gly Cys Ser Gly
            580                 585                 590

Lys Leu Ile Cys Thr Thr Thr Val Pro Trp Asn Ser Ser Trp Ser Asn
        595                 600                 605

Lys Ser Gln Asp Glu Ile Trp Asp Asn Met Thr Trp Met Glu Trp Glu
    610                 615                 620

Arg Glu Ile Asn Asn Tyr Thr Asp Ile Ile Tyr Ser Leu Ile Glu Glu
625                 630                 635                 640

Ser Gln Asn Gln Gln Glu Lys Asn Glu Gln Glu Leu Leu Ala Leu Asp
                645                 650                 655

Lys Trp Ala Ser Leu Trp Asn Trp Phe Asp Ile Thr Asn Trp Leu Trp
            660                 665                 670

<210> SEQ ID NO 38
<211> LENGTH: 497
<212> TYPE: PRT
<213> ORGANISM: Artificial Sequence
<220> FEATURE:
<223> OTHER INFORMATION: Description of Artificial Sequence: Synthetic consensus sequence

<400> SEQUENCE: 38

```
Met Gly Ala Arg Ala Ser Val Leu Ser Gly Gly Lys Leu Asp Ala Trp
1               5                   10                  15

Glu Lys Ile Arg Leu Arg Pro Gly Gly Lys Lys Tyr Arg Leu Lys
            20                  25                  30

His Leu Val Trp Ala Ser Arg Glu Leu Glu Arg Phe Ala Leu Asn Pro
        35                  40                  45

Gly Leu Leu Glu Thr Ser Glu Gly Cys Lys Gln Ile Ile Gly Gln Leu
    50                  55                  60

Gln Pro Ala Leu Gln Thr Gly Ser Glu Glu Leu Arg Ser Leu Tyr Asn
65                  70                  75                  80

Thr Val Ala Thr Leu Tyr Cys Val His Gln Arg Ile Glu Val Lys Asp
                85                  90                  95

Thr Lys Glu Ala Leu Glu Lys Ile Glu Glu Gln Asn Lys Ser Gln
            100                 105                 110

Gln Lys Thr Gln Gln Ala Ala Ala Asp Lys Gly Asn Ser Ser Lys Val
        115                 120                 125

Ser Gln Asn Tyr Pro Ile Val Gln Asn Leu Gln Gly Gln Met Val His
    130                 135                 140

Gln Ala Ile Ser Pro Arg Thr Leu Asn Ala Trp Val Lys Val Ile Glu
145                 150                 155                 160

Glu Lys Ala Phe Ser Pro Glu Val Ile Pro Met Phe Ser Ala Leu Ser
                165                 170                 175

Glu Gly Ala Thr Pro Gln Asp Leu Asn Thr Met Leu Asn Thr Val Gly
            180                 185                 190

Gly His Gln Ala Ala Met Gln Met Leu Lys Asp Thr Ile Asn Glu Glu
        195                 200                 205

Ala Ala Glu Trp Asp Arg Leu His Pro Val His Ala Gly Pro Ile Pro
    210                 215                 220

Pro Gly Gln Met Arg Glu Pro Arg Gly Ser Asp Ile Ala Gly Thr Thr
225                 230                 235                 240

Ser Thr Leu Gln Glu Gln Ile Ala Trp Met Thr Ser Asn Pro Pro Ile
                245                 250                 255

Pro Val Gly Glu Ile Tyr Lys Arg Trp Ile Ile Leu Gly Leu Asn Lys
            260                 265                 270

Ile Val Arg Met Tyr Ser Pro Val Ser Ile Leu Asp Ile Arg Gln Gly
        275                 280                 285

Pro Lys Glu Pro Phe Arg Asp Tyr Val Asp Arg Phe Phe Lys Thr Leu
    290                 295                 300

Arg Ala Glu Gln Ala Thr Gln Asp Val Lys Asn Trp Met Thr Asp Thr
305                 310                 315                 320

Leu Leu Val Gln Asn Ala Asn Pro Asp Cys Lys Thr Ile Leu Lys Ala
                325                 330                 335

Leu Gly Pro Gly Ala Thr Leu Glu Glu Met Met Thr Ala Cys Gln Gly
            340                 345                 350

Val Gly Gly Pro Gly His Lys Ala Arg Val Leu Ala Glu Ala Met Ser
        355                 360                 365
```

```
Gln Val Thr Asn Ala Ala Ile Met Met Gln Arg Gly Asn Phe Lys Gly
    370                 375                 380

Gln Arg Arg Ile Ile Lys Cys Phe Asn Cys Gly Lys Glu Gly His Ile
385                 390                 395                 400

Ala Arg Asn Cys Arg Ala Pro Arg Lys Lys Gly Cys Trp Lys Cys Gly
                405                 410                 415

Lys Glu Gly His Gln Met Lys Asp Cys Thr Glu Arg Gln Ala Asn Phe
            420                 425                 430

Leu Gly Lys Ile Trp Pro Ser Asn Lys Gly Arg Pro Gly Asn Phe Leu
        435                 440                 445

Gln Ser Arg Pro Glu Pro Thr Ala Pro Pro Ala Glu Ser Phe Gly Phe
450                 455                 460

Gly Glu Glu Ile Thr Pro Ser Pro Lys Gln Glu Pro Lys Asp Lys Glu
465                 470                 475                 480

Pro Pro Leu Thr Ser Leu Lys Ser Leu Phe Gly Asn Asp Pro Leu Ser
                485                 490                 495

Gln

<210> SEQ ID NO 39
<211> LENGTH: 850
<212> TYPE: PRT
<213> ORGANISM: Artificial Sequence
<220> FEATURE:
<223> OTHER INFORMATION: Description of Artificial Sequence: Synthetic
      consensus sequence

<400> SEQUENCE: 39

Met Ala Pro Ile Ser Pro Ile Glu Thr Val Pro Val Lys Leu Lys Pro
1               5                   10                  15

Gly Met Asp Gly Pro Lys Val Lys Gln Trp Pro Leu Thr Glu Glu Lys
            20                  25                  30

Ile Lys Ala Leu Thr Glu Ile Cys Thr Glu Met Glu Lys Glu Gly Lys
        35                  40                  45

Ile Ser Lys Ile Gly Pro Glu Asn Pro Tyr Asn Thr Pro Ile Phe Ala
    50                  55                  60

Ile Lys Lys Lys Asp Ser Thr Lys Trp Arg Lys Leu Val Asp Phe Arg
65                  70                  75                  80

Glu Leu Asn Lys Arg Thr Gln Asp Phe Trp Glu Val Gln Leu Gly Ile
                85                  90                  95

Pro His Pro Ala Gly Leu Lys Lys Lys Lys Ser Val Thr Val Leu Asp
            100                 105                 110

Val Gly Asp Ala Tyr Phe Ser Val Pro Leu Asp Glu Asp Phe Arg Lys
        115                 120                 125

Tyr Thr Ala Phe Thr Ile Pro Ser Ile Asn Asn Glu Thr Pro Gly Ile
    130                 135                 140

Arg Tyr Gln Tyr Asn Val Leu Pro Gln Gly Trp Lys Gly Ser Pro Ala
145                 150                 155                 160

Ile Phe Gln Ser Ser Met Thr Lys Ile Leu Glu Pro Phe Arg Thr Gln
                165                 170                 175

Asn Pro Glu Ile Val Ile Tyr Gln Tyr Met Asp Asp Leu Tyr Val Gly
            180                 185                 190

Ser Asp Leu Glu Ile Gly Gln His Arg Ala Lys Ile Glu Glu Leu Arg
        195                 200                 205

Glu His Leu Leu Arg Trp Gly Phe Thr Thr Pro Asp Lys Lys His Gln
    210                 215                 220
```

-continued

Lys Glu Pro Pro Phe Leu Trp Met Gly Tyr Glu Leu His Pro Asp Lys
225                 230                 235                 240

Trp Thr Val Gln Pro Ile Gln Leu Pro Glu Lys Asp Ser Trp Thr Val
            245                 250                 255

Asn Asp Ile Gln Lys Leu Val Gly Lys Leu Asn Trp Ala Ser Gln Ile
                260                 265                 270

Tyr Pro Gly Ile Lys Val Lys Gln Leu Cys Lys Leu Leu Arg Gly Ala
            275                 280                 285

Lys Ala Leu Thr Asp Ile Val Pro Leu Thr Glu Glu Ala Glu Leu Glu
    290                 295                 300

Leu Ala Glu Asn Arg Glu Ile Leu Lys Glu Pro Val His Gly Val Tyr
305                 310                 315                 320

Tyr Asp Pro Ser Lys Asp Leu Ile Ala Glu Ile Gln Lys Gln Gly Gln
            325                 330                 335

Asp Gln Trp Thr Tyr Gln Ile Tyr Gln Glu Pro Phe Lys Asn Leu Lys
            340                 345                 350

Thr Gly Lys Tyr Ala Lys Met Arg Ser Ala His Thr Asn Asp Val Lys
            355                 360                 365

Gln Leu Thr Glu Ala Val Gln Lys Ile Ala Thr Glu Ser Ile Val Ile
    370                 375                 380

Trp Gly Lys Thr Pro Lys Phe Arg Leu Pro Ile Gln Lys Glu Thr Trp
385                 390                 395                 400

Glu Thr Trp Trp Thr Glu Tyr Trp Gln Ala Thr Trp Ile Pro Glu Trp
                405                 410                 415

Glu Phe Val Asn Thr Pro Pro Leu Val Lys Leu Trp Tyr Gln Leu Glu
            420                 425                 430

Lys Glu Pro Ile Ala Gly Ala Glu Thr Phe Tyr Val Asp Gly Ala Ala
            435                 440                 445

Asn Arg Glu Thr Lys Leu Gly Lys Ala Gly Tyr Val Thr Asp Arg Gly
    450                 455                 460

Arg Gln Lys Val Val Ser Leu Thr Glu Thr Thr Asn Gln Lys Thr Glu
465                 470                 475                 480

Leu Gln Ala Ile His Leu Ala Leu Gln Asp Ser Gly Ser Glu Val Asn
                485                 490                 495

Ile Val Thr Asp Ser Gln Tyr Ala Leu Gly Ile Ile Gln Ala Gln Pro
            500                 505                 510

Asp Lys Ser Glu Ser Glu Leu Val Asn Gln Ile Ile Glu Gln Leu Ile
            515                 520                 525

Lys Lys Glu Lys Val Tyr Leu Ser Trp Val Pro Ala His Lys Gly Ile
    530                 535                 540

Gly Gly Asn Glu Gln Val Asp Lys Leu Val Ser Thr Gly Ile Arg Lys
545                 550                 555                 560

Val Leu Phe Leu Asp Gly Ile Asp Lys Ala Gln Glu Glu His Glu Lys
                565                 570                 575

Tyr His Ser Asn Trp Arg Ala Met Ala Ser Asp Phe Asn Leu Pro Pro
            580                 585                 590

Ile Val Ala Lys Glu Ile Val Ala Ser Cys Asp Lys Cys Gln Leu Lys
            595                 600                 605

Gly Glu Ala Met His Gly Gln Val Asp Cys Ser Pro Gly Ile Trp Gln
    610                 615                 620

Leu Ala Cys Thr His Leu Glu Gly Lys Ile Ile Leu Val Ala Val His
625                 630                 635                 640

Val Ala Ser Gly Tyr Ile Glu Ala Glu Val Ile Pro Ala Glu Thr Gly

-continued

```
                    645                 650                 655
Gln Glu Thr Ala Tyr Phe Ile Leu Lys Leu Ala Gly Arg Trp Pro Val
                660                 665                 670
Lys Val Ile His Thr Asp Asn Gly Ser Asn Phe Thr Ser Ala Ala Val
            675                 680                 685
Lys Ala Ala Cys Trp Trp Ala Gly Ile Gln Gln Glu Phe Gly Ile Pro
        690                 695                 700
Tyr Asn Pro Gln Ser Gln Gly Val Val Glu Ser Met Asn Lys Glu Leu
705                 710                 715                 720
Lys Lys Ile Ile Gly Gln Val Arg Asp Gln Ala Glu His Leu Lys Thr
                725                 730                 735
Ala Val Gln Met Ala Val Phe Ile His Asn Phe Lys Arg Lys Gly Gly
                740                 745                 750
Ile Gly Gly Tyr Ser Ala Gly Glu Arg Ile Ile Asp Ile Ile Ala Thr
            755                 760                 765
Asp Ile Gln Thr Lys Glu Leu Gln Lys Gln Ile Thr Lys Ile Gln Asn
        770                 775                 780
Phe Arg Val Tyr Tyr Arg Asp Ser Arg Asp Pro Ile Trp Lys Gly Pro
785                 790                 795                 800
Ala Lys Leu Leu Trp Lys Gly Glu Gly Ala Val Val Ile Gln Asp Asn
                805                 810                 815
Ser Asp Ile Lys Val Val Pro Arg Arg Lys Ala Lys Ile Ile Arg Asp
                820                 825                 830
Tyr Gly Lys Gln Met Ala Gly Asp Asp Cys Val Ala Gly Arg Gln Asp
            835                 840                 845
Glu Asp
    850

<210> SEQ ID NO 40
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
tctagagaat cgccaccat g                                              21

<210> SEQ ID NO 41
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
taatgaggat ccgctagc                                                 18

<210> SEQ ID NO 42
<211> LENGTH: 500
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Met Gly Ala Arg Ala Ser Val Leu Ser Gly Gly Glu Leu Asp Arg Trp
```

-continued

```
  1               5                   10                  15
Glu Lys Ile Arg Leu Arg Pro Gly Gly Lys Lys Tyr Lys Leu Lys
                 20                  25                  30

His Ile Val Trp Ala Ser Arg Glu Leu Glu Arg Phe Ala Val Asn Pro
                 35                  40                  45

Gly Leu Leu Glu Thr Ser Glu Gly Cys Arg Gln Ile Leu Gly Gln Leu
 50                  55                  60

Gln Pro Ser Leu Gln Thr Gly Ser Glu Glu Leu Arg Ser Leu Tyr Asn
 65                  70                  75                  80

Thr Val Ala Thr Leu Tyr Cys Val His Gln Arg Ile Glu Ile Lys Asp
                 85                  90                  95

Thr Lys Glu Ala Leu Asp Lys Ile Glu Glu Gln Asn Lys Ser Lys
                100                 105                 110

Lys Lys Ala Gln Gln Ala Ala Ala Asp Thr Gly His Ser Asn Gln Val
                115                 120                 125

Ser Gln Asn Tyr Pro Ile Val Gln Asn Ile Gln Gly Gln Met Val His
 130                 135                 140

Gln Ala Ile Ser Pro Arg Thr Leu Asn Ala Trp Val Lys Val Val Glu
145                 150                 155                 160

Glu Lys Ala Phe Ser Pro Glu Val Ile Pro Met Phe Ser Ala Leu Ser
                165                 170                 175

Glu Gly Ala Thr Pro Gln Asp Leu Asn Thr Met Leu Asn Thr Val Gly
                180                 185                 190

Gly His Gln Ala Ala Met Gln Met Leu Lys Glu Thr Ile Asn Glu Glu
                195                 200                 205

Ala Ala Glu Trp Asp Arg Val His Pro Val His Ala Gly Pro Ile Ala
210                 215                 220

Pro Gly Gln Met Arg Glu Pro Arg Gly Ser Asp Ile Ala Gly Thr Thr
225                 230                 235                 240

Ser Thr Leu Gln Glu Gln Ile Gly Trp Met Thr Asn Asn Pro Pro Ile
                245                 250                 255

Pro Val Gly Glu Ile Tyr Lys Arg Trp Ile Ile Leu Gly Leu Asn Lys
                260                 265                 270

Ile Val Arg Met Tyr Ser Pro Thr Ser Ile Leu Asp Ile Arg Gln Gly
                275                 280                 285

Pro Lys Glu Pro Phe Arg Asp Tyr Val Asp Arg Phe Tyr Lys Thr Leu
                290                 295                 300

Arg Ala Glu Gln Ala Ser Gln Glu Val Lys Asn Trp Met Thr Glu Thr
305                 310                 315                 320

Leu Leu Val Gln Asn Ala Asn Pro Asp Cys Lys Thr Ile Leu Lys Ala
                325                 330                 335

Leu Gly Pro Ala Ala Thr Leu Glu Glu Met Met Thr Ala Cys Gln Gly
                340                 345                 350

Val Gly Gly Pro Gly His Lys Ala Arg Val Leu Ala Glu Ala Met Ser
                355                 360                 365

Gln Val Thr Asn Ser Ala Thr Ile Met Met Gln Arg Gly Asn Phe Arg
                370                 375                 380

Asn Gln Arg Lys Ile Val Lys Cys Phe Asn Cys Gly Lys Glu Gly His
385                 390                 395                 400

Thr Ala Arg Asn Cys Arg Ala Pro Arg Lys Lys Gly Cys Trp Lys Cys
                405                 410                 415

Gly Lys Glu Gly His Gln Met Lys Asp Cys Thr Glu Arg Gln Ala Asn
                420                 425                 430
```

```
Phe Leu Gly Lys Ile Trp Pro Ser Tyr Lys Gly Arg Pro Gly Asn Phe
        435                 440                 445

Leu Gln Ser Arg Pro Glu Pro Thr Ala Pro Pro Glu Glu Ser Phe Arg
    450                 455                 460

Ser Gly Val Glu Thr Thr Thr Pro Pro Gln Lys Gln Glu Pro Ile Asp
465                 470                 475                 480

Lys Glu Leu Tyr Pro Leu Thr Ser Leu Arg Ser Leu Phe Gly Asn Asp
                485                 490                 495

Pro Ser Ser Gln
            500

<210> SEQ ID NO 43
<211> LENGTH: 500
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Met Gly Ala Arg Ala Ser Val Leu Ser Gly Gly Glu Leu Asp Arg Trp
1               5                   10                  15

Glu Lys Ile Arg Leu Arg Pro Gly Gly Lys Lys Tyr Lys Leu Lys
            20                  25                  30

His Ile Val Trp Ala Ser Arg Glu Leu Glu Arg Phe Ala Val Asn Pro
        35                  40                  45

Gly Leu Leu Glu Thr Ser Glu Gly Cys Arg Gln Ile Leu Gly Gln Leu
    50                  55                  60

Gln Pro Ser Leu Gln Thr Gly Ser Glu Glu Leu Arg Ser Leu Tyr Asn
65                  70                  75                  80

Thr Val Ala Thr Leu Tyr Cys Val His Gln Arg Ile Glu Ile Lys Asp
                85                  90                  95

Thr Lys Glu Ala Leu Asp Lys Ile Glu Glu Glu Gln Asn Lys Ser Lys
            100                 105                 110

Lys Lys Ala Gln Gln Ala Ala Ala Asp Thr Gly His Ser Asn Gln Val
        115                 120                 125

Ser Gln Asn Tyr Pro Ile Val Gln Asn Ile Gln Gly Gln Met Val His
    130                 135                 140

Gln Ala Ile Ser Pro Arg Thr Leu Asn Ala Trp Val Lys Val Val Glu
145                 150                 155                 160

Glu Lys Ala Phe Ser Pro Glu Val Ile Pro Met Phe Ser Ala Leu Ser
                165                 170                 175

Glu Gly Ala Thr Pro Gln Asp Leu Asn Thr Met Leu Asn Thr Val Gly
            180                 185                 190

Gly His Gln Ala Ala Met Gln Met Leu Lys Glu Thr Ile Asn Glu Glu
        195                 200                 205

Ala Ala Glu Trp Asp Arg Val His Pro Val His Ala Gly Pro Ile Ala
    210                 215                 220

Pro Gly Gln Met Arg Glu Pro Arg Gly Ser Asp Ile Ala Gly Thr Thr
225                 230                 235                 240

Ser Thr Leu Gln Glu Gln Ile Gly Trp Met Thr Asn Asn Pro Pro Ile
                245                 250                 255

Pro Val Gly Glu Ile Tyr Lys Arg Trp Ile Ile Leu Gly Leu Asn Lys
            260                 265                 270

Ile Val Arg Met Tyr Ser Pro Thr Ser Ile Leu Asp Ile Arg Gln Gly
```

```
            275                 280                 285
Pro Lys Glu Pro Phe Arg Asp Tyr Val Asp Arg Phe Tyr Lys Thr Leu
        290                 295                 300
Arg Ala Glu Gln Ala Ser Gln Glu Val Lys Asn Trp Met Thr Glu Thr
305                 310                 315                 320
Leu Leu Val Gln Asn Ala Asn Pro Asp Cys Lys Thr Ile Leu Lys Ala
                325                 330                 335
Leu Gly Pro Ala Ala Thr Leu Glu Glu Met Met Thr Ala Cys Gln Gly
            340                 345                 350
Val Gly Gly Pro Gly His Lys Ala Arg Val Leu Ala Glu Ala Met Ser
        355                 360                 365
Gln Val Thr Asn Ser Ala Thr Ile Met Met Gln Arg Gly Asn Phe Arg
    370                 375                 380
Asn Gln Arg Lys Ile Val Lys Cys Phe Asn Cys Gly Lys Glu Gly His
385                 390                 395                 400
Thr Ala Arg Asn Cys Arg Ala Pro Arg Lys Lys Gly Cys Trp Lys Cys
                405                 410                 415
Gly Lys Glu Gly His Gln Met Lys Asp Cys Thr Glu Arg Gln Ala Asn
            420                 425                 430
Phe Leu Gly Lys Ile Trp Pro Ser Tyr Lys Gly Arg Pro Gly Asn Phe
        435                 440                 445
Leu Gln Ser Arg Pro Glu Pro Thr Ala Pro Pro Glu Glu Ser Phe Arg
    450                 455                 460
Ser Gly Val Glu Thr Thr Thr Pro Pro Gln Lys Gln Glu Pro Ile Asp
465                 470                 475                 480
Lys Glu Leu Tyr Pro Leu Thr Ser Leu Arg Ser Leu Phe Gly Asn Asp
                485                 490                 495
Pro Ser Ser Gln
            500

<210> SEQ ID NO 44
<211> LENGTH: 16
<212> TYPE: PRT
<213> ORGANISM: Human immunodeficiency virus

<400> SEQUENCE: 44

Ile Val Gln Gln Gln Ser Asn Leu Leu Arg Ala Ile Glu Ala Gln Gln
1               5                   10                  15

<210> SEQ ID NO 45
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Val Val Gln Gln Gln Ser Asn Leu Leu Arg Ala Ile Glu Ala Gln
1               5                   10                  15

<210> SEQ ID NO 46
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46
```

Val Gln Gln Gln Asn Asn Leu Leu Arg Ala Ile Glu Ala Gln His
1               5                   10                  15

<210> SEQ ID NO 47
<211> LENGTH: 16
<212> TYPE: PRT
<213> ORGANISM: Human immunodeficiency virus

<400> SEQUENCE: 47

Ala Val Phe Ile His Asn Phe Lys Arg Lys Gly Gly Ile Gly Gly Tyr
1               5                   10                  15

<210> SEQ ID NO 48
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Ala Val Phe Ile His Asn Phe Lys Arg Lys Gly Gly Ile Gly Gly
1               5                   10                  15

<210> SEQ ID NO 49
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Val Leu Ile His Asn Phe Lys Arg Lys Gly Gly Ile Gly Gly Tyr
1               5                   10                  15

<210> SEQ ID NO 50
<211> LENGTH: 15
<212> TYPE: PRT
<213> ORGANISM: Human immunodeficiency virus

<400> SEQUENCE: 50

Met Ala Ile Cys Glu Glu Met Glu Lys Glu Gly Lys Ile Thr Lys
1               5                   10                  15

<210> SEQ ID NO 51
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Thr Ala Ile Cys Glu Glu Met Glu Lys Glu Gly Lys Ile Thr Lys
1               5                   10                  15

<210> SEQ ID NO 52
<211> LENGTH: 15
<212> TYPE: PRT
<213> ORGANISM: Human immunodeficiency virus

<400> SEQUENCE: 52

Cys Thr His Gly Ile Lys Pro Val Val Ser Thr Gln Leu Leu Leu
1               5                   10                  15

<210> SEQ ID NO 53
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 53

Cys Thr His Gly Ile Lys Pro Val Val Ser Thr Gln Leu Leu Leu
1               5                   10                  15

<210> SEQ ID NO 54
<211> LENGTH: 15
<212> TYPE: PRT
<213> ORGANISM: Human immunodeficiency virus

<400> SEQUENCE: 54

Gly Gly Pro Ser His Lys Ala Arg Val Leu Ala Glu Ala Met Ser
1               5                   10                  15

<210> SEQ ID NO 55
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 55

Gly Gly Pro Ser His Lys Ala Arg Val Leu Ala Glu Ala Met Gly
1               5                   10                  15

<210> SEQ ID NO 56
<211> LENGTH: 15
<212> TYPE: PRT
<213> ORGANISM: Human immunodeficiency virus

<400> SEQUENCE: 56

Ile Ile Gly Gln Val Arg Asp Gln Ala Glu His Leu Lys Thr Ala
1               5                   10                  15

<210> SEQ ID NO 57
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 57

Leu Ile Gly Gln Val Arg Asp Gln Ala Glu His Leu Lys Thr Ala
1               5                   10                  15

<210> SEQ ID NO 58
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 58

Ile Cys Thr Thr Thr Val Pro Trp Asn Ala Ser Trp Ser Asn Lys Ser
1               5                   10                  15

Leu

```
<210> SEQ ID NO 59
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Ile Cys Thr Thr Ala Val Pro Trp Asn Thr Ser Trp Ser Asn Lys Ser
1               5                   10                  15

Gln

<210> SEQ ID NO 60
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Ile Cys Thr Thr Thr Val Pro Trp Asn Ala Ser Trp Ser Asn Arg
1               5                   10                  15

<210> SEQ ID NO 61
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Cys Thr Thr Thr Val Pro Trp Asn Ser Ser Trp Ser Asn Lys Thr
1               5                   10                  15

<210> SEQ ID NO 62
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Thr Thr Ala Val Pro Trp Asn Ala Ser Trp Ser Asn Lys Ser Leu
1               5                   10                  15

<210> SEQ ID NO 63
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Thr Thr Ala Val Pro Trp Asn Thr Ser Trp Ser Asn Lys Ser Leu
1               5                   10                  15

<210> SEQ ID NO 64
<211> LENGTH: 21
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 64

Glu Gln Leu Ile Lys Lys Glu Arg Val Tyr Leu Ser Trp Val Pro Ala
1               5                   10                  15

His Lys Gly Ile Gly
            20

<210> SEQ ID NO 65
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Glu Gln Leu Ile Lys Lys Glu Lys Val Tyr Leu Ala Trp Val Pro Ala
1               5                   10                  15

His Lys Gly Ile Gly
            20

<210> SEQ ID NO 66
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Glu Glu Leu Ile Lys Lys Glu Lys Val Tyr Leu Ala Trp Val Pro
1               5                   10                  15

<210> SEQ ID NO 67
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Glu Pro Leu Ile Lys Lys Glu Lys Val Tyr Leu Ser Trp Val Pro
1               5                   10                  15

<210> SEQ ID NO 68
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Lys Leu Ile Glu Lys Asp Lys Val Tyr Leu Ser Trp Val Pro Ala
1               5                   10                  15

<210> SEQ ID NO 69
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 69

Leu Ile Lys Lys Glu Arg Val Tyr Leu Ser Trp Val Pro Ala His
1               5                   10                  15

<210> SEQ ID NO 70
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Glu Lys Val Tyr Leu Ala Trp Val Pro Ala His Lys Gly Ile Gly
1               5                   10                  15

<210> SEQ ID NO 71
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Glu Lys Val Tyr Leu Ser Trp Val Pro Ala His Lys Gly Ile Gly
1               5                   10                  15

<210> SEQ ID NO 72
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Cys Thr His Gly Ile Arg Pro Val Val Ser Thr Gln Leu Leu Leu
1               5                   10                  15

<210> SEQ ID NO 73
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Cys Thr His Gly Ile Lys Pro Val Val Ser Thr Gln Leu Leu Leu
1               5                   10                  15

<210> SEQ ID NO 74
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Cys Thr His Gly Ile Lys Pro Val Val Ser Thr Gln Leu Leu Leu
1               5                   10                  15

<210> SEQ ID NO 75
<211> LENGTH: 15
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 75

Cys Thr His Gly Ile Arg Pro Val Val Ser Thr Gln Leu Leu Leu
1               5                   10                  15

<210> SEQ ID NO 76
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Ile Cys Thr Thr Thr Val Pro Trp Asn Ala Ser Trp Ser Asn Lys Ser
1               5                   10                  15

Leu

<210> SEQ ID NO 77
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Ile Cys Thr Thr Ala Val Pro Trp Asn Thr Ser Trp Ser Asn Lys Ser
1               5                   10                  15

Gln

<210> SEQ ID NO 78
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Ile Cys Thr Thr Thr Val Pro Trp Asn Ala Ser Trp Ser Asn Arg
1               5                   10                  15

<210> SEQ ID NO 79
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Cys Thr Thr Thr Val Pro Trp Asn Ser Ser Trp Ser Asn Lys Thr
1               5                   10                  15

<210> SEQ ID NO 80
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 80

Thr Thr Ala Val Pro Trp Asn Ala Ser Trp Ser Asn Lys Ser Leu
1               5                   10                  15

<210> SEQ ID NO 81
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Thr Thr Ala Val Pro Trp Asn Thr Ser Trp Ser Asn Lys Ser Leu
1               5                   10                  15

<210> SEQ ID NO 82
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Ala Cys Gln Gly Val Gly Gly Pro Gly His Lys Ala Arg Val Leu Ala
1               5                   10                  15

Glu Ala Met Ser
            20

<210> SEQ ID NO 83
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Ala Cys Gln Gly Val Gly Gly Pro Ser His Lys Ala Arg Val Leu Ala
1               5                   10                  15

Glu Ala Met Ser
            20

<210> SEQ ID NO 84
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Ala Cys Gln Glu Val Gly Gly Pro Gly His Lys Ala Arg Val Leu
1               5                   10                  15

<210> SEQ ID NO 85
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Gly Gly Pro Ser His Lys Ala Arg Val Leu Ala Glu Ala Met Gly
```

<210> SEQ ID NO 86
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Ala Ala Glu Trp Asp Arg Val His Pro Val His Ala Gly Pro Ile Ala
1               5                   10                  15

Pro Gly Gln

<210> SEQ ID NO 87
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Ala Ala Glu Trp Asp Arg Leu His Pro Val His Ala Gly Pro Val Ala
1               5                   10                  15

Pro Gly Gln

<210> SEQ ID NO 88
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Ala Ala Glu Asp Arg Leu His Pro Val His Ala Gly Pro Ile Pro
1               5                   10                  15

<210> SEQ ID NO 89
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Ala Asp Trp Asp Arg Leu His Pro Val His Ala Gly Pro Val Ala
1               5                   10                  15

<210> SEQ ID NO 90
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Ala Glu Trp Asp Arg Leu His Pro Val His Ala Gly Pro Ile Ala
1               5                   10                  15

<210> SEQ ID NO 91
<211> LENGTH: 15

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Trp Asp Arg Val His Pro Val His Ala Gly Pro Asn Pro Pro Gly
1               5                   10                  15

<210> SEQ ID NO 92
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Asp Arg Val His Pro Val His Ala Gly Pro Ile Pro Pro Gly Gln
1               5                   10                  15

<210> SEQ ID NO 93
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

His Ser Asn Trp Arg Ala Met Ala Ser Asp Phe Asn Leu Pro Pro
1               5                   10                  15

<210> SEQ ID NO 94
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

His Ser Asn Trp Arg Ala Met Ala Ser Glu Phe Asn Leu Pro Pro
1               5                   10                  15

<210> SEQ ID NO 95
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

His Ser Asn Trp Arg Ala Met Ala Ser Asp Phe Asn Leu Pro Pro
1               5                   10                  15

<210> SEQ ID NO 96
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Lys Gly Arg Pro Gly Asn Phe Leu Gln Asn Arg Pro Glu Pro Thr
```

```
                 1               5                  10                 15

<210> SEQ ID NO 97
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Lys Gly Arg Pro Gly Asn Phe Leu Gln Ser Arg Pro Glu Pro Thr
1               5                  10                 15

<210> SEQ ID NO 98
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Lys Gly Arg Pro Gly Asn Phe Leu Gln Asn Arg Pro Glu Pro Thr
1               5                  10                 15

<210> SEQ ID NO 99
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Ser Arg Glu Leu Glu Arg Phe Ala Val Asn Pro Gly Leu Leu Glu
1               5                  10                 15

<210> SEQ ID NO 100
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Ser Arg Glu Leu Glu Arg Phe Ala Leu Asn Pro Gly Leu Leu Glu
1               5                  10                 15

<210> SEQ ID NO 101
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Ser Arg Glu Leu Glu Arg Phe Ala Leu Asn Pro Gly Leu Leu Glu
1               5                  10                 15

<210> SEQ ID NO 102
<211> LENGTH: 16
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 102

Arg Ser Leu Tyr Asn Thr Val Ala Thr Leu Tyr Cys Val His Gln Arg
1               5                   10                  15

<210> SEQ ID NO 103
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Arg Ser Leu Phe Asn Thr Val Ala Thr Leu Tyr Cys Val His Ala Glu
1               5                   10                  15

<210> SEQ ID NO 104
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Lys Ser Leu Phe Asn Thr Val Ala Thr Leu Tyr Cys Val His Ala
1               5                   10                  15

<210> SEQ ID NO 105
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Ser Leu Tyr Asn Thr Val Ala Thr Leu Tyr Cys Val His Gln Arg
1               5                   10                  15

<210> SEQ ID NO 106
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Tyr Val Thr Asp Arg Gly Arg Gln Lys Ile Val Ser Leu Thr Glu
1               5                   10                  15

<210> SEQ ID NO 107
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Tyr Val Thr Asp Arg Gly Arg Gln Lys Val Val Ser Leu Thr Asp
1               5                   10                  15

<210> SEQ ID NO 108

<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Tyr Val Thr Asp Arg Gly Arg Gln Lys Val Val Ser Leu Thr Glu
1               5                   10                  15

<210> SEQ ID NO 109
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Cys Thr Thr Thr Val Pro Trp Asn Ala Ser Trp Ser Asn Lys Ser
1               5                   10                  15

<210> SEQ ID NO 110
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Cys Thr Thr Ala Val Pro Trp Asn Thr Ser Trp Ser Asn Lys Ser
1               5                   10                  15

<210> SEQ ID NO 111
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Cys Thr Thr Asn Val Pro Trp Asn Ser Ser Trp Ser Asn Lys Ser
1               5                   10                  15

<210> SEQ ID NO 112
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Trp Trp Ala Gly Ile Gln Gln Glu Phe Gly Ile Pro Tyr Asn Pro
1               5                   10                  15

<210> SEQ ID NO 113
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

```
Trp Trp Ala Gly Ile Lys Gln Glu Phe Gly Ile Pro Tyr Asn Pro
1               5                   10                  15

<210> SEQ ID NO 114
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Trp Trp Ala Gly Ile Gln Gln Glu Phe Gly Ile Pro Tyr Asn Pro
1               5                   10                  15

<210> SEQ ID NO 115
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Gly Pro Gly His Lys Ala Arg Val Leu Ala Glu Ala Met Ser Gln
1               5                   10                  15

<210> SEQ ID NO 116
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Gly Pro Ser His Lys Ala Arg Val Leu Ala Glu Ala Met Ser Gln
1               5                   10                  15

<210> SEQ ID NO 117
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Gly Pro Gly His Lys Ala Arg Val Leu Ala Glu Ala Met Ser Gln
1               5                   10                  15

<210> SEQ ID NO 118
<211> LENGTH: 500
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 118

Met Gly Ala Arg Ala Ser Val Leu Ser Gly Gly Glu Leu Asp Arg Trp
1               5                   10                  15

Glu Lys Ile Arg Leu Arg Pro Gly Gly Lys Lys Tyr Lys Leu Lys
                20                  25                  30

His Ile Val Trp Ala Ser Arg Glu Leu Glu Arg Phe Ala Val Asn Pro
            35                  40                  45
```

Gly Leu Leu Glu Thr Ser Glu Gly Cys Arg Gln Ile Leu Gly Gln Leu
        50                  55                  60

Gln Pro Ser Leu Gln Thr Gly Ser Glu Glu Leu Arg Ser Leu Tyr Asn
 65                  70                  75                  80

Thr Val Ala Thr Leu Tyr Cys Val His Gln Arg Ile Glu Ile Lys Asp
                 85                  90                  95

Thr Lys Glu Ala Leu Asp Lys Ile Glu Glu Glu Gln Asn Lys Ser Lys
                100                 105                 110

Lys Lys Ala Gln Gln Ala Ala Ala Asp Thr Gly His Ser Asn Gln Val
            115                 120                 125

Ser Gln Asn Tyr Pro Ile Val Gln Asn Ile Gln Gly Gln Met Val His
130                 135                 140

Gln Ala Ile Ser Pro Arg Thr Leu Asn Ala Trp Val Lys Val Val Glu
145                 150                 155                 160

Glu Lys Ala Phe Ser Pro Glu Val Ile Pro Met Phe Ser Ala Leu Ser
                165                 170                 175

Glu Gly Ala Thr Pro Gln Asp Leu Asn Thr Met Leu Asn Thr Val Gly
            180                 185                 190

Gly His Gln Ala Ala Met Gln Met Leu Lys Glu Thr Ile Asn Glu Glu
        195                 200                 205

Ala Ala Glu Trp Asp Arg Val His Pro Val His Ala Gly Pro Ile Ala
210                 215                 220

Pro Gly Gln Met Arg Glu Pro Arg Gly Ser Asp Ile Ala Gly Thr Thr
225                 230                 235                 240

Ser Thr Leu Gln Glu Gln Ile Gly Trp Met Thr Asn Asn Pro Pro Ile
                245                 250                 255

Pro Val Gly Glu Ile Tyr Lys Arg Trp Ile Ile Leu Gly Leu Asn Lys
            260                 265                 270

Ile Val Arg Met Tyr Ser Pro Thr Ser Ile Leu Asp Ile Arg Gln Gly
        275                 280                 285

Pro Lys Glu Pro Phe Arg Asp Tyr Val Asp Arg Phe Tyr Lys Thr Leu
290                 295                 300

Arg Ala Glu Gln Ala Ser Gln Glu Val Lys Asn Trp Met Thr Glu Thr
305                 310                 315                 320

Leu Leu Val Gln Asn Ala Asn Pro Asp Cys Lys Thr Ile Leu Lys Ala
                325                 330                 335

Leu Gly Pro Ala Ala Thr Leu Glu Glu Met Met Thr Ala Cys Gln Gly
            340                 345                 350

Val Gly Gly Pro Gly His Lys Ala Arg Val Leu Ala Glu Ala Met Ser
        355                 360                 365

Gln Val Thr Asn Ser Ala Thr Ile Met Met Gln Arg Gly Asn Phe Arg
370                 375                 380

Asn Gln Arg Lys Ile Val Lys Cys Phe Asn Cys Gly Lys Glu Gly His
385                 390                 395                 400

Thr Ala Arg Asn Cys Arg Ala Pro Arg Lys Lys Gly Cys Trp Lys Cys
                405                 410                 415

Gly Lys Glu Gly His Gln Met Lys Asp Cys Thr Glu Arg Gln Ala Asn
            420                 425                 430

Phe Leu Gly Lys Ile Trp Pro Ser Tyr Lys Gly Arg Pro Gly Asn Phe
        435                 440                 445

Leu Gln Ser Arg Pro Glu Pro Thr Ala Pro Pro Glu Glu Ser Phe Arg
450                 455                 460

Ser Gly Val Glu Thr Thr Thr Pro Pro Gln Lys Gln Glu Pro Ile Asp

```
                465                 470                 475                 480
Lys Glu Leu Tyr Pro Leu Thr Ser Leu Arg Ser Leu Phe Gly Asn Asp
                    485                 490                 495

Pro Ser Ser Gln
            500

<210> SEQ ID NO 119
<211> LENGTH: 1003
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 119

Phe Phe Arg Glu Asp Leu Ala Phe Leu Gln Gly Lys Ala Arg Glu Phe
1               5                   10                  15

Ser Ser Glu Gln Thr Arg Ala Asn Ser Pro Thr Arg Arg Glu Leu Gln
            20                  25                  30

Val Trp Gly Arg Asp Asn Asn Ser Pro Ser Glu Ala Gly Ala Asp Arg
        35                  40                  45

Gln Gly Thr Val Ser Phe Asn Phe Pro Gln Val Thr Leu Trp Gln Arg
    50                  55                  60

Pro Leu Val Thr Ile Lys Ile Gly Gly Gln Leu Lys Glu Ala Leu Leu
65                  70                  75                  80

Asp Thr Gly Ala Asp Asp Thr Val Leu Glu Glu Met Ser Leu Pro Gly
                85                  90                  95

Arg Trp Lys Pro Lys Met Ile Gly Ile Gly Gly Phe Ile Lys Val
            100                 105                 110

Arg Gln Tyr Asp Gln Ile Leu Ile Glu Ile Cys Gly His Lys Ala Ile
        115                 120                 125

Gly Thr Val Leu Val Gly Pro Thr Pro Val Asn Ile Ile Gly Arg Asn
    130                 135                 140

Leu Leu Thr Gln Ile Gly Cys Thr Leu Asn Phe Pro Ile Ser Pro Ile
145                 150                 155                 160

Glu Thr Val Pro Val Lys Leu Lys Pro Gly Met Asp Gly Pro Lys Val
                165                 170                 175

Lys Gln Trp Pro Leu Thr Glu Glu Lys Ile Lys Ala Leu Val Glu Ile
            180                 185                 190

Cys Thr Glu Met Glu Lys Glu Gly Lys Ile Ser Lys Ile Gly Pro Glu
        195                 200                 205

Asn Pro Tyr Asn Thr Pro Val Phe Ala Ile Lys Lys Lys Asp Ser Thr
    210                 215                 220

Lys Trp Arg Lys Leu Val Asp Phe Arg Glu Leu Asn Lys Arg Thr Gln
225                 230                 235                 240

Asp Phe Trp Glu Val Gln Leu Gly Ile Pro His Pro Ala Gly Leu Lys
                245                 250                 255

Lys Lys Lys Ser Val Thr Val Leu Asp Val Gly Asp Ala Tyr Phe Ser
            260                 265                 270

Val Pro Leu Asp Glu Asp Phe Arg Lys Tyr Thr Ala Phe Thr Ile Pro
        275                 280                 285

Ser Ile Asn Asn Glu Thr Pro Gly Ile Arg Tyr Gln Tyr Asn Val Leu
    290                 295                 300

Pro Gln Gly Trp Lys Gly Ser Pro Ala Ile Phe Gln Ser Ser Met Thr
305                 310                 315                 320
```

```
Lys Ile Leu Glu Pro Phe Arg Lys Gln Asn Pro Asp Ile Val Ile Tyr
                325                 330                 335
Gln Tyr Met Asp Asp Leu Tyr Val Gly Ser Asp Leu Glu Ile Gly Gln
            340                 345                 350
His Arg Thr Lys Ile Glu Glu Leu Arg Gln His Leu Leu Arg Trp Gly
        355                 360                 365
Leu Thr Thr Pro Asp Lys Lys His Gln Lys Glu Pro Pro Phe Leu Trp
    370                 375                 380
Met Gly Tyr Glu Leu His Pro Asp Lys Trp Thr Val Gln Pro Ile Val
385                 390                 395                 400
Leu Pro Glu Lys Asp Ser Trp Thr Val Asn Asp Ile Gln Lys Leu Val
                405                 410                 415
Gly Lys Leu Asn Trp Ala Ser Gln Ile Tyr Pro Gly Ile Lys Val Arg
            420                 425                 430
Gln Leu Cys Lys Leu Leu Arg Gly Thr Lys Ala Leu Thr Glu Val Ile
        435                 440                 445
Pro Leu Thr Glu Glu Ala Glu Leu Glu Leu Ala Glu Asn Arg Glu Ile
    450                 455                 460
Leu Lys Glu Pro Val His Gly Val Tyr Tyr Asp Pro Ser Lys Asp Leu
465                 470                 475                 480
Ile Ala Glu Ile Gln Lys Gln Gly Gln Gly Gln Trp Thr Tyr Gln Ile
                485                 490                 495
Tyr Gln Glu Pro Phe Lys Asn Leu Lys Thr Gly Lys Tyr Ala Arg Met
            500                 505                 510
Arg Gly Ala His Thr Asn Asp Val Lys Gln Leu Thr Glu Ala Val Gln
        515                 520                 525
Lys Ile Thr Thr Glu Ser Ile Val Ile Trp Gly Lys Thr Pro Lys Phe
    530                 535                 540
Lys Leu Pro Ile Gln Lys Glu Thr Trp Glu Thr Trp Trp Thr Glu Tyr
545                 550                 555                 560
Trp Gln Ala Thr Trp Ile Pro Glu Trp Glu Phe Val Asn Thr Pro Pro
                565                 570                 575
Leu Val Lys Leu Trp Tyr Gln Leu Glu Lys Glu Pro Ile Val Gly Ala
            580                 585                 590
Glu Thr Phe Tyr Val Asp Gly Ala Ala Asn Arg Glu Thr Lys Leu Gly
        595                 600                 605
Lys Ala Gly Tyr Val Thr Asn Arg Gly Arg Gln Lys Val Val Thr Leu
    610                 615                 620
Thr Asp Thr Thr Asn Gln Lys Thr Glu Leu Gln Ala Ile Tyr Leu Ala
625                 630                 635                 640
Leu Gln Asp Ser Gly Leu Glu Val Asn Ile Val Thr Asp Ser Gln Tyr
                645                 650                 655
Ala Leu Gly Ile Ile Gln Ala Gln Pro Asp Gln Ser Glu Ser Glu Leu
            660                 665                 670
Val Asn Gln Ile Ile Glu Gln Leu Ile Lys Lys Glu Lys Val Tyr Leu
        675                 680                 685
Ala Trp Val Pro Ala His Lys Gly Ile Gly Gly Asn Glu Gln Val Asp
    690                 695                 700
Lys Leu Val Ser Ala Gly Ile Arg Lys Val Leu Phe Leu Asp Gly Ile
705                 710                 715                 720
Asp Lys Ala Gln Asp Glu His Glu Lys Tyr His Ser Asn Trp Arg Ala
                725                 730                 735
Met Ala Ser Asp Phe Asn Leu Pro Pro Val Val Ala Lys Glu Ile Val
```

```
            740                 745                 750
Ala Ser Cys Asp Lys Cys Gln Leu Lys Gly Glu Ala Met His Gly Gln
        755                 760                 765

Val Asp Cys Ser Pro Gly Ile Trp Gln Leu Asp Cys Thr His Leu Glu
    770                 775                 780

Gly Lys Val Ile Leu Val Ala Val His Val Ala Ser Gly Tyr Ile Glu
785                 790                 795                 800

Ala Glu Val Ile Pro Ala Glu Thr Gly Gln Glu Thr Ala Tyr Phe Leu
                805                 810                 815

Leu Lys Leu Ala Gly Arg Trp Pro Val Lys Thr Ile His Thr Asp Asn
            820                 825                 830

Gly Ser Asn Phe Thr Gly Ala Thr Val Arg Ala Ala Cys Trp Trp Ala
        835                 840                 845

Gly Ile Lys Gln Glu Phe Gly Ile Pro Tyr Asn Pro Gln Ser Gln Gly
    850                 855                 860

Val Val Glu Ser Met Asn Lys Glu Leu Lys Lys Ile Ile Gly Gln Val
865                 870                 875                 880

Arg Asp Gln Ala Glu His Leu Lys Thr Ala Val Gln Met Ala Val Phe
                885                 890                 895

Ile His Asn Phe Lys Arg Lys Gly Gly Ile Gly Gly Tyr Ser Ala Gly
            900                 905                 910

Glu Arg Ile Val Asp Ile Ile Ala Thr Asp Ile Gln Thr Lys Glu Leu
        915                 920                 925

Gln Lys Gln Ile Thr Lys Ile Gln Asn Phe Arg Val Tyr Tyr Arg Asp
    930                 935                 940

Ser Arg Asn Pro Leu Trp Lys Gly Pro Ala Lys Leu Leu Trp Lys Gly
945                 950                 955                 960

Glu Gly Ala Val Val Ile Gln Asp Asn Ser Asp Ile Lys Val Val Pro
                965                 970                 975

Arg Arg Lys Ala Lys Ile Ile Arg Asp Tyr Gly Lys Gln Met Ala Gly
            980                 985                 990

Asp Asp Cys Val Ala Ser Arg Gln Asp Glu Asp
        995                 1000

<210> SEQ ID NO 120
<211> LENGTH: 856
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 120

Met Arg Val Lys Glu Lys Tyr Gln His Leu Trp Arg Trp Gly Trp Arg
1               5                   10                  15

Trp Gly Thr Met Leu Leu Gly Met Leu Met Ile Cys Ser Ala Thr Glu
            20                  25                  30

Lys Leu Trp Val Thr Val Tyr Tyr Gly Val Pro Val Trp Lys Glu Ala
        35                  40                  45

Thr Thr Thr Leu Phe Cys Ala Ser Asp Ala Lys Ala Tyr Asp Thr Glu
    50                  55                  60

Val His Asn Val Trp Ala Thr His Ala Cys Val Pro Thr Asp Pro Asn
65                  70                  75                  80

Pro Gln Glu Val Val Leu Val Asn Val Thr Glu Asn Phe Asn Met Trp
                85                  90                  95
```

```
Lys Asn Asp Met Val Glu Gln Met His Glu Asp Ile Ile Ser Leu Trp
                100                 105                 110

Asp Gln Ser Leu Lys Pro Cys Val Lys Leu Thr Pro Leu Cys Val Ser
            115                 120                 125

Leu Lys Cys Thr Asp Leu Lys Asn Asp Thr Asn Thr Asn Ser Ser Ser
130                 135                 140

Gly Arg Met Ile Met Glu Lys Gly Glu Ile Lys Asn Cys Ser Phe Asn
145                 150                 155                 160

Ile Ser Thr Ser Ile Arg Gly Lys Val Gln Lys Glu Tyr Ala Phe Phe
                165                 170                 175

Tyr Lys Leu Asp Ile Ile Pro Ile Asp Asn Asp Thr Thr Ser Tyr Lys
            180                 185                 190

Leu Thr Ser Cys Asn Thr Ser Val Ile Thr Gln Ala Cys Pro Lys Val
        195                 200                 205

Ser Phe Glu Pro Ile Pro Ile His Tyr Cys Ala Pro Ala Gly Phe Ala
    210                 215                 220

Ile Leu Lys Cys Asn Asn Lys Thr Phe Asn Gly Thr Gly Pro Cys Thr
225                 230                 235                 240

Asn Val Ser Thr Val Gln Cys Thr His Gly Ile Arg Pro Val Val Ser
                245                 250                 255

Thr Gln Leu Leu Leu Asn Gly Ser Leu Ala Glu Glu Val Val Ile
            260                 265                 270

Arg Ser Val Asn Phe Thr Asp Asn Ala Lys Thr Ile Ile Val Gln Leu
        275                 280                 285

Asn Thr Ser Val Glu Ile Asn Cys Thr Arg Pro Asn Asn Asn Thr Arg
    290                 295                 300

Lys Arg Ile Arg Ile Gln Arg Gly Pro Gly Arg Ala Phe Val Thr Ile
305                 310                 315                 320

Gly Lys Ile Gly Asn Met Arg Gln Ala His Cys Asn Ile Ser Arg Ala
                325                 330                 335

Lys Trp Asn Asn Thr Leu Lys Gln Ile Ala Ser Lys Leu Arg Glu Gln
            340                 345                 350

Phe Gly Asn Asn Lys Thr Ile Ile Phe Lys Gln Ser Ser Gly Gly Asp
        355                 360                 365

Pro Glu Ile Val Thr His Ser Phe Asn Cys Gly Gly Glu Phe Phe Tyr
    370                 375                 380

Cys Asn Ser Thr Gln Leu Phe Asn Ser Thr Trp Phe Asn Ser Thr Trp
385                 390                 395                 400

Ser Thr Glu Gly Ser Asn Asn Thr Glu Gly Ser Asp Thr Ile Thr Leu
                405                 410                 415

Pro Cys Arg Ile Lys Gln Ile Ile Asn Met Trp Gln Lys Val Gly Lys
            420                 425                 430

Ala Met Tyr Ala Pro Pro Ile Ser Gly Gln Ile Arg Cys Ser Ser Asn
        435                 440                 445

Ile Thr Gly Leu Leu Leu Thr Arg Asp Gly Gly Asn Ser Asn Asn Glu
    450                 455                 460

Ser Glu Ile Phe Arg Pro Gly Gly Gly Asp Met Arg Asp Asn Trp Arg
465                 470                 475                 480

Ser Glu Leu Tyr Lys Tyr Lys Val Val Lys Ile Glu Pro Leu Gly Val
                485                 490                 495

Ala Pro Thr Lys Ala Lys Arg Arg Val Val Gln Arg Glu Lys Arg Ala
            500                 505                 510

Val Gly Ile Gly Ala Leu Phe Leu Gly Phe Leu Gly Ala Ala Gly Ser
```

```
                515                 520                 525
Thr Met Gly Ala Ala Ser Met Thr Leu Thr Val Gln Ala Arg Gln Leu
    530                 535                 540
Leu Ser Gly Ile Val Gln Gln Asn Asn Leu Leu Arg Ala Ile Glu
545                 550                 555                 560
Ala Gln Gln His Leu Leu Gln Leu Thr Val Trp Gly Ile Lys Gln Leu
                565                 570                 575
Gln Ala Arg Ile Leu Ala Val Glu Arg Tyr Leu Lys Asp Gln Gln Leu
            580                 585                 590
Leu Gly Ile Trp Gly Cys Ser Gly Lys Leu Ile Cys Thr Thr Ala Val
                595                 600                 605
Pro Trp Asn Ala Ser Trp Ser Asn Lys Ser Leu Glu Gln Ile Trp Asn
    610                 615                 620
His Thr Thr Trp Met Glu Trp Asp Arg Glu Ile Asn Asn Tyr Thr Ser
625                 630                 635                 640
Leu Ile His Ser Leu Ile Glu Glu Ser Gln Asn Gln Gln Glu Lys Asn
                645                 650                 655
Glu Gln Glu Leu Leu Glu Leu Asp Lys Trp Ala Ser Leu Trp Asn Trp
            660                 665                 670
Phe Asn Ile Thr Asn Trp Leu Trp Tyr Ile Lys Leu Phe Ile Met Ile
                675                 680                 685
Val Gly Gly Leu Val Gly Leu Arg Ile Val Phe Ala Val Leu Ser Ile
    690                 695                 700
Val Asn Arg Val Arg Gln Gly Tyr Ser Pro Leu Ser Phe Gln Thr His
705                 710                 715                 720
Leu Pro Thr Pro Arg Gly Pro Asp Arg Pro Glu Gly Ile Glu Glu Glu
                725                 730                 735
Gly Gly Glu Arg Asp Arg Asp Arg Ser Ile Arg Leu Val Asn Gly Ser
            740                 745                 750
Leu Ala Leu Ile Trp Asp Asp Leu Arg Ser Leu Cys Leu Phe Ser Tyr
                755                 760                 765
His Arg Leu Arg Asp Leu Leu Leu Ile Val Thr Arg Ile Val Glu Leu
    770                 775                 780
Leu Gly Arg Arg Gly Trp Glu Ala Leu Lys Tyr Trp Trp Asn Leu Leu
785                 790                 795                 800
Gln Tyr Trp Ser Gln Glu Leu Lys Asn Ser Ala Val Ser Leu Leu Asn
                805                 810                 815
Ala Thr Ala Ile Ala Val Ala Glu Gly Thr Asp Arg Val Ile Glu Val
            820                 825                 830
Val Gln Gly Ala Cys Arg Ala Ile Arg His Ile Pro Arg Arg Ile Arg
                835                 840                 845
Gln Gly Leu Glu Arg Ile Leu Leu
    850                 855

<210> SEQ ID NO 121
<211> LENGTH: 500
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 121

Met Gly Ala Arg Ala Ser Val Leu Ser Gly Gly Glu Leu Asp Arg Trp
1               5                   10                  15
```

-continued

```
Glu Lys Ile Arg Leu Arg Pro Gly Gly Lys Lys Tyr Lys Leu Lys
             20                  25                  30
His Ile Val Trp Ala Ser Arg Glu Leu Glu Arg Phe Ala Val Asn Pro
         35                  40                  45
Gly Leu Leu Glu Thr Ser Glu Gly Cys Arg Gln Ile Leu Gly Gln Leu
 50                  55                  60
Gln Pro Ser Leu Gln Thr Gly Ser Glu Glu Leu Arg Ser Leu Tyr Asn
 65                  70                  75                  80
Thr Val Ala Thr Leu Tyr Cys Val His Gln Arg Ile Glu Ile Lys Asp
                 85                  90                  95
Thr Lys Glu Ala Leu Asp Lys Ile Glu Glu Gln Asn Lys Ser Lys
            100                 105                 110
Lys Lys Ala Gln Gln Ala Ala Ala Asp Thr Gly His Ser Asn Gln Val
            115                 120                 125
Ser Gln Asn Tyr Pro Ile Val Gln Asn Ile Gln Gly Gln Met Val His
130                 135                 140
Gln Ala Ile Ser Pro Arg Thr Leu Asn Ala Trp Val Lys Val Val Glu
145                 150                 155                 160
Glu Lys Ala Phe Ser Pro Glu Val Ile Pro Met Phe Ser Ala Leu Ser
                165                 170                 175
Glu Gly Ala Thr Pro Gln Asp Leu Asn Thr Met Leu Asn Thr Val Gly
            180                 185                 190
Gly His Gln Ala Ala Met Gln Met Leu Lys Glu Thr Ile Asn Glu Glu
            195                 200                 205
Ala Ala Glu Trp Asp Arg Val His Pro Val His Ala Gly Pro Ile Ala
210                 215                 220
Pro Gly Gln Met Arg Glu Pro Arg Gly Ser Asp Ile Ala Gly Thr Thr
225                 230                 235                 240
Ser Thr Leu Gln Glu Gln Ile Gly Trp Met Thr Asn Asn Pro Pro Ile
                245                 250                 255
Pro Val Gly Glu Ile Tyr Lys Arg Trp Ile Ile Leu Gly Leu Asn Lys
            260                 265                 270
Ile Val Arg Met Tyr Ser Pro Thr Ser Ile Leu Asp Ile Arg Gln Gly
            275                 280                 285
Pro Lys Glu Pro Phe Arg Asp Tyr Val Asp Arg Phe Tyr Lys Thr Leu
290                 295                 300
Arg Ala Glu Gln Ala Ser Gln Glu Val Lys Asn Trp Met Thr Glu Thr
305                 310                 315                 320
Leu Leu Val Gln Asn Ala Asn Pro Asp Cys Lys Thr Ile Leu Lys Ala
                325                 330                 335
Leu Gly Pro Ala Ala Thr Leu Glu Glu Met Met Thr Ala Cys Gln Gly
            340                 345                 350
Val Gly Gly Pro Gly His Lys Ala Arg Val Leu Ala Glu Ala Met Ser
            355                 360                 365
Gln Val Thr Asn Ser Ala Thr Ile Met Met Gln Arg Gly Asn Phe Arg
370                 375                 380
Asn Gln Arg Lys Ile Val Lys Cys Phe Asn Cys Gly Lys Glu Gly His
385                 390                 395                 400
Thr Ala Arg Asn Cys Arg Ala Pro Arg Lys Lys Gly Cys Trp Lys Cys
                405                 410                 415
Gly Lys Glu Gly His Gln Met Lys Asp Cys Thr Glu Arg Gln Ala Asn
            420                 425                 430
Phe Leu Gly Lys Ile Trp Pro Ser Tyr Lys Gly Arg Pro Gly Asn Phe
```

-continued

```
                 435                 440                 445

Leu Gln Ser Arg Pro Glu Pro Thr Ala Pro Pro Glu Glu Ser Phe Arg
    450                 455                 460

Ser Gly Val Glu Thr Thr Thr Pro Pro Gln Lys Gln Glu Pro Ile Asp
465                 470                 475                 480

Lys Glu Leu Tyr Pro Leu Thr Ser Leu Arg Ser Leu Phe Gly Asn Asp
                485                 490                 495

Pro Ser Ser Gln
            500

<210> SEQ ID NO 122
<211> LENGTH: 1003
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 122

Phe Phe Arg Glu Asp Leu Ala Phe Leu Gln Gly Lys Ala Arg Glu Phe
1               5                   10                  15

Ser Ser Glu Gln Thr Arg Ala Asn Ser Pro Thr Arg Arg Glu Leu Gln
                20                  25                  30

Val Trp Gly Arg Asp Asn Asn Ser Pro Ser Glu Ala Gly Ala Asp Arg
            35                  40                  45

Gln Gly Thr Val Ser Phe Asn Phe Pro Gln Val Thr Leu Trp Gln Arg
        50                  55                  60

Pro Leu Val Thr Ile Lys Ile Gly Gly Gln Leu Lys Glu Ala Leu Leu
65                  70                  75                  80

Asp Thr Gly Ala Asp Asp Thr Val Leu Glu Glu Met Ser Leu Pro Gly
                85                  90                  95

Arg Trp Lys Pro Lys Met Ile Gly Gly Ile Gly Gly Phe Ile Lys Val
                100                 105                 110

Arg Gln Tyr Asp Gln Ile Leu Ile Glu Ile Cys Gly His Lys Ala Ile
            115                 120                 125

Gly Thr Val Leu Val Gly Pro Thr Pro Val Asn Ile Ile Gly Arg Asn
        130                 135                 140

Leu Leu Thr Gln Ile Gly Cys Thr Leu Asn Phe Pro Ile Ser Pro Ile
145                 150                 155                 160

Glu Thr Val Pro Val Lys Leu Lys Pro Gly Met Asp Gly Pro Lys Val
                165                 170                 175

Lys Gln Trp Pro Leu Thr Glu Glu Lys Ile Lys Ala Leu Val Glu Ile
            180                 185                 190

Cys Thr Glu Met Glu Lys Glu Gly Lys Ile Ser Lys Ile Gly Pro Glu
        195                 200                 205

Asn Pro Tyr Asn Thr Pro Val Phe Ala Ile Lys Lys Lys Asp Ser Thr
    210                 215                 220

Lys Trp Arg Lys Leu Val Asp Phe Arg Glu Leu Asn Lys Arg Thr Gln
225                 230                 235                 240

Asp Phe Trp Glu Val Gln Leu Gly Ile Pro His Pro Ala Gly Leu Lys
                245                 250                 255

Lys Lys Lys Ser Val Thr Val Leu Asp Val Gly Asp Ala Tyr Phe Ser
            260                 265                 270

Val Pro Leu Asp Glu Asp Phe Arg Lys Tyr Thr Ala Phe Thr Ile Pro
        275                 280                 285
```

```
Ser Ile Asn Asn Glu Thr Pro Gly Ile Arg Tyr Gln Tyr Asn Val Leu
    290                 295                 300

Pro Gln Gly Trp Lys Gly Ser Pro Ala Ile Phe Gln Ser Ser Met Thr
305                 310                 315                 320

Lys Ile Leu Glu Pro Phe Arg Lys Gln Asn Pro Asp Ile Val Ile Tyr
                325                 330                 335

Gln Tyr Met Asp Asp Leu Tyr Val Gly Ser Asp Leu Glu Ile Gly Gln
            340                 345                 350

His Arg Thr Lys Ile Glu Glu Leu Arg Gln His Leu Leu Arg Trp Gly
        355                 360                 365

Leu Thr Thr Pro Asp Lys Lys His Gln Lys Glu Pro Pro Phe Leu Trp
370                 375                 380

Met Gly Tyr Glu Leu His Pro Asp Lys Trp Thr Val Gln Pro Ile Val
385                 390                 395                 400

Leu Pro Glu Lys Asp Ser Trp Thr Val Asn Asp Ile Gln Lys Leu Val
                405                 410                 415

Gly Lys Leu Asn Trp Ala Ser Gln Ile Tyr Pro Gly Ile Lys Val Arg
            420                 425                 430

Gln Leu Cys Lys Leu Leu Arg Gly Thr Lys Ala Leu Thr Glu Val Ile
        435                 440                 445

Pro Leu Thr Glu Glu Ala Glu Leu Glu Leu Ala Glu Asn Arg Glu Ile
450                 455                 460

Leu Lys Glu Pro Val His Gly Val Tyr Tyr Asp Pro Ser Lys Asp Leu
465                 470                 475                 480

Ile Ala Glu Ile Gln Lys Gln Gly Gln Gly Gln Trp Thr Tyr Gln Ile
                485                 490                 495

Tyr Gln Glu Pro Phe Lys Asn Leu Lys Thr Gly Lys Tyr Ala Arg Met
            500                 505                 510

Arg Gly Ala His Thr Asn Asp Val Lys Gln Leu Thr Glu Ala Val Gln
        515                 520                 525

Lys Ile Thr Thr Glu Ser Ile Val Ile Trp Gly Lys Thr Pro Lys Phe
530                 535                 540

Lys Leu Pro Ile Gln Lys Glu Thr Trp Glu Thr Trp Trp Thr Glu Tyr
545                 550                 555                 560

Trp Gln Ala Thr Trp Ile Pro Glu Trp Glu Phe Val Asn Thr Pro Pro
                565                 570                 575

Leu Val Lys Leu Trp Tyr Gln Leu Glu Lys Glu Pro Ile Val Gly Ala
            580                 585                 590

Glu Thr Phe Tyr Val Asp Gly Ala Ala Asn Arg Glu Thr Lys Leu Gly
        595                 600                 605

Lys Ala Gly Tyr Val Thr Asn Arg Gly Arg Gln Lys Val Val Thr Leu
610                 615                 620

Thr Asp Thr Thr Asn Gln Lys Thr Glu Leu Gln Ala Ile Tyr Leu Ala
625                 630                 635                 640

Leu Gln Asp Ser Gly Leu Glu Val Asn Ile Val Thr Asp Ser Gln Tyr
                645                 650                 655

Ala Leu Gly Ile Ile Gln Ala Gln Pro Asp Gln Ser Glu Ser Glu Leu
            660                 665                 670

Val Asn Gln Ile Ile Glu Gln Leu Ile Lys Lys Glu Lys Val Tyr Leu
        675                 680                 685

Ala Trp Val Pro Ala His Lys Gly Ile Gly Gly Asn Glu Gln Val Asp
690                 695                 700

Lys Leu Val Ser Ala Gly Ile Arg Lys Val Leu Phe Leu Asp Gly Ile
```

```
                705                 710                 715                 720
Asp Lys Ala Gln Asp Glu His Glu Lys Tyr His Ser Asn Trp Arg Ala
            725                 730                 735

Met Ala Ser Asp Phe Asn Leu Pro Pro Val Ala Lys Glu Ile Val
        740                 745                 750

Ala Ser Cys Asp Lys Cys Gln Leu Lys Gly Glu Ala Met His Gly Gln
            755                 760                 765

Val Asp Cys Ser Pro Gly Ile Trp Gln Leu Asp Cys Thr His Leu Glu
    770                 775                 780

Gly Lys Val Ile Leu Val Ala Val His Val Ala Ser Gly Tyr Ile Glu
785                 790                 795                 800

Ala Glu Val Ile Pro Ala Glu Thr Gly Gln Glu Thr Ala Tyr Phe Leu
                805                 810                 815

Leu Lys Leu Ala Gly Arg Trp Pro Val Lys Thr Ile His Thr Asp Asn
            820                 825                 830

Gly Ser Asn Phe Thr Gly Ala Thr Val Arg Ala Ala Cys Trp Trp Ala
        835                 840                 845

Gly Ile Lys Gln Glu Phe Gly Ile Pro Tyr Asn Pro Gln Ser Gln Gly
    850                 855                 860

Val Val Glu Ser Met Asn Lys Glu Leu Lys Lys Ile Ile Gly Gln Val
865                 870                 875                 880

Arg Asp Gln Ala Glu His Leu Lys Thr Ala Val Gln Met Ala Val Phe
                885                 890                 895

Ile His Asn Phe Lys Arg Lys Gly Gly Ile Gly Gly Tyr Ser Ala Gly
            900                 905                 910

Glu Arg Ile Val Asp Ile Ile Ala Thr Asp Ile Gln Thr Lys Glu Leu
        915                 920                 925

Gln Lys Gln Ile Thr Lys Ile Gln Asn Phe Arg Val Tyr Tyr Arg Asp
    930                 935                 940

Ser Arg Asn Pro Leu Trp Lys Gly Pro Ala Lys Leu Leu Trp Lys Gly
945                 950                 955                 960

Glu Gly Ala Val Val Ile Gln Asp Asn Ser Asp Ile Lys Val Val Pro
                965                 970                 975

Arg Arg Lys Ala Lys Ile Ile Arg Asp Tyr Gly Lys Gln Met Ala Gly
            980                 985                 990

Asp Asp Cys Val Ala Ser Arg Gln  Asp Glu Asp
        995                 1000

<210> SEQ ID NO 123
<211> LENGTH: 856
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 123

Met Arg Val Lys Glu Lys Tyr Gln His Leu Trp Arg Trp Gly Trp Arg
1               5                   10                  15

Trp Gly Thr Met Leu Leu Gly Met Leu Met Ile Cys Ser Ala Thr Glu
            20                  25                  30

Lys Leu Trp Val Thr Val Tyr Tyr Gly Val Pro Val Trp Lys Glu Ala
        35                  40                  45

Thr Thr Thr Leu Phe Cys Ala Ser Asp Ala Lys Ala Tyr Asp Thr Glu
    50                  55                  60
```

```
Val His Asn Val Trp Ala Thr His Ala Cys Val Pro Thr Asp Pro Asn
 65                  70                  75                  80

Pro Gln Glu Val Val Leu Val Asn Val Thr Glu Asn Phe Asn Met Trp
                 85                  90                  95

Lys Asn Asp Met Val Glu Gln Met His Glu Asp Ile Ile Ser Leu Trp
            100                 105                 110

Asp Gln Ser Leu Lys Pro Cys Val Lys Leu Thr Pro Leu Cys Val Ser
        115                 120                 125

Leu Lys Cys Thr Asp Leu Lys Asn Asp Thr Asn Thr Asn Ser Ser Ser
130                 135                 140

Gly Arg Met Ile Met Glu Lys Gly Glu Ile Lys Asn Cys Ser Phe Asn
145                 150                 155                 160

Ile Ser Thr Ser Ile Arg Gly Lys Val Gln Lys Glu Tyr Ala Phe Phe
                165                 170                 175

Tyr Lys Leu Asp Ile Ile Pro Ile Asp Asn Asp Thr Thr Ser Tyr Lys
            180                 185                 190

Leu Thr Ser Cys Asn Thr Ser Val Ile Thr Gln Ala Cys Pro Lys Val
        195                 200                 205

Ser Phe Glu Pro Ile Pro Ile His Tyr Cys Ala Pro Ala Gly Phe Ala
210                 215                 220

Ile Leu Lys Cys Asn Asn Lys Thr Phe Asn Gly Thr Gly Pro Cys Thr
225                 230                 235                 240

Asn Val Ser Thr Val Gln Cys Thr His Gly Ile Arg Pro Val Val Ser
                245                 250                 255

Thr Gln Leu Leu Leu Asn Gly Ser Leu Ala Glu Glu Val Val Ile
            260                 265                 270

Arg Ser Val Asn Phe Thr Asp Asn Ala Lys Thr Ile Ile Val Gln Leu
        275                 280                 285

Asn Thr Ser Val Glu Ile Asn Cys Thr Arg Pro Asn Asn Asn Thr Arg
290                 295                 300

Lys Arg Ile Arg Ile Gln Arg Gly Pro Gly Arg Ala Phe Val Thr Ile
305                 310                 315                 320

Gly Lys Ile Gly Asn Met Arg Gln Ala His Cys Asn Ile Ser Arg Ala
                325                 330                 335

Lys Trp Asn Asn Thr Leu Lys Gln Ile Ala Ser Lys Leu Arg Glu Gln
            340                 345                 350

Phe Gly Asn Asn Lys Thr Ile Ile Phe Lys Gln Ser Ser Gly Gly Asp
        355                 360                 365

Pro Glu Ile Val Thr His Ser Phe Asn Cys Gly Gly Glu Phe Phe Tyr
370                 375                 380

Cys Asn Ser Thr Gln Leu Phe Asn Ser Thr Trp Phe Asn Ser Thr Trp
385                 390                 395                 400

Ser Thr Glu Gly Ser Asn Asn Thr Glu Gly Ser Asp Thr Ile Thr Leu
                405                 410                 415

Pro Cys Arg Ile Lys Gln Ile Ile Asn Met Trp Gln Lys Val Gly Lys
            420                 425                 430

Ala Met Tyr Ala Pro Pro Ile Ser Gly Gln Ile Arg Cys Ser Ser Asn
        435                 440                 445

Ile Thr Gly Leu Leu Leu Thr Arg Asp Gly Gly Ser Asn Asn Glu
450                 455                 460

Ser Glu Ile Phe Arg Pro Gly Gly Gly Asp Met Arg Asp Asn Trp Arg
465                 470                 475                 480

Ser Glu Leu Tyr Lys Tyr Lys Val Val Lys Ile Glu Pro Leu Gly Val
```

```
                    485                 490                 495
Ala Pro Thr Lys Ala Lys Arg Val Val Gln Arg Glu Lys Arg Ala
                500                 505                 510

Val Gly Ile Gly Ala Leu Phe Leu Gly Phe Leu Gly Ala Ala Gly Ser
            515                 520                 525

Thr Met Gly Ala Ala Ser Met Thr Leu Thr Val Gln Ala Arg Gln Leu
        530                 535                 540

Leu Ser Gly Ile Val Gln Gln Gln Asn Asn Leu Leu Arg Ala Ile Glu
545                 550                 555                 560

Ala Gln Gln His Leu Leu Gln Leu Thr Val Trp Gly Ile Lys Gln Leu
                565                 570                 575

Gln Ala Arg Ile Leu Ala Val Glu Arg Tyr Leu Lys Asp Gln Gln Leu
                580                 585                 590

Leu Gly Ile Trp Gly Cys Ser Gly Lys Leu Ile Cys Thr Thr Ala Val
                595                 600                 605

Pro Trp Asn Ala Ser Trp Ser Asn Lys Ser Leu Glu Gln Ile Trp Asn
                610                 615                 620

His Thr Thr Trp Met Glu Trp Asp Arg Glu Ile Asn Asn Tyr Thr Ser
625                 630                 635                 640

Leu Ile His Ser Leu Ile Glu Glu Ser Gln Asn Gln Gln Glu Lys Asn
                645                 650                 655

Glu Gln Glu Leu Leu Glu Leu Asp Lys Trp Ala Ser Leu Trp Asn Trp
                660                 665                 670

Phe Asn Ile Thr Asn Trp Leu Trp Tyr Ile Lys Leu Phe Ile Met Ile
                675                 680                 685

Val Gly Gly Leu Val Gly Leu Arg Ile Val Phe Ala Val Leu Ser Ile
                690                 695                 700

Val Asn Arg Val Arg Gln Gly Tyr Ser Pro Leu Ser Phe Gln Thr His
705                 710                 715                 720

Leu Pro Thr Pro Arg Gly Pro Asp Arg Pro Glu Gly Ile Glu Glu Glu
                725                 730                 735

Gly Gly Glu Arg Asp Arg Asp Arg Ser Ile Arg Leu Val Asn Gly Ser
                740                 745                 750

Leu Ala Leu Ile Trp Asp Asp Leu Arg Ser Leu Cys Leu Phe Ser Tyr
                755                 760                 765

His Arg Leu Arg Asp Leu Leu Leu Ile Val Thr Arg Ile Val Glu Leu
                770                 775                 780

Leu Gly Arg Arg Gly Trp Glu Ala Leu Lys Tyr Trp Trp Asn Leu Leu
785                 790                 795                 800

Gln Tyr Trp Ser Gln Glu Leu Lys Asn Ser Ala Val Ser Leu Leu Asn
                805                 810                 815

Ala Thr Ala Ile Ala Val Ala Glu Gly Thr Asp Arg Val Ile Glu Val
                820                 825                 830

Val Gln Gly Ala Cys Arg Ala Ile Arg His Ile Pro Arg Arg Ile Arg
                835                 840                 845

Gln Gly Leu Glu Arg Ile Leu Leu
                850                 855

<210> SEQ ID NO 124
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 124

Ala Ala Glu Trp Asp Arg Leu His Pro Val His Ala Gly Pro Ile Ala
1               5                   10                  15

<210> SEQ ID NO 125
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Ala Ala Glu Trp Asp Arg Leu His Pro Val His Ala Gly Pro Ile Ala
1               5                   10                  15

<210> SEQ ID NO 126
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Ala Ala Glu Asp Arg Leu His Pro Val His Ala Gly Pro Ile Pro
1               5                   10                  15

<210> SEQ ID NO 127
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Asp Gln Met His Glu Asp Ile Ile Ser Leu Trp Asp Gln Ser Leu Lys
1               5                   10                  15

<210> SEQ ID NO 128
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Glu Gln Met His Glu Asp Ile Ile Ser Leu Trp Asp Gln Ser Leu Lys
1               5                   10                  15

<210> SEQ ID NO 129
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Glu Gln Met His Glu Asp Ile Ile Ser Leu Trp Asp Gln Ser Leu
1               5                   10                  15

<210> SEQ ID NO 130
<211> LENGTH: 15

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

His Met His Glu Asp Ile Ile Ser Leu Trp Asp Glu Ser Leu Lys
1               5                   10                  15

<210> SEQ ID NO 131
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Lys Leu Asn Trp Ala Ser Gln Ile Tyr Ser Gly Ile Lys Val Arg
1               5                   10                  15

<210> SEQ ID NO 132
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Lys Leu Asn Trp Ala Ser Gln Ile Tyr Pro Gly Ile Lys Val Arg
1               5                   10                  15

<210> SEQ ID NO 133
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Lys Leu Asn Trp Ala Ser Gln Ile Tyr Ala Gly Ile Lys Val Lys
1               5                   10                  15

<210> SEQ ID NO 134
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Lys His Leu Val Trp Ala Ser Arg Glu Leu Glu Arg Phe Ala Leu
1               5                   10                  15

<210> SEQ ID NO 135
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Lys His Ile Val Trp Ala Ser Arg Glu Leu Glu Arg Phe Ala Val
```

```
1               5                   10                  15

<210> SEQ ID NO 136
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Lys His Leu Val Trp Ala Ser Arg Glu Leu Glu Arg Phe Ala Leu
1               5                   10                  15

<210> SEQ ID NO 137
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Leu Gln Glu Gln Ile Ala Trp Met Thr Asn Asn Pro Pro Val Pro
1               5                   10                  15

<210> SEQ ID NO 138
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Leu Gln Glu Gln Ile Gly Trp Met Thr Asn Asn Pro Pro Ile Pro
1               5                   10                  15

<210> SEQ ID NO 139
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Leu Ala Glu Gln Ile Ala Trp Met Thr Ser Asn Pro Pro Ile Pro
1               5                   10                  15

<210> SEQ ID NO 140
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Gln Met His Glu Asp Ile Ile Ser Leu Trp Asp Gln Ser Leu Lys
1               5                   10                  15

<210> SEQ ID NO 141
<211> LENGTH: 15
<212> TYPE: PRT
<213> ORGANISM: Artificial Sequence
<220> FEATURE:
<223> OTHER INFORMATION: Description of Artificial Sequence: Synthetic
```

-continued

```
      peptide

<400> SEQUENCE: 141

Gln Met His Glu Asp Ile Ile Ser Leu Trp Asp Gln Ser Leu Lys
1               5                   10                  15

<210> SEQ ID NO 142
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

His Met His Glu Asp Ile Ile Ser Leu Trp Asp Glu Ser Leu Lys
1               5                   10                  15

<210> SEQ ID NO 143
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Asp Ile Trp Asp Asn Met Thr Trp Met Gln Trp Asp Arg Glu Ile
1               5                   10                  15

<210> SEQ ID NO 144
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Glu Ile Trp Asp Asn Met Thr Trp Met Glu Trp Glu Arg Glu Ile
1               5                   10                  15

<210> SEQ ID NO 145
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Glu Ile Trp Asn Asn Met Thr Trp Met Glu Trp Glu Lys Glu Ile
1               5                   10                  15

<210> SEQ ID NO 146
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Trp Pro Val Lys Val Ile His Thr Ala Asn Gly Ser Asn Phe Thr
1               5                   10                  15

<210> SEQ ID NO 147
```

```
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Trp Pro Val Lys Thr Ile His Thr Ala Asn Gly Ser Asn Phe Thr
1               5                   10                  15

<210> SEQ ID NO 148
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Trp Pro Val Lys Val Val His Thr Asp Asn Gly Ser Asn Phe Thr
1               5                   10                  15

<210> SEQ ID NO 149
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Ala Gln Thr Gly Thr Glu Glu Leu Arg Ser Leu Tyr Asn Thr Val
1               5                   10                  15

<210> SEQ ID NO 150
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Leu Gln Thr Gly Ser Glu Glu Leu Arg Ser Leu Tyr Asn Thr Val
1               5                   10                  15

<210> SEQ ID NO 151
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Leu Gln Thr Gly Ser Glu Glu Leu Lys Ser Leu Phe Asn Thr Val
1               5                   10                  15

<210> SEQ ID NO 152
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152
```

```
Tyr Phe Asn Met Trp Lys Asn Asp Met Val Asp Gln Met His Glu
1               5                   10                  15
```

<210> SEQ ID NO 153
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

```
Asn Phe Asn Met Trp Lys Asn Asn Met Val Glu Gln Met His Glu
1               5                   10                  15
```

<210> SEQ ID NO 154
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

```
Asn Phe Asn Met Trp Lys Asn Asn Met Val Glu Gln Met His Glu
1               5                   10                  15
```

<210> SEQ ID NO 155
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

```
Gly Arg Pro Gly Asn Phe Leu Gln Ser Arg Pro Glu Pro Thr
1               5                   10
```

<210> SEQ ID NO 156
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

```
Gly Arg Pro Gly Asn Phe Leu Gln Ser Arg Pro Glu Pro Thr
1               5                   10
```

<210> SEQ ID NO 157
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

```
Gly Arg Pro Gly Asn Phe Leu Gln Asn Arg Pro Glu Pro Thr
1               5                   10
```

<210> SEQ ID NO 158
<211> LENGTH: 13
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 158

His Ala Gly Pro Ile Ala Pro Gly Gln Met Arg Glu Pro
1               5                   10

<210> SEQ ID NO 159
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Pro Val His Ala Gly Pro Ile Ala Pro Gly Gln Met Arg Glu Pro
1               5                   10                  15

<210> SEQ ID NO 160
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Pro Val Gln Ala Gly Pro Ile Ala Pro Gly Gln Met Arg Glu Pro
1               5                   10                  15

<210> SEQ ID NO 161
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Val Gln Gln Gln Ser Asn Leu Leu Arg Ala Ile Glu Ala Gln Gln
1               5                   10                  15

<210> SEQ ID NO 162
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Val Gln Gln Gln Asn Asn Leu Leu Arg Ala Ile Glu Ala Gln Gln
1               5                   10                  15

<210> SEQ ID NO 163
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Val Gln Gln Gln Asn Asn Leu Leu Arg Ala Ile Glu Ala Gln His
1               5                   10                  15

```
<210> SEQ ID NO 164
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Leu Leu Glu Glu Ser Gln Asn Gln Gln Glu Lys Asn Glu Lys Asp
1               5                   10                  15

<210> SEQ ID NO 165
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

Leu Ile Glu Glu Ser Gln Asn Gln Gln Glu Lys Asn Glu Gln Glu
1               5                   10                  15

<210> SEQ ID NO 166
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Leu Ile Glu Glu Ser Gln Asn Gln Gln Glu Lys Asn Glu Gln Asp
1               5                   10                  15

<210> SEQ ID NO 167
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

Asp Arg Leu His Pro Val His Ala Gly Pro Ile Ala Pro Gly Gln
1               5                   10                  15

<210> SEQ ID NO 168
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

Asp Arg Leu His Pro Val His Ala Gly Pro Ile Ala Pro Gly Gln
1               5                   10                  15

<210> SEQ ID NO 169
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169
```

```
Asp Arg Val His Pro Val His Ala Gly Pro Ile Pro Pro Gly Gln
1               5                   10                  15

<210> SEQ ID NO 170
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

Gly Asp Ile Ile Gly Asp Ile Arg Gln Ala His Cys Asn Ile Ser
1               5                   10                  15

<210> SEQ ID NO 171
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

Gly Glu Ile Ile Gly Asp Ile Arg Gln Ala His Cys Asn Ile Ser
1               5                   10                  15

<210> SEQ ID NO 172
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Gly Asp Ile Ile Gly Asp Ile Arg Gln Ala His Cys Asn Ile Ser
1               5                   10                  15

<210> SEQ ID NO 173
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

Thr Gly Met Leu Arg Asn Cys Gln Pro Trp Trp Ile Trp Gly Ile
1               5                   10                  15

<210> SEQ ID NO 174
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Lys Gly Ile Arg Lys Asn Tyr Gln His Leu Trp Arg Trp Gly Thr
1               5                   10                  15

<210> SEQ ID NO 175
<211> LENGTH: 15
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 175

Lys Glu Ile Arg Lys Asn Tyr Gln His Leu Trp Arg Trp Gly Thr
1               5                   10                  15

<210> SEQ ID NO 176
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

Met Thr Lys Ile Leu Glu Pro Phe Arg Ala Lys Asn Pro Glu Ile
1               5                   10                  15

<210> SEQ ID NO 177
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 177

Met Thr Lys Ile Leu Glu Pro Phe Arg Lys Gln Asn Pro Asp Ile
1               5                   10                  15

<210> SEQ ID NO 178
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

Met Thr Lys Ile Leu Glu Pro Phe Arg Lys Gln Asn Pro Asp Ile
1               5                   10                  15

<210> SEQ ID NO 179
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

Arg Ala Met Ala Ser Glu Phe Asn Leu Pro Pro Val Val Ala Lys
1               5                   10                  15

<210> SEQ ID NO 180
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 180

Arg Ala Met Ala Ser Asp Phe Asn Leu Pro Pro Val Val Ala Lys
1               5                   10                  15
```

<210> SEQ ID NO 181
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 181

Lys Ala Met Ala Ser Asp Phe Asn Leu Pro Pro Ile Val Ala Lys
1               5                   10                  15

<210> SEQ ID NO 182
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

Ala Ala Glu Trp Asp Arg Leu His Pro Val His Ala Gly Pro Ile Ala
1               5                   10                  15

Pro Gly Gln

<210> SEQ ID NO 183
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

Ala Ala Glu Trp Asp Arg Leu His Pro Val His Ala Gly Pro Ile Ala
1               5                   10                  15

Pro Gly Gln

<210> SEQ ID NO 184
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

Ala Ala Glu Asp Arg Leu His Pro Val His Ala Gly Pro Ile Pro
1               5                   10                  15

<210> SEQ ID NO 185
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185

Ala Glu Trp Asp Arg Leu His Pro Val His Ala Gly Pro Ile Ala
1               5                   10                  15

<210> SEQ ID NO 186
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186

Asp Arg Val His Pro Val His Ala Gly Pro Ile Pro Pro Gly Gln
1               5                   10                  15

<210> SEQ ID NO 187
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 187

Gln Leu Ile Asn Lys Glu Arg Val Tyr Leu Ser Trp Val Pro Ala His
1               5                   10                  15

Lys Gly Ile Gly
            20

<210> SEQ ID NO 188
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 188

Gln Leu Ile Lys Lys Glu Lys Val Tyr Leu Ala Trp Val Pro Ala His
1               5                   10                  15

Lys Gly Ile Gly
            20

<210> SEQ ID NO 189
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 189

Lys Leu Ile Glu Lys Asp Lys Val Tyr Leu Ser Trp Val Pro Ala
1               5                   10                  15

<210> SEQ ID NO 190
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190

Leu Ile Lys Lys Glu Arg Val Tyr Leu Ser Trp Val Pro Ala His
1               5                   10                  15

<210> SEQ ID NO 191
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 191

Glu Lys Val Tyr Leu Ser Trp Val Pro Ala His Lys Gly Ile Gly
1               5                   10                  15

<210> SEQ ID NO 192
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192

Ser Leu Tyr Asn Thr Val Ala Thr Leu Tyr Cys Val His Ala Gly
1               5                   10                  15

<210> SEQ ID NO 193
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 193

Ser Leu Tyr Asn Thr Val Ala Thr Leu Tyr Cys Val His Gln Lys
1               5                   10                  15

<210> SEQ ID NO 194
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194

Ser Leu Tyr Asn Thr Val Ala Thr Leu Tyr Cys Val His Gln Arg
1               5                   10                  15

<210> SEQ ID NO 195
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 195

His Gln Ala Ala Met Gln Met Leu Lys Asp Thr Ile Asn Glu Glu
1               5                   10                  15

<210> SEQ ID NO 196
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 196

His Gln Ala Ala Met Gln Met Leu Lys Glu Thr Ile Asn Glu Glu
1               5                   10                  15

<210> SEQ ID NO 197
<211> LENGTH: 15

-continued

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 197

His Gln Ala Ala Met Gln Met Leu Lys Asp Thr Ile Asn Glu Glu
1               5                   10                  15

<210> SEQ ID NO 198
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 198

His Gln Ala Ala Met Gln Met Leu Lys Glu Thr Ile Asn Glu Glu
1               5                   10                  15

<210> SEQ ID NO 199
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 199

Ala Val Phe Ile His Asn Phe Lys Arg Lys Gly Gly Ile Gly Gly
1               5                   10                  15

<210> SEQ ID NO 200
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 200

Ala Val Phe Ile His Asn Phe Lys Arg Lys Gly Gly Ile Gly Gly
1               5                   10                  15

<210> SEQ ID NO 201
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 201

Ala Val Phe Ile His Asn Phe Lys Arg Lys Gly Gly Ile Gly Gly
1               5                   10                  15

<210> SEQ ID NO 202
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 202

Tyr Phe Asn Met Trp Lys Asn Asp Met Val Asp Gln Met His Glu
```

```
<210> SEQ ID NO 203
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 203

Asn Phe Asn Met Trp Lys Asn Asn Met Val Glu Gln Met His Glu
1               5                   10                  15

<210> SEQ ID NO 204
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 204

Asn Phe Asn Met Trp Lys Asn Asn Met Val Glu Gln Met His Glu
1               5                   10                  15

<210> SEQ ID NO 205
<211> LENGTH: 22
<212> TYPE: PRT
<213> ORGANISM: Artificial Sequence
<220> FEATURE:
<223> OTHER INFORMATION: Description of Artificial Sequence: Synthetic
      consensus sequence

<400> SEQUENCE: 205

Glu Gln Ala Thr Gln Asp Val Lys Asn Trp Met Thr Asp Thr Leu Leu
1               5                   10                  15

Val Gln Asn Ala Asn Pro
            20

<210> SEQ ID NO 206
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 206

Glu Gln Ser Thr Gln Glu Val Lys Asn Trp Met Thr Asp Thr Leu
1               5                   10                  15

<210> SEQ ID NO 207
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 207

Thr Gln Asp Val Lys Asn Trp Met Thr Asp Thr Leu Leu Ile Gln
1               5                   10                  15

<210> SEQ ID NO 208
<211> LENGTH: 15
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 208

Lys Asn Trp Met Thr Asp Thr Leu Leu Val Gln Asn Ala Asn Pro
1               5                   10                  15

<210> SEQ ID NO 209
<211> LENGTH: 16
<212> TYPE: PRT
<213> ORGANISM: Artificial Sequence
<220> FEATURE:
<223> OTHER INFORMATION: Description of Artificial Sequence: Synthetic
      consensus sequence

<400> SEQUENCE: 209

Ile Val Gln Gln Gln Ser Asn Leu Leu Arg Ala Ile Glu Ala Gln Gln
1               5                   10                  15

<210> SEQ ID NO 210
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 210

Val Val Gln Gln Gln Ser Asn Leu Leu Arg Ala Ile Glu Ala Gln
1               5                   10                  15

<210> SEQ ID NO 211
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 211

Val Gln Gln Gln Asn Asn Leu Leu Arg Ala Ile Glu Ala Gln His
1               5                   10                  15

<210> SEQ ID NO 212
<211> LENGTH: 16
<212> TYPE: PRT
<213> ORGANISM: Artificial Sequence
<220> FEATURE:
<223> OTHER INFORMATION: Description of Artificial Sequence: Synthetic
      consensus sequence

<400> SEQUENCE: 212

Ala Val Phe Ile His Asn Phe Lys Arg Lys Gly Gly Ile Gly Gly Tyr
1               5                   10                  15

<210> SEQ ID NO 213
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 213

Ala Val Phe Ile His Asn Phe Lys Arg Lys Gly Gly Ile Gly Gly
1               5                   10                  15
```

<210> SEQ ID NO 214
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 214

Val Leu Ile His Asn Phe Lys Arg Lys Gly Gly Ile Gly Gly Tyr
1               5                   10                  15

<210> SEQ ID NO 215
<211> LENGTH: 15
<212> TYPE: PRT
<213> ORGANISM: Artificial Sequence
<220> FEATURE:
<223> OTHER INFORMATION: Description of Artificial Sequence: Synthetic
      consensus sequence

<400> SEQUENCE: 215

Ser Glu Leu Tyr Lys Tyr Lys Val Val Lys Ile Glu Pro Leu Gly
1               5                   10                  15

<210> SEQ ID NO 216
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 216

Ser Glu Leu Tyr Lys Tyr Lys Val Val Lys Ile Glu Pro Leu Gly
1               5                   10                  15

<210> SEQ ID NO 217
<211> LENGTH: 15
<212> TYPE: PRT
<213> ORGANISM: Artificial Sequence
<220> FEATURE:
<223> OTHER INFORMATION: Description of Artificial Sequence: Synthetic
      consensus sequence

<400> SEQUENCE: 217

Asn Phe Asn Met Trp Lys Asn Asn Met Val Glu Gln Met His Glu
1               5                   10                  15

<210> SEQ ID NO 218
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 218

Asn Phe Asn Met Trp Lys Asn Asn Met Val Glu Gln Met His Glu
1               5                   10                  15

<210> SEQ ID NO 219
<211> LENGTH: 15
<212> TYPE: PRT
<213> ORGANISM: Artificial Sequence
<220> FEATURE:
<223> OTHER INFORMATION: Description of Artificial Sequence: Synthetic
      consensus sequence

```
<400> SEQUENCE: 219

Gly Lys Lys Lys Tyr Arg Leu Lys His Leu Val Trp Ala Ser Arg
1               5                   10                  15

<210> SEQ ID NO 220
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 220

Gly Arg Lys Lys Tyr Arg Leu Lys His Ile Val Trp Ala Ser Arg
1               5                   10                  15

<210> SEQ ID NO 221
<211> LENGTH: 15
<212> TYPE: PRT
<213> ORGANISM: Artificial Sequence
<220> FEATURE:
<223> OTHER INFORMATION: Description of Artificial Sequence: Synthetic
      consensus sequence

<400> SEQUENCE: 221

Asp Ile Lys Val Val Pro Arg Arg Lys Ala Lys Ile Ile Arg Asp
1               5                   10                  15

<210> SEQ ID NO 222
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 222

Asp Ile Lys Val Val Pro Arg Arg Lys Val Lys Ile Ile Arg Asp
1               5                   10                  15

<210> SEQ ID NO 223
<211> LENGTH: 20
<212> TYPE: PRT
<213> ORGANISM: Artificial Sequence
<220> FEATURE:
<223> OTHER INFORMATION: Description of Artificial Sequence: Synthetic
      consensus sequence

<400> SEQUENCE: 223

Lys His Leu Val Trp Ala Ser Arg Glu Leu Glu Arg Phe Ala Leu Asn
1               5                   10                  15

Pro Gly Leu Leu
            20

<210> SEQ ID NO 224
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 224

Lys His Leu Val Trp Ala Ser Arg Glu Leu Glu Arg Phe Ala Leu
1               5                   10                  15
```

<210> SEQ ID NO 225
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 225

Ala Ser Arg Glu Leu Glu Arg Phe Ala Val Asn Pro Gly Leu Leu
1               5                   10                  15

<210> SEQ ID NO 226
<211> LENGTH: 16
<212> TYPE: PRT
<213> ORGANISM: Artificial Sequence
<220> FEATURE:
<223> OTHER INFORMATION: Description of Artificial Sequence: Synthetic
      consensus sequence

<400> SEQUENCE: 226

Ile Val Gln Gln Gln Ser Asn Leu Leu Arg Ala Ile Glu Ala Gln Gln
1               5                   10                  15

<210> SEQ ID NO 227
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 227

Val Val Gln Gln Gln Ser Asn Leu Leu Arg Ala Ile Glu Ala Gln
1               5                   10                  15

<210> SEQ ID NO 228
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 228

Val Gln Gln Gln Asn Asn Leu Leu Arg Ala Ile Glu Ala Gln His
1               5                   10                  15

<210> SEQ ID NO 229
<211> LENGTH: 16
<212> TYPE: PRT
<213> ORGANISM: Artificial Sequence
<220> FEATURE:
<223> OTHER INFORMATION: Description of Artificial Sequence: Synthetic
      consensus sequence

<400> SEQUENCE: 229

Ala Val Phe Ile His Asn Phe Lys Arg Lys Gly Gly Ile Gly Gly Tyr
1               5                   10                  15

<210> SEQ ID NO 230
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 230

Ala Val Phe Ile His Asn Phe Lys Arg Lys Gly Gly Ile Gly Gly
1               5                   10                  15

<210> SEQ ID NO 231
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 231

Val Leu Ile His Asn Phe Lys Arg Lys Gly Gly Ile Gly Gly Tyr
1               5                   10                  15

<210> SEQ ID NO 232
<211> LENGTH: 15
<212> TYPE: PRT
<213> ORGANISM: Artificial Sequence
<220> FEATURE:
<223> OTHER INFORMATION: Description of Artificial Sequence: Synthetic
      consensus sequence

<400> SEQUENCE: 232

Lys Asn Trp Met Thr Asp Thr Leu Leu Val Gln Asn Ala Asn Pro
1               5                   10                  15

<210> SEQ ID NO 233
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 233

Lys Asn Trp Met Thr Asp Thr Leu Leu Val Gln Asn Ala Asn Pro
1               5                   10                  15

<210> SEQ ID NO 234
<211> LENGTH: 15
<212> TYPE: PRT
<213> ORGANISM: Artificial Sequence
<220> FEATURE:
<223> OTHER INFORMATION: Description of Artificial Sequence: Synthetic
      consensus sequence

<400> SEQUENCE: 234

Trp Lys Gly Ser Pro Ala Ile Phe Gln Ser Ser Met Thr Lys Ile
1               5                   10                  15

<210> SEQ ID NO 235
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 235

Trp Lys Gly Ser Pro Ala Ile Phe Gln Ala Ser Met Thr Lys Ile
1               5                   10                  15

<210> SEQ ID NO 236
<211> LENGTH: 15
<212> TYPE: PRT
```

```
<213> ORGANISM: Artificial Sequence
<220> FEATURE:
<223> OTHER INFORMATION: Description of Artificial Sequence: Synthetic
      consensus sequence

<400> SEQUENCE: 236

Gln Pro Ala Leu Gln Thr Gly Ser Glu Glu Leu Arg Ser Leu Tyr
1               5                   10                  15

<210> SEQ ID NO 237
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 237

Leu Pro Ala Leu Lys Thr Gly Ser Glu Glu Leu Arg Ser Leu Tyr
1               5                   10                  15

<210> SEQ ID NO 238
<211> LENGTH: 15
<212> TYPE: PRT
<213> ORGANISM: Artificial Sequence
<220> FEATURE:
<223> OTHER INFORMATION: Description of Artificial Sequence: Synthetic
      consensus sequence

<400> SEQUENCE: 238

Ile Val Gln Gln Gln Ser Asn Leu Leu Arg Ala Ile Glu Ala Gln
1               5                   10                  15

<210> SEQ ID NO 239
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 239

Val Val Gln Gln Gln Ser Asn Leu Leu Arg Ala Ile Glu Ala Gln
1               5                   10                  15

<210> SEQ ID NO 240
<211> LENGTH: 15
<212> TYPE: PRT
<213> ORGANISM: Artificial Sequence
<220> FEATURE:
<223> OTHER INFORMATION: Description of Artificial Sequence: Synthetic
      consensus sequence

<400> SEQUENCE: 240

Cys Ser Gly Lys Leu Ile Cys Thr Thr Thr Val Pro Trp Asn Ser
1               5                   10                  15

<210> SEQ ID NO 241
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 241

Cys Ser Gly Lys Leu Ile Cys Thr Thr Ala Val Pro Trp Asn Ser
1               5                   10                  15
```

```
<210> SEQ ID NO 242
<211> LENGTH: 15
<212> TYPE: PRT
<213> ORGANISM: Artificial Sequence
<220> FEATURE:
<223> OTHER INFORMATION: Description of Artificial Sequence: Synthetic
      consensus sequence

<400> SEQUENCE: 242

Ala Lys Ala Tyr Asp Thr Glu Val His Asn Val Trp Ala Thr His
1               5                   10                  15

<210> SEQ ID NO 243
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 243

Ala Lys Ala Tyr Glu Lys Glu Val His Asn Val Trp Ala Thr His
1               5                   10                  15

<210> SEQ ID NO 244
<211> LENGTH: 15
<212> TYPE: PRT
<213> ORGANISM: Artificial Sequence
<220> FEATURE:
<223> OTHER INFORMATION: Description of Artificial Sequence: Synthetic
      consensus sequence

<400> SEQUENCE: 244

Lys Lys Asp Ser Thr Lys Trp Arg Lys Leu Val Asp Phe Arg Glu
1               5                   10                  15

<210> SEQ ID NO 245
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 245

Lys Lys Asp Ser Thr Lys Trp Arg Lys Leu Val Asp Phe Arg Glu
1               5                   10                  15

<210> SEQ ID NO 246
<211> LENGTH: 15
<212> TYPE: PRT
<213> ORGANISM: Artificial Sequence
<220> FEATURE:
<223> OTHER INFORMATION: Description of Artificial Sequence: Synthetic
      consensus sequence

<400> SEQUENCE: 246

Val Phe Ile His Asn Phe Lys Arg Lys Gly Gly Ile Gly Gly Tyr
1               5                   10                  15

<210> SEQ ID NO 247
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 247

Val Leu Ile His Asn Phe Lys Arg Lys Gly Gly Ile Gly Gly Tyr
1               5                   10                  15

<210> SEQ ID NO 248
<211> LENGTH: 15
<212> TYPE: PRT
<213> ORGANISM: Artificial Sequence
<220> FEATURE:
<223> OTHER INFORMATION: Description of Artificial Sequence: Synthetic
      consensus sequence

<400> SEQUENCE: 248

Asn Lys Ile Val Arg Met Tyr Ser Pro Val Ser Ile Leu Asp Ile
1               5                   10                  15

<210> SEQ ID NO 249
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 249

Asn Lys Ile Val Arg Met Tyr Ser Pro Val Ser Ile Leu Asp Ile
1               5                   10                  15

<210> SEQ ID NO 250
<211> LENGTH: 15
<212> TYPE: PRT
<213> ORGANISM: Artificial Sequence
<220> FEATURE:
<223> OTHER INFORMATION: Description of Artificial Sequence: Synthetic
      consensus sequence

<400> SEQUENCE: 250

Lys Gly Asn Ser Ser Lys Val Ser Gln Asn Tyr Pro Ile Val Gln
1               5                   10                  15

<210> SEQ ID NO 251
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 251

Thr Gly Asn Ser Ser Gln Val Ser Gln Asn Tyr Pro Ile Val Gln
1               5                   10                  15

<210> SEQ ID NO 252
<211> LENGTH: 15
<212> TYPE: PRT
<213> ORGANISM: Artificial Sequence
<220> FEATURE:
<223> OTHER INFORMATION: Description of Artificial Sequence: Synthetic
      consensus sequence

<400> SEQUENCE: 252

Gly Cys Lys Gln Ile Ile Gly Gln Leu Gln Pro Ala Leu Gln Thr
1               5                   10                  15

<210> SEQ ID NO 253
<211> LENGTH: 15
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 253

Gly Cys Arg Gln Ile Leu Gly Gln Leu Gln Pro Ser Leu Gln Thr
1               5                   10                  15

<210> SEQ ID NO 254
<211> LENGTH: 15
<212> TYPE: PRT
<213> ORGANISM: Artificial Sequence
<220> FEATURE:
<223> OTHER INFORMATION: Description of Artificial Sequence: Synthetic
      consensus sequence

<400> SEQUENCE: 254

Pro Val His Ala Gly Pro Ile Pro Pro Gly Gln Met Arg Glu Pro
1               5                   10                  15

<210> SEQ ID NO 255
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 255

Pro Val Gln Ala Gly Pro Ile Ala Pro Gly Gln Met Arg Glu Pro
1               5                   10                  15

<210> SEQ ID NO 256
<211> LENGTH: 22
<212> TYPE: PRT
<213> ORGANISM: Artificial Sequence
<220> FEATURE:
<223> OTHER INFORMATION: Description of Artificial Sequence: Synthetic
      consensus sequence

<400> SEQUENCE: 256

Glu Gln Ala Thr Gln Asp Val Lys Asn Trp Met Thr Asp Thr Leu Leu
1               5                   10                  15

Val Gln Asn Ala Asn Pro
            20

<210> SEQ ID NO 257
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 257

Glu Gln Ser Thr Gln Glu Val Lys Asn Trp Met Thr Asp Thr Leu
1               5                   10                  15

<210> SEQ ID NO 258
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 258

Lys Asn Trp Met Thr Asp Thr Leu Leu Val Gln Asn Ala Asn Pro
1               5                   10                  15

<210> SEQ ID NO 259
<211> LENGTH: 16
<212> TYPE: PRT
<213> ORGANISM: Artificial Sequence
<220> FEATURE:
<223> OTHER INFORMATION: Description of Artificial Sequence: Synthetic
      consensus sequence

<400> SEQUENCE: 259

Ile Val Gln Gln Gln Ser Asn Leu Leu Arg Ala Ile Glu Ala Gln Gln
1               5                   10                  15

<210> SEQ ID NO 260
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 260

Val Val Gln Gln Gln Ser Asn Leu Leu Arg Ala Ile Glu Ala Gln
1               5                   10                  15

<210> SEQ ID NO 261
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 261

Val Gln Gln Gln Asn Asn Leu Leu Arg Ala Ile Glu Ala Gln His
1               5                   10                  15

<210> SEQ ID NO 262
<211> LENGTH: 15
<212> TYPE: PRT
<213> ORGANISM: Artificial Sequence
<220> FEATURE:
<223> OTHER INFORMATION: Description of Artificial Sequence: Synthetic
      consensus sequence

<400> SEQUENCE: 262

His Ser Asn Trp Arg Ala Met Ala Ser Asp Phe Asn Leu Pro Pro
1               5                   10                  15

<210> SEQ ID NO 263
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 263

His Ser Asn Trp Arg Ala Met Ala Ser Asp Phe Asn Leu Pro Pro
1               5                   10                  15

<210> SEQ ID NO 264
<211> LENGTH: 15
<212> TYPE: PRT
```

<213> ORGANISM: Artificial Sequence
<220> FEATURE:
<223> OTHER INFORMATION: Description of Artificial Sequence: Synthetic
      consensus sequence

<400> SEQUENCE: 264

Gly Ser Pro Ala Ile Phe Gln Ser Ser Met Thr Lys Ile Leu Glu
1               5                   10                  15

<210> SEQ ID NO 265
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 265

Gly Ser Pro Ala Ile Phe Gln Ser Ser Met Thr Lys Ile Leu Asp
1               5                   10                  15

<210> SEQ ID NO 266
<211> LENGTH: 15
<212> TYPE: PRT
<213> ORGANISM: Artificial Sequence
<220> FEATURE:
<223> OTHER INFORMATION: Description of Artificial Sequence: Synthetic
      consensus sequence

<400> SEQUENCE: 266

Ile Ile Gly Asp Ile Arg Gln Ala His Cys Asn Ile Ser Gly Thr
1               5                   10                  15

<210> SEQ ID NO 267
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 267

Ile Thr Gly Asp Ile Arg Gln Ala His Cys Asn Val Ser Arg Ser
1               5                   10                  15

<210> SEQ ID NO 268
<211> LENGTH: 18
<212> TYPE: PRT
<213> ORGANISM: Artificial Sequence
<220> FEATURE:
<223> OTHER INFORMATION: Description of Artificial Sequence: Synthetic
      consensus sequence

<400> SEQUENCE: 268

Ser Asn Trp Arg Ala Met Ala Ser Asp Phe Asn Leu Pro Pro Ile Val
1               5                   10                  15

Ala Lys

<210> SEQ ID NO 269
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 269

```
Ser Asn Trp Arg Ala Met Ala Ser Asp Phe Asn Leu Pro Pro
1               5                   10
```

<210> SEQ ID NO 270
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 270

```
Arg Thr Met Ala Ser Asp Phe Asn Leu Pro Pro Val Val Ala Lys
1               5                   10                  15
```

<210> SEQ ID NO 271
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 271

```
Lys Ala Met Ala Ser Asp Phe Asn Leu Pro Pro Ile Val Ala Lys
1               5                   10                  15
```

<210> SEQ ID NO 272
<211> LENGTH: 15
<212> TYPE: PRT
<213> ORGANISM: Artificial Sequence
<220> FEATURE:
<223> OTHER INFORMATION: Description of Artificial Sequence: Synthetic
      consensus sequence

<400> SEQUENCE: 272

```
Gly Ser Pro Ala Ile Phe Gln Ser Ser Met Thr Lys Ile Leu Glu
1               5                   10                  15
```

<210> SEQ ID NO 273
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 273

```
Gly Ser Pro Ala Ile Phe Gln Ser Ser Met Thr Lys Ile Leu Asp
1               5                   10                  15
```

<210> SEQ ID NO 274
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 274

```
Ala Ala Glu Trp Asp Arg Val His Pro Val His Ala Gly Pro Ile Ala
1               5                   10                  15

Pro Gly Gln
```

<210> SEQ ID NO 275
<211> LENGTH: 19
<212> TYPE: PRT

-continued

<213> ORGANISM: Artificial Sequence
<220> FEATURE:
<223> OTHER INFORMATION: Description of Artificial Sequence: Synthetic
      peptide

<400> SEQUENCE: 275

Ala Ala Glu Trp Asp Arg Leu His Pro Val His Ala Gly Pro Val Ala
1               5                   10                  15

Pro Gly Gln

<210> SEQ ID NO 276
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 276

Ala Ala Glu Asp Arg Leu His Pro Val His Ala Gly Pro Ile Pro
1               5                   10                  15

<210> SEQ ID NO 277
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 277

Ala Glu Trp Asp Arg Leu His Pro Val His Ala Gly Pro Ile Ala
1               5                   10                  15

<210> SEQ ID NO 278
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 278

Ala Asp Trp Asp Arg Leu His Pro Val His Ala Gly Pro Val Ala
1               5                   10                  15

<210> SEQ ID NO 279
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 279

Trp Asp Arg Val His Pro Val His Ala Gly Pro Asn Pro Pro Gly
1               5                   10                  15

<210> SEQ ID NO 280
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 280

```
Asp Arg Val His Pro Val His Ala Gly Pro Ile Pro Pro Gly Gln
 1               5                  10                  15

<210> SEQ ID NO 281
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 281

Ile Val Gln Gln Gln Asn Asn Leu Leu Arg Ala Ile Glu Ala Gln Gln
 1               5                  10                  15

<210> SEQ ID NO 282
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 282

Ile Val Gln Gln Gln Ser Asn Leu Leu Arg Ala Ile Glu Ala Gln Gln
 1               5                  10                  15

<210> SEQ ID NO 283
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 283

Val Val Gln Gln Gln Ser Asn Leu Leu Arg Ala Ile Glu Ala Gln
 1               5                  10                  15

<210> SEQ ID NO 284
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 284

Val Gln Gln Gln Asn Asn Leu Leu Arg Ala Ile Glu Ala Gln His
 1               5                  10                  15

<210> SEQ ID NO 285
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 285

Val Gln Gln Gln Ser Asn Leu Leu Lys Ala Ile Glu Ala Gln Gln
 1               5                  10                  15

<210> SEQ ID NO 286
<211> LENGTH: 15
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 286

Ala Ser Gln Asp Val Lys Asn Trp Met Thr Glu Thr Leu Leu Val
1               5                   10                  15

<210> SEQ ID NO 287
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 287

Ala Thr Gln Asp Val Lys Asn Trp Met Thr Asp Thr Leu Leu Val
1               5                   10                  15

<210> SEQ ID NO 288
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 288

Ala Ser Gln Glu Val Lys Asn Trp Met Thr Glu Thr Leu Leu Ile
1               5                   10                  15

<210> SEQ ID NO 289
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 289

Ala Val Phe Ile His Asn Phe Lys Arg Lys Gly Gly Ile Gly Gly Tyr
1               5                   10                  15

<210> SEQ ID NO 290
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 290

Ala Val Phe Ile His Asn Phe Lys Arg Lys Gly Gly Ile Gly Glu Tyr
1               5                   10                  15

<210> SEQ ID NO 291
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 291

Ala Val Phe Ile His Asn Phe Lys Arg Lys Gly Gly Ile Gly Gly
1               5                   10                  15
```

<210> SEQ ID NO 292
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 292

Val Leu Ile His Asn Phe Lys Arg Lys Gly Gly Ile Gly Gly Tyr
1               5                   10                  15

<210> SEQ ID NO 293
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 293

Pro Leu Val Lys Leu Trp Tyr Gln Leu Glu Lys Asp Pro Ile Ala
1               5                   10                  15

<210> SEQ ID NO 294
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 294

Pro Leu Val Lys Leu Trp Tyr Gln Leu Glu Lys Glu Pro Ile Val
1               5                   10                  15

<210> SEQ ID NO 295
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 295

Pro Leu Val Lys Leu Trp Tyr Gln Leu Glu Lys Glu Pro Ile Val
1               5                   10                  15

<210> SEQ ID NO 296
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 296

Thr Ile Pro Ser Thr Asn Asn Glu Thr Pro Gly Ile Arg Tyr Gln
1               5                   10                  15

<210> SEQ ID NO 297
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 297

```
Thr Ile Pro Ser Ile Asn Asn Glu Thr Pro Gly Ile Arg Tyr Gln
1               5                   10                  15

<210> SEQ ID NO 298
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 298

Thr Ile Pro Ser Ile Asn Asn Glu Thr Pro Gly Ile Arg Tyr Gln
1               5                   10                  15

<210> SEQ ID NO 299
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 299

Tyr Pro Gly Ile Lys Val Arg Gln Leu Cys Lys Leu Leu Arg Gly
1               5                   10                  15

<210> SEQ ID NO 300
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 300

Tyr Ala Gly Ile Lys Val Lys Gln Leu Cys Lys Leu Leu Arg Gly
1               5                   10                  15

<210> SEQ ID NO 301
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 301

Tyr Pro Gly Ile Lys Val Arg Gln Leu Cys Lys Leu Leu Arg Gly
1               5                   10                  15

<210> SEQ ID NO 302
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 302

Leu Ile Lys Lys Glu Arg Val Tyr Leu Ser Trp Val Pro Ala His Lys
1               5                   10                  15

Gly Ile Gly

<210> SEQ ID NO 303
<211> LENGTH: 19
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 303

Leu Ile Lys Lys Glu Lys Val Tyr Leu Ala Trp Val Pro Ala His Lys
1               5                   10                  15

Gly Ile Gly

<210> SEQ ID NO 304
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 304

Leu Ile Lys Lys Glu Arg Val Tyr Leu Ser Trp Val Pro Ala His
1               5                   10                  15

<210> SEQ ID NO 305
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 305

Glu Lys Val Tyr Leu Ser Trp Val Pro Ala His Lys Gly Ile Gly
1               5                   10                  15

<210> SEQ ID NO 306
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 306

Ser Leu Tyr Asn Thr Val Ala Thr Leu Tyr Cys Val His Gln Arg
1               5                   10                  15

<210> SEQ ID NO 307
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 307

Ser Leu Phe Asn Thr Val Ala Thr Leu Tyr Cys Val His Ala Glu
1               5                   10                  15

<210> SEQ ID NO 308
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 308
```

```
Ser Leu Tyr Asn Thr Val Ala Thr Leu Tyr Cys Val His Gln Arg
1               5                   10                  15

<210> SEQ ID NO 309
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 309

Ala Asn Pro Asp Cys Lys Thr Ile Leu Lys Ala Leu Gly Pro Ala
1               5                   10                  15

<210> SEQ ID NO 310
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 310

Ala Asn Pro Asp Cys Lys Thr Ile Leu Arg Ala Leu Gly Pro Gly
1               5                   10                  15

<210> SEQ ID NO 311
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 311

Ala Asn Pro Asp Cys Lys Thr Ile Leu Arg Ala Leu Gly Pro Gly
1               5                   10                  15

<210> SEQ ID NO 312
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 312

Glu Gln Leu Ile Lys Lys Glu Arg Val Tyr Leu Ser Trp Val Pro Ala
1               5                   10                  15

His Lys Gly Ile Gly
            20

<210> SEQ ID NO 313
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 313

Glu Gln Leu Ile Lys Lys Glu Lys Val Tyr Leu Ala Trp Val Pro Ala
1               5                   10                  15

His Lys Gly Ile Gly
            20
```

```
<210> SEQ ID NO 314
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 314

Glu Pro Leu Ile Lys Lys Glu Lys Val Tyr Leu Ser Trp Val Pro
1               5                   10                  15

<210> SEQ ID NO 315
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 315

Lys Leu Ile Glu Lys Asp Lys Val Tyr Leu Ser Trp Val Pro Ala
1               5                   10                  15

<210> SEQ ID NO 316
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 316

Leu Ile Lys Lys Glu Arg Val Tyr Leu Ser Trp Val Pro Ala His
1               5                   10                  15

<210> SEQ ID NO 317
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 317

Glu Lys Val Tyr Leu Ala Trp Val Pro Ala His Lys Gly Ile Gly
1               5                   10                  15

<210> SEQ ID NO 318
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 318

Glu Lys Val Tyr Leu Ser Trp Val Pro Ala His Lys Gly Ile Gly
1               5                   10                  15

<210> SEQ ID NO 319
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 319

Ile Val Gln Gln Gln Asn Asn Leu Leu Arg Ala Ile Glu Ala Gln Gln
1               5                   10                  15

<210> SEQ ID NO 320
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 320

Ile Val Gln Gln Gln Ser Asn Leu Leu Arg Ala Ile Glu Ala Gln Gln
1               5                   10                  15

<210> SEQ ID NO 321
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 321

Val Val Gln Gln Gln Ser Asn Leu Leu Arg Ala Ile Glu Ala Gln
1               5                   10                  15

<210> SEQ ID NO 322
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 322

Val Gln Gln Gln Asn Asn Leu Leu Arg Ala Ile Glu Ala Gln His
1               5                   10                  15

<210> SEQ ID NO 323
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 323

Glu Gln Ala Ser Gln Asp Val Lys Asn Trp Met Thr Glu Thr Leu Leu
1               5                   10                  15

Val Gln Asn Ala Asn Pro
            20

<210> SEQ ID NO 324
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 324

Glu Gln Ala Thr Gln Asp Val Lys Asn Trp Met Thr Asp Thr Leu Leu
1               5                   10                  15
```

Val Gln Asn Ala Asn Pro
            20

<210> SEQ ID NO 325
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 325

Glu Gln Ser Thr Gln Glu Val Lys Asn Trp Met Thr Asp Thr Leu
1               5                   10                  15

<210> SEQ ID NO 326
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 326

Lys Asn Trp Met Thr Asp Thr Leu Leu Val Gln Asn Ala Asn Pro
1               5                   10                  15

<210> SEQ ID NO 327
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 327

His Ser Asn Trp Arg Ala Met Ala Ser Asp Phe Asn Leu Pro Pro Val
1               5                   10                  15

Val Ala Lys

<210> SEQ ID NO 328
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 328

His Ser Asn Trp Arg Ala Met Ala Ser Glu Phe Asn Leu Pro Pro Ile
1               5                   10                  15

Val Ala Lys

<210> SEQ ID NO 329
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 329

His Ser Asn Trp Arg Ala Met Ala Ser Asp Phe Asn Leu Pro Pro
1               5                   10                  15

<210> SEQ ID NO 330

```
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 330

Ser Asn Trp Arg Ala Met Ala Ser Glu Phe Asn Leu Pro Pro Ile
1               5                   10                  15

<210> SEQ ID NO 331
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 331

Asn Trp Arg Thr Met Ala Ser Asp Phe Asn Leu Pro Pro Val Ile
1               5                   10                  15

<210> SEQ ID NO 332
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 332

Arg Thr Met Ala Ser Asp Phe Asn Leu Pro Pro Val Val Ala Lys
1               5                   10                  15

<210> SEQ ID NO 333
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 333

Lys Ala Met Ala Ser Asp Phe Asn Leu Pro Pro Ile Val Ala Lys
1               5                   10                  15

<210> SEQ ID NO 334
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 334

Ala Glu Trp Asp Arg Val His Pro Val His Ala Gly Pro Ile Ala Pro
1               5                   10                  15

Gly Gln

<210> SEQ ID NO 335
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 335

Ala Glu Trp Asp Arg Leu His Pro Val His Ala Gly Pro Val Ala Pro
1               5                   10                  15

Gly Gln

<210> SEQ ID NO 336
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 336

Ala Ala Glu Asp Arg Leu His Pro Val His Ala Gly Pro Ile Pro
1               5                   10                  15

<210> SEQ ID NO 337
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 337

Ala Asp Trp Asp Arg Leu His Pro Val His Ala Gly Pro Val Ala
1               5                   10                  15

<210> SEQ ID NO 338
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 338

Ala Glu Trp Asp Arg Leu His Pro Val His Ala Gly Pro Ile Ala
1               5                   10                  15

<210> SEQ ID NO 339
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 339

Trp Asp Arg Val His Pro Val His Ala Gly Pro Asn Pro Pro Gly
1               5                   10                  15

<210> SEQ ID NO 340
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 340

Asp Arg Val His Pro Val His Ala Gly Pro Ile Pro Pro Gly Gln
1               5                   10                  15

<210> SEQ ID NO 341
```

```
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 341

Ala Val Phe Ile His Asn Phe Lys Arg Lys Gly Gly Ile Gly Gly Tyr
1               5                   10                  15

<210> SEQ ID NO 342
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 342

Ala Val Phe Ile His Asn Phe Lys Arg Lys Gly Gly Ile Gly Glu Tyr
1               5                   10                  15

<210> SEQ ID NO 343
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 343

Ala Val Phe Ile His Asn Phe Lys Arg Lys Gly Gly Ile Gly Gly
1               5                   10                  15

<210> SEQ ID NO 344
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 344

Val Leu Ile His Asn Phe Lys Arg Lys Gly Gly Ile Gly Gly Tyr
1               5                   10                  15

<210> SEQ ID NO 345
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 345

Pro Leu Asp Glu Gly Phe Arg Lys Tyr Thr Ala Phe Thr Ile Pro
1               5                   10                  15

<210> SEQ ID NO 346
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 346
```

Pro Leu Asp Glu Asp Phe Arg Lys Tyr Thr Ala Phe Thr Ile Pro
1               5                   10                  15

<210> SEQ ID NO 347
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 347

Pro Leu Asp Glu Ser Phe Arg Lys Tyr Thr Ala Phe Thr Ile Pro
1               5                   10                  15

<210> SEQ ID NO 348
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 348

Thr Arg Ile Leu Glu Pro Phe Arg Ala Lys Asn Pro Glu Ile Val
1               5                   10                  15

<210> SEQ ID NO 349
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 349

Thr Lys Ile Leu Glu Pro Phe Arg Lys Gln Asn Pro Asp Ile Val
1               5                   10                  15

<210> SEQ ID NO 350
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 350

Thr Lys Ile Leu Glu Pro Phe Arg Ala Gln Asn Pro Glu Leu Val
1               5                   10                  15

<210> SEQ ID NO 351
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 351

Ile Cys Glu Glu Met Glu Lys Glu Gly Lys Ile Thr Lys Ile Gly
1               5                   10                  15

<210> SEQ ID NO 352
<211> LENGTH: 15
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 352

Ile Cys Thr Glu Met Glu Lys Glu Gly Lys Ile Ser Lys Ile Gly
1               5                   10                  15

<210> SEQ ID NO 353
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 353

Ile Cys Thr Glu Met Glu Lys Glu Gly Lys Ile Ser Lys Ile Gly
1               5                   10                  15

<210> SEQ ID NO 354
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 354

Val Lys Leu Trp Tyr Gln Leu Glu Lys Asp Pro Ile Ala Gly Val
1               5                   10                  15

<210> SEQ ID NO 355
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 355

Val Lys Leu Trp Tyr Gln Leu Glu Lys Glu Pro Ile Val Gly Ala
1               5                   10                  15

<210> SEQ ID NO 356
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 356

Val Lys Leu Trp Tyr Gln Leu Glu Lys Asp Pro Ile Val Gly Ala
1               5                   10                  15

<210> SEQ ID NO 357
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 357

Gly Asp Ile Ile Gly Asp Ile Arg Gln Ala His Cys Asn Ile Ser
1               5                   10                  15
```

```
<210> SEQ ID NO 358
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 358

Gly Asp Ile Ile Gly Asp Ile Arg Gln Ala His Cys Asn Leu Ser
1               5                   10                  15

<210> SEQ ID NO 359
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 359

Gly Asp Ile Ile Gly Asp Ile Arg Gln Ala His Cys Asn Ile Ser
1               5                   10                  15

<210> SEQ ID NO 360
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 360

Ile Cys Thr Thr Thr Val Pro Trp Asn Ala Ser Trp Ser Asn Lys
1               5                   10                  15

<210> SEQ ID NO 361
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 361

Ile Cys Thr Thr Ala Val Pro Trp Asn Thr Ser Trp Ser Asn Lys
1               5                   10                  15

<210> SEQ ID NO 362
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 362

Ile Cys Thr Thr Thr Val Pro Trp Asn Ala Ser Trp Ser Asn Arg
1               5                   10                  15

<210> SEQ ID NO 363
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 363
```

Ile Gly Gln Val Arg Asp Gln Ala Glu His Leu Lys Thr Ala Val
1               5                   10                  15

<210> SEQ ID NO 364
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 364

Ile Gly Gln Val Arg Asp Gln Ala Glu His Leu Lys Thr Ala Val
1               5                   10                  15

<210> SEQ ID NO 365
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 365

Ile Gly Gln Val Arg Glu Gln Ala Glu His Leu Lys Thr Ala Val
1               5                   10                  15

<210> SEQ ID NO 366
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 366

Gly Lys Gln Met Ala Gly Ala Asp Cys Val Ala Gly Arg Gln Asp
1               5                   10                  15

<210> SEQ ID NO 367
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 367

Gly Lys Gln Met Ala Gly Asp Asp Cys Val Ala Ser Arg Gln Asp
1               5                   10                  15

<210> SEQ ID NO 368
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 368

Gly Lys Gln Met Ala Gly Asp Asp Cys Val Ala Gly Arg Gln Asp
1               5                   10                  15

<210> SEQ ID NO 369
<211> LENGTH: 15
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 369

Lys Tyr Ala Lys Met Arg Thr Ala His Thr Asn Asp Val Lys Gln
1               5                   10                  15

<210> SEQ ID NO 370
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 370

Lys Tyr Ala Arg Met Arg Gly Ala His Thr Asn Asp Val Lys Gln
1               5                   10                  15

<210> SEQ ID NO 371
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 371

Lys Tyr Ala Lys Met Arg Thr Ala His Thr Asn Asp Val Arg Gln
1               5                   10                  15

<210> SEQ ID NO 372
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 372

Ala Gly Asp Ile Ile Gly Asp Ile Arg Gln Ala His Cys Asn Ile
1               5                   10                  15

<210> SEQ ID NO 373
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 373

Thr Gly Asp Ile Ile Gly Asp Ile Arg Gln Ala His Cys Asn Leu
1               5                   10                  15

<210> SEQ ID NO 374
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 374

Thr Gly Glu Ile Ile Gly Asp Ile Arg Gln Ala His Cys Asn Leu
1               5                   10                  15
```

<210> SEQ ID NO 375
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 375

Asn Gln Gln Glu Lys Asn Glu Lys Asp Leu Leu Ala Leu Asp Ser
1               5                   10                  15

<210> SEQ ID NO 376
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 376

Asn Gln Gln Glu Lys Asn Glu Gln Glu Leu Leu Glu Leu Asp Lys
1               5                   10                  15

<210> SEQ ID NO 377
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 377

Asn Gln Gln Glu Lys Asn Glu Gln Asp Leu Leu Ala Leu Asp Lys
1               5                   10                  15

<210> SEQ ID NO 378
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 378

Asp Ile Lys Val Val Pro Arg Arg Lys Val Lys Ile Ile Lys Asp
1               5                   10                  15

<210> SEQ ID NO 379
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 379

Asp Ile Lys Val Val Pro Arg Arg Lys Ala Lys Ile Ile Arg Asp
1               5                   10                  15

<210> SEQ ID NO 380
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 380

Asp Ile Lys Val Val Pro Arg Arg Lys Val Lys Ile Ile Arg Asp
1               5                   10                  15

<210> SEQ ID NO 381
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 381

Leu Ile Lys Lys Glu Arg Val Tyr Leu Ser Trp Val Pro Ala His Lys
1               5                   10                  15

Gly Ile Gly

<210> SEQ ID NO 382
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 382

Leu Ile Lys Lys Glu Lys Val Tyr Leu Ala Trp Val Pro Ala His Lys
1               5                   10                  15

Gly Ile Gly

<210> SEQ ID NO 383
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 383

Leu Ile Lys Lys Glu Arg Val Tyr Leu Ser Trp Val Pro Ala His
1               5                   10                  15

<210> SEQ ID NO 384
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 384

Glu Lys Val Tyr Leu Ser Trp Val Pro Ala His Lys Gly Ile Gly
1               5                   10                  15

<210> SEQ ID NO 385
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 385

Ile Val Gln Gln Gln Asn Asn Leu Leu Arg Ala Ile Glu Ala Gln Gln
1               5                   10                  15
```

-continued

His Leu Leu Gln Leu
        20

<210> SEQ ID NO 386
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 386

Ile Val Gln Gln Gln Ser Asn Leu Leu Arg Ala Ile Glu Ala Gln Gln
1               5                   10                  15

His Met Leu Gln Leu
        20

<210> SEQ ID NO 387
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 387

Val Val Gln Gln Gln Ser Asn Leu Leu Arg Ala Ile Glu Ala Gln
1               5                   10                  15

<210> SEQ ID NO 388
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 388

Val Gln Gln Gln Ser Asn Leu Leu Lys Ala Ile Glu Ala Gln Gln
1               5                   10                  15

<210> SEQ ID NO 389
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 389

Val Gln Gln Gln Asn Asn Leu Leu Arg Ala Ile Glu Ala Gln His
1               5                   10                  15

<210> SEQ ID NO 390
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 390

Asn Leu Leu Arg Ala Ile Glu Ala Gln Gln His Leu Leu Gln Leu
1               5                   10                  15

<210> SEQ ID NO 391
<211> LENGTH: 16

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 391

Ala Val Phe Ile His Asn Phe Lys Arg Lys Gly Gly Ile Gly Gly Tyr
1               5                   10                  15

<210> SEQ ID NO 392
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 392

Ala Val Phe Ile His Asn Phe Lys Arg Lys Gly Gly Ile Gly Glu Tyr
1               5                   10                  15

<210> SEQ ID NO 393
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 393

Ala Val Phe Ile His Asn Phe Lys Arg Lys Gly Gly Ile Gly Gly
1               5                   10                  15

<210> SEQ ID NO 394
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 394

Val Leu Ile His Asn Phe Lys Arg Lys Gly Gly Ile Gly Gly Tyr
1               5                   10                  15

<210> SEQ ID NO 395
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 395

Glu Gln Ala Ser Gln Asp Val Lys Asn Trp Met Thr Glu Thr Leu Leu
1               5                   10                  15

Val Gln Asn Ala Asn Pro
            20

<210> SEQ ID NO 396
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 396

Glu Gln Ala Thr Gln Asp Val Lys Asn Trp Met Thr Asp Thr Leu Leu
1               5                   10                  15

Val Gln Asn Ala Asn Pro
            20

<210> SEQ ID NO 397
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 397

Glu Gln Ala Ser Gln Asp Val Lys Asn Trp Met Thr Glu Thr Leu
1               5                   10                  15

<210> SEQ ID NO 398
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 398

Glu Gln Ser Thr Gln Glu Val Lys Asn Trp Met Thr Asp Thr Leu
1               5                   10                  15

<210> SEQ ID NO 399
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 399

Ala Ser Gln Glu Val Lys Asn Trp Met Thr Glu Thr Leu Leu Ile
1               5                   10                  15

<210> SEQ ID NO 400
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 400

Thr Gln Asp Val Lys Asn Trp Met Thr Asp Thr Leu Leu Ile Gln
1               5                   10                  15

<210> SEQ ID NO 401
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 401

Lys Asn Trp Met Thr Glu Thr Leu Leu Val Gln Asn Ala Asn Pro
1               5                   10                  15
```

```
<210> SEQ ID NO 402
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 402

Lys Asn Trp Met Thr Asp Thr Leu Leu Val Gln Asn Ala Asn Pro
1               5                   10                  15

<210> SEQ ID NO 403
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 403

Ala Glu Trp Asp Arg Val His Pro Val His Ala Gly Pro Ile Ala Pro
1               5                   10                  15

Gly Gln

<210> SEQ ID NO 404
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 404

Ala Glu Trp Asp Arg Leu His Pro Val His Ala Gly Pro Val Ala Pro
1               5                   10                  15

Gly Gln

<210> SEQ ID NO 405
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 405

Ala Ala Glu Asp Arg Leu His Pro Val His Ala Gly Pro Ile Pro
1               5                   10                  15

<210> SEQ ID NO 406
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 406

Ala Glu Trp Asp Arg Leu His Pro Val His Ala Gly Pro Ile Ala
1               5                   10                  15

<210> SEQ ID NO 407
<211> LENGTH: 15
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 407

Asp Arg Val His Pro Val His Ala Gly Pro Ile Pro Pro Gly Gln
1               5                   10                  15

<210> SEQ ID NO 408
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 408

Trp Lys Gly Ser Pro Ala Ile Phe Gln Cys Ser Met Thr Arg Ile
1               5                   10                  15

<210> SEQ ID NO 409
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 409

Trp Lys Gly Ser Pro Ala Ile Phe Gln Ser Ser Met Thr Lys Ile
1               5                   10                  15

<210> SEQ ID NO 410
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 410

Trp Lys Gly Ser Pro Ala Ile Phe Gln Cys Ser Met Thr Lys Ile
1               5                   10                  15

<210> SEQ ID NO 411
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 411

Met Thr Arg Ile Leu Glu Pro Phe Arg Ala Lys Asn Pro Glu Ile
1               5                   10                  15

<210> SEQ ID NO 412
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 412

Met Thr Lys Ile Leu Glu Pro Phe Arg Lys Gln Asn Pro Asp Ile
1               5                   10                  15

```
<210> SEQ ID NO 413
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 413

Met Thr Lys Ile Leu Glu Pro Phe Arg Lys Gln Asn Pro Asp Ile
1               5                   10                  15

<210> SEQ ID NO 414
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 414

Gly Ser Pro Ala Ile Phe Gln Cys Ser Met Thr Arg Ile Leu Glu
1               5                   10                  15

<210> SEQ ID NO 415
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 415

Gly Ser Pro Ala Ile Phe Gln Ser Ser Met Thr Lys Ile Leu Glu
1               5                   10                  15

<210> SEQ ID NO 416
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 416

Gly Ser Pro Ala Ile Phe Gln Ser Ser Met Thr Lys Ile Leu Asp
1               5                   10                  15

<210> SEQ ID NO 417
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 417

His Gly Gln Val Asp Cys Ser Pro Gly Ile Trp Gln Leu Ala Cys
1               5                   10                  15

<210> SEQ ID NO 418
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 418
```

```
His Gly Gln Val Asp Cys Ser Pro Gly Ile Trp Gln Leu Ala Cys
1               5                   10                  15

<210> SEQ ID NO 419
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 419

His Gly Gln Val Asp Cys Ser Pro Gly Ile Trp Gln Leu Asp Cys
1               5                   10                  15

<210> SEQ ID NO 420
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 420

Asp Arg Phe Tyr Lys Thr Leu Arg Ala Glu Gln Ala Ser Gln Asp
1               5                   10                  15

<210> SEQ ID NO 421
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 421

Asp Arg Phe Phe Lys Thr Leu Arg Ala Glu Gln Ala Thr Gln Asp
1               5                   10                  15

<210> SEQ ID NO 422
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 422

Asp Arg Phe Tyr Lys Thr Leu Arg Ala Glu Gln Ala Ser Gln Glu
1               5                   10                  15

<210> SEQ ID NO 423
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 423

Leu Ile Lys Lys Glu Arg Val Tyr Leu Ser Trp Val Pro Ala His Lys
1               5                   10                  15

Gly Ile Gly

<210> SEQ ID NO 424
<211> LENGTH: 19
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 424

Leu Ile Lys Lys Glu Lys Val Tyr Leu Ala Trp Val Pro Ala His Lys
1               5                   10                  15

Gly Ile Gly

<210> SEQ ID NO 425
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 425

Leu Ile Lys Lys Glu Arg Val Tyr Leu Ser Trp Val Pro Ala His
1               5                   10                  15

<210> SEQ ID NO 426
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 426

Glu Lys Val Tyr Leu Ser Trp Val Pro Ala His Lys Gly Ile Gly
1               5                   10                  15

<210> SEQ ID NO 427
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 427

Ala Glu Trp Asp Arg Val His Pro Val His Ala Gly Pro Ile Ala Pro
1               5                   10                  15

Gly Gln

<210> SEQ ID NO 428
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 428

Ala Glu Trp Asp Arg Leu His Pro Val His Ala Gly Pro Val Ala Pro
1               5                   10                  15

Gly Gln

<210> SEQ ID NO 429
<211> LENGTH: 15
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 429

Ala Glu Trp Asp Arg Leu His Pro Val His Ala Gly Pro Ile Ala
1               5                   10                  15

<210> SEQ ID NO 430
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 430

Asp Arg Val His Pro Val His Ala Gly Pro Ile Pro Pro Gly Gln
1               5                   10                  15

<210> SEQ ID NO 431
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 431

Ala Ile Phe Gln Cys Ser Met Thr Arg Ile Leu Glu Pro Phe Arg
1               5                   10                  15

<210> SEQ ID NO 432
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 432

Ala Ile Phe Gln Ser Ser Met Thr Lys Ile Leu Glu Pro Phe Arg
1               5                   10                  15

<210> SEQ ID NO 433
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 433

Ala Ile Phe Gln Ser Ser Met Thr Arg Ile Leu Glu Pro Phe Arg
1               5                   10                  15

<210> SEQ ID NO 434
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 434

Ala Ser Gln Ile Tyr Pro Gly Ile Lys Val Arg Gln Leu Cys Lys
1               5                   10                  15

```
<210> SEQ ID NO 435
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 435

Ala Ser Gln Ile Tyr Ala Gly Ile Lys Val Lys Gln Leu Cys Lys
1               5                   10                  15

<210> SEQ ID NO 436
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 436

Trp Ser Gln Ile Tyr Ala Gly Ile Lys Val Arg Gln Leu Cys Lys
1               5                   10                  15

<210> SEQ ID NO 437
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 437

Arg Glu Leu Asn Lys Arg Thr Gln Asp Phe Trp Glu Val Gln Leu
1               5                   10                  15

<210> SEQ ID NO 438
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 438

Arg Glu Leu Asn Lys Arg Thr Gln Asp Phe Trp Glu Val Gln Leu
1               5                   10                  15

<210> SEQ ID NO 439
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 439

Arg Glu Leu Asn Arg Arg Thr Gln Asp Phe Trp Glu Val Gln Leu
1               5                   10                  15

<210> SEQ ID NO 440
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 440
```

Leu Leu Arg Ala Ile Glu Ala Gln Gln His Leu Leu Gln Leu Thr
1               5                   10                  15

<210> SEQ ID NO 441
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 441

Leu Leu Arg Ala Ile Glu Ala Gln Gln His Met Leu Gln Leu Thr
1               5                   10                  15

<210> SEQ ID NO 442
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 442

Leu Leu Met Ala Ile Glu Ala Gln Gln His Leu Leu Gln Leu Thr
1               5                   10                  15

<210> SEQ ID NO 443
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 443

Leu Ile Cys Thr Thr Thr Val Pro Trp Asn Ala Ser Trp Ser Asn
1               5                   10                  15

<210> SEQ ID NO 444
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 444

Leu Ile Cys Thr Thr Ala Val Pro Trp Asn Thr Ser Trp Ser Asn
1               5                   10                  15

<210> SEQ ID NO 445
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 445

His Ile Cys Thr Thr Asn Val Pro Trp Asn Ala Ser Trp Ser Asn
1               5                   10                  15

<210> SEQ ID NO 446
<211> LENGTH: 15
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 446

Lys His Ile Val Trp Ala Ser Arg Glu Leu Glu Arg Phe Ala Val
1               5                   10                  15

<210> SEQ ID NO 447
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 447

Lys His Leu Val Trp Ala Ser Arg Glu Leu Glu Arg Phe Ala Leu
1               5                   10                  15

<210> SEQ ID NO 448
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 448

Lys His Leu Val Trp Ala Ser Arg Glu Leu Glu Arg Phe Ala Leu
1               5                   10                  15

<210> SEQ ID NO 449
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 449

Arg Ser Leu Tyr Asn Thr Val Ala Thr Leu Tyr Cys Val His Gln
1               5                   10                  15

<210> SEQ ID NO 450
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 450

Arg Ser Leu Phe Asn Thr Val Ala Thr Leu Tyr Cys Val His Ala
1               5                   10                  15

<210> SEQ ID NO 451
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 451

Lys Ser Leu Tyr Asn Thr Val Ala Val Leu Tyr Cys Val His Gln
1               5                   10                  15
```

<210> SEQ ID NO 452
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 452

Glu Glu Lys Ala Phe Ser Pro Glu Val Ile Pro Met Phe Ser Ala
1               5                   10                  15

<210> SEQ ID NO 453
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 453

Glu Glu Lys Ala Phe Ser Pro Glu Val Ile Pro Met Phe Thr Ala
1               5                   10                  15

<210> SEQ ID NO 454
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 454

Glu Glu Lys Ala Phe Ser Pro Glu Val Ile Pro Met Phe Ser Ala
1               5                   10                  15

<210> SEQ ID NO 455
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 455

Trp Lys Gly Ser Pro Ala Ile Phe Gln Cys Ser Met Thr Arg Ile Leu
1               5                   10                  15

Glu Pro Phe Arg Ala
            20

<210> SEQ ID NO 456
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 456

Trp Lys Gly Ser Pro Ala Ile Phe Gln Ser Ser Met Thr Lys Ile Leu
1               5                   10                  15

Glu Pro Phe Arg Lys
            20

<210> SEQ ID NO 457
<211> LENGTH: 15

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 457

Trp Lys Gly Ser Pro Ala Ile Phe Gln Ala Ser Met Thr Lys Ile
1               5                   10                  15

<210> SEQ ID NO 458
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 458

Gly Ser Pro Ala Ile Phe Gln Ser Ser Met Thr Lys Ile Leu Asp
1               5                   10                  15

<210> SEQ ID NO 459
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 459

Ile Phe Gln Cys Ser Met Thr Lys Ile Leu Glu Pro Phe Arg Ala
1               5                   10                  15

<210> SEQ ID NO 460
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 460

Lys Ala Arg Val Leu Ala Glu Ala Met Ser Gln Val Thr Asn Ser Ala
1               5                   10                  15

Thr

<210> SEQ ID NO 461
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 461

Lys Ala Arg Val Leu Ala Glu Ala Met Ser Gln Thr Asn Ser Thr Ile
1               5                   10                  15

Leu

<210> SEQ ID NO 462
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 462

Lys Ala Lys Val Leu Ala Glu Ala Met Ser Gln Val Gln Gln Thr
1               5                   10                  15

<210> SEQ ID NO 463
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 463

Arg Val Leu Ala Glu Ala Met Ser Gln Val Thr Asn Ser Ala Thr
1               5                   10                  15

<210> SEQ ID NO 464
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 464

Ser Asp Leu Glu Ile Gly Gln His Arg Ala Lys Ile Glu Glu Leu Arg
1               5                   10                  15

<210> SEQ ID NO 465
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 465

Ser Asp Leu Glu Ile Gly Gln His Arg Thr Lys Ile Glu Glu Leu Arg
1               5                   10                  15

<210> SEQ ID NO 466
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 466

Ser Asp Leu Glu Ile Gly Gln His Arg Ile Lys Ile Glu Glu Leu
1               5                   10                  15

<210> SEQ ID NO 467
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 467

Asp Leu Glu Ile Gly Gln His Arg Ala Lys Ile Glu Glu Leu Arg
1               5                   10                  15

<210> SEQ ID NO 468
<211> LENGTH: 16

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 468

Gln Met His Glu Asp Ile Ile Ser Leu Trp Asp Gln Ser Leu Lys Pro
1               5                   10                  15

<210> SEQ ID NO 469
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 469

Gln Met His Glu Asp Ile Ile Arg Leu Trp Asp Gln Ser Leu Lys Pro
1               5                   10                  15

<210> SEQ ID NO 470
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 470

His Met His Glu Asp Ile Ile Ser Leu Trp Asp Glu Ser Leu Lys
1               5                   10                  15

<210> SEQ ID NO 471
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 471

Met His Glu Asp Val Ile Ser Leu Trp Asp Gln Ser Leu Lys Pro
1               5                   10                  15

<210> SEQ ID NO 472
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 472

Glu Glu Lys Ala Phe Ser Pro Glu Val Ile Pro Met Phe Ser Ala Leu
1               5                   10                  15

<210> SEQ ID NO 473
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 473

Glu Glu Lys Ala Phe Ser Pro Glu Val Ile Pro Met Phe Thr Ala Leu
```

```
<210> SEQ ID NO 474
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 474

Glu Glu Lys Ala Phe Ser Pro Glu Val Ile Pro Met Phe Ser Ala
1               5                   10                  15

<210> SEQ ID NO 475
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 475

Glu Glu Lys Gly Phe Asn Pro Glu Val Ile Pro Met Phe Ser Ala
1               5                   10                  15

<210> SEQ ID NO 476
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 476

Glu Lys Gly Phe Ser Pro Glu Val Ile Pro Met Phe Thr Ala Leu
1               5                   10                  15

<210> SEQ ID NO 477
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 477

Lys Tyr Thr Ala Phe Thr Ile Pro Ser Thr Asn Asn Glu Thr Pro
1               5                   10                  15

<210> SEQ ID NO 478
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 478

Lys Tyr Thr Ala Phe Thr Ile Pro Ser Ile Asn Asn Glu Thr Pro
1               5                   10                  15

<210> SEQ ID NO 479
<211> LENGTH: 15
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 479

Lys Tyr Thr Ala Phe Thr Ile Pro Ser Thr Asn Asn Glu Thr Pro
1               5                   10                  15

<210> SEQ ID NO 480
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 480

Glu Lys Ile Lys Ala Leu Thr Ala Ile Cys Glu Glu Met Glu Lys
1               5                   10                  15

<210> SEQ ID NO 481
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 481

Glu Lys Ile Lys Ala Leu Val Glu Ile Cys Thr Glu Met Glu Lys
1               5                   10                  15

<210> SEQ ID NO 482
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 482

Glu Lys Ile Glu Ala Leu Thr Ala Ile Cys Glu Glu Met Glu Lys
1               5                   10                  15

<210> SEQ ID NO 483
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 483

Gly Lys Tyr Ala Lys Met Arg Thr Ala His Thr Asn Asp Val Lys
1               5                   10                  15

<210> SEQ ID NO 484
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 484

Gly Lys Tyr Ala Arg Met Arg Gly Ala His Thr Asn Asp Val Lys
1               5                   10                  15

<210> SEQ ID NO 485

```
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 485

Gly Lys Tyr Ala Arg Met Arg Gly Ala His Thr Asn Asp Val Arg
1               5                   10                  15

<210> SEQ ID NO 486
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 486

Leu Pro Ile Gln Lys Glu Thr Trp Glu Thr Trp Trp Thr Asp Tyr
1               5                   10                  15

<210> SEQ ID NO 487
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 487

Leu Pro Ile Gln Lys Glu Thr Trp Glu Ala Trp Trp Thr Glu Tyr
1               5                   10                  15

<210> SEQ ID NO 488
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 488

Leu Pro Ile Gln Lys Glu Thr Trp Glu Ala Trp Trp Thr Glu Tyr
1               5                   10                  15

<210> SEQ ID NO 489
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 489

Trp Tyr Gln Leu Glu Lys Asp Pro Ile Ala Gly Val Glu Thr Phe
1               5                   10                  15

<210> SEQ ID NO 490
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 490
```

Trp Tyr Gln Leu Glu Lys Glu Pro Ile Val Gly Ala Glu Thr Phe
1               5                   10                  15

<210> SEQ ID NO 491
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 491

Trp Tyr Gln Leu Glu Lys Asp Pro Ile Ala Gly Ala Glu Thr Phe
1               5                   10                  15

<210> SEQ ID NO 492
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 492

Glu Asn Val Thr Glu Asn Phe Asn Met Trp Lys Asn Asn Met Val
1               5                   10                  15

<210> SEQ ID NO 493
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 493

Glu Asn Val Thr Glu Asn Phe Asn Met Trp Lys Asn Asp Met Val
1               5                   10                  15

<210> SEQ ID NO 494
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 494

Glu Asn Val Thr Glu Glu Phe Asn Met Trp Lys Asn Asn Met Val
1               5                   10                  15

<210> SEQ ID NO 495
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 495

Val Ile Gln Asp Asn Ser Asp Ile Lys Val Val Pro Arg Arg Lys
1               5                   10                  15

<210> SEQ ID NO 496
<211> LENGTH: 15
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 496

Val Ile Gln Asp Asn Ser Asp Ile Lys Val Val Pro Arg Arg Lys
1               5                   10                  15

<210> SEQ ID NO 497
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 497

Val Ile Gln Asp Asn Ser Asp Ile Lys Val Val Pro Arg Arg Lys
1               5                   10                  15

<210> SEQ ID NO 498
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 498

Val Ser Gln Asn Tyr Pro Ile Val Gln Asn Ile Gln Gly Gln Met
1               5                   10                  15

<210> SEQ ID NO 499
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 499

Val Ser Gln Asn Tyr Pro Ile Val Gln Asn Leu Gln Gly Gln Met
1               5                   10                  15

<210> SEQ ID NO 500
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 500

Val Ser Gln Asn Tyr Pro Ile Val Gln Asn Leu Gln Gly Gln Met
1               5                   10                  15

<210> SEQ ID NO 501
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 501

Val Leu Ala Glu Ala Met Ser Gln Val Thr Asn Ser Ala Thr Ile Met
1               5                   10                  15
```

```
<210> SEQ ID NO 502
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 502

Val Leu Ala Glu Ala Met Ser Gln Thr Asn Ser Thr Ile Leu Met
1               5                   10                  15

<210> SEQ ID NO 503
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 503

Val Leu Ala Glu Ala Met Ser Gln Ala Gln Gln Thr Asn Ile Met
1               5                   10                  15

<210> SEQ ID NO 504
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 504

His Gly Gln Val Asp Cys Ser Pro Gly Ile Trp Gln Leu Ala Cys
1               5                   10                  15

<210> SEQ ID NO 505
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 505

His Gly Gln Val Asp Cys Ser Pro Gly Ile Trp Gln Leu Ala Cys
1               5                   10                  15

<210> SEQ ID NO 506
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 506

His Gly Gln Val Asp Cys Ser Pro Gly Ile Trp Gln Leu Asp Cys
1               5                   10                  15

<210> SEQ ID NO 507
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 507
```

```
Arg Val Leu Ala Glu Ala Met Ser Gln Val Thr Asn Ser Ala Thr
1               5                   10                  15

<210> SEQ ID NO 508
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 508

Arg Val Leu Ala Glu Ala Met Ser Gln Thr Asn Ser Thr Ile Leu
1               5                   10                  15

<210> SEQ ID NO 509
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 509

Arg Val Leu Ala Glu Ala Met Ser Gln Thr Asn Ser Ala Ile Leu
1               5                   10                  15

<210> SEQ ID NO 510
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 510

Glu Gln Leu Ile Lys Lys Glu Arg Val Tyr Leu Ser Trp Val Pro Ala
1               5                   10                  15

His Lys Gly Ile Gly
            20

<210> SEQ ID NO 511
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 511

Glu Gln Leu Ile Lys Lys Glu Lys Val Tyr Leu Ala Trp Val Pro Ala
1               5                   10                  15

His Lys Gly Ile Gly
            20

<210> SEQ ID NO 512
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 512

Glu Glu Leu Ile Lys Lys Glu Lys Val Tyr Leu Ala Trp Val Pro
1               5                   10                  15
```

<210> SEQ ID NO 513
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 513

Glu Pro Leu Ile Lys Lys Glu Lys Val Tyr Leu Ser Trp Val Pro
1               5                   10                  15

<210> SEQ ID NO 514
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 514

Lys Leu Ile Glu Lys Asp Lys Val Tyr Leu Ser Trp Val Pro Ala
1               5                   10                  15

<210> SEQ ID NO 515
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 515

Leu Ile Lys Lys Glu Arg Val Tyr Leu Ser Trp Val Pro Ala His
1               5                   10                  15

<210> SEQ ID NO 516
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 516

Glu Lys Val Tyr Leu Ala Trp Val Pro Ala His Lys Gly Ile Gly
1               5                   10                  15

<210> SEQ ID NO 517
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 517

Glu Lys Val Tyr Leu Ser Trp Val Pro Ala His Lys Gly Ile Gly
1               5                   10                  15

<210> SEQ ID NO 518
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 518

Cys Thr His Gly Ile Arg Pro Val Val Ser Thr Gln Leu Leu Leu
1               5                   10                  15

<210> SEQ ID NO 519
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 519

Cys Thr His Gly Ile Lys Pro Val Val Ser Thr Gln Leu Leu Leu
1               5                   10                  15

<210> SEQ ID NO 520
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 520

Cys Thr His Gly Ile Lys Pro Val Val Ser Thr Gln Leu Leu Leu
1               5                   10                  15

<210> SEQ ID NO 521
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 521

Cys Thr His Gly Ile Arg Pro Val Val Ser Thr Gln Leu Leu Leu
1               5                   10                  15

<210> SEQ ID NO 522
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 522

Ile Cys Thr Thr Thr Val Pro Trp Asn Ala Ser Trp Ser Asn Lys Ser
1               5                   10                  15

Leu

<210> SEQ ID NO 523
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 523

Ile Cys Thr Thr Ala Val Pro Trp Asn Thr Ser Trp Ser Asn Lys Ser
1               5                   10                  15

Gln
```

<210> SEQ ID NO 524
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 524

Ile Cys Thr Thr Thr Val Pro Trp Asn Ala Ser Trp Ser Asn Arg
1               5                   10                  15

<210> SEQ ID NO 525
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 525

Cys Thr Thr Thr Val Pro Trp Asn Ser Ser Trp Ser Asn Lys Thr
1               5                   10                  15

<210> SEQ ID NO 526
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 526

Thr Thr Ala Val Pro Trp Asn Ala Ser Trp Ser Asn Lys Ser Leu
1               5                   10                  15

<210> SEQ ID NO 527
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 527

Thr Thr Ala Val Pro Trp Asn Thr Ser Trp Ser Asn Lys Ser Leu
1               5                   10                  15

<210> SEQ ID NO 528
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 528

Ala Cys Gln Gly Val Gly Gly Pro Gly His Lys Ala Arg Val Leu Ala
1               5                   10                  15

Glu Ala Met Ser
            20

<210> SEQ ID NO 529
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 529

Ala Cys Gln Gly Val Gly Gly Pro Ser His Lys Ala Arg Val Leu Ala
1               5                   10                  15

Glu Ala Met Ser
            20

<210> SEQ ID NO 530
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 530

Ala Cys Gln Glu Val Gly Gly Pro Gly His Lys Ala Arg Val Leu
1               5                   10                  15

<210> SEQ ID NO 531
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 531

Gly Gly Pro Ser His Lys Ala Arg Val Leu Ala Glu Ala Met Gly
1               5                   10                  15

<210> SEQ ID NO 532
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 532

Ala Ala Glu Trp Asp Arg Val His Pro Val His Ala Gly Pro Ile Ala
1               5                   10                  15

Pro Gly Gln

<210> SEQ ID NO 533
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 533

Ala Ala Glu Trp Asp Arg Leu His Pro Val His Ala Gly Pro Val Ala
1               5                   10                  15

Pro Gly Gln

<210> SEQ ID NO 534
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 534

Ala Ala Glu Asp Arg Leu His Pro Val His Ala Gly Pro Ile Pro
1               5                   10                  15

<210> SEQ ID NO 535
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 535

Ala Asp Trp Asp Arg Leu His Pro Val His Ala Gly Pro Val Ala
1               5                   10                  15

<210> SEQ ID NO 536
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 536

Ala Glu Trp Asp Arg Leu His Pro Val His Ala Gly Pro Ile Ala
1               5                   10                  15

<210> SEQ ID NO 537
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 537

Trp Asp Arg Val His Pro Val His Ala Gly Pro Asn Pro Pro Gly
1               5                   10                  15

<210> SEQ ID NO 538
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 538

Asp Arg Val His Pro Val His Ala Gly Pro Ile Pro Pro Gly Gln
1               5                   10                  15

<210> SEQ ID NO 539
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 539

His Ser Asn Trp Arg Ala Met Ala Ser Asp Phe Asn Leu Pro Pro
1               5                   10                  15

<210> SEQ ID NO 540

```
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 540

His Ser Asn Trp Arg Ala Met Ala Ser Glu Phe Asn Leu Pro Pro
1               5                   10                  15

<210> SEQ ID NO 541
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 541

His Ser Asn Trp Arg Ala Met Ala Ser Asp Phe Asn Leu Pro Pro
1               5                   10                  15

<210> SEQ ID NO 542
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 542

Lys Gly Arg Pro Gly Asn Phe Leu Gln Asn Arg Pro Glu Pro Thr
1               5                   10                  15

<210> SEQ ID NO 543
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 543

Lys Gly Arg Pro Gly Asn Phe Leu Gln Ser Arg Pro Glu Pro Thr
1               5                   10                  15

<210> SEQ ID NO 544
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 544

Lys Gly Arg Pro Gly Asn Phe Leu Gln Asn Arg Pro Glu Pro Thr
1               5                   10                  15

<210> SEQ ID NO 545
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 545
```

```
Arg Ser Leu Tyr Asn Thr Val Ala Thr Leu Tyr Cys Val His Gln Arg
1               5                   10                  15

<210> SEQ ID NO 546
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 546

Arg Ser Leu Phe Asn Thr Val Ala Thr Leu Tyr Cys Val His Ala Glu
1               5                   10                  15

<210> SEQ ID NO 547
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 547

Lys Ser Leu Phe Asn Thr Val Ala Thr Leu Tyr Cys Val His Ala
1               5                   10                  15

<210> SEQ ID NO 548
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 548

Ser Leu Tyr Asn Thr Val Ala Thr Leu Tyr Cys Val His Gln Arg
1               5                   10                  15

<210> SEQ ID NO 549
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 549

Tyr Val Thr Asp Arg Gly Arg Gln Lys Ile Val Ser Leu Thr Glu
1               5                   10                  15

<210> SEQ ID NO 550
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 550

Tyr Val Thr Asp Arg Gly Arg Gln Lys Val Val Ser Leu Thr Asp
1               5                   10                  15

<210> SEQ ID NO 551
<211> LENGTH: 15
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 551

Tyr Val Thr Asp Arg Gly Arg Gln Lys Val Val Ser Leu Thr Glu
1               5                   10                  15

<210> SEQ ID NO 552
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 552

Cys Thr Thr Thr Val Pro Trp Asn Ala Ser Trp Ser Asn Lys Ser
1               5                   10                  15

<210> SEQ ID NO 553
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 553

Cys Thr Thr Ala Val Pro Trp Asn Thr Ser Trp Ser Asn Lys Ser
1               5                   10                  15

<210> SEQ ID NO 554
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 554

Cys Thr Thr Asn Val Pro Trp Asn Ser Ser Trp Ser Asn Lys Ser
1               5                   10                  15

<210> SEQ ID NO 555
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 555

Trp Trp Ala Gly Ile Gln Gln Glu Phe Gly Ile Pro Tyr Asn Pro
1               5                   10                  15

<210> SEQ ID NO 556
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 556

Trp Trp Ala Gly Ile Lys Gln Glu Phe Gly Ile Pro Tyr Asn Pro
1               5                   10                  15
```

```
<210> SEQ ID NO 557
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 557

Trp Trp Ala Gly Ile Gln Gln Glu Phe Gly Ile Pro Tyr Asn Pro
1               5                   10                  15

<210> SEQ ID NO 558
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 558

Gly Pro Gly His Lys Ala Arg Val Leu Ala Glu Ala Met Ser Gln
1               5                   10                  15

<210> SEQ ID NO 559
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 559

Gly Pro Ser His Lys Ala Arg Val Leu Ala Glu Ala Met Ser Gln
1               5                   10                  15

<210> SEQ ID NO 560
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 560

Gly Pro Gly His Lys Ala Arg Val Leu Ala Glu Ala Met Ser Gln
1               5                   10                  15

<210> SEQ ID NO 561
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 561

Cys Thr His Gly Ile Arg Pro Val Val Ser Thr Gln Leu Leu Leu
1               5                   10                  15

<210> SEQ ID NO 562
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 562
```

Cys Thr His Gly Ile Lys Pro Val Val Ser Thr Gln Leu Leu Leu
1               5                   10                  15

<210> SEQ ID NO 563
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 563

Cys Thr His Gly Ile Lys Pro Val Val Ser Thr Gln Leu Leu Leu
1               5                   10                  15

<210> SEQ ID NO 564
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 564

Cys Thr His Gly Ile Arg Pro Val Val Ser Thr Gln Leu Leu Leu
1               5                   10                  15

<210> SEQ ID NO 565
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 565

Lys His Ile Val Trp Ala Ser Arg Glu Leu Glu Arg Phe Ala Val Asn
1               5                   10                  15

Pro Gly Leu Leu
            20

<210> SEQ ID NO 566
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 566

Lys His Leu Val Trp Ala Ser Arg Glu Leu Glu Arg Phe Ala Leu Asn
1               5                   10                  15

Pro Gly Leu Leu
            20

<210> SEQ ID NO 567
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 567

Lys His Leu Val Trp Ala Ser Arg Glu Leu Glu Arg Phe Ala Leu
1               5                   10                  15

<210> SEQ ID NO 568
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 568

Ala Ser Arg Glu Leu Glu Arg Phe Ala Val Asn Pro Gly Leu Leu
1               5                   10                  15

<210> SEQ ID NO 569
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 569

Gln Pro Ser Leu Gln Thr Gly Ser Glu Glu Leu Arg Ser Leu Tyr Asn
1               5                   10                  15

Thr Val Ala Thr Leu
            20

<210> SEQ ID NO 570
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 570

Gln Pro Ala Leu Gln Thr Gly Thr Glu Glu Leu Arg Ser Leu Phe Asn
1               5                   10                  15

Thr Val Ala Thr Leu
            20

<210> SEQ ID NO 571
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 571

Leu Pro Ala Leu Lys Thr Gly Ser Glu Glu Leu Arg Ser Leu Tyr
1               5                   10                  15

<210> SEQ ID NO 572
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 572

Ala Leu Gln Thr Gly Ser Glu Glu Leu Arg Ser Leu Phe Asn Thr
1               5                   10                  15

<210> SEQ ID NO 573

```
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 573

Leu Gln Thr Gly Thr Glu Glu Leu Arg Ser Leu Phe Asn Thr Val
1               5                   10                  15

<210> SEQ ID NO 574
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 574

Gly Ser Glu Glu Leu Arg Ser Leu Tyr Asn Thr Val Ala Thr Leu
1               5                   10                  15

<210> SEQ ID NO 575
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 575

Ala Cys Gln Gly Val Gly Gly Pro Gly His Lys Ala Arg Val Leu Ala
1               5                   10                  15

Glu Ala Met Ser
            20

<210> SEQ ID NO 576
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 576

Ala Cys Gln Gly Val Gly Gly Pro Ser His Lys Ala Arg Val Leu Ala
1               5                   10                  15

Glu Ala Met Ser
            20

<210> SEQ ID NO 577
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 577

Ala Cys Gln Glu Val Gly Gly Pro Gly His Lys Ala Arg Val Leu
1               5                   10                  15

<210> SEQ ID NO 578
<211> LENGTH: 15
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 578

Gly Gly Pro Ser His Lys Ala Arg Val Leu Ala Glu Ala Met Gly
1               5                   10                  15

<210> SEQ ID NO 579
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 579

Arg Glu Leu Asn Lys Arg Thr Gln Asp Phe Trp Glu Val Gln Leu
1               5                   10                  15

<210> SEQ ID NO 580
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 580

Arg Glu Leu Asn Lys Arg Thr Gln Asp Phe Trp Glu Val Gln Leu
1               5                   10                  15

<210> SEQ ID NO 581
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 581

Arg Glu Leu Asn Arg Arg Thr Gln Asp Phe Trp Glu Val Gln Leu
1               5                   10                  15

<210> SEQ ID NO 582
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 582

Leu Leu Arg Ala Ile Glu Ala Gln Gln His Leu Leu Gln Leu Thr
1               5                   10                  15

<210> SEQ ID NO 583
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 583

Leu Leu Arg Ala Ile Glu Ala Gln Gln His Met Leu Gln Leu Thr
1               5                   10                  15
```

<210> SEQ ID NO 584
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 584

Leu Leu Met Ala Ile Glu Ala Gln Gln His Leu Leu Gln Leu Thr
1               5                   10                  15

<210> SEQ ID NO 585
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 585

Lys Thr Ala Val Gln Met Ala Val Phe Ile His Asn Phe Lys Arg
1               5                   10                  15

<210> SEQ ID NO 586
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 586

Lys Thr Ala Val Gln Met Ala Val Phe Ile His Asn Phe Lys Arg
1               5                   10                  15

<210> SEQ ID NO 587
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 587

Lys Thr Ala Val Gln Met Ala Val Phe Ile His Asn Phe Lys Arg
1               5                   10                  15

<210> SEQ ID NO 588
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 588

Lys Leu Asn Trp Ala Ser Gln Ile Tyr Pro Gly Ile Lys Val Arg
1               5                   10                  15

<210> SEQ ID NO 589
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 589

Lys Leu Asn Trp Ala Ser Gln Ile Tyr Ala Gly Ile Lys Val Lys
1               5                   10                  15

<210> SEQ ID NO 590
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 590

Lys Leu Asn Trp Ala Ser Gln Ile Tyr Ala Gly Ile Lys Val Lys
1               5                   10                  15

<210> SEQ ID NO 591
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 591

Tyr Ala Lys Met Arg Thr Ala His Thr Asn Asp Val Lys Gln Leu
1               5                   10                  15

<210> SEQ ID NO 592
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 592

Tyr Ala Arg Met Arg Gly Ala His Thr Asn Asp Val Lys Gln Leu
1               5                   10                  15

<210> SEQ ID NO 593
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 593

Tyr Ala Arg Lys Arg Ser Ala His Thr Asn Asp Val Lys Gln Leu
1               5                   10                  15

<210> SEQ ID NO 594
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 594

Asp Gln Ala Glu His Leu Lys Thr Ala Val Gln Met Ala Val Phe
1               5                   10                  15

<210> SEQ ID NO 595
<211> LENGTH: 15
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 595

Asp Gln Ala Glu His Leu Lys Thr Ala Val Gln Met Ala Val Phe
1               5                   10                  15

<210> SEQ ID NO 596
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 596

Asp Gln Ala Glu His Leu Lys Thr Ala Val Gln Met Ala Val Phe
1               5                   10                  15

<210> SEQ ID NO 597
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 597

Ser Leu Gln Thr Gly Ser Glu Glu Leu Arg Ser Leu Tyr Asn Thr
1               5                   10                  15

<210> SEQ ID NO 598
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 598

Ala Leu Gln Thr Gly Thr Glu Glu Leu Arg Ser Leu Phe Asn Thr
1               5                   10                  15

<210> SEQ ID NO 599
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 599

Ala Leu Lys Thr Gly Thr Glu Glu Leu Arg Ser Leu Tyr Asn Thr
1               5                   10                  15

<210> SEQ ID NO 600
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 600

Gly Pro Gly His Lys Ala Arg Val Leu Ala Glu Ala Met Ser Gln
1               5                   10                  15
```

```
<210> SEQ ID NO 601
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 601

Gly Pro Ser His Lys Ala Arg Val Leu Ala Glu Ala Met Ser Gln
1               5                   10                  15

<210> SEQ ID NO 602
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 602

Gly Pro Gly His Lys Ala Arg Val Leu Ala Glu Ala Met Ser Gln
1               5                   10                  15

<210> SEQ ID NO 603
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 603

Gln Pro Ala Leu Gln Thr Gly Thr Glu Glu Leu Arg Ser Leu Tyr Asn
1               5                   10                  15

Thr Val Ala Thr Leu
            20

<210> SEQ ID NO 604
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 604

Leu Pro Ala Leu Lys Thr Gly Ser Glu Glu Leu Arg Ser Leu Tyr
1               5                   10                  15

<210> SEQ ID NO 605
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 605

Gly Ser Glu Glu Leu Arg Ser Leu Tyr Asn Thr Val Ala Thr Leu
1               5                   10                  15

<210> SEQ ID NO 606
<211> LENGTH: 15
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 606

Ala His Thr Asn Asp Val Lys Gln Leu Thr Glu Ala Val Gln Lys
1               5                   10                  15

<210> SEQ ID NO 607
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 607

Ala His Thr Asn Asp Val Lys Gln Leu Thr Glu Ala Val Gln Lys
1               5                   10                  15

<210> SEQ ID NO 608
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 608

Gly Asp Ile Ile Gly Asp Ile Arg Gln Ala His Cys Asn Ile Ser
1               5                   10                  15

<210> SEQ ID NO 609
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 609

Gly Asp Ile Ile Gly Asp Ile Arg Gln Ala His Cys Asn Ile Ser
1               5                   10                  15

<210> SEQ ID NO 610
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 610

Ser Glu Lys Ser Ala Val Gly Ile Gly Ala Val Phe Leu Gly Phe
1               5                   10                  15

<210> SEQ ID NO 611
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 611

Arg Glu Lys Arg Ala Val Gly Leu Gly Ala Val Phe Leu Gly Phe
1               5                   10                  15
```

<210> SEQ ID NO 612
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 612

Arg Ala Ser Ile Leu Arg Gly Gly Lys Leu Asp Lys Trp Glu Lys
1               5                   10                  15

<210> SEQ ID NO 613
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 613

Ser Ala Ser Ile Leu Arg Gly Gly Lys Leu Asp Lys Trp Glu Lys
1               5                   10                  15

<210> SEQ ID NO 614
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 614

Thr Asn Asn Pro Pro Val Pro Val Gly Asp Ile Tyr Lys Arg Trp
1               5                   10                  15

<210> SEQ ID NO 615
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 615

Thr Ser Asn Pro Pro Val Pro Val Gly Asp Ile Tyr Lys Arg Trp
1               5                   10                  15

<210> SEQ ID NO 616
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 616

Cys Lys Ser Asn Ile Thr Gly Leu Leu Leu Thr Arg Asp Gly Gly
1               5                   10                  15

<210> SEQ ID NO 617
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 617

Cys Thr Ser Asn Ile Thr Gly Leu Leu Leu Val Arg Asp Gly Gly
1               5                   10                  15

<210> SEQ ID NO 618
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 618

Ser Leu Tyr Asn Thr Val Ala Thr Leu Tyr Cys Val His Ala Gly
1               5                   10                  15

<210> SEQ ID NO 619
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 619

Ser Leu Tyr Asn Thr Val Ala Thr Leu Tyr Cys Val His Gln Arg
1               5                   10                  15

<210> SEQ ID NO 620
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 620

Glu Gln Leu Ile Asn Lys Glu Arg Val Tyr Leu Ser Trp Val Pro
1               5                   10                  15

<210> SEQ ID NO 621
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 621

Glu Pro Leu Ile Lys Lys Glu Lys Val Tyr Leu Ser Trp Val Pro
1               5                   10                  15

<210> SEQ ID NO 622
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 622

Ala Glu Trp Asp Arg Leu His Pro Val His Ala Gly Pro Ile Ala
1               5                   10                  15

<210> SEQ ID NO 623
<211> LENGTH: 15
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 623

Ala Glu Trp Asp Arg Leu His Pro Val His Ala Gly Pro Ile Ala
1               5                   10                  15

<210> SEQ ID NO 624
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 624

His Gln Ala Ala Met Gln Met Leu Lys Asp Thr Ile Asn Glu Glu
1               5                   10                  15

<210> SEQ ID NO 625
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 625

His Gln Ala Ala Met Gln Met Leu Lys Asp Thr Ile Asn Glu Glu
1               5                   10                  15

<210> SEQ ID NO 626
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 626

Ile Val Gln Gln Gln Ser Asn Leu Leu Arg Ala Ile Glu Ala Gln Gln
1               5                   10                  15

<210> SEQ ID NO 627
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 627

Val Val Gln Gln Gln Ser Asn Leu Leu Arg Ala Ile Glu Ala Gln
1               5                   10                  15

<210> SEQ ID NO 628
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 628

Val Gln Gln Gln Asn Asn Leu Leu Arg Ala Ile Glu Ala Gln His
1               5                   10                  15
```

<210> SEQ ID NO 629
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 629

Ala Val Phe Ile His Asn Phe Lys Arg Lys Gly Gly Ile Gly Gly Tyr
1               5                   10                  15

<210> SEQ ID NO 630
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 630

Ala Val Phe Ile His Asn Phe Lys Arg Lys Gly Gly Ile Gly Gly
1               5                   10                  15

<210> SEQ ID NO 631
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 631

Val Leu Ile His Asn Phe Lys Arg Lys Gly Gly Ile Gly Gly Tyr
1               5                   10                  15

<210> SEQ ID NO 632
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 632

Met Ala Ile Cys Glu Glu Met Glu Lys Glu Gly Lys Ile Thr Lys
1               5                   10                  15

<210> SEQ ID NO 633
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 633

Thr Ala Ile Cys Glu Glu Met Glu Lys Glu Gly Lys Ile Thr Lys
1               5                   10                  15

<210> SEQ ID NO 634
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 634

Gly Gly Pro Ser His Lys Ala Arg Val Leu Ala Glu Ala Met Ser
1               5                   10                  15

<210> SEQ ID NO 635
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 635

Gly Gly Pro Ser His Lys Ala Arg Val Leu Ala Glu Ala Met Gly
1               5                   10                  15

<210> SEQ ID NO 636
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 636

Ile Ile Gly Gln Val Arg Asp Gln Ala Glu His Leu Lys Thr Ala
1               5                   10                  15

<210> SEQ ID NO 637
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 637

Leu Ile Gly Gln Val Arg Asp Gln Ala Glu His Leu Lys Thr Ala
1               5                   10                  15

<210> SEQ ID NO 638
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 638

Ala Val Phe Ile His Asn Phe Lys Arg Lys Gly Gly Ile Gly Gly Tyr
1               5                   10                  15

<210> SEQ ID NO 639
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 639

Ala Val Phe Ile His Asn Phe Lys Arg Lys Gly Gly Ile Gly Gly
1               5                   10                  15

<210> SEQ ID NO 640
<211> LENGTH: 15
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 640

Val Leu Ile His Asn Phe Lys Arg Lys Gly Gly Ile Gly Gly Tyr
1               5                   10                  15

<210> SEQ ID NO 641
<211> LENGTH: 16
<212> TYPE: PRT
<213> ORGANISM: Human immunodeficiency virus

<400> SEQUENCE: 641

Ile Val Gln Gln Gln Ser Asn Leu Leu Arg Ala Ile Glu Ala Gln Gln
1               5                   10                  15

<210> SEQ ID NO 642
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 642

Val Val Gln Gln Gln Ser Asn Leu Leu Arg Ala Ile Glu Ala Gln
1               5                   10                  15

<210> SEQ ID NO 643
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 643

Val Gln Gln Gln Asn Asn Leu Leu Arg Ala Ile Glu Ala Gln His
1               5                   10                  15

<210> SEQ ID NO 644
<211> LENGTH: 16
<212> TYPE: PRT
<213> ORGANISM: Human immunodeficiency virus

<400> SEQUENCE: 644

Ala Val Phe Ile His Asn Phe Lys Arg Lys Gly Gly Ile Gly Gly Tyr
1               5                   10                  15

<210> SEQ ID NO 645
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 645

Ala Val Phe Ile His Asn Phe Lys Arg Lys Gly Gly Ile Gly Gly
1               5                   10                  15

<210> SEQ ID NO 646
<211> LENGTH: 15
<212> TYPE: PRT
```

-continued

```
<213> ORGANISM: Artificial Sequence
<220> FEATURE:
<223> OTHER INFORMATION: Description of Artificial Sequence: Synthetic
      peptide

<400> SEQUENCE: 646

Val Leu Ile His Asn Phe Lys Arg Lys Gly Gly Ile Gly Gly Tyr
1               5                   10                  15

<210> SEQ ID NO 647
<211> LENGTH: 15
<212> TYPE: PRT
<213> ORGANISM: Human immunodeficiency virus

<400> SEQUENCE: 647

Met Ala Ile Cys Glu Glu Met Glu Lys Glu Gly Lys Ile Thr Lys
1               5                   10                  15

<210> SEQ ID NO 648
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 648

Thr Ala Ile Cys Glu Glu Met Glu Lys Glu Gly Lys Ile Thr Lys
1               5                   10                  15

<210> SEQ ID NO 649
<211> LENGTH: 15
<212> TYPE: PRT
<213> ORGANISM: Human immunodeficiency virus

<400> SEQUENCE: 649

Gly Gly Pro Ser His Lys Ala Arg Val Leu Ala Glu Ala Met Ser
1               5                   10                  15

<210> SEQ ID NO 650
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 650

Gly Gly Pro Ser His Lys Ala Arg Val Leu Ala Glu Ala Met Gly
1               5                   10                  15

<210> SEQ ID NO 651
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 651

Glu Gln Leu Ile Lys Lys Glu Arg Val Tyr Leu Ser Trp Val Pro Ala
1               5                   10                  15

His Lys Gly Ile Gly
            20

<210> SEQ ID NO 652
```

```
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 652

Glu Gln Leu Ile Lys Lys Glu Lys Val Tyr Leu Ala Trp Val Pro Ala
1               5                   10                  15

His Lys Gly Ile Gly
            20

<210> SEQ ID NO 653
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 653

Glu Glu Leu Ile Lys Lys Glu Lys Val Tyr Leu Ala Trp Val Pro
1               5                   10                  15

<210> SEQ ID NO 654
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 654

Glu Pro Leu Ile Lys Lys Glu Lys Val Tyr Leu Ser Trp Val Pro
1               5                   10                  15

<210> SEQ ID NO 655
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 655

Lys Leu Ile Glu Lys Asp Lys Val Tyr Leu Ser Trp Val Pro Ala
1               5                   10                  15

<210> SEQ ID NO 656
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 656

Leu Ile Lys Lys Glu Arg Val Tyr Leu Ser Trp Val Pro Ala His
1               5                   10                  15

<210> SEQ ID NO 657
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 657

Glu Lys Val Tyr Leu Ala Trp Val Pro Ala His Lys Gly Ile Gly
1               5                   10                  15

<210> SEQ ID NO 658
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 658

Glu Lys Val Tyr Leu Ser Trp Val Pro Ala His Lys Gly Ile Gly
1               5                   10                  15

<210> SEQ ID NO 659
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 659

Cys Thr His Gly Ile Arg Pro Val Val Ser Thr Gln Leu Leu Leu
1               5                   10                  15

<210> SEQ ID NO 660
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 660

Cys Thr His Gly Ile Lys Pro Val Val Ser Thr Gln Leu Leu Leu
1               5                   10                  15

<210> SEQ ID NO 661
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 661

Cys Thr His Gly Ile Lys Pro Val Val Ser Thr Gln Leu Leu Leu
1               5                   10                  15

<210> SEQ ID NO 662
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 662

Cys Thr His Gly Ile Arg Pro Val Val Ser Thr Gln Leu Leu Leu
1               5                   10                  15

<210> SEQ ID NO 663
<211> LENGTH: 17

<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 663

Ile Cys Thr Thr Thr Val Pro Trp Asn Ala Ser Trp Ser Asn Lys Ser
1               5                   10                  15
Leu

<210> SEQ ID NO 664
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 664

Ile Cys Thr Thr Ala Val Pro Trp Asn Thr Ser Trp Ser Asn Lys Ser
1               5                   10                  15
Gln

<210> SEQ ID NO 665
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 665

Ile Cys Thr Thr Thr Val Pro Trp Asn Ala Ser Trp Ser Asn Arg
1               5                   10                  15

<210> SEQ ID NO 666
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 666

Cys Thr Thr Thr Val Pro Trp Asn Ser Ser Trp Ser Asn Lys Thr
1               5                   10                  15

<210> SEQ ID NO 667
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 667

Thr Thr Ala Val Pro Trp Asn Ala Ser Trp Ser Asn Lys Ser Leu
1               5                   10                  15

<210> SEQ ID NO 668
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 668

Thr Thr Ala Val Pro Trp Asn Thr Ser Trp Ser Asn Lys Ser Leu
1               5                   10                  15

<210> SEQ ID NO 669
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 669

Ala Cys Gln Gly Val Gly Gly Pro Gly His Lys Ala Arg Val Leu Ala
1               5                   10                  15

Glu Ala Met Ser
            20

<210> SEQ ID NO 670
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 670

Ala Cys Gln Gly Val Gly Gly Pro Ser His Lys Ala Arg Val Leu Ala
1               5                   10                  15

Glu Ala Met Ser
            20

<210> SEQ ID NO 671
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 671

Ala Cys Gln Glu Val Gly Gly Pro Gly His Lys Ala Arg Val Leu
1               5                   10                  15

<210> SEQ ID NO 672
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 672

Gly Gly Pro Ser His Lys Ala Arg Val Leu Ala Glu Ala Met Gly
1               5                   10                  15

<210> SEQ ID NO 673
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 673

Ala Ala Glu Trp Asp Arg Val His Pro Val His Ala Gly Pro Ile Ala
1               5                   10                  15

Pro Gly Gln

<210> SEQ ID NO 674
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 674

Ala Ala Glu Trp Asp Arg Leu His Pro Val His Ala Gly Pro Val Ala
1               5                   10                  15

Pro Gly Gln

<210> SEQ ID NO 675
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 675

Ala Ala Glu Asp Arg Leu His Pro Val His Ala Gly Pro Ile Pro
1               5                   10                  15

<210> SEQ ID NO 676
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 676

Ala Asp Trp Asp Arg Leu His Pro Val His Ala Gly Pro Val Ala
1               5                   10                  15

<210> SEQ ID NO 677
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 677

Ala Glu Trp Asp Arg Leu His Pro Val His Ala Gly Pro Ile Ala
1               5                   10                  15

<210> SEQ ID NO 678
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 678

Trp Asp Arg Val His Pro Val His Ala Gly Pro Asn Pro Pro Gly
1               5                   10                  15

<210> SEQ ID NO 679

```
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 679

Asp Arg Val His Pro Val His Ala Gly Pro Ile Pro Pro Gly Gln
1               5                   10                  15

<210> SEQ ID NO 680
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 680

His Ser Asn Trp Arg Ala Met Ala Ser Asp Phe Asn Leu Pro Pro
1               5                   10                  15

<210> SEQ ID NO 681
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 681

His Ser Asn Trp Arg Ala Met Ala Ser Glu Phe Asn Leu Pro Pro
1               5                   10                  15

<210> SEQ ID NO 682
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 682

His Ser Asn Trp Arg Ala Met Ala Ser Asp Phe Asn Leu Pro Pro
1               5                   10                  15

<210> SEQ ID NO 683
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 683

Lys Gly Arg Pro Gly Asn Phe Leu Gln Asn Arg Pro Glu Pro Thr
1               5                   10                  15

<210> SEQ ID NO 684
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 684
```

-continued

```
Lys Gly Arg Pro Gly Asn Phe Leu Gln Ser Arg Pro Glu Pro Thr
1               5                   10                  15

<210> SEQ ID NO 685
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 685

Lys Gly Arg Pro Gly Asn Phe Leu Gln Asn Arg Pro Glu Pro Thr
1               5                   10                  15
```